(12) United States Patent
Lazarides et al.

(10) Patent No.: US 7,977,344 B2
(45) Date of Patent: Jul. 12, 2011

(54) COMPOUNDS

(75) Inventors: Linos Lazarides, Stevenage (GB);
Stephen Allan Smith, Stevenage (GB);
Richard Stocker, Stevenage (GB);
Colin Jack Theobald, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 609 days.

(21) Appl. No.: 12/031,764

(22) Filed: Feb. 15, 2008

(65) Prior Publication Data

US 2009/0131458 A1    May 21, 2009

Related U.S. Application Data

(60) Provisional application No. 60/890,523, filed on Feb. 19, 2007, provisional application No. 60/972,313, filed on Sep. 14, 2007, provisional application No. 61/021,921, filed on Jan. 18, 2008.

(51) Int. Cl.
   - C07D 473/16    (2006.01)
   - C07D 473/18    (2006.01)
   - A61K 31/522    (2006.01)
   - A61P 11/06     (2006.01)
   - A61P 37/08     (2006.01)
   - C07D 307/10    (2006.01)
   - C07D 307/12    (2006.01)
   - C07D 309/04    (2006.01)
   - C07D 309/06    (2006.01)
   - C07D 473/40    (2006.01)

(52) U.S. Cl. .............. 514/263.23; 544/276; 544/277; 549/425; 549/427; 549/428; 549/502; 549/504

(58) Field of Classification Search .............. 514/263.23; 544/276
See application file for complete search history.

(56) References Cited

U.S. PATENT DOCUMENTS

| | | | |
|---|---|---|---|
| 5,962,479 A | 10/1999 | Chen | |
| 6,376,501 B1 | 4/2002 | Isobe et al. | |
| 6,552,192 B1 | 4/2003 | Hanuset et al. | |
| 7,125,880 B1 | 10/2006 | Chen | |
| 7,642,350 B2 * | 1/2010 | Pryde | 544/61 |
| 2001/0020030 A1 | 9/2001 | Stewart et al. | |
| 2003/0187261 A1 | 10/2003 | Havlicek et al. | |
| 2003/0236216 A1 | 12/2003 | Devos et al. | |
| 2005/0054590 A1 | 3/2005 | Averett | |
| 2006/0029642 A1 | 2/2006 | Miljkovic et al. | |
| 2006/0148805 A1 | 7/2006 | Chen et al. | |
| 2006/0264448 A1 | 11/2006 | Pryde | |
| 2007/0190071 A1 * | 8/2007 | Kurimoto et al. | 424/184.1 |
| 2007/0197478 A1 | 8/2007 | Jones et al. | |
| 2008/0008682 A1 * | 1/2008 | Chong et al. | 424/85.6 |
| 2008/0269240 A1 * | 10/2008 | Hashimoto et al. | 514/252.16 |
| 2008/0300244 A1 * | 12/2008 | Bonnert et al. | 514/232.5 |
| 2009/0047249 A1 * | 2/2009 | Graupe et al. | 424/85.6 |
| 2009/0082332 A1 * | 3/2009 | Abbot et al. | 514/210.21 |
| 2009/0099216 A1 * | 4/2009 | Millichip et al. | 514/263.38 |
| 2009/0105212 A1 * | 4/2009 | Isobe et al. | 514/210.21 |
| 2009/0118263 A1 * | 5/2009 | Hashimoto et al. | 514/218 |
| 2009/0131458 A1 * | 5/2009 | Lazarides et al. | 514/263.23 |
| 2009/0143400 A1 * | 6/2009 | McInally et al. | 514/252.16 |
| 2009/0192153 A1 * | 7/2009 | Hashimoto et al. | 514/234.2 |
| 2009/0202484 A1 * | 8/2009 | Chong et al. | 424/85.6 |
| 2009/0324551 A1 * | 12/2009 | Carson et al. | 424/93.4 |
| 2009/0325877 A1 * | 12/2009 | Grunt et al. | 514/12 |
| 2010/0075995 A1 * | 3/2010 | Biggadike et al. | 514/263.22 |
| 2010/0087443 A1 * | 4/2010 | Bonnert et al. | 514/252.16 |
| 2010/0093998 A1 * | 4/2010 | Isobe et al. | 540/575 |
| 2010/0099870 A1 * | 4/2010 | Isobe et al. | 544/276 |
| 2010/0120799 A1 * | 5/2010 | Lazarides et al. | 514/263.23 |
| 2010/0130491 A1 * | 5/2010 | Bonnert et al. | 514/234.2 |
| 2010/0240623 A1 * | 9/2010 | Cook et al. | 514/171 |

FOREIGN PATENT DOCUMENTS

| | | |
|---|---|---|
| EP | 1939198 A1 | 7/2008 |
| WO | 2004029054 A1 | 4/2004 |
| WO | 2007028129 A1 | 3/2007 |
| WO | 2007041863 A1 | 4/2007 |
| WO | WO 2008004948 A1 * | 1/2008 |
| WO | 2008114008 A1 | 9/2008 |
| WO | WO 2010018130 A1 * | 2/2010 |
| WO | WO 2010018131 A1 * | 2/2010 |
| WO | WO 2010018132 A1 * | 2/2010 |
| WO | WO 2010018134 A1 * | 2/2010 |

OTHER PUBLICATIONS

Kurimoto et al.; "Prodrugs of 9-Benzyl-8-Hydroxy-2-(2-Hydroxyethylthio)Adenine: Potent Interferon Inducing Agents in Monkeys"; Chem. Pharm. Bull.; 2004; vol. 52, No. 4; pp. 466-469.

Hirota et al; "Discovery of 8-Hydroxyadenines as a Novel Type of Interferon Inducer"; J. Med. Chem.; 2002; vol. 45; pp. 5419-5422.

Isobe et al.; "Synthesis and Biological Evaluation of Novel 9-Substituted-8-Hydroxyadenine Derivatives as Potent Interferon Inducers"; J. Med. Chem.; 2006; vol. 49; pp. 2088-2095.

* cited by examiner

*Primary Examiner* — Mark L Berch

(74) *Attorney, Agent, or Firm* — Kathryn L. Coulter

(57) ABSTRACT

The present invention includes novel compounds useful in the treatment of various disorders in particular infectious diseases, cancer, and allergic diseases and other inflammatory conditions for example allergic rhinitis and asthma, and as vaccine adjuvants.

28 Claims, 6 Drawing Sheets

XRPD diffractogram of 6-amino-2-butylamino-9-(tetrahydro-2*H*-pyran-4-ylmethyl)-7,9-dihydro-8*H*-purin-8-one XRPD diffractogram of 6-amino-2-(butyloxy)-9-(tetrahydro-3-furanylmethyl)-7,9-dihydro-8H-purin-8-one, Isomer 1

XRPD diffractogram of 6-amino-2-(butyloxy)-9-(tetrahydro-3-furanylmethyl)-7,9-dihydro-8H-purin-8-one, Isomer 2

XRPD diffractogram of 6-amino-2-(butylamino)-9-(tetrahydro-3-furanylmethyl)-7,9-dihydro-8*H*-purin-8-one, Isomer 1

XRPD diffractogram of 6-amino-2-(butylamino)-9-(tetrahydro-3-furanylmethyl)-7,9-dihydro-8*H*-purin-8-one, Isomer 2

XRPD diffractogram of 6-amino-2-[(2-cyclopropylethyl)oxy]-9-(tetrahydro-3-furanylmethyl)-7,9-dihydro-8H-purin-8-one, Isomer 1

XRPD diffractogram of 6-amino-2-[(2-cyclopropylethyl)oxy]-9-[tetrahydro-3-furanylmethyl]-7,9-dihydro-8H-purin-8-one, Isomer 2

DSC thermogram of 6-amino-2-butylamino-9-(tetrahydro-2H-pyran-4-ylmethyl)-7,9-dihydro-8H-purin-8-one DSC thermogram of 6-amino-2-(butyloxy)-9-(tetrahydro-3-furanylmethyl)-7,9-dihydro-8H-purin-8-one, Isomer 1

DSC thermogram of 6-amino-2-(butyloxy)-9-(tetrahydro-3-furanylmethyl)-7,9-dihydro-8H-purin-8-one, Isomer 2

DSC thermogram of 6-amino-2-(butylamino)-9-(tetrahydro-3-furanylmethyl)-7,9-dihydro-8H-purin-8-one, Isomer 2

DSC thermogram of 6-amino-2-[(2-cyclopropylethyl)oxy]-9-(tetrahydro-3-furanylmethyl)-7,9-dihydro-8H-purin-8-one, Isomer 1

COMPOUNDS

CROSS-REFERENCE TO RELATED APPLICATIONS

This application claims benefit of U.S. Provisional Application Nos. 60/890,523 filed on Feb. 19, 2007, U.S. 60/972,313 filed on Sep. 14, 2007 and U.S. 61/021,921 filed on Jan. 18, 2008.

BACKGROUND OF THE INVENTION

The present invention relates to compounds, processes for their preparation, compositions containing them, to their use in the treatment of various disorders in particular infectious diseases, cancer, and allergic diseases and other inflammatory conditions for example allergic rhinitis and asthma, and as vaccine adjuvants.

Vertebrates are constantly threatened by the invasion of microorganisms and have evolved mechanisms of immune defense to eliminate infective pathogens. In mammals, this immune system comprises two branches; innate immunity and acquired immunity. The first line of host defense is the innate immune system, which is mediated by macrophages and dendritic cells. Acquired immunity involves the elimination of pathogens at the late stages of infection and also enables the generation of immunological memory. Acquired immunity is highly specific, due to the vast repertoire of lymphocytes with antigen-specific receptors that have undergone gene rearrangement.

The innate immune response was originally thought to be non-specific, but is now known to be able to discriminate between self and a variety of pathogens. The innate immune system recognises microbes via a limited number of germline-encoded pattern-recognition receptors (PRRs) which have a number of important characteristics. PRRs recognise microbial components, known as pathogen-associated molecular patterns (PAMPs), which are essential for the survival of the microorganism. PRRs are constitutively expressed in the host on all cells of a given type and are independent of immunological memory. These receptors include the recently-identified Toll-like receptors (TLRs), nucleotide oligomerisation domain-like receptors (NLRs) and retinoic acid-inducible gene-like receptors (RLRs) (Creagh E M, O'Neill L A., Trends Immunol. 2006 27(8):352-7).

Central to the generation of an effective innate immune response in mammals are mechanisms which bring about the induction of interferons and other cytokines which act upon cells to induce a number of effects. These effects can include the activation of anti-infective gene expression, the activation of antigen presentation in cells to drive strong antigen-specific immunity and the promotion of phagocytosis in phagocytic cells.

Interferon was first described as a substance which could protect cells from viral infection (Isaacs & Lindemann, J. Virus Interference. Proc. R. Soc. Lon. Ser. B. Biol. Sci. 1957, 147:258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

As a first-line therapy for hepatitis C virus (HCV) disease, interferon combinations can be highly effective at reducing viral load and in some subjects in eliminating viral replication. However, many patients fail to show a sustained viral response and in these patients viral load is not controlled. Additionally, therapy with injected interferon may be associated with a number of unwanted adverse effects which are shown to affect compliance (Dudley T. O'Donnell K, Haydon G, Mutimer D. Gut. 2006 55(9):1362-3).

Administration of a small molecule compound which could stimulate the innate immune response, including the activation of type I interferons and other cytokines, could become an important strategy for the treatment or prevention of human diseases including viral infections. This type of immunomodulatory strategy has the potential to identify compounds which may be useful not only in infectious diseases but in cancer (Krieg. Curr. Oncol. Rep. 2004; 6(2):88-95), allergic diseases (Moisan et al., Am. J. Physiol. Lung Cell Mol. Physiol. 2005; 290(5):L987-95), other inflammatory conditions such as irritable bowel disease (Rakoff-Nahoum S., Cell. 2004, 23; 118(2):229-41), and as vaccine adjuvants (Persing et al. Trends Microbiol. 2002; 10(10 Suppl):S32-7).

Mechanisms which lead to induction of type I interferons are only partly understood. One mechanism which can lead to the induction of interferon in many cell types is the recognition of double-stranded viral RNA by the RNA helicases RIG-I and MDA5. This mechanism is thought to be the primary mechanism by which interferons are induced by Sendai virus infection of cells.

Further mechanisms for the induction of interferons are via TLR-dependent signalling events. In man, plasmacytoid dendritic cells (pDCs) are professional interferon-producing cells, able to make large amounts of interferons in response to, for example, viral infection. These pDCs are shown to preferentially express TLR7 and TLR9 and stimulation of these receptors with viral RNA or DNA respectively can induce expression of interferon alpha.

Oligonucleotide agonists of TLR7 and TLR9, and small molecule purine-based agonists of TLR7 have been described which can induce interferon alpha from these cell types in animals and in man (Takeda K. et al, Annu. Rev. Immunol., 2003, 21:335-76). TLR7 agonists include imidazoquinoline compounds such as imiquimod and resiquimod, oxoadenine analogues and also nucleoside analogues such as loxoribine and 7-thia-8-oxoguanosine which have long been known to induce interferon alpha.

It remains unclear how small molecule purine-like compounds can induce type I interferons and other cytokines since the molecular targets of these known inducers have not been identified. However, an assay strategy has been developed to characterise small molecule inducers of human interferon IFNα (regardless of mechanism) which is based on stimulation of primary human donor cells with compounds, and is disclosed herein.

BRIEF DESCRIPTION OF THE INVENTION

The compounds of the invention have been shown to be inducers of human interferon and may possess an improved profile with respect to known inducers of human interferon, for example enhanced potency. Compounds which induce human interferon may be useful in the treatment of various disorders, for example the treatment of infectious diseases, cancer, and allergic diseases and other inflammatory conditions for example allergic rhinitis and asthma, and may also be useful as vaccine adjuvants.

SUMMARY OF THE INVENTION

In a first aspect, there are provided compounds of formula (I):

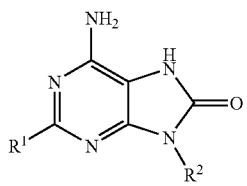

(I)

wherein

R$^1$ is C$_{1-8}$alkylamino, C$_{1-8}$alkoxy, C$_{3-7}$cycloalkylC$_{1-6}$alkylamino, C$_{3-7}$cycloalkylC$_{1-6}$alkoxy, C$_{1-3}$alkoxyC$_{2-3}$alkoxy, or Het$^b$-C$_{1-3}$alkoxy;

Het$^b$ is a 5- or 6-membered saturated aliphatic heterocyle containing one oxygen atom;

R$^2$ is —(CH$_2$)$_n$-Het;

n is an integer having a value of 1 to 4;

Het is a 5- or 6-membered saturated aliphatic heterocycle containing one oxygen heteroatom, which heterocycle may be substituted by one or two C$_{1-4}$alkyl groups;

and salts and solvates thereof.

In a further embodiment, R$^1$ is C$_{1-6}$alkylamino, C$_{1-8}$alkoxy, C$_{3-7}$cycloalkylC$_{1-6}$alkylamino, C$_{3-7}$cycloalkylC$_{1-6}$alkoxy, C$_{1-3}$alkoxyC$_{2-3}$alkoxy, or Het$^b$-C$_{1-3}$alkoxy.

In a further embodiment, R$^1$ is n-butoxy, n-butylamino, 2,2-dimethylpentyloxy, n-pentylamino, 3-methylbutoxy, 2-methylbutoxy, 1-methylbutoxy, 2-methylbutylamino, 3-methylbutylamino, 1-methylbutylamino, 2-(cyclopropyl)ethoxy, 2-(ethoxy)ethoxy, (1-methyl-2-methoxy)ethoxy, cyclohexylmethylamino, cyclopentylmethylamino, 2-(cyclopropyl)ethylamino, 2-(methyl)propoxy, cyclohexylmethoxy, methoxyethoxy, (2-tetrahydrofuranyl)methoxy, (2-tetrahydro-2H-pyranyl)methoxy, or 2-(iso-propoxy)ethoxy.

In a further embodiment, R$^1$ is n-butylamino, n-butoxy, or 2-(cyclopropyl)ethoxy.

In a further embodiment, R$^1$ is n-butylamino, n-butoxy, (R)-1-methylbutyloxy, (S)-1-methylbutyloxy, or 2-(cyclopropyl)ethoxy.

In a further embodiment, n is 1.
In a further embodiment, n is 2.
In a further embodiment, n is 3.
In a further embodiment, n is 4.

In a further embodiment, Het is tetrahydrofuran-3-yl, tetrahydro-2H-pyran-3-yl, tetrahydro-2H-pyran-4-yl, tetrahydrofuran-2-yl, 2,2-dimethyltetrahydro-2H-pyran-4-yl, or tetrahydro-2H-pyran-2-yl.

In a further embodiment, Het is tetrahydro-2H-pyran-4-yl, tetrahydrofuran-2-yl, tetrahydro-2H-pyran-3-yl, tetrahydro-2H-pyran-2-yl, or tetrahydrofuran-3-yl.

In a further embodiment, Het is tetrahydro-2H-pyran-3-yl.

In a further embodiment, Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydro-2H-pyran-2-yl.

In a further embodiment, when n is 1, then Het is tetrahydrofuran-3-yl, tetrahydro-2H-pyran-3-yl, tetrahydro-2H-pyran-4-yl, tetrahydrofuran-2-yl, 2,2-dimethyltetrahydro-2H-pyran-4-yl, or tetrahydro-2H-pyran-2-yl.

In a further embodiment, when n is 2, then Het is tetrahydro-2H-pyran-4-yl, tetrahydrofuran-2-yl, tetrahydro-2H-pyran-3-yl, tetrahydro-2H-pyran-2-yl, or tetrahydrofuran-3-yl.

In a further embodiment, when n is 3, then Het is tetrahydro-2H-pyran-3-yl.

In a further embodiment, when n is 4, then Het is tetrahydro-2H-pyran-3-yl.

In a further embodiment, when n is 1, then R$^2$ is tetrahydro-2H-pyran-4-yl or tetrahydrofuran-3-yl.

In a further embodiment, when n is 2, then Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydrofuran-2-yl.

In a further embodiment, when n is 3, then Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydrofuran-2-yl.

In a further embodiment, when n is 4, then Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydrofuran-2-yl.

In a further aspect of the invention, there is provided a subset of compounds of formula (I), being compounds of formula (I'):

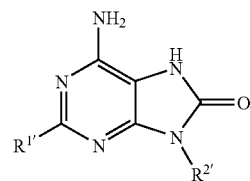

(I')

wherein

R$^{1'}$ is n-butylamino, n-butoxy, or cyclopropylethoxy;

R$^{2'}$ is —(CH$_2$)$_n$-Het;

n is 1;

Het is tetrahydro-2H-pyran-4-yl or tetrahydro-3-furanyl;

and salts and solvates thereof.

In a further aspect of the invention, there is provided a subset of compounds of formula (I), being compounds of formula (I''):

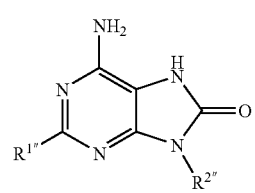

(I'')

wherein

R$^{1''}$ is n-butylamino, n-butoxy, (R)-1-methylbutyloxy, (S)-1-methylbutyloxy, or 2-(cyclopropyl)ethoxy;

R$^{2''}$ is —(CH$_2$)$_n$-Het'';

n is 2, 3, or 4;

Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydrofuran-2-yl;

and salts and solvates thereof.

In a further aspect of the invention, there is provided a subset of compounds of formula (I), being compounds of formula (IA):

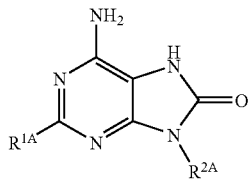

wherein
$R^{1A}$ is $C_{1-6}$alkylamino, or $C_{1-6}$alkoxy;
$R^{2A}$ is —$(CH_2)_{n^A}$-$Het^A$;
n is an integer having a value of 1 to 4;
$Het^A$ is a 5- or 6-membered saturated aliphatic heterocycle containing one oxygen heteroatom;
and salts and solvates thereof.
In a further embodiment, $R^{1A}$ is n-butoxy or n-butylamino.
In a further embodiment, $n^A$ is 1 or 2.
In a further embodiment, when $n^A$ is 1, then $Het^A$ is tetrahydrofuran-3-yl, tetrahydro-2H-pyran-3-yl, or tetrahydro-2H-pyran-4-yl.

Examples of compounds of formula (I) are provided in the following list, and form a further aspect of the invention:
6-amino-2-butoxy-9-(tetrahydro-2H-pyran-4-ylmethyl)-7,9-dihydro-8H-purin-8-one;
6-amino-2-butoxy-9-(tetrahydro-2H-pyran-2-ylmethyl)-7,9-dihydro-8H-purin-8-one;
6-amino-2-butoxy-9-(tetrahydrofuran-2-ylmethyl)-7,9-dihydro-8H-purin-8-one;
6-amino-2-butylamino-9-(tetrahydro-2H-pyran-4-ylmethyl)-7,9-dihydro-8H-purin-8-one;
6-amino-2-butylamino-9-(tetrahydro-2H-pyran-2-ylmethyl)-7,9-dihydro-8H-purin-8-one;
6-amino-2-butylamino-9-(tetrahydrofuran-2-ylmethyl)-7,9-dihydro-8H-purin-8-one;
6-amino-2-butylamino-9-[2-(tetrahydro-2H-pyran-4-yl)ethyl]-7,9-dihydro-8H-purin-8-one;
6-amino-2-butylamino-9-(tetrahydrofuran-3-ylmethyl)-7,9-dihydro-8H-purin-8-one;
6-amino-2-butylamino-9-(tetrahydro-2H-pyran-3-ylmethyl)-7,9-dihydro-8H-purin-8-one;
6-amino-2-butoxy-9-(tetrahydrofuran-3-ylmethyl)-7,9-dihydro-8H-purin-8-one;
6-amino-2-butoxy-9-[2-(tetrahydro-2H-pyran-4-yl)ethyl]-7,9-dihydro-8H-purin-8-one;
6-amino-2-butoxy-9-(tetrahydro-2H-pyran-3-ylmethyl)-7,9-dihydro-8H-purin-8-one;
6-amino-2-butoxy-9-[2-(tetrahydrofuran-2-yl)ethyl]-7,9-dihydro-8H-purin-8-one;
6-amino-2-butylamino-9-[2-(tetrahydrofuran-2-yl)ethyl]-7,9-dihydro-8H-purin-8-one;
6-amino-2-butoxy-9-[2-(tetrahydro-2H-pyran-3-yl)ethyl]-7,9-dihydro-8H-purin-8-one;
6-amino-2-butylamino-9-[2-(tetrahydro-2H-pyran-3-yl)ethyl]-7,9-dihydro-8H-purin-8-one;
6-amino-2-[(2,2-dimethylpentyl)oxy]-9-(tetrahydro-2H-pyran-4-ylmethyl)-7,9-dihydro-8H-purin-8-one;
6-amino-2-(pentylamino)-9-(tetrahydro-2H-pyran-4-ylmethyl)-7,9-dihydro-8H-purin-8-one;
6-amino-2-[(3-methylbutyl)oxy]-9-(tetrahydro-2H-pyran-4-ylmethyl)-7,9-dihydro-8H-purin-8-one;
6-amino-2-[(2-methylbutyl)oxy]-9-(tetrahydro-2H-pyran-4-ylmethyl)-7,9-dihydro-8H-purin-8-one;
6-amino-2-[(1-methylbutyl)oxy]-9-(tetrahydro-2H-pyran-4-ylmethyl)-7,9-dihydro-8H-purin-8-one;
6-amino-2-[(2-methylbutyl)amino]-9-(tetrahydro-2H-pyran-4-ylmethyl)-7,9-dihydro-8H-purin-8-one;
6-amino-2-[(3-methylbutyl)amino]-9-(tetrahydro-2H-pyran-4-ylmethyl)-7,9-dihydro-8H-purin-8-one;
6-amino-2-[(1-methylbutyl)amino]-9-(tetrahydro-2H-pyran-4-ylmethyl)-7,9-dihydro-8H-purin-8-one;
6-amino-2-[(2-cyclopropylethyl)oxy]-9-(tetrahydro-3-furanylmethyl)-7,9-dihydro-8H-purin-8-one;
6-amino-2-butyloxy-9-[2-(tetrahydro-2H-pyran-2-yl)ethyl]-7,9-dihydro-8H-purin-8-one;
6-amino-2-butyloxy-9-[(2,2-dimethyltetrahydro-2H-pyran-4-yl)methyl]-7,9-dihydro-8H-purin-8-one;
6-amino-2-(butylamino)-9-[(2,2-dimethyltetrahydro-2H-pyran-4-yl)methyl]-7,9-dihydro-8H-purin-8-one;
6-amino-2-butyloxy-9-[2-(tetrahydro-3-furanyl)ethyl]-7,9-dihydro-8H-purin-8-one;
6-amino-2-(butylamino)-9-[2-(tetrahydro-2H-pyran-2-yl)ethyl]-7,9-dihydro-8H-purin-8-one;
6-amino-2-(butylamino)-9-[2-(tetrahydro-3-furanyl)ethyl]-7,9-dihydro-8H-purin-8-one;
6-amino-2-(butyloxy)-9-(tetrahydro-3-furanylmethyl)-7,9-dihydro-8H-purin-8-one, isomer 1;
6-amino-2-(butyloxy)-9-(tetrahydro-3-furanylmethyl)-7,9-dihydro-8H-purin-8-one, isomer 2;
6-amino-2-{[2-(ethyloxy)ethyl]oxy}-9-(tetrahydro-2H-pyran-4-ylmethyl)-7,9-dihydro-8H-purin-8-one;
6-amino-2-{[1-methyl-2-(methoxy)ethyl]oxy}-9-(tetrahydro-2H-pyran-4-ylmethyl)-7,9-dihydro-8H-purin-8-one;
6-amino-2-{[2-(ethyloxy)ethyl]oxy}-9-(tetrahydro-2H-pyran-3-ylmethyl)-7,9-dihydro-8H-purin-8-one;
6-amino-2-{[1-methyl-2-(methoxy)ethyl]oxy}-9-(tetrahydro-2H-pyran-3-ylmethyl)-7,9-dihydro-8H-purin-8-one;
6-amino-2-[(cyclohexylmethyl)amino]-9-(tetrahydro-2H-pyran-4-ylmethyl)-7,9-dihydro-8H-purin-8-one;
6-amino-2-[(cyclopentylmethyl)amino]-9-(tetrahydro-2H-pyran-4-ylmethyl)-7,9-dihydro-8H-purin-8-one;
6-amino-2-[(2-cyclopropylethyl)amino]-9-(tetrahydro-2H-pyran-4-ylmethyl)-7,9-dihydro-8H-purin-8-one;
6-amino-2-(butylamino)-9-(tetrahydro-3-furanylmethyl)-7,9-dihydro-8H-purin-8-one, isomer 1;
6-amino-2-(butylamino)-9-(tetrahydro-3-furanylmethyl)-7,9-dihydro-8H-purin-8-one, isomer 2;
6-amino-2-[(2-methylpropyl)oxy]-9-(tetrahydro-2H-pyran-4-ylmethyl)-7,9-dihydro-8H-purin-8-one;
6-amino-2-[(2-cyclopropylethyl)oxy]-9-(tetrahydro-2H-pyran-4-ylmethyl)-7,9-dihydro-8H-purin-8-one;
6-amino-2-[(cyclohexyl methyl)oxy]-9-(tetrahydro-2H-pyran-4-ylmethyl)-7,9-dihydro-8H-purin-8-one;
6-amino-2-{[2-(methoxy)ethyl]oxy}-9-(tetrahydro-2H-pyran-4-ylmethyl)-7,9-dihydro-8H-purin-8-one;
6-amino-2-{[2-(methoxy)ethyl]oxy}-9-(tetrahydro-3-furanyl methyl)-7,9-dihydro-8H-purin-8-one;
6-amino-2-[(tetrahydro-2-furanylmethyl)oxy]-9-(tetrahydro-2H-pyran-4-ylmethyl)-7,9-dihydro-8H-purin-8-one;
6-amino-2-(butylamino)-9-[3-(tetrahydro-2H-pyran-3-yl)propyl]-7,9-dihydro-8H-purin-8-one;
6-amino-9-(tetrahydro-2H-pyran-4-ylmethyl)-2-[(tetrahydro-2H-pyran-2-ylmethoxy]-7,9-dihydro-8H-purin-8-one;
6-amino-2-({2-[(1-methylethyl)oxy]ethyl}oxy)-9-(tetrahydro-2H-pyran-4-ylmethyl)-7,9-dihydro-8H-purin-8-one;
6-amino-2-(butylamino)-9-[4-(tetrahydro-2H-pyran-3-yl)butyl]-7,9-dihydro-8H-purin-8-one;

6-amino-2-[(2-cyclopropylethyl)amino]-9-(tetrahydro-3-furanylmethyl)-7,9-dihydro-8H-purin-8-one;
6-amino-2-[(2-cyclopropylethyl)amino]-9-(tetrahydro-2H-pyran-3-ylmethyl)-7,9-dihydro-8H-purin-8-one;
6-amino-2-[(2-cyclopropylethyl)oxy]-9-(tetrahydro-3-furanylmethyl)-7,9-dihydro-8H-purin-8-one, isomer 1, and;
6-amino-2-[(2-cyclopropylethyl)oxy]-9-[tetrahydro-3-furanylmethyl]-7,9-dihydro-8H-purin-8-one, isomer 2; and salts and solvates thereof.

The following compounds of formula (I) form a further aspect of the invention:
6-amino-2-(butyloxy)-9-(tetrahydro-3-furanylmethyl)-7,9-dihydro-8H-purin-8-one, isomer 1;
6-amino-2-butylamino-9-(tetrahydro-2H-pyran-4-ylmethyl)-7,9-dihydro-8H-purin-8-one;
6-amino-2-(butyloxy)-9-(tetrahydro-3-furanylmethyl)-7,9-dihydro-8H-purin-8-one, isomer 2;
6-amino-2-(butylamino)-9-(tetrahydro-3-furanylmethyl)-7,9-dihydro-8H-purin-8-one, isomer 1;
6-amino-2-(butylamino)-9-(tetrahydro-3-furanylmethyl)-7,9-dihydro-8H-purin-8-one, isomer 2;
6-amino-2-[(2-cyclopropylethyl)oxy]-9-(tetrahydro-3-furanylmethyl)-7,9-dihydro-8H-purin-8-one, isomer 1, and;
6-amino-2-[(2-cyclopropylethyl)oxy]-9-[tetrahydro-3-furanylmethyl]-7,9-dihydro-8H-purin-8-one, isomer 2; and salts and solvates thereof.

The following compounds of formula (I) form a further aspect of the invention:
6-amino-2-butoxy-9-[2-(tetrahydrofuran-2-yl)ethyl]-7,9-dihydro-8H-purin-8-one, isomer 1;
6-amino-2-butoxy-9-[2-(tetrahydrofuran-2-yl)ethyl]-7,9-dihydro-8H-purin-8-one, isomer 2;
6-amino-2-butylamino-9-[2-(tetrahydro-2H-pyran-3-yl)ethyl]-7,9-dihydro-8H-purin-8-one, isomer 1;
6-amino-2-butylamino-9-[2-(tetrahydro-2H-pyran-3-yl)ethyl]-7,9-dihydro-8H-purin-8-one, isomer 2;
6-amino-2-butyloxy-9-[2-(tetrahydro-2H-pyran-2-yl)ethyl]-7,9-dihydro-8H-purin-8-one, isomer 1;
6-amino-2-butyloxy-9-[2-(tetrahydro-2H-pyran-2-yl)ethyl]-7,9-dihydro-8H-purin-8-one, isomer 2;
6-amino-2-butyloxy-9-[(2,2-dimethyltetrahydro-2H-pyran-4-yl)methyl]-7,9-dihydro-8H-purin-8-one, isomer 1;
6-amino-2-butyloxy-9-[(2,2-dimethyltetrahydro-2H-pyran-4-yl)methyl]-7,9-dihydro-8H-purin-8-one, isomer 2;
6-amino-2-(butylamino)-9-[3-(tetrahydro-2-furanyl)propyl]-7,9-dihydro-8H-purin-8-one;
6-amino-2-(butylamino)-9-[4-(tetrahydro-2-furanyl)butyl]-7,9-dihydro-8H-purin-8-one;
6-amino-2-(utylamino)-9-{2-[(3S)-tetrahydro-3-furanyl]ethyl}-7,9-dihydro-8H-purin-8-one;
6-amino-2-(butylamino)-9-{2-[(3R)-tetrahydro-3-furanyl]ethyl}-7,9-dihydro-8H-purin-8-one;
6-amino-2-(butylamino)-9-[3-(tetrahydro-3-furanyl)propyl]-7,9-dihydro-8H-purin-8-one;
6-amino-2-(butylamino)-9-[4-(tetrahydro-3-furanyl)butyl]-7,9-dihydro-8H-purin-8-one;
6-amino-2-(butylamino)-9-[3-(tetrahydro-2H-pyran-2-yl)propyl]-7,9-dihydro-8H-purin-8-one;
6-amino-2-(butylamino)-9-[4-(tetrahydro-2H-pyran-2-yl)butyl]-7,9-dihydro-8H-purin-8-one;
6-amino-2-(butylamino)-9-[3-(tetrahydro-2H-pyran-4-yl)propyl]-7,9-dihydro-8H-purin-8-one;
6-amino-2-(butylamino)-9-[4-(tetrahydro-2H-pyran-4-yl)butyl]-7,9-dihydro-8H-purin-8-one;
6-amino-2-(butylamino)-9-[2-(2,2-dimethyltetrahydro-2H-pyran-4-yl)ethyl]-7,9-dihydro-8H-purin-8-one;
6-amino-2-(butylamino)-9-[3-(2,2-dimethyltetrahydro-2H-pyran-4-yl)propyl]-7,9-dihydro-8H-purin-8-one;
6-amino-2-(butylamino)-9-[4-(2,2-dimethyltetrahydro-2H-pyran-4-yl)butyl]-7,9-dihydro-8H-purin-8-one;
6-amino-2-(butyloxy)-9-[3-(tetrahydro-2-furanyl)propyl]-7,9-dihydro-8H-purin-8-one;
6-amino-2-(butyloxy)-9-[4-(tetrahydro-2-furanyl)butyl]-7,9-dihydro-8H-purin-8-one;
6-amino-2-(butyloxy)-9-{2-[(3S)-tetrahydro-3-furanyl]ethyl}-7,9-dihydro-8H-purin-8-one;
6-amino-2-(butyloxy)-9-{2-[(3R)-tetrahydro-3-furanyl]ethyl}-7,9-dihydro-8H-purin-8-one;
6-amino-2-(butyloxy)-9-[3-(tetrahydro-3-furanyl)propyl]-7,9-dihydro-8H-purin-8-one;
6-amino-2-(butyloxy)-9-[4-(tetrahydro-3-furanyl)butyl]-7,9-dihydro-8H-purin-8-one;
6-amino-2-(butyloxy)-9-[3-(tetrahydro-2H-pyran-2-yl)propyl]-7,9-dihydro-8H-purin-8-one;
6-amino-2-(butyloxy)-9-[4-(tetrahydro-2H-pyran-2-yl)butyl]-7,9-dihydro-8H-purin-8-one;
6-amino-2-(butyloxy)-9-[3-(tetrahydro-2H-pyran-3-yl)propyl]-7,9-dihydro-8H-purin-8-one;
6-amino-2-(butyloxy)-9-[4-(tetrahydro-2H-pyran-3-yl)butyl]-7,9-dihydro-8H-purin-8-one;
6-amino-2-(butyloxy)-9-[3-(tetrahydro-2H-pyran-4-yl)propyl]-7,9-dihydro-8H-purin-8-one;
6-amino-2-(butyloxy)-9-[4-(tetrahydro-2H-pyran-4-yl)butyl]-7,9-dihydro-8H-purin-8-one;
6-amino-2-(butyloxy)-9-[2-(2,2-dimethyltetrahydro-2H-pyran-4-yl)ethyl]-7,9-dihydro-8H-purin-8-one;
6-amino-2-(butyloxy)-9-[3-(2,2-dimethyltetrahydro-2H-pyran-4-yl)propyl]-7,9-dihydro-8H-purin-8-one;
6-amino-2-(butyloxy)-9-[4-(2,2-dimethyltetrahydro-2H-pyran-4-yl)butyl]-7,9-dihydro-8H-purin-8-one;
6-amino-2-[(2-cyclopropylethyl)oxy]-9-[2-(tetrahydro-2-furanyl)ethyl]-7,9-dihydro-8H-purin-8-one;
6-amino-2-[(2-cyclopropylethyl)oxy]-9-[3-(tetrahydro-2-furanyl)propyl]-7,9-dihydro-8H-purin-8-one;
6-amino-2-[(2-cyclopropylethyl)oxy]-9-[4-(tetrahydro-2-furanyl)butyl]-7,9-dihydro-8H-purin-8-one;
6-amino-2-[(2-cyclopropylethyl)oxy]-9-[2-(tetrahydro-3-furanyl)ethyl]-7,9-dihydro-8H-purin-8-one;
6-amino-2-[(2-cyclopropylethyl)oxy]-9-{2-[(3S)-tetrahydro-3-furanyl]ethyl}-7,9-dihydro-8H-purin-8-one;
6-amino-2-[(2-cyclopropylethyl)oxy]-9-{2-[(3R)-tetrahydro-3-furanyl]ethyl}-7,9-dihydro-8H-purin-8-one
6-amino-2-[(2-cyclopropylethyl)oxy]-9-[3-(tetrahydro-3-furanyl)propyl]-7,9-dihydro-8H-purin-8-one;
6-amino-2-[(2-cyclopropylethyl)oxy]-9-[4-(tetrahydro-3-furanyl)butyl]-7,9-dihydro-8H-purin-8-one;
6-amino-2-[(2-cyclopropylethyl)oxy]-9-[2-(tetrahydro-2H-pyran-2-yl)ethyl]-7,9-dihydro-8H-purin-8-one;
6-amino-2-[(2-cyclopropylethyl)oxy]-9-[3-(tetrahydro-2H-pyran-2-yl)propyl]-7,9-dihydro-8H-purin-8-one;
6-amino-2-[(2-cyclopropylethyl)oxy]-9-[4-(tetrahydro-2H-pyran-2-yl)butyl]-7,9-dihydro-8H-purin-8-one;
6-amino-2-[(2-cyclopropylethyl)oxy]-9-[2-(tetrahydro-2H-pyran-3-yl)ethyl]-7,9-dihydro-8H-purin-8-one;
6-amino-2-[(2-cyclopropylethyl)oxy]-9-[4-(tetrahydro-2H-pyran-3-yl)butyl]-7,9-dihydro-8H-purin-8-one;
6-amino-2-[(2-cyclopropylethyl)oxy]-9-[2-(tetrahydro-2H-pyran-4-yl)ethyl]-7,9-dihydro-8H-purin-8-one;
6-amino-2-[(2-cyclopropylethyl)oxy]-9-[3-(tetrahydro-2H-pyran-4-yl)propyl]-7,9-dihydro-8H-purin-8-one;
6-amino-2-[(2-cyclopropylethyl)oxy]-9-[4-(tetrahydro-2H-pyran-4-yl)butyl]-7,9-dihydro-8H-purin-8-one;

6-amino-2-[(2-cyclopropylethyl)oxy]-9-[2-(2,2-dimethyltetrahydro-2H-pyran-4-yl)ethyl]-7,9-dihydro-8H-purin-8-one;

6-amino-2-[(2-cyclopropylethyl)oxy]-9-[3-(2,2-dimethyltetrahydro-2H-pyran-4-yl)propyl]-7,9-dihydro-8H-purin-8-one;

6-amino-2-[(2-cyclopropylethyl)oxy]-9-[4-(2,2-dimethyltetrahydro-2H-pyran-4-yl)butyl]-7,9-dihydro-8H-purin-8-one;

6-amino-2-{[(1S)-1-methylbutyl]oxy}-9-[2-(tetrahydro-2-furanyl)ethyl]-7,9-dihydro-8H-purin-8-one;

6-amino-2-{[(1S)-1-methylbutyl]oxy}-9-[3-(tetrahydro-2-furanyl)propyl]-7,9-dihydro-8H-purin-8-one;

6-amino-2-{[(1S)-1-methylbutyl]oxy}-9-{2-[(3S)-tetrahydro-3-furanyl]ethyl}-7,9-dihydro-8H-purin-8-one;

6-amino-2-{[(1S)-1-methylbutyl]oxy}-9-{2-[(3R)-tetrahydro-3-furanyl]ethyl}-7,9-dihydro-8H-purin-8-one;

6-amino-2-{[(1S)-1-methylbutyl]oxy}-9-[3-(tetrahydro-3-furanyl)propyl]-7,9-dihydro-8H-purin-8-one;

6-amino-2-{[(1S)-1-methylbutyl]oxy}-9-[4-(tetrahydro-3-furanyl)butyl]-7,9-dihydro-8H-purin-8-one;

6-amino-2-{[(1S)-1-methylbutyl]oxy}-9-[2-(tetrahydro-2H-pyran-2-yl)ethyl]-7,9-dihydro-8H-purin-8-one;

6-amino-2-{[(1S)-1-methylbutyl]oxy}-9-[3-(tetrahydro-2H-pyran-2-yl)propyl]-7,9-dihydro-8H-purin-8-one;

6-amino-2-{[(1S)-1-methylbutyl]oxy}-9-[4-(tetrahydro-2H-pyran-2-yl)butyl]-7,9-dihydro-8H-purin-8-one;

6-amino-2-{[(1S)-1-methylbutyl]oxy}-9-[2-(tetrahydro-2H-pyran-3-yl)ethyl]-7,9-dihydro-8H-purin-8-one;

6-amino-2-{[(1S)-1-methylbutyl]oxy}-9-[4-(tetrahydro-2H-pyran-3-yl)butyl]-7,9-dihydro-8H-purin-8-one;

6-amino-2-{[(1S)-1-methylbutyl]oxy}-9-[2-(tetrahydro-2H-pyran-4-yl)ethyl]-7,9-dihydro-8H-purin-8-one;

6-amino-2-{[(1S)-1-methylbutyl]oxy}-9-[3-(tetrahydro-2H-pyran-4-yl)propyl]-7,9-dihydro-8H-purin-8-one;

6-amino-2-{[(1S)-1-methylbutyl]oxy}-9-[4-(tetrahydro-2H-pyran-4-yl)butyl]-7,9-dihydro-8H-purin-8-one;

6-amino-9-[2-(2,2-dimethyltetrahydro-2H-pyran-4-yl)ethyl]-2-{[(1S)-1-methylbutyl]oxy}-7,9-dihydro-8H-purin-8-one;

6-amino-9-[3-(2,2-dimethyltetrahydro-2H-pyran-4-yl)propyl]-2-{[(1S)-1-methylbutyl]oxy}-7,9-dihydro-8H-purin-8-one;

6-amino-9-[4-(2,2-dimethyltetrahydro-2H-pyran-4-yl)butyl]-2-{[(1S)-1-methylbutyl]oxy}-7,9-dihydro-8H-purin-8-one;

6-amino-2-{[(1R)-1-methylbutyl]oxy}-9-[2-(tetrahydro-2-furanyl)ethyl]-7,9-dihydro-8H-purin-8-one;

6-amino-2-{[(1R)-1-methylbutyl]oxy}-9-[3-(tetrahydro-2-furanyl)propyl]-7,9-dihydro-8H-purin-8-one;

6-amino-2-{[(1R)-1-methylbutyl]oxy}-9-{2-[(3S)-tetrahydro-3-furanyl]ethyl}-7,9-dihydro-8H-purin-8-one;

6-amino-2-{[(1R)-1-methylbutyl]oxy}-9-{2-[(3R)-tetrahydro-3-furanyl]ethyl}-7,9-dihydro-8H-purin-8-one;

6-amino-2-{[(1R)-1-methylbutyl]oxy}-9-[3-(tetrahydro-3-furanyl)propyl]-7,9-dihydro-8H-purin-8-one;

6-amino-2-{[(1R)-1-methylbutyl]oxy}-9-[4-(tetrahydro-3-furanyl)butyl]-7,9-dihydro-8H-purin-8-one;

6-amino-2-{[(1R)-1-methylbutyl]oxy}-9-[2-(tetrahydro-2H-pyran-2-yl)ethyl]-7,9-dihydro-8H-purin-8-one;

6-amino-2-{[(1R)-1-methylbutyl]oxy}-9-[3-(tetrahydro-2H-pyran-2-yl)propyl]-7,9-dihydro-8H-purin-8-one;

6-amino-2-{[(1R)-1-methylbutyl]oxy}-9-[4-(tetrahydro-2H-pyran-2-yl)butyl]-7,9-dihydro-8H-purin-8-one;

6-amino-2-{[(1R)-1-methylbutyl]oxy}-9-[2-(tetrahydro-2H-pyran-3-yl)ethyl]-7,9-dihydro-8H-purin-8-one;

6-amino-2-{[(1R)-1-methylbutyl]oxy}-9-[4-(tetrahydro-2H-pyran-3-yl)butyl]-7,9-dihydro-8H-purin-8-one;

6-amino-2-{[(1R)-1-methylbutyl]oxy}-9-[2-(tetrahydro-2H-pyran-4-yl)ethyl]-7,9-dihydro-8H-purin-8-one;

6-amino-2-{[(1R)-1-methylbutyl]oxy}-9-[3-(tetrahydro-2H-pyran-4-yl)propyl]-7,9-dihydro-8H-purin-8-one;

6-amino-2-{[(1R)-1-methylbutyl]oxy}-9-[4-(tetrahydro-2H-pyran-4-yl)butyl]-7,9-dihydro-8H-purin-8-one;

6-amino-9-[2-(2,2-dimethyltetrahydro-2H-pyran-4-yl)ethyl]-2-{[(1R)-1-methylbutyl]oxy}-7,9-dihydro-8H-purin-8-one;

6-amino-9-[3-(2,2-dimethyltetrahydro-2H-pyran-4-yl)propyl]-2-{[(1R)-1-methylbutyl]oxy}-7,9-dihydro-8H-purin-8-one;

6-amino-9-[4-(2,2-dimethyltetrahydro-2H-pyran-4-yl)butyl]-2-{[(1R)-1-methylbutyl]oxy}-7,9-dihydro-8H-purin-8-one; and salts and solvates thereof.

There is thus provided as a further aspect of the invention a compound of formula (I), or a pharmaceutically acceptable salt or solvate thereof, for use as an active therapeutic agent.

There is also therefore provided a compound of formula (I), or a pharmaceutically acceptable salt or solvate thereof, for use in the treatment of infectious diseases, cancer, allergic diseases and other inflammatory conditions.

There is also therefore provided a compound of formula (I), or a pharmaceutically acceptable salt or solvate thereof, for use as a vaccine adjuvant.

There is further provided the use of a compound of formula (I), or a pharmaceutically acceptable salt or solvate thereof, for the manufacture of a medicament for the treatment of infectious diseases, cancer, allergic diseases and other inflammatory conditions.

In a further aspect of the invention, there is provided a method for the treatment of infectious diseases, cancer, allergic diseases and other inflammatory conditions, which method comprises administering an effective amount of a compound of formula (I), or a pharmaceutically acceptable salt or solvate thereof.

The invention thus provides, in a further aspect, a combination comprising at least one compound of formula (I), or pharmaceutically acceptable salts or solvates thereof, together with at least one other therapeutically active agent.

There is further provided a pharmaceutical composition comprising a compound of formula (I), or a pharmaceutically acceptable salt or solvate thereof, and optionally one or more pharmaceutically acceptable diluents or carriers.

There is also provided a process for preparing a pharmaceutical composition which comprises admixing a compound of formula (I), or a pharmaceutically acceptable salt or solvate thereof, with one or more pharmaceutically acceptable diluents or carriers.

The compounds of formula (I) and salts and solvates thereof may be prepared by the methodology described herein, and constitutes a further aspect of this invention.

Accordingly, there is provided a process for the preparation of a compound of formula (I), which process comprises the deprotection of a compound of formula (IIA):

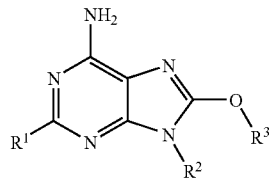

(IIA)

wherein $R^1$ and $R^2$ are as hereinbefore defined for a compound of formula (I) and $R^3$ is $C_{1-6}$alkyl, and thereafter, if required, carrying out one or more of the following optional steps:
(i). converting a compound of formula (I) to a further compound of formula (I);
(ii). preparing a salt or solvate of the compound so-formed.

In one aspect of the invention, a compound of formula (IIA) may be prepared by reaction of a compound of formula (II):

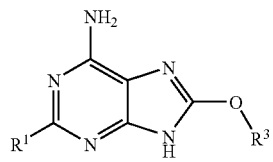

(II)

wherein $R^1$ is as hereinbefore defined for a compound of formula (I) and $R^3$ is as hereinbefore defined for a compound of formula (IIA), with a compound of formula (IIB):

$R^2$-L           (IIB)

wherein $R^2$ is as hereinbefore defined for a compound of formula (I) and L is a suitable leaving group, for example an alkylsulphonyloxy group such as a methanesulphonyloxy group, or a halogen atom, such as bromine.

In one aspect of the invention, a compound of formula (II) is used in the form of a salt, for example the trifluoroacetate salt. This salt results from the deprotection of a compound of formula (III) with, for example, trifluoroacetic acid, as hereinbelow described.

Alternatively, a compound of formula (I) may be prepared by reaction of a compound of formula (II) as hereinbefore defined, typically as a salt, for example the trifluoroacetate salt, with a compound of formula (IIB) as hereinbefore defined, without isolation of the intermediate compound (IIA).

In one aspect of the invention, a compound of formula (II) may be prepared by reaction of a compound of formula (III):

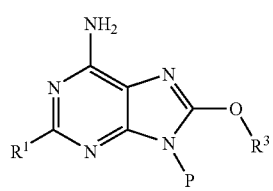

(III)

wherein $R^1$ is as hereinbefore defined for a compound of formula (I), P is a protecting group, typically a tetrahydro-2H-pyran-2-yl group, and $R^3$ is as hereinbefore defined for a compound of formula (IIA), with a suitable deprotecting agent, for example trifluoroacetic acid (the use of trifluoroacetic acid results in a compound of formula (II) being formed as a trifluoroacetate salt).

In one aspect of the invention, a compound of formula (IIB) wherein L is a halogen atom may be prepared by reaction of a compound of formula (IX):

$R^2$—OG           (IX)

wherein $R^2$ is as hereinbefore defined for a compound of formula (I) and OG is a leaving group, for example an alkanesulphonate group such as a methanesulphonate group, with an anhydrous alkali metal halide such as anhydrous lithium bromide.

In one aspect of the invention, a compound of formula (IX), or a compound of formula (IIB) wherein L is an alkylsulphonyl group, may be prepared by reaction of a compound of formula (X):

$R^2$—OH           (X)

wherein $R^2$ is as hereinbefore defined for a compound of formula (I), with a suitable activating agent, for example an alkylsulphonyl halide such as methanesulphonyl chloride.

In one aspect of the invention, a compound of formula (X) may be prepared by reaction of a compound of formula (XI):

Het-$(CH_2)_{(n-1)}$—COO$C_{1-6}$alkyl           (XI)

wherein Het and n are as hereinbefore defined for a compound of formula (I) with a suitable reducing agent, such as lithium aluminium hydride.

In one aspect of the invention, a compound of formula (X) wherein Het is 3-tetrahydropyranyl and n is an integer having a value of 2 may be prepared by reaction of the compound of formula (XII):

Het-$(CH_2)$—CHO           (XII)

wherein Het is 3-tetrahydropyranyl, with a suitable reducing agent, for example sodium borohydride.

In one aspect of the invention, a compound of formula (XII) may be prepared by reaction of a compound of formula (XIII):

Het-CH=CH(O$C_{1-6}$alkyl)           (XIII)

wherein Het is 3-tetrahydropyranyl, with a suitable mineral acid, for example hydrochloric acid.

In one aspect of the invention, a compound of formula (XIII) may be prepared by reaction of the compound of formula (XIV):

Het-CHO           (XIV)

wherein Het is 3-tetrahydropyranyl, with a compound of formula (XV):

$C_{1-6}$alkoxy-$(CH_2)$—$P^+(Ph)_3$ $Cl^-$           (XV)

In one aspect of the invention, a compound of formula (XIV) may be prepared by hydrogenation of the compound of formula (XVI):

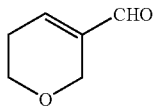

(XVI)

In one aspect of the invention, a compound of formula (III) may be prepared by reaction of a compound of formula (IV):

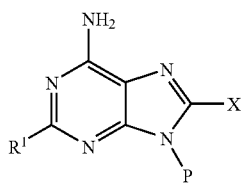

(IV)

wherein $R^1$ is as hereinbefore defined for a compound of formula (I), P is as hereinbefore defined for a compound of formula (III), and X is a halogen atom, for example bromine, with an alkali metal alkoxide, for example sodium methoxide.

In one aspect of the invention, a compound of formula (IV) may be prepared by reaction of a compound of formula (V):

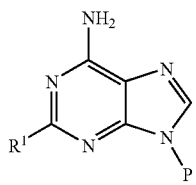

(V)

wherein $R^1$ is as hereinbefore defined for a compound of formula (I) and P is as hereinbefore defined for a compound of formula (III), with a suitable halogenating agent, for example N-bromosuccinimide.

In one aspect of the invention, a compound of formula (V), wherein $R^1$ is $C_{1-8}$alkoxy, $C_{3-7}$cycloalkyl$C_{1-6}$alkoxy, $C_{1-6}$alkoxy$C_{1-6}$alkoxy, or $Het^b$-$C_{1-3}$alkoxy, may be prepared by reaction of a compound of formula (VI):

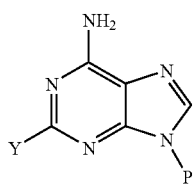

(VI)

wherein P is as hereinbefore defined for a compound of formula (III) and Y is a halogen atom, for example chlorine, with a compound of formula (VIA):

$R^1$—H    (VIA)

wherein $R^1$ is $C_{1-8}$alkoxy, $C_{3-7}$cycloalkyl$C_{1-6}$alkoxy, $C_{1-6}$alkoxy$C_{1-6}$alkoxy, or $Het^b$-$C_{1-3}$alkoxy, in the presence of a strong base of appropriate strength, for example sodium metal, sodium hydride, or sodium tert-butoxide.

In one aspect of the invention, a compound of formula (V), wherein $R^1$ is $C_{1-8}$alkylamino or $C_{3-7}$cycloalkyl$C_{1-6}$alkylamino may be prepared by reaction of a compound of formula (VI) as hereinbefore defined, with a compound of formula (VIB):

$R^1$—H    (VIB)

wherein $R^1$ is $C_{1-6}$alkylamino or $C_{3-7}$cycloalkyl$C_{1-6}$-amino.

In one aspect of the invention, a compound of formula (VI) may be prepared by reaction of a compound of formula (VII):

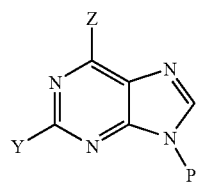

(VII)

wherein P is as hereinbefore defined for a compound of formula (III), Y is as hereinbefore defined for a compound of formula (VI), and Z is a halogen atom, for example chlorine, with an alcoholic solution of ammonia.

In one aspect of the invention, a compound of formula (VII) may be prepared from a compound of formula (VIII):

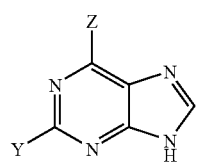

(VIII)

wherein Y is as hereinbefore defined for a compound of formula (VI) and Z is as hereinbefore defined for a compound of formula (VII), by reaction with a suitable protecting reagent, for example 3,4-dihydro-2H-pyran.

There is further provided in a further aspect of the invention, a process for the preparation of a compound of formula (I), which process comprises the hydrolysis of a compound of formula (XXI):

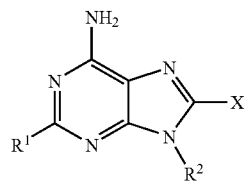

(XXI)

wherein $R^1$ and $R^2$ are as hereinbefore defined for a compound of formula (I) and X is as hereinbefore defined for a compound of formula (IV).

In one aspect of the invention, a compound of formula (XXI) wherein may be prepared by halogenation of a compound of formula (XX):

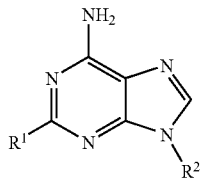

(XX)

wherein $R^1$ and $R^2$ are as hereinbefore defined for a compound of formula (I).

In one aspect of the present invention, a compound of formula (XX), wherein $R^1$ is $C_{1-8}$alkoxy, $C_{3-7}$cycloalkyl$C_{1-6}$alkoxy, $C_{1-6}$alkoxy$C_{1-6}$alkoxy, or $Het^b$-$C_{1-3}$alkoxy may be prepared by reaction of a compound of formula (XIX):

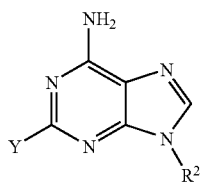

(XIX)

wherein Y is as hereinbefore defined for a compound of formula (VI) and $R^2$ is as hereinbefore defined for a compound of formula (I), with a compound of formula (VIA) as hereinbefore defined.

In one aspect of the invention, a compound of formula (XIX) may be prepared by reaction of a compound of formula (XVIII):

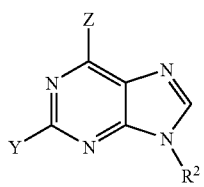

(XVIII)

wherein Y is as hereinbefore defined for a compound of formula (VI), Z is as hereinbefore defined for a compound of formula (VII), and $R^2$ is as hereinbefore defined for a compound of formula (I), with ammonia.

A compound of formula (XIX) may also be prepared by reaction of a compound of formula (XVII):

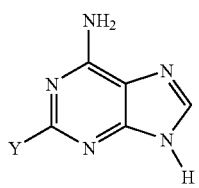

(XVII)

wherein Y is as hereinbefore defined for a compound of formula (VI), with a compound of formula (IIB) as hereinbefore defined.

In one aspect of the invention, a compound of formula (XVIII) may be prepared by reaction of a compound of formula (VIII) as hereinbefore defined with a compound of formula $R^2$—OH, wherein $R^2$ is as hereinbefore defined for a compound of formula (I).

In one aspect of the invention, a compound of formula (XVII) may be prepared by reaction of a compound of formula (VIII) as hereinbefore defined with ammonia.

In a further aspect of the invention, a compound of formula (I), wherein $R^1$ is $C_{1-8}$alkylamino or $C_{3-7}$cycloalkyl$C_{1-6}$alkylamino, may be prepared by reaction of a compound of formula (XXIII):

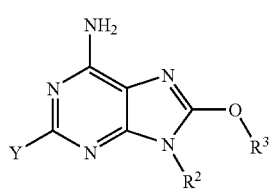

(XXIII)

wherein Y is as hereinbefore defined for a compound of formula (VI), $R^2$ is as hereinbefore defined for a compound of formula (I), and $R^3$ is as hereinbefore defined for a compound of formula (IIA), with a compound of formula (VIB) as hereinbefore defined.

In one aspect of the invention, a compound of formula (XXIII) may be prepared by reaction of a compound of formula (XXII):

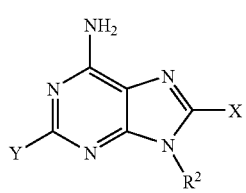

(XXII)

wherein X is as hereinbefore defined for a compound of formula (IV), Y is as hereinbefore defined for a compound of formula (VI) and $R^2$ is as hereinbefore defined for a compound of formula (I), with a source of alkoxide anion.

The present invention covers all combinations of embodiments and aspects herein described.

DETAILED DESCRIPTION OF THE INVENTION

Figure 1:
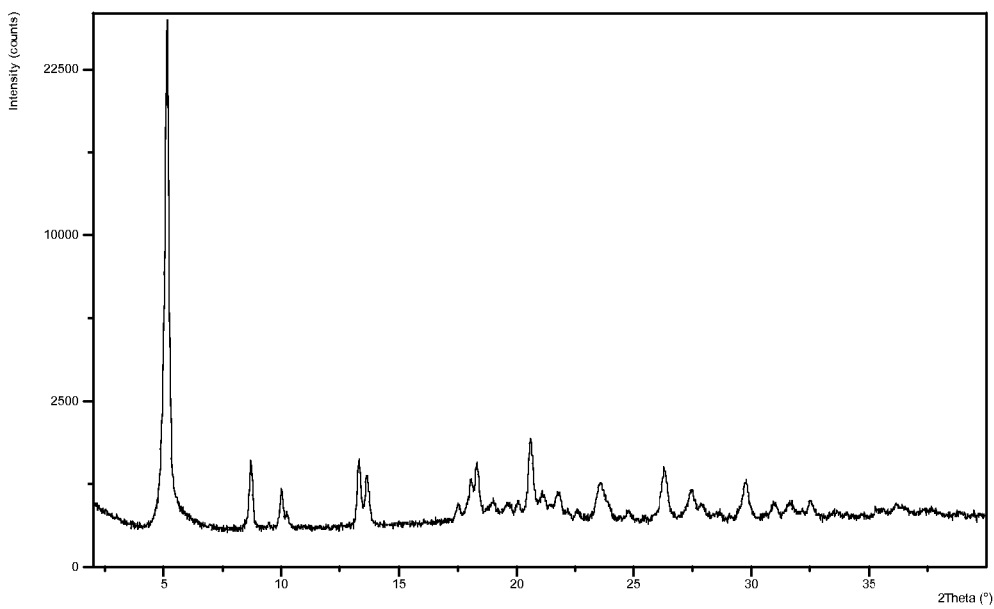
FIG. 1 shows an XRPD diffractogram of 6-amino-2-butylamino-9-(tetrahydro-2H-pyran-4-ylmethyl)-7,9-dihydro-8H-purin-8-one.

The present invention is described in terms known and appreciated by those skilled in the art. For ease of reference certain terms hereinafter are defined. The fact that certain terms are defined, however, should not be considered as indicative that defined terms are used in a manner inconsistent with the ordinary meaning or, alternatively, that any term that is undefined is indefinite or not used within the ordinary and accepted meaning. Rather, all terms used herein are believed to describe the invention such that one of ordinary skill can appreciate the scope of the present invention. The following definitions are meant to clarify, but not limit, the terms defined.

References to 'alkyl' include references to both straight-chain and branched-chain aliphatic isomers of the corresponding alkyl suitably containing up to eight carbon atoms, for example up to four carbon atoms or up to three carbon atoms. Such references to 'alkyl' are also applicable when an alkyl group is part of another group, for example an alkylamino or alkoxy group. Examples of such alkyl groups and groups containing alkyl groups are $C_{1-4}$alkyl, $C_{1-6}$alkylamino, $C_{1-8}$alkoxy, $C_{3-7}$cycloalkyl$C_{1-6}$alkylamino, $C_{3-7}$cycloalkyl$C_{1-6}$alkoxy, and $C_{1-3}$alkoxy$C_{2-3}$alkoxy.

References to 'heterocycle' or 'heterocyclyl' refer to monocyclic saturated heterocyclic aliphatic rings containing 5 or 6 carbon atoms, and one heteroatom, which heteroatom is oxygen. Examples of such heterocyclic rings are tetrahydrofuranyl and tetrahydropyranyl.

References to 'cycloalkyl' refer to monocyclic alkyl groups containing between three and seven carbon atoms, for example three carbon atoms, or five carbon atoms, or six carbon atoms. Examples of such cycloalkyl groups are cyclopropyl, cyclopentyl, and cyclohexyl.

References to 'halogen' refer to iodine, bromine, chlorine or fluorine, typically bromine or chlorine.

It is to be understood that references hereinafter to compounds of the invention mean a compound of formula (I) as the free base, or as a salt, or as a solvate.

It will be appreciated from the foregoing that included within the scope of the invention are all solvates, hydrates, complexes, isomers and polymorphic forms of the compounds of formula (I) and salts and solvates thereof.

Salts of the compounds of formula (I) include pharmaceutically acceptable salts and salts which may not be pharmaceutically acceptable but may be useful in the preparation of compounds of formula (I) and pharmaceutically acceptable salts thereof. Salts may be derived from certain inorganic or organic acids, or certain inorganic or organic bases.

The invention includes within its scope all possible stoichiometric and non-stoichiometric forms of the salts of the compounds of formula (I).

Examples of salts are pharmaceutically acceptable salts. Pharmaceutically acceptable salts include acid addition salts and base addition salts. For a review on suitable salts see Berge et al., *J. Pharm. Sci.*, 66:1-19 (1977).

Examples of pharmaceutically acceptable acid addition salts of a compound of formula (I) include hydrobromide, hydrochloride, sulphate, p-toluenesulphonate, methanesulphonate, naphthalenesulphonate, and phenylsulphonate salts.

Examples of pharmaceutically acceptable base salts include alkali metal salts such as those of sodium and potassium, and alkaline earth metal salts such as those of calcium and magnesium.

Salts may be formed using techniques well-known in the art, for example by precipitation from solution followed by filtration, or by evaporation of the solvent.

Typically, a pharmaceutically acceptable acid addition salt can be formed by reaction of a compound of formula (I) with a suitable strong acid (such as hydrobromic, hydrochloric, sulphuric, p-toluenesulphonic, methanesulphonic or naphthalenesulphonic acids), optionally in a suitable solvent such as an organic solvent, to give the salt which is usually isolated for example by crystallisation and filtration.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methylpyrrolidinone may be used to form solvates. Solvates of the compounds of formula (I) are within the scope of the invention. As used herein, the term solvate encompasses solvates of both a free base compound as well as any salt thereof.

Certain of the compounds of the invention may contain chiral atoms and/or multiple bonds, and hence may exist in one or more stereoisomeric forms. The present invention encompasses all of the stereoisomers of the compounds of the invention, including geometric isomers and optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

As used herein, the terms "Isomer 1" and "Isomer 2" and "Diastereoisomer 1" and "Diastereoisomer 2" refer to the first- and second-eluting isomer or diastereoisomer respectively when the separations are performed using the chromatographic conditions specified in the relevant text. It will be appreciated that the order of elution may change depending on the particular chromatographic conditions employed.

Certain of the compounds of the invention may exist in tautomeric forms. It will be understood that the present invention encompasses all of the tautomers of the compounds of the invention whether as individual tautomers or as mixtures thereof.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

Examples of disease states in which the compounds of formula (I) and pharmaceutically acceptable salts or solvates thereof have potentially beneficial effects include infectious diseases, cancer, allergic diseases and other inflammatory conditions. The compounds of formula (I) and pharmaceutically acceptable salts or solvates thereof are also of potential use as vaccine adjuvants.

The compounds of formula (I) and pharmaceutically acceptable salts or solvates thereof may therefore be useful in the treatment of various disorders, in particular the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compounds of formula (I) and pharmaceutically acceptable salts or solvates thereof may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis.

As potent modulators of the immune response the compounds of formula (I) and pharmaceutically acceptable salts or solvates thereof may therefore be useful in the treatment of inflammation, including but not limited to inflammatory or allergic diseases such as asthma, allergic rhinitis, hypersensitivity lung diseases, eosinophilic pneumonitis, delayed-type hypersensitivity, atherosclerosis, pancreatitis, gastritis, osteoarthritis, psoriasis, sarcoidosis, pulmonary fibrosis, respiratory distress syndrome, bronchiolitis, chronic obstructive pulmonary disease, sinusitis, cystic fibrosis, and dermatitis.

The compounds of formula (I) and pharmaceutically acceptable salts or solvates thereof may also be useful in the treatment of autoimmune diseases including but not limited to rheumatoid arthritis, psoriatic arthritis, systemic lupus erythematosus, sjöegrens disease, ankylosing spondylitis, scleroderma, diabetes, graft rejection, including graft-versus-host disease, inflammatory bowel diseases including, but not limited to, Crohn's disease and ulcerative colitis.

The compounds of formula (I) and pharmaceutically acceptable salts or solvates thereof may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

It will be appreciated by those skilled in the art that references herein to treatment or therapy extend to prophylaxis as well as the treatment of established conditions.

As mentioned herein, compounds of formula (I) and pharmaceutically acceptable salts or solvates thereof may be useful as therapeutic agents.

As noted, the present invention includes a compound of formula (I), or a pharmaceutically acceptable salt or solvate thereof, for use as an active therapeutic agent.

There is also therefore provided a compound of formula (I), or a pharmaceutically acceptable salt or solvate thereof, for use in the treatment of infectious diseases, cancer, allergic diseases and other inflammatory conditions.

There is also therefore provided a compound of formula (I), or a pharmaceutically acceptable salt or solvate thereof, for use as a vaccine adjuvant.

There is also therefore provided a compound of formula (I), or a pharmaceutically acceptable salt or solvate thereof, for use in the treatment of allergic rhinitis.

There is also therefore provided a compound of formula (I), or a pharmaceutically acceptable salt or solvate thereof, for use in the treatment of asthma.

There is further provided the use of a compound of formula (I), or a pharmaceutically acceptable salt or solvate thereof, for the manufacture of a medicament for the treatment of infectious diseases, cancer, allergic diseases and other inflammatory conditions.

The present invention also includes a method for the treatment of infectious diseases, cancer, allergic diseases and other inflammatory conditions, which method comprises administering an effective amount of a compound of formula (I), or a pharmaceutically acceptable salt or solvate thereof.

There is further provided the use of a compound of formula (I), or a pharmaceutically acceptable salt or solvate thereof, for the manufacture of a medicament for the treatment of allergic rhinitis.

The present invention also includes a method for the treatment of allergic rhinitis, which method comprises administering an effective amount of a compound of formula (I), or a pharmaceutically acceptable salt or solvate thereof.

There is further provided the use of a compound of formula (I), or a pharmaceutically acceptable salt or solvate thereof, for the manufacture of a medicament for the treatment of asthma.

The present invention also includes a method for the treatment of asthma, which method comprises administering an effective amount of a compound of formula (I), or a pharmaceutically acceptable salt or solvate thereof.

The compounds according to the invention, and pharmaceutically acceptable salts and solvates thereof, may be formulated for administration in any convenient way.

The compounds according to the invention, and pharmaceutically acceptable salts and solvates thereof, may, for example, be formulated for oral, topical, inhaled, intranasal, buccal, parenteral (for example intravenous, subcutaneous, intradermal, or intramuscular) or rectal administration. In one aspect, the compounds of formula (I), and pharmaceutically acceptable salts and solvates thereof, are formulated for oral administration. In a further aspect, the compounds of formula (I), and pharmaceutically acceptable salts and solvates thereof, are formulated for topical administration, for example intranasal administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use.

Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Formulations for intranasal administration include aqueous formulations administered to the nose by drops or by pressurised pump. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose or other regions of the respiratory tract by nebulisation.

Formulations for inhaled administration include aqueous, organic or aqueous/organic mixtures, dry powder or crystalline formulations administered to the respiratory tract by pressurised pump or inhaler. Suitable formulations contain water as the diluent or carrier for this purpose and may be provided with conventional excipients such as buffering agents, tonicity modifying agents and the like. Aqueous formulations may also be administered to the nose and other regions of the respiratory tract by nebulisation. Such formulations may be aqueous solutions or suspensions or aerosols delivered from pressurised packs, such as a metered dose inhaler, with the use of a suitable liquefied propellant. Aerosol compositions suitable for inhalation can be either a suspension or a solution and may contain a compound of formula (I) or a salt or solvate thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid or derivative thereof e.g. as described in WO 94/21229 and WO 98/34596 (Minnesota Mining and Manufacturing Company) and co-solvents e.g. ethanol.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, wool-fat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

The compounds according to the invention and pharmaceutically acceptable salts or solvates thereof may, for example, be formulated for transdermal delivery by formulation into patches or other devices (e.g. pressurised gas devices) which deliver the active component into the skin.

For buccal administration the compositions may take the form of tablets or lozenges formulated in the conventional manner.

The compounds and pharmaceutically acceptable salts or solvates thereof may also be formulated as suppositories, e.g. containing conventional suppository bases such as cocoa butter or other glycerides.

The compounds according to the invention or pharmaceutically acceptable salts or solvates thereof may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds according to the invention or pharmaceutically acceptable salts or solvates thereof may also be formulated with vaccines as adjuvants to modulate their activity. Such formulations may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

The compounds of the present invention or pharmaceutically acceptable salts or solvates thereof may be employed alone or in combination with other therapeutic agents. The compound(s) of the present invention or pharmaceutically acceptable salts or solvates thereof and the other pharmaceutically active agent(s) may be administered together or separately and, when administered separately, administration may occur simultaneously or sequentially, in any order. The amounts of the compound(s) of the present invention and pharmaceutically acceptable salts or solvates thereof and the other pharmaceutically active agent(s) and the relative timings of administration will be selected in order to achieve the desired combined therapeutic effect. The administration in combination of a compound of the present invention and pharmaceutically acceptable salts or solvates thereof with other treatment agents may be in combination by administration concomitantly in a unitary pharmaceutical composition including both compounds, or in separate pharmaceutical compositions each including one of the compounds. Alternatively, the combination may be administered separately in a sequential manner wherein one treatment agent is administered first and the other second or vice versa. Such sequential administration may be close in time or remote in time.

The present invention may be used in combination with one or more agents useful in the prevention or treatment of viral infections. Examples of such agents include; polymerase inhibitors such as those disclosed in WO 2004/037818-A1, as well as those disclosed in WO 2004/037818 and WO 2006/045613; JTK-003, JTK-019, NM-283, HCV- 796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, and similar agents; entry inhibitors such as enfuvirtide (T-20), T-1249, PRO-542, PRO-140, TNX-355, BMS-806, 5-Helix and similar agents; integrase inhibitors such as L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; neuraminidase inhibitors such as zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, and WO 2006/122011, and similar agents. The present invention may also be used in combination with one or more other agents which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, antifibrotic agents, anti-inflammatory agents such as corticosteroids or NSAIDs and similar agents.

The scope of combinations of compounds of this invention and pharmaceutically acceptable salts or solvates thereof with antiviral agents is not limited to those mentioned above, but includes in principle any combination with any pharmaceutical composition useful for the treatment of viral disease. As noted, in such combinations the compounds of the present invention and pharmaceutically acceptable salts or solvates thereof and other antiviral agents may be administered separately or in conjunction. In addition, one agent may be prior to, concurrent to, or subsequent to the administration of other agent(s).

The compounds of the present invention and pharmaceutically acceptable salts or solvates thereof may be used in combination with one or more other agents which may be useful in the prevention or treatment of allergic disease, inflammatory disease, autoimmune disease or similar, for example; antigen immunotherapy, anti-histamines, steroids, non-steroidal anti-inflammatory agents, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF anti-IL-5, anti-IL-6, anti-IL-12, anti-IL-1 and similar agents; receptor therapies e.g. entanercept and similar agents; antigen non-specific immunotherapies (e.g. interferon or other cytokines/chemokines, cytokine/chemokine receptor modulators, cytokine agonists or antagonists, TLR agonists and similar agents).

The compounds of the present invention and pharmaceutically acceptable salts or solvates thereof may be used in combination with one or more other agents which may be useful in the prevention or treatment of cancer, for example chemotherapeutics such as alkylating agents, topoisomerase inhibitors, antimetabolites, antimitotic agents, kinase inhibitors and similar agents; monoclonal antibody therapy such as trastuzumab, gemtuzumab and other similar agents; immunotherapies (e.g. interferon or other cytokines/chemokines, cytokine/chemokine receptor modulators, cytokine agonists or antagonists, TLR agonists and similar agents); and hormone therapy such as tamoxifen, goserelin and similar agents.

The pharmaceutical compositions according to the invention may also be used alone or in combination with at least one other therapeutic agent in other therapeutic areas, for example gastrointestinal disease. The compositions according to the invention may also be used in combination with gene replacement therapy.

The invention includes a combination comprising at least one compound of formula (I), or (a) pharmaceutically acceptable salt(s) or solvate(s) thereof, together with at least one other therapeutically active agent.

The combinations referred to above may conveniently be presented for use in the form of a pharmaceutical formulation and thus pharmaceutical formulations comprising a combination as defined above together with at least one pharmaceutically acceptable diluent or carrier thereof represent a further aspect of the invention.

A therapeutically effective amount of a compound of the present invention or pharmaceutically acceptable salts or solvates thereof will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician. Regardless, an effective amount of a compound of the present invention for the treatment of humans suffering from frailty, generally, should be in the range of 0.01 to 100 mg/kg body weight of recipient (mammal) per day. More usually the effective amount should be in the range of 0.1 to 10 mg/kg body weight per day. Thus, for a 70 kg adult mammal one example of an actual amount per day would usually be from 7 to 700 mg. This amount may be given in a single dose per day or in a number (such as two, three, four, five, or more) of sub-doses per day such that the total daily dose is the same. An effective amount of a pharmaceutically acceptable salt or solvate of a compound of formula (I) may be determined as a proportion of the effective amount of the compound of the present invention per se. Similar dosages should be appropriate for treatment of the other conditions referred to herein.

Compounds of formula (I) and pharmaceutically acceptable salts or solvates thereof may also be administered at any appropriate frequency e.g. 1-7 times per week. The precise dosing regimen will of course depend on factors such as the therapeutic indication, the age and condition of the patient, and the particular route of administration chosen.

Pharmaceutical formulations may be presented in unit-dose forms containing a predetermined amount of active ingredient per unit dose. Such a unit may contain, as a non-limiting example, 0.5 mg to 1 g of a compound of formula (I) or pharmaceutically acceptable salts or solvates thereof, depending on the condition being treated, the route of administration, and the age, weight, and condition of the patient. Preferred unit-dosage formulations are those containing a daily dose or sub-dose, as herein above recited, or an appropriate fraction thereof, of an active ingredient. Such pharmaceutical formulations may be prepared by any of the methods well-known in the pharmacy art.

There is thus further provided a pharmaceutical composition comprising a compound of formula (I), or a pharmaceutically acceptable salt or solvate thereof, and optionally one or more pharmaceutically acceptable diluents or carriers.

There is also provided a process for preparing such a pharmaceutical composition which comprises admixing a compound of formula (I), or a pharmaceutically acceptable salt or solvate thereof, with one or more pharmaceutically acceptable diluents or carriers.

Throughout the description and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The compounds of formula (I) and salts and solvates thereof may be prepared by the methodology described hereinafter, constituting further aspects of this invention.

Accordingly, there is provided a process for the preparation of a compound of formula (I), which process comprises the deprotection of a compound of formula (IIA):

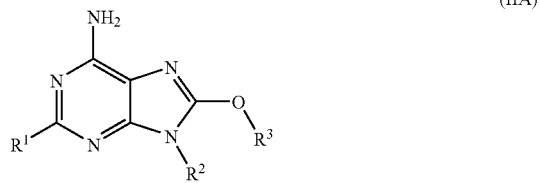

(IIA)

wherein $R^1$ and $R^2$ are as hereinbefore defined for a compound of formula (I) and $R^3$ is $C_{1-6}$alkyl, and thereafter, if required, carrying out one or more of the following optional steps:
(i). converting a compound of formula (I) to a further compound of formula (I);
(ii). preparing a salt or solvate of the compound so-formed.

For example, a compound of formula (IIA) is dissolved in a suitable solvent, for example methanol, and treated with a solution of a suitable mineral acid in a suitable solvent, for example 4N hydrogen chloride in 1,4-dioxane. The reaction is stirred at a suitable temperature, for example room temperature, for a suitable period of time, for example 4-18 hours, and the solvent removed under reduced pressure to give a material that is then suspended in water. A sufficient amount of a suitable alcohol, for example methanol, may be added until a solution is obtained. A suitable aqueous base, for example 2N sodium hydroxide solution, is added to bring the mixture to pH7, and the solution may be concentrated until a suspension is formed. The solid is then filtered and washed with water before being dried to give a compound of formula (I). Alternatively, the reaction mixture may be neutralised without prior removal of the solvent, and the resultant product recovered by filtration before or after removal of a proportion of the solvent.

A compound of formula (IIA) may be prepared by reaction of a compound of formula (I):

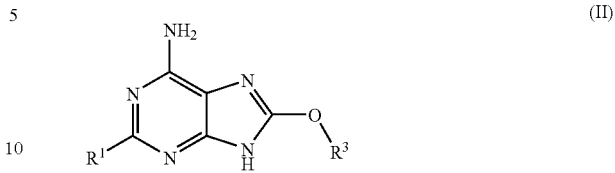

(II)

wherein $R^1$ is as hereinbefore defined for a compound of formula (I) and $R^3$ is as hereinbefore defined for a compound of formula (IIA), with a compound of formula (IIB):

$R^2$-L         (IIB)

wherein $R^2$ is as hereinbefore defined for a compound of formula (I) and L is a suitable leaving group, for example an alkylsulphonyloxy group such as a methanesulphonyloxy group, or a halogen atom, such as bromine.

For example, the trifluoroacetate salt of a compound of formula (II) is heated to a suitable temperature, for example 60° C., for a suitable period of time, for example 1 hour, with anhydrous potassium carbonate in a suitable dry solvent, for example dry DMF, and allowed to cool to room temperature before adding a compound of formula (IIB). The reaction may be stirred at room temperature for a suitable period of time, for example 20-40 hours, and may be heated if necessary for a suitable period of time, for example 1-2 hours, at a suitable temperature, for example up to 90° C. The reaction mixture is poured into water and extracted into a suitable solvent, for example ethyl acetate. The solvent extracts are dried, evaporated to dryness under reduced pressure, and purified. It will be appreciated that the reaction times and reaction temperatures required to effect the reaction of a compound of formula (II) with a compound of formula (IIB) to give a compound of formula (IIA) will vary depending on the precise nature of the individual reactants used, for example reaction times and reaction temperatures must be chosen to ensure that a compound of formula (IIA) is obtained, but that N-alkylation at the 7-position is minimised or avoided.

A compound of formula (II) may be used in the form of a salt, for example the trifluoroacetate salt. This salt results from the deprotection of a compound of formula (III) with, for example, trifluoroacetic acid, as hereinbelow described.

Alternatively, a compound of formula (I) may be prepared by reaction of a compound of formula (II) as hereinbefore defined, typically as a salt, for example the trifluoroacetate salt, with a compound of formula (IIB) as hereinbefore defined, without isolation of the intermediate compound (IIA).

For example, to the trifluoroacetate salt of a compound of formula (II) in a suitable solvent, for example dry N,N-dimethylformamide (DMF), is added a suitable base, for example anhydrous potassium carbonate. The mixture is heated to a suitable temperature, for example 60° C., for a suitable period of time, for example 1 hour, and cooled to room temperature. A compound of formula (IIB) is then added and the reaction mixture heated to a suitable temperature, for example 50° C., for a suitable period of time, for example 12-18 hours. The reaction is quenched with water and extracted with a suitable solvent, for example ethyl acetate. The organic phase is separated and dried. Evaporation of the organic phase and purification of the oil so formed yields a product which is then dissolved in a suitable solvent, for example methanol, treated with a solution of a suitable mineral acid in a suitable solvent, for example 4N hydrogen chloride in 1,4-dioxane, and stirred overnight at room temperature. The reaction mixture is evaporated to dryness under reduced pressure to give a compound of formula (I), which may be purified. It will be appreciated that the reaction times and reaction temperatures required to effect the reaction of a trifluoroacetate salt of a compound of formula (II) with a compound of formula (IIB) to give a compound of formula (IIA) will vary depending on the precise nature of the individual reactants used, for example reaction times and reaction temperatures must be chosen to ensure that a compound of formula (IIA) is obtained, but that N-alkylation at the 7-position is minimised or avoided.

A compound of formula (II) may be prepared by reaction of a compound of formula (III):

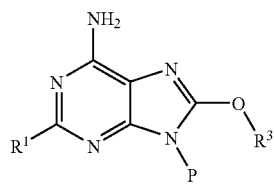

(III)

wherein $R^1$ is as hereinbefore defined for a compound of formula (I), P is a protecting group, typically a tetrahydro-2H-pyran-2-yl group, and $R^3$ is as hereinbefore defined for a compound of formula (IIA), with a suitable deprotecting agent, for example trifluoroacetic acid (the use of trifluoroacetic acid results in a compound of formula (II) being formed as a trifluoroacetate salt).

For example, to a solution of a compound of formula (III) in a suitable solvent, for example dry methanol, is added a suitable deprotecting agent, for example trifluoroacetic acid. The mixture is stirred at a suitable temperature, for example ambient temperature, for 24-48 hours. The reaction mixture is concentrated to a slurry before being diluted with a suitable solvent, for example ethyl acetate. The slurry is filtered and washed with a small volume of solvent, for example ethyl acetate, until the filtrate is colourless. The solid remaining is dried by air and then in vacuo to give, in the case where trifluoroacetic acid is used as the deprotecting agent, the trifluoroacetate salt of a compound of formula (II). The filtrate obtained previously may be concentrated to give a slurry which is then diluted with a small volume of solvent, for example ethyl acetate and then filtered and dried to yield a second crop of the trifluoroacetate salt of a compound of formula (II). Alternatively, the reaction mixture may be concentrated under reduced pressure to yield a solid, which solid may then be triturated in the presence of a suitable solvent, for example diethyl ether.

A compound of formula (IIB) wherein L is a halogen atom may be prepared by reaction of a compound of formula (IX):

$R^2$—OG (IX)

wherein $R^2$ is as hereinbefore defined for a compound of formula (I) and OG is a leaving group, for example an alkanesulphonate group such as a methanesulphonate group, with an anhydrous alkali metal halide such as anhydrous lithium bromide.

For example, a compound of formula (IX) and a suitable halogenating agent, for example anhydrous lithium bromide, in a suitable solvent, for example, acetone, are refluxed with stirring for a suitable period of time, for example 3 hours.

After allowing to cool the solvent is removed under reduced pressure, the residue treated with water, and extracted with a suitable solvent, for example dichloromethane. The combined solvent extracts are washed, dried, and the solvent removed under reduced pressure to give a compound of formula (IIB).

A compound of formula (IX), or a compound of formula (IIB) wherein L is an alkylsulphonyl group, may be prepared by reaction of a compound of formula (X):

$R^2$—OH (X)

wherein $R^2$ is as hereinbefore defined for a compound of formula (I), with a suitable activating agent, for example an alkylsulphonyl halide such as methanesulphonyl chloride.

For example, to an ice-cooled stirring solution of a compound of formula (X) and a suitable base, for example triethylamine, in a suitable dry solvent, for example dry dichloromethane, is added, dropwise, a suitable activating agent, for example methanesulphonyl chloride. The mixture is allowed to warm slowly to ambient temperature over a suitable period of time, for example 16 hours, then washed with saturated sodium hydrogen carbonate. The aqueous layer is further extracted with a suitable organic solvent, for example dichloromethane, and the organic extracts washed, dried, and the solvent removed under reduced pressure to give a compound of formula (IX).

A compound of formula (X) may be prepared by reaction of a compound of formula (XI):

Het-$(CH_2)_{(n-1)}$—COOC$_{1-6}$alkyl (XI)

wherein Het and n are as hereinbefore defined for a compound of formula (I) with a suitable reducing agent, such as lithium aluminium hydride.

For example, a stirring solution of a compound of formula (XI) in a suitable dry solvent, for example dry tetrahydrofuran, is cooled, for example using an ice-bath, and a solution of lithium aluminium hydride in a suitable solvent, for example dry tetrahydrofuran, added dropwise under a suitable atmosphere, for example an atmosphere of nitrogen, at a suitable temperature, for example less than 15° C. The reaction is allowed to warm to ambient temperature and, after a suitable period of time, for example 3 hours, re-cooled using, for example, an ice-bath, and a suitable base, for example 5N sodium hydroxide added while maintaining a suitable temperature, for example less than 10° C. A suitable organic solvent, for example diethyl ether, is then added and the resulting solid filtered and washed with further organic solvent, for example diethyl ether. The combined filtrate is then evaporated to give a compound of formula (X).

A compound of formula (X) wherein Het is 3-tetrahydropyranyl and n is an integer having a value of 2 may be prepared by reaction of the compound of formula (XII):

Het-$(CH_2)$—CHO (XII)

wherein Het is 3-tetrahydropyranyl, with a suitable reducing agent, for example sodium borohydride.

For example, a suspension of a suitable reducing agent, for example sodium borohydride, in a suitable solvent, for example ethanol, is cooled, for example using an ice-bath, and a solution of the compound of formula (XII) in a suitable solvent, for example ethanol added dropwise with stirring over a suitable period of time, for example 10 minutes. After a suitable period of time, for example 15 minutes, the ice-bath is removed and after a further period of time, for example 3 hours, the mixture is heated at a suitable temperature, for example 50° C. for a suitable period of time, for example 1 hour. After cooling, the solvent is evaporated and the residue treated with water and extracted with a suitable organic solvent, for example dichloromethane. The combined extracts were washed, dried, and evaporated to give the compound of formula (X) wherein Het is 3-tetrahydropyranyl and n is an integer having a value of 2.

The compound of formula (XII) may be prepared by reaction of a compound of formula (XIII):

Het-CH=CH(OC$_{1-6}$alkyl)        (XIII)

wherein Het is 3-tetrahydropyranyl, with a suitable mineral acid, for example hydrochloric acid.

For example, to a stirring solution of a compound of formula (XIII) in a suitable solvent, for example tetrahydrofuran, is added a suitable mineral acid, for example 2N hydrochloric acid. After a suitable period of time, for example 1 hour, the mixture is diluted with water and extracted with a suitable organic solvent, for example ether. The organic extract is then washed, dried, and evaporated to give the compound of formula (XII).

A compound of formula (XIII) may be prepared by reaction of the compound of formula (XIV):

Het-CHO        (XIV)

wherein Het is 3-tetrahydropyranyl, with a compound of formula (XV):

C$_{1-6}$alkoxy-(CH$_2$)—P$^+$(Ph)$_3$ Cl$^-$        (XV)

For example, a suspension of a compound of formula (XV) in a suitable dry solvent, for example dry tetrahydrofuran, is cooled to a suitable temperature, for example minus 40° C. using, for example, a cooling bath containing a mixture of dry ice and acetone, and a solution of a suitable strong base, for example potassium tert-butoxide in a suitable dry solvent, for example dry tetrahydrofuran, added dropwise with stirring under a suitable atmosphere, for example an atmosphere of nitrogen. After a suitable period of time, for example, 45 minutes, the mixture is further cooled to minus 65° C. using, for example, a cooling bath containing a mixture of dry ice and acetone, and a solution of the compound of formula (XIV) in a suitable dry solvent, for example dry tetrahydrofuran is added dropwise. The cooling bath is removed and the reaction mixture allowed to warm to ambient temperature. The reaction mixture is then stirred for a further period of time, for example 30 minutes, and then quenched by pouring onto ice. The mixture is then extracted with a suitable solvent, for example ether, and the combined extracts washed, dried and evaporated to give a crude compound of formula (XIII), which may be purified by, for example, chromatography.

The compound of formula (XIV) may be prepared by hydrogenation of the compound of formula (XVI):

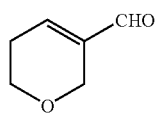

(XVI)

For example, the compound of formula (XVI) in a suitable solvent, for example ethanol, is treated with 10% wetted palladium on carbon catalyst under a suitable atmosphere, for example an atmosphere of nitrogen, then hydrogenated at ambient temperature and pressure for a suitable period of time, for example 30 minutes. The catalyst removed by filtration and the filtrate evaporated to give the compound of formula (XIV).

The compound of formula (XVI) may be prepared from acrolein.

For example, concentrated hydrochloric acid is added to water followed by acrolein and a suitable solvent, for example toluene. The stirred mixture is heated under reflux at 75° C. for a suitable period of time, for example 1 hour when reflux will gradually abate. After allowing to cool, a suitable base, for example potassium carbonate, is added until the mixture is basic and the mixture extracted with a suitable organic solvent, for example diethyl ether. The organic extracts are washed with brine, dried, and evaporated to yield a crude product. The compound of formula (XVI) is obtained from the crude mixture by distillation.

A compound of formula (III) may be prepared by reaction of a compound of formula (IV):

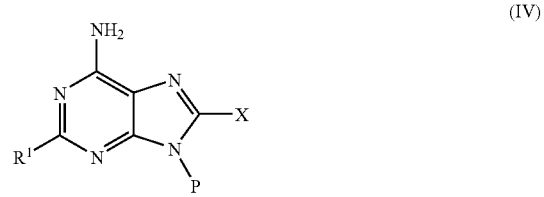

(IV)

wherein R$^1$ is as hereinbefore defined for a compound of formula (I), P is as hereinbefore defined for a compound of formula (III), and X is a halogen atom, for example bromine, with an alkali metal alkoxide, for example sodium methoxide.

For example, a compound of formula (IV) is heated to a suitable temperature, for example to reflux temperature to or just below reflux temperature, with an alcoholic solution of an alkali metal alkoxide, for example 25% sodium methoxide in methanol, in a suitable solvent, for example methanol, for a suitable period of time, for example 2-8 hours. The reaction mixture is concentrated under reduced pressure and partitioned between suitable aqueous and non-aqueous phases, for example ethyl acetate and saturated ammonium chloride solution. The organic phase is separated and the aqueous phase extracted repeatedly into ethyl acetate. The combined organic phases are washed, dried, evaporated, and then placed under reduced pressure to give a compound of formula (III).

A compound of formula (IV) may be prepared by reaction of a compound of formula (V):

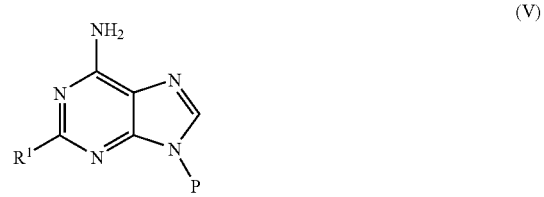

(V)

wherein R$^1$ is as hereinbefore defined for a compound of formula (I) and P is as hereinbefore defined for a compound of formula (III), with a suitable halogenating agent, for example N-bromosuccinimide.

For example, a compound of formula (V) is dissolved in a suitable solvent, for example chloroform, and cooled to a suitable temperature, for example 0° C. To this solution is added portionwise N-bromosuccinimide, whilst maintaining a suitable temperature, for example less than 3° C. The resulting mixture is stirred at a suitable temperature, for example 2-3° C., for a suitable period of time, for example 30 minutes, before allowing to warm to room temperature and then stirring for a further period of time, for example 6 hours. The reaction mixture is then washed with water. The organic phase is dried/separated using a hydrophobic frit and evaporated to give a crude compound of formula (IV), which may be purified.

A compound of formula (V), wherein $R^1$ is $C_{1-8}$alkoxy, $C_{3-7}$cycloalkyl$C_{1-6}$alkoxy, $C_{1-6}$alkoxy$C_{1-6}$alkoxy, or Het$^b$-$C_{1-3}$alkoxy, may be prepared by reaction of a compound of formula (VI):

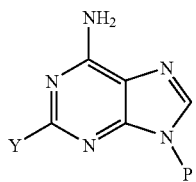

(VI)

wherein P is as hereinbefore defined for a compound of formula (III) and Y is a halogen atom, for example chlorine, with a compound of formula (VIA):

wherein $R^1$ is $C_{1-8}$alkoxy, $C_{3-7}$cycloalkyl$C_{1-6}$alkoxy, $C_{1-6}$alkoxy$C_{1-6}$alkoxy, or Het$^b$-$C_{1-3}$alkoxy, in the presence of a strong base of appropriate strength, for example sodium metal, sodium hydride, or sodium tert-butoxide.

For example, to a compound of formula (VIA), for example butan-1-ol, is added portion-wise a strong base, for example sodium tert-butoxide. The mixture is stirred until homogeneous before a compound of formula (VI) is added to the solution. The reaction mixture is then heated to a suitable temperature, for example 100° C., for a suitable period of time, for example 12-18 hours. The reaction mixture is placed under reduced pressure to remove as much of a compound of formula (VIA) as possible before being partitioned between a suitable organic solvent, for example diethyl ether, and water. The organic phase is separated and the aqueous phase may be re-extracted with further organic solvent. The combined organic phases are dried over a suitable drying agent, for example anhydrous magnesium sulphate. The drying agent is removed by filtration and the filtrate evaporated under reduced pressure to give a compound of formula (V) wherein $R^1$ is $C_{1-6}$alkoxy, which may then be further treated by, for example, being azeotroped with toluene and placed under reduced pressure.

A compound of formula (V), wherein $R^1$ is $C_{1-8}$alkylamino or $C_{3-7}$cycloalkyl$C_{1-6}$alkylamino may be prepared by reaction of a compound of formula (VI) as hereinbefore defined, with a compound of formula (VIB):

wherein $R^1$ is $C_{1-6}$alkylamino or $C_{3-7}$cycloalkyl$C_{1-6}$-amino.

For example, to a solution of a compound of formula (VI) in a suitable dry solvent, for example dry ethylene glycol, at a suitable temperature, for example room temperature, and under a suitable atmosphere, for example an atmosphere of nitrogen, is added a compound of formula (VIB). The reaction is heated at a suitable temperature, for example 120° C., for a suitable period of time, for example 12-18 hours. The reaction is cooled to room temperature, diluted with a suitable solvent, for example ethyl acetate, and washed with water. The organic layer is dried over a suitable drying agent, for example anhydrous magnesium sulphate, filtered and concentrated in vacuo to afford a compound of formula (V) wherein $R^1$ is $C_{1-6}$alkylamino.

A compound of formula (VI) may be prepared by reaction of a compound of formula (VII):

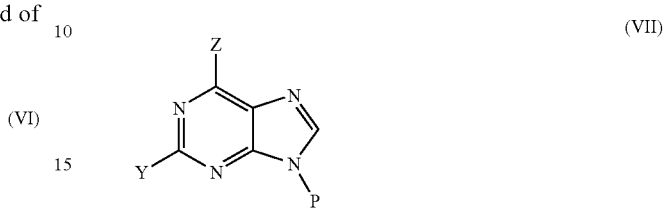

(VII)

wherein P is as hereinbefore defined for a compound of formula (III), Y is as hereinbefore defined for a compound of formula (VI), and Z is a halogen atom, for example chlorine, with an alcoholic solution of ammonia.

For example, a compound of formula (VII) is heated with 2M solution of ammonia in a suitable alcohol, for example, iso-propyl alcohol, at a suitable temperature, for example 50° C., for a suitable period of time, for example 5 hours. After standing at ambient temperature for a suitable period of time, for example 12-18 hours, a further quantity of the alcoholic ammonia is added to break up the resultant cake and the reaction mixture heated for a further suitable period of time, for example 9 hours, until the reaction is complete. To the reaction mixture is added water and the solid product filtered off. The solid is then washed, for example with a mixture of iso-propyl alcohol and water, and then air-dried under suction to give a first crop. The filtrate may be re-filtered after standing for 12-18 hours to afford a second crop and the crops then dried in vacuo.

A compound of formula (VII) may be prepared from a compound of formula (VIII):

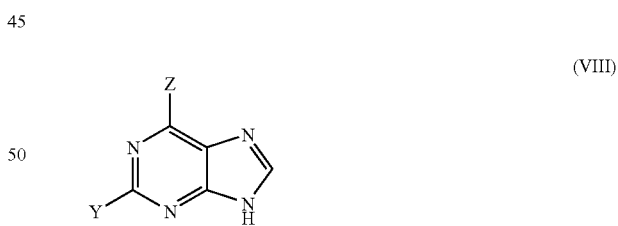

(VIII)

wherein Y is as hereinbefore defined for a compound of formula (VI) and Z is as hereinbefore defined for a compound of formula (VII), by reaction with a suitable protecting reagent, for example 3,4-dihydro-2H-pyran.

For example, a compound of formula (VIII) is added a suitable solvent, for example ethyl acetate, followed by p-toluenesulfonic acid. The mixture is heated to a suitable temperature, for example 50° C., and then 3,4-dihydro-2H-pyran added. The reaction mixture is then heated at a suitable temperature, for example 50° C., for a suitable period of time, for example 4 hours. The reaction mixture is then evaporated in vacuo to give a compound of formula (VII).

The present invention includes a process for the preparation of a compound of formula (I), which process comprises the hydrolysis of a compound of formula (XXI):

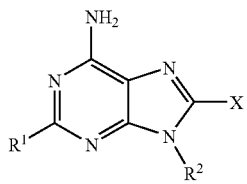

(XXI)

wherein $R^1$ and $R^2$ are as hereinbefore defined for a compound of formula (I) and X is as hereinbefore defined for a compound of formula (IV).

For example, to a solution of a compound of formula (XXI) in a suitable solvent, for example dry n-butanol, is added a suitable concentrated mineral acid, for example concentrated hydrochloric acid at a suitable temperature, for example ambient temperature. The reaction is then heated to a suitable temperature, for example 80-120° C. for a suitable period of time, for example 0.5-8 hours. The volume of the reaction mixture is then was reduced, for example by concentration in vacuo, water added, and the mixture neutralised by the addition of a suitable aqueous base, for example sodium hydroxide solution. The product is then isolated and purified by conventional means, for example the product may be isolated by filtration and purified by chromatography.

A compound of formula (XXI) may be prepared by halogenation of a compound of formula (XX):

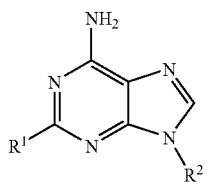

(XX)

wherein $R^1$ and $R^2$ are as hereinbefore defined for a compound of formula (I).

When $R^1$ is $C_{1-8}$alkylamino or $C_{3-7}$cycloalkyl$C_{1-6}$alkylamino, the halogenation of a compound of formula (XX) may be undertaken, for example, as follows:

To a solution of a compound of formula (XX) in a suitable dry solvent, for example dry chloroform, at a suitable temperature, for example ambient temperature is added N-bromosuccinimide. The reaction mixture is stirred at a suitable temperature, for example ambient temperature, for a suitable period of time, for example one hour. The reaction mixture is then diluted with a suitable solvent, for example dichloromethane, and washed with water. The organic phase is then dried, for example by passage through a hydrophobic frit, and concentrated.

When $R^1$ is $C_{1-8}$alkoxy, $C_{3-7}$cycloalkyl$C_{1-6}$alkoxy, $C_{1-3}$alkoxy$C_{2-3}$alkoxy, or $Het^b$-$C_{1-3}$alkoxy, the halogenation of a compound of formula (XX) may be undertaken, for example, as follows:

A compound of formula (XX) is dissolved in glacial acetic acid before adding sodium acetate. The mixture is then cooled to a suitable temperature, for example in an ice-bath, and bromine gradually added. The reaction mixture is warmed to a suitable temperature, for example ambient temperature, before being heated to a suitable temperature, for example in a heating device set to a temperature of 60-80° C. for a suitable period of time, for example 3-6 hours. The reaction mixture is quenched with sodium thiosulphate solution and then the pH adjusted to 6-7 by the addition of a suitable base, for example aqueous sodium hydroxide solution. The mixture is then extracted into a suitable organic solvent, for example ethyl acetate, the organic layer separated, dried, and the solvent removed.

A compound of formula (XX), wherein $R^1$ is $C_{1-8}$alkoxy, $C_{3-7}$cycloalkyl$C_{1-6}$alkoxy, $C_{1-6}$alkoxy$C_{1-6}$alkoxy, or $Het^b$-$C_{1-3}$alkoxy may be prepared by reaction of a compound of formula (XIX):

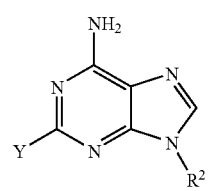

(XIX)

wherein Y is as hereinbefore defined for a compound of formula (VI) and $R^2$ is as hereinbefore defined for a compound of formula (I), with a compound of formula (VIA) as hereinbefore defined.

For example, a compound of formula (XIX) is added to a suspension of a compound of formula (VIA) and a strong base, for example sodium tert-butoxide. The reaction mixture is then heated, for example in a microwave oven, for a suitable period of time, for example 20-45 minutes at a suitable temperature, for example 90-120° C. The reaction mixture is then diluted with a suitable solvent, for example ethyl acetate, and washed with water. The organic phase is separated and dried, for example by passage through a hydrophobic frit, and concentrated. The compound of formula (XX) may be isolated by conventional means, for example trituration followed by filtration.

A compound of formula (XX), wherein $R^1$ is $C_{1-8}$alkylamino, $C_{3-7}$cycloalkyl$C_{1-6}$alkylamino, may be prepared by reaction of a compound of formula (XIX) with a compound of formula (VIB) as hereinbefore defined.

For example, a solution of a compound of formula (XIX) in a suitable solvent, for example cyclohexylamine, is heated, for example in a microwave oven, at a suitable temperature, for example 150-180° C., for a suitable period of time, for example five minutes. The crude reaction mixture is then purified by, for example chromatography.

A compound of formula (XIX) may be prepared by reaction of a compound of formula (XVIII):

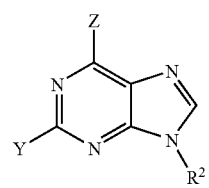

(XVIII)

wherein Y is as hereinbefore defined for a compound of formula (VI), Z is as hereinbefore defined for a compound of formula (VII), and $R^2$ is as hereinbefore defined for a compound of formula (I), with ammonia.

For example, a compound of formula (XVIII) (which may contain residual triphenylphosphine oxide as an impurity from the synthesis of a compound of formula (XVIII), is heated with an alcoholic solution of ammonia, for example 2M ammonia in iso-propyl alcohol, at a suitable temperature, for example 40-60° C., for a suitable period of time, for example 12-18 hours. The reaction mixture is then evaporated to dryness and the product purified by recrystallisation from a suitable solvent, for example methanol.

A compound of formula (XIX) may also be prepared by reaction of a compound of formula (XVII):

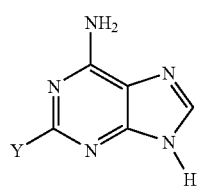
(XVII)

wherein Y is as hereinbefore defined for a compound of formula (VI), with a compound of formula (IIB) as hereinbefore defined.

For example, to a suspension of a compound of formula (XVII) and a suitable base, for example potassium carbonate, in a suitable solvent, for example N,N-dimethylformamide, is added a compound of formula (IIB). The mixture is stirred at a suitable temperature, for example 80-100° C., for a suitable period of time, for example 12-18 hours. The reaction mixture is then taken up in a suitable solvent, for example a mixture of chloroform and iso-propyl alcohol and extracted with water. The organic phase is then separated, dried by, for example passage through a hydrophobic frit, and concentrated.

A compound of formula (XVIII) may be prepared by reaction of a compound of formula (VIII) as hereinbefore defined with a compound of formula $R^2$—OH, wherein $R^2$ is as hereinbefore defined for a compound of formula (I).

For example, a mixture of a compound of formula (VIII) and a compound of formula $R^2$—OH is dissolved in a suitable dry solvent, for example dry tetrahydrofuran. To this solution is added triphenylphosphine, followed by diisopropyl azodicarboxylate (dropwise). The temperature of the reaction mixture is kept below about 45° C. by cooling, for example with a water-bath. The reaction mixture is then stirred for a suitable period of time, for example 12-18 hours, at a suitable temperature, for example ambient temperature, quenched with water, and extracted into a suitable organic solvent, for example ethyl acetate. The organic phase is separated, washed with water, and then dried by, for example, passage through a hydrophobic frit, and concentrated under reduced pressure. The crude product may be purified by conventional means, for example chromatography.

A compound of formula (XVII) may be prepared by reaction of a compound of formula (VIII) as hereinbefore defined with ammonia.

For example, a mixture of a compound of formula (VIII) and ammonia solution in a suitable solvent, for example iso-propyl alcohol, is stirred and heated at a suitable temperature, for example 100-140° C. in an autoclave for a suitable period of time, for example 12-18 hours. The reaction is then cooled and concentrated to give a compound of formula (XVII).

The present invention includes a synthetic process for, a compound of formula (I), wherein $R^1$ is $C_{1-8}$alkylamino or $C_{3-7}$cycloalkyl$C_{1-6}$alkylamino, which may be prepared by reaction of a compound of formula (XXIII):

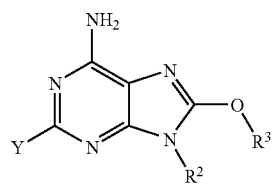
(XXIII)

wherein Y is as hereinbefore defined for a compound of formula (VI), $R^2$ is as hereinbefore defined for a compound of formula (I), and $R^3$ is as hereinbefore defined for a compound of formula (IIA), with a compound of formula (VIB) as hereinbefore defined.

For example, a mixture of a compound of formula (XXIII) and a compound of formula (VIB) is heated, for example in a microwave oven, at a suitable temperature, for example 150-190° C. for a suitable period of time, for example 10-20 minutes. The reaction mixture is then concentrated to yield a crude product which is purified by conventional means, for example chromatography.

A compound of formula (XXIII) may be prepared by reaction of a compound of formula (XXII):

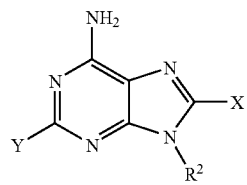
(XXII)

wherein X is as hereinbefore defined for a compound of formula (IV), Y is as hereinbefore defined for a compound of formula (VI) and $R^2$ is as hereinbefore defined for a compound of formula (I), with a source of alkoxide anion.

For example, a solution of a compound of formula (XXII) in a suitable solvent, for example dry methanol, was added a suitable base, for example aqueous sodium hydroxide solution and the mixture was stirred at reflux for a suitable period of time, for example 15-45 minutes. The reaction mixture is cooled to a suitable temperature, for example ambient temperature, and concentrated. The residue obtained is triturated with water and extracted with a suitable solvent, for example ethyl acetate. The organic layer is separated, washed, dried, filtered and concentrated to give a solid product which may be purified by conventional means, for example chromatography.

A compound of formula (XXII) may be prepared by reaction of a compound of formula (XIX) as hereinbefore defined, with a halogenating agent.

For example, a solution of a compound of formula (XIX) in a suitable dry solvent, for example chloroform, at a suitable temperature, for example ambient temperature, is added a suitable halogenating agent, for example N-bromosuccinimide. The reaction mixture is stirred at a suitable temperature, for example 50-70° C. for a suitable period of time, for example 5-7 hours. The reaction mixture is cooled, for example to ambient temperature, taken up in a suitable solvent, for example dichloromethane, and washed with water. The organic phase is then dried by, for example passage through a hydrophobic frit, and concentrated.

ABBREVIATIONS

The following list provides definitions of certain abbreviations as used herein. It will be appreciated that the list is not exhaustive, but the meaning of those abbreviations not hereinbelow defined will be readily apparent to those skilled in the art.

| | |
|---|---|
| DCM | Dichloromethane |
| DME | 1,2-Dimethoxyethane |
| DMF | N,N-Dimethylformamide |
| EtOAc | Ethyl acetate |
| Et$_2$O | Diethyl ether |
| h | hours |
| HCl | Hydrochloric acid |
| HPLC | High performance liquid chromatography |
| ISCO Companion | Automated flash chromatography equipment with fraction analysis by UV absorption available from Presearch Limited, Basingstoke, Hants., RG24 8PZ, UK |
| MDAP HPLC | Reverse phase HPLC on a C$_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. |
| MeOH | Methanol |
| mins | minutes |
| NBS | N-Bromosuccinimide |
| Stripped | Removal of solvent under reduced pressure |
| TBME | Tertiary butyl methyl ether |
| TFA | Trifluoroacetic acid |
| iPr | iso-Propyl |
| t-Bu | tert-Butyl |
| Ms | Mesyl |
| Ac | Acetyl |
| n-Bu | n-Butyl |
| Ph | Phenyl |

The synthetic processes hereinbefore described are summarised in Scheme 1.

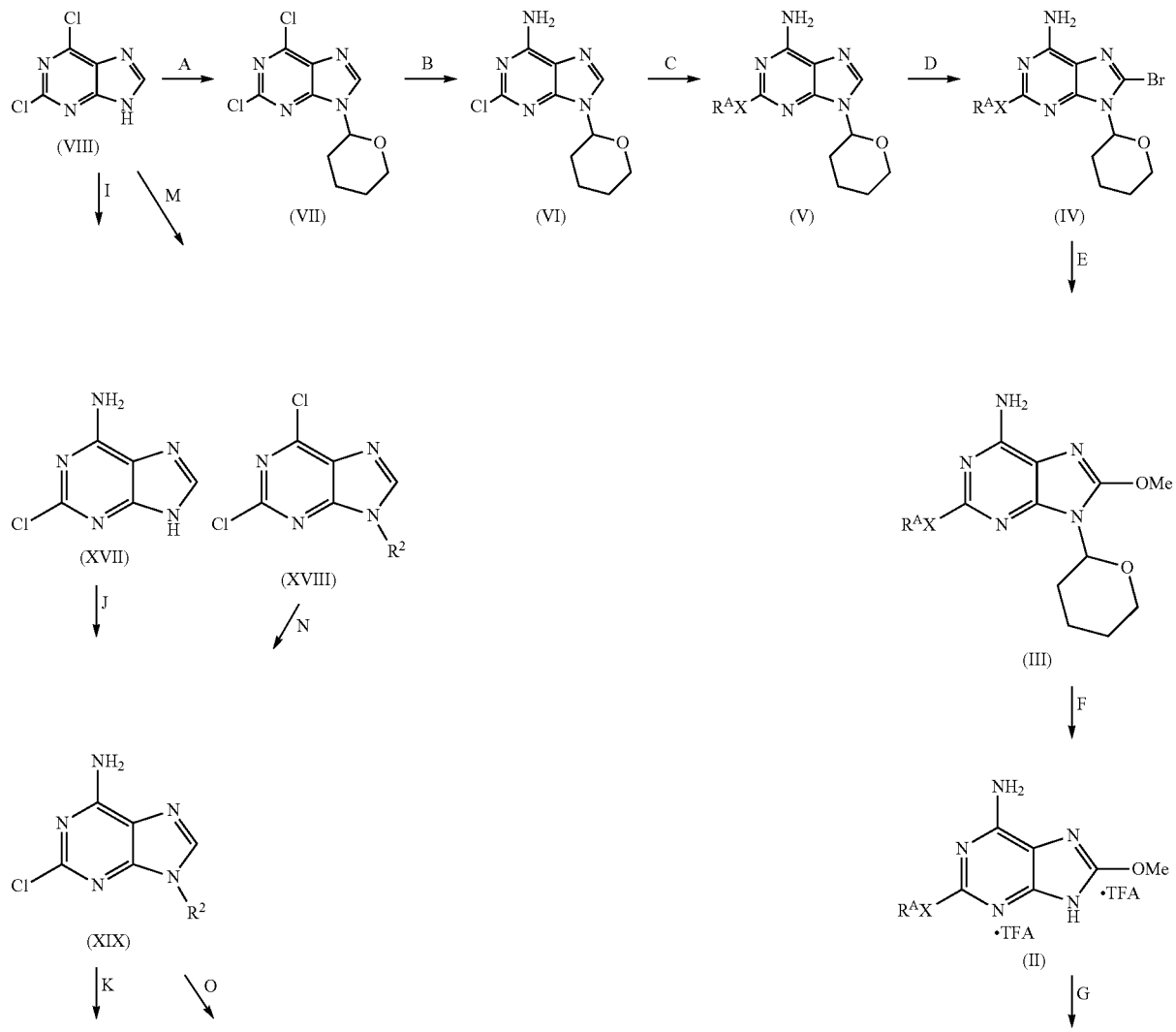

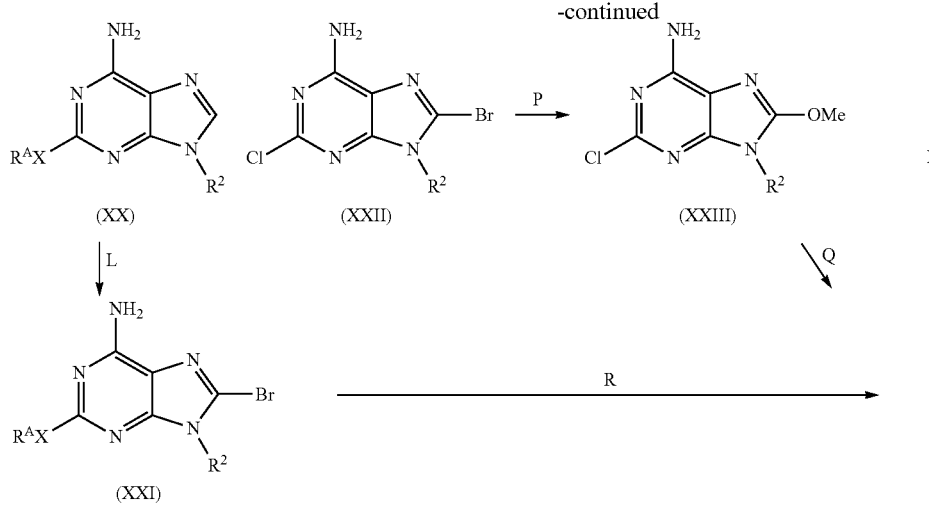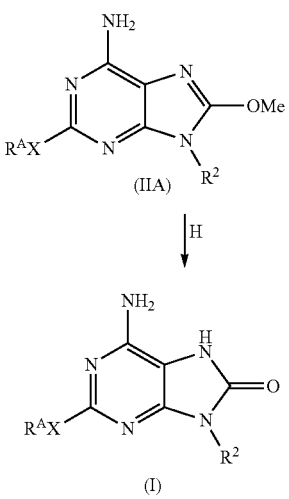

Typical reaction conditions for each of the synthetic steps of Scheme 1 are provided below:

A Dihydropyran/paratoluene sulphonic acid, e.g. 50° C. for 4 hours.
B Ammonia/iPrOH, e.g. 50° C. for 5 hours, then ambient temperature for 12-18 hours, then 50° C. for 9 hours; or 60° C. for 4 hours.
C For X=NH:—$R^4NH_2$/ethylene glycol e.g. 120° C. for 12-18 hours.
  For X=O:—$R^4OH$/KOtBu/dimethoxyethane e.g. 93-110° C. for 12-18 hours.
  $R^4OH$/KOtBu or NaH e.g. 50° C. for 72 hours; or 12-18 hours, then 72 hours, or 80-90° C. for 2-4 hours, or 100° C. for 12-18 hours.
D NBS in $CH_2Cl_2$ or $CHCl_3$ e.g. 0-20° C. for 10 minutes to 6.5 hours, or ambient temperature for 0.25-2 hours.
E NaOMe/MeOH e.g. reflux 1-18 hours or 60° C. for 12-48 hours.
F TFA/MeOH e.g. ambient temperature for 18-65 hours.
G $K_2CO_3$/DMF then $R^2L$ where L=halogen-Br e.g. 60° C. for 1-1.5 hours, then;
  a) 50° C. for 2-18 hours, or;
  b) 60° C. for 2-16 hours, or;
  c) 50° C. for 12-18 hours, then 70° C. for 8 hours, or;
  d) ambient temperature for 39 hours then 50° C. for 2 hours, or
  e) 50° C. for 12-18 hours then 70° C. for 8 hours, or;
  f) 50° C. for 12-18 hours, then 90° C. for 2 hours.
  or where L=OMs e.g. 60° C. for 1-1.5 hours then;
  a) 90° C. for 2-3.5 hours, or;
  b) 50° C. 5 h, ambient temperature 16 hours, LiBr at 90° C. for 8 hours, or;
  c) 60° C. for 3-16 hours.
H HCl/1,4-dioxane e.g. ambient temperature for 1-18 hours.
I Ammonia/iPrOH e.g. 120° C. for 12-18 hours.
J $K_2CO_3$/DMF then $R^2L$ where L=halogen, for example 90° C. for 12-18 hours.
K X=O: $R^1OH$/KOtBu e.g. 30 mins. At 105° C. in a microwave oven.
  X=NH: $R^1NH_2$ e.g. 170° C. in microwave oven for 2-5 min.
L X=O: $Br_2$/AcOH e.g. ice-bath—ambient temperature then 70° C. for 4 hours.
  X=NH: NBS in $CHCl_3$ e.g. ambient temperature for 40 min –1 hour.
M $R^2OH$/$PPh_3$/diisopropyl azodicarboxylate e.g. ambient temperature –43° C.
N Ammonia/iPrOH e.g. 50° C. for 12-18 hours.
O NBS in $CHCl_3$ e.g. 60° C. for 6 hours.
P NaOH MeOH e.g. reflux 0.5 hours.
Q $R^1NH_2$ neat e.g. 170° C. in microwave oven for 10-15 mins.
  $R^1NH_2$/ethylene glycol e.g. 170° C. in microwave oven for 2×30 min. then 180° C. in microwave oven for 30 min.
R c.HCl/nBuOH e.g. 100° C. for 0.5-6 hours.

Compounds of formulae (VIA), (VIB), (VIII), (X), (XI), (XII), (XIII), (XIV), XV), (XVI), and acrolein are commercially available and may be obtained from, for example, Sigma-Aldrich, UK; TCI Europe, Belgium; ABCR GmbH & Co. KG, Germany; PharmaCore Inc., USA; Chemical Block Ltd., Russia; Lancaster Synthesis (Alfa Aesar), UK, or may be prepared by analogy with known procedures, for example those disclosed in standard reference texts of synthetic methodology such as J. March, *Advanced Organic Chemistry*, 4th Edition (1992), Wiley Interscience, or *Comprehensive Organic Synthesis* (Trost B. M. and Fleming I., (Eds.), *Pergamon Press*, 1991), each incorporated herein by reference as it relates to such procedures.

Examples of other protecting groups that may be employed in the synthetic routes described herein and the means for their removal can be found in T. W. Greene 'Protective Groups in Organic Synthesis', 3rd edition, J. Wiley and Sons, 1999, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with magnesium sulphate, or sodium sulphate, or passing through a hydrophobic frit, may be employed. Conventional methods of purification, for example crystallisation and chromatography, for example silica chromatography or reverse-phase chromatography, may be used as required. Crystallisation may be performed using conventional solvents such as methanol, ethanol, or butanol, or aqueous mixtures thereof. It will be appreciated that specific reaction times temperatures may typically be determined by reaction-monitoring techniques, for example thin-layer chromatography and LC-MS.

Where appropriate individual isomeric forms of the compounds of formula (I) may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

The invention is illustrated by reference to, but is in no way limited by, the following Examples.

Experimental Details

Experimental details of LCMS systems A and B as referred to herein are as follows:

System A
Column: 3.3 cm×4.6 mm ID, 3 µm ABZ+PLUS from Supelco
Flow Rate: 3 mL/min.
Injection Volume: 5 µL
Temp: RT
UV Detection Range: 215 to 330 nm
Solvents: A: 0.1% formic acid+10 mM ammonium acetate
  B: 95% acetonitrile+0.05% formic acid

| Gradient: | | |
|---|---|---|
| Time (min.) | A % | B % |
| 0 | 100 | 0 |
| 0.7 | 100 | 0 |
| 4.2 | 0 | 100 |
| 5.3 | 0 | 100 |
| 5.5 | 100 | 0 |

System B
Column: 50 mm×2.1 mm ID, 1.7 µm Acquity HPLC BEH $C_{18}$
Flow Rate: 1 mL/min.
Injection Volume: 0.5 µL
Temp: 40° C.
UV Detection Range: 220 to 330 nm
Solvents: A: 0.1% formic acid+10 mM ammonium acetate
  B: 95% acetonitrile+0.05% formic acid

| Gradient: | | |
|---|---|---|
| Time (min.) | A % | B % |
| 0 | 97 | 3 |
| 0.7 | 97 | 3 |
| 4.2 | 0 | 100 |
| 5.3 | 0 | 100 |
| 5.5 | 97 | 3 |

For Intermediates 219-292 and Examples 61-141, chromatographic purification was undertaken as detailed below.

Chromatographic purification was typically performed using pre-packed silica gel cartridges. The Flashmaster II is an automated multi-user flash chromatography system, available from Argonaut Technologies Ltd, which utilises disposable, normal phase, Solid Phase Extraction (SPE) cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength UV-detector and two Gilson FC204 fraction-collectors enabling automated peak cutting, collection and tracking.

For Intermediates 219-292 and Examples 61-141, NMR spectra were recorded as detailed below.

$^1$H NMR spectra were recorded in either $CDCl_3$ or DMSO-$d_6$ on either a Bruker DPX 400 or Bruker Avance DRX or Varian Unity 400 spectrometer all working at 400 MHz. The internal standard used was either tetramethylsilane or the residual protonated solvent at 7.25 ppm for $CDCl_3$ or 2.50 ppm for DMSO-$d_6$.

For Intermediates 219-292, mass-directed autopreparation was undertaken under the conditions given below.

Mass directed autopreparative HPLC was conducted on an XBridge C18 column (100 mm×19 mm i.d. 5 µm packing diameter) at ambient temperature. The solvents employed were:

A=10 mM aqueous Ammonium Bicarbonate adjusted to pH 10 with Ammonia solution.

B=Acetonitrile.

A flow rate of 20 ml/min was employed. A typical gradient was:

| Time (min.) | A % | B % |
|---|---|---|
| 0 | 70 | 30 |
| 1 | 70 | 30 |
| 10 | 15 | 85 |
| 11 | 1 | 99 |
| 15 | 1 | 99 |

The UV detection was an averaged signal from wavelength of 210 nm to 350 nm and mass spectra were recorded on a mass spectrometer using alternate-scan positive and negative mode electrospray ionization.

EXAMPLES

Intermediate 1

2,6-Dichloro-9-(tetrahydro-2H-pyran-2-yl)-9H-purine

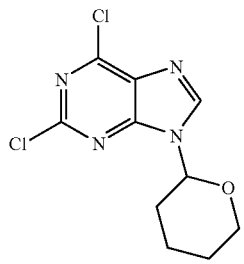

To 2,6-dichloropurine (25.0 g) was added ethyl acetate (260 mL), followed by p-toluenesulfonic acid (0.253 g). The mixture was heated to 50° C. and then 3,4-dihydro-2H-pyran (16.8 g) was added. The reaction mixture was then heated at 50° C. for 4 hours. The reaction mixture was evaporated in vacuo to give the title compound as a yellow solid (36.9 g).

¹H NMR (CDCl₃): 8.35 (1H, s), 5.77 (1H, dd), 4.20 (1H, m), 3.79 (1H, m), 2.20-1.65 (6H, m).

Intermediate 2

2-Chloro-9-(tetrahydro-2H-pyran-2-yl)-9H-purin-6-amine

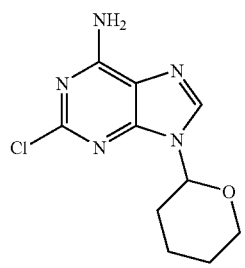

2,6-Dichloro-9-(tetrahydro-2H-pyran-2-yl)-9H-purine (36.9 g) was heated with 2M ammonia in isopropanol (250 mL) at 50° C. for 5 hours. After standing at ambient temperature overnight, a further quantity of 2M ammonia in isopropanol (100 mL) was added to break up the resultant cake and the reaction mixture was heated for a further 9 hours until the reaction was complete. To the reaction mixture was added water (70 mL) and the yellow solid filtered off. The solid was washed with isopropyl alcohol:water (5:1 (v/v), 60 mL) and then air-dried under suction to give a first crop. The filtrate was re-filtered after standing overnight to isolate precipitate and both solids were dried in vacuo. The first crop was pure with the second crop material showing a very minor impurity (isolated broad signal 3.5 ppm not seen in first crop) but was otherwise identical. Solid first crop (28.4 g), solid second crop (3.42 g).

¹H NMR (CDCl₃): 8.01 (1H, s), 5.98 (2H, broad s), 5.70 (1H, dd), 4.16 (1H, m), 3.78 (1H, m), 2.15-1.60 (6H, overlapping m).

Intermediate 2 (Alternative Method)

2-Chloro-9-(tetrahydro-2H-pyran-2-yl)-9H-purin-6-amine

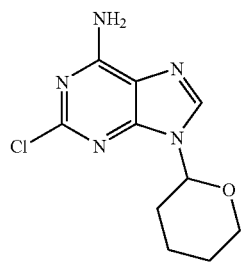

To a solution of 2,6-dichloropurine (25 g) in dry ethyl acetate (200 ml) was added p-toluenesulfonic acid monohydrate (235 mg). The reaction was heated to 50° C. and 3,4-dihydro-2H-pyran (18.1 ml) was added in one go. The reaction was allowed to stir at 50° C. for 1 hour and the solvent was removed under reduced pressure. This afforded a yellow solid. A suspension of this solid (~36 g) in 2.0M ammonia in isopropanol (460 ml) was heated under nitrogen at 60° C. for 4 hours with an attached condenser. The reaction was poured into water (50 ml) and left to cool overnight. The precipitate was filtered and dried on a rotary evaporator (60° C.) for 30 minutes to afford the title compound as an off-white solid (31 g, 93%, 2 steps).

MS calcd for $(C_{10}H_{12}ClN_5O)^+$=254, 256

MS found (electrospray): $(M)^+$=254, 256 (3:1)

¹H NMR((CD₃)₂SO): δ 8.43 (1H, s), 7.82 (2H, s), 5.55 (1H, dd), 4.00 (1H, m), 3.69 (1H, m), 2.21 (1H, m), 1.95 (2H, m), 1.74 (1H, m), 1.56 (2H, m).

Intermediate 3

2-(Butoxy)-9-(tetrahydro-2H-pyran-2-yl)-9H-purin-6-amine

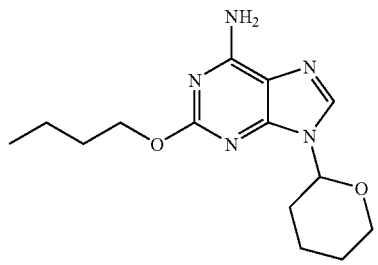

To butan-1-ol (76 mL) was added portion wise sodium tert-butoxide (15.2 g) (Note: reaction mixture gets warm). The above was stirred until homogeneous (~15 min) before 2-chloro-9-(tetrahydro-2H-pyran-2-yl)-9H-purin-6-amine (10.0 g) was then added to the resultant pale yellow solution. The reaction mixture was then heated to 100° C., overnight. The reaction mixture was stripped to remove as much butan-1-ol as possible before being partitioned between diethyl ether and water. The diethyl ether phase was separated and the aqueous re-extracted further with diethyl ether. Combined organic layers dried over magnesium sulphate (anhydrous). Magnesium sulphate was filtered off and filtrate stripped to give brown viscous oil which was azeotroped with toluene (3 times) and placed under high vacuum overnight, transferred to new flask with dichloromethane and stripped, placed under high vacuum to give the title compound as a brown glass (9.45 g).

1H NMR (CDCl₃): 7.85 (1H, s), 5.92 (2H, broad s), 5.64 (1H, d), 4.32 (2H, t), 4.14 (1H, m), 3.75 (1H, m), 2.10-1.95 (3H, overlapping m), 1.81-1.58 (5H, overlapping m), 1.50 (2H, m), 0.97 (3H, t).

Intermediate 4

8-Bromo-2-butoxy-9-(tetrahydro-2H-pyran-2-yl)-9H-purin-6-amine

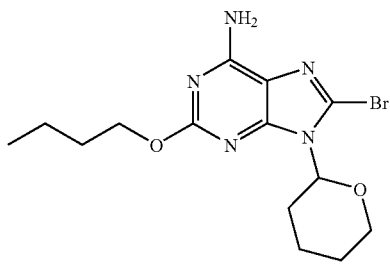

2-Butoxy-9-(tetrahydro-2H-pyran-2-yl)-9H-purin-6-amine (9.45 g) was dissolved in chloroform (50 mL) and cooled to 0° C. (ice-bath). To this solution was added portion wise N-bromosuccinimide (6.07 g) keeping the temperature below 3° C. This gave a dark green solution, stirred at 2.5° C. for 30 minutes before allowing to warm to room temperature and then stirring for 6 hours. The reaction mixture was then washed with water (100 mL, twice). Organic phase was dried/separated using a hydrophobic frit and evaporated to give a dark brown gum which was purified by silica chromatography (120 g) (ISCO) using a gradient elution of 0-50% ethyl acetate: cyclohexane to afford the title compound as a pale yellow solid (8.37 g).

1H NMR (CDCl$_3$): 5.61 (1H, dd), 5.49 (2H, broad s), 4.32 (2H, m), 4.17 (1H, m), 3.71 (1H, m), 3.04 (1H, m), 2.11 (1H, broad d), 1.89-1.45 (6H, overlapping m), 1.50 (2H, m), 0.97 (3H, t).

Intermediate 5

2-Butoxy-8-methoxy-9-(tetrahydro-2H-pyran-2-yl)-9H-purin-6-amine

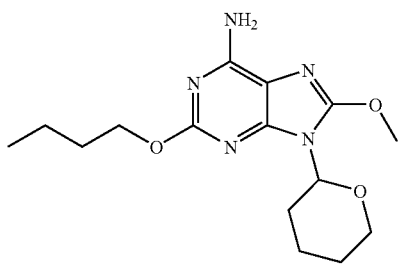

8-Bromo-2-butoxy-9-(tetrahydro-2H-pyran-2-yl)-9H-purin-6-amine (8.37 g) was heated to reflux with 25% sodium methoxide in methanol (14.4 mL) and methanol (65 mL) for 4.5 hours. The reaction mixture was concentrated under reduced pressure and partitioned between ethyl acetate and saturated ammonium chloride solution. Separated organic phase and repeated extraction into ethyl acetate. Combined organic phases and washed with brine (twice). The organic phase was passed through a hydrophobic frit after separating aqueous and was evaporated to give a light brown gum which was placed under high vacuum to give a foam (7.52 g) which collapsed to a gum (7.34 g) at ambient pressure and solidified overnight to give the title compound as a yellow amorphous solid.

MS calcd for $(C_{15}H_{23}N_5O_3)^+=321$
MS found (electrospray): $(M+H)^+=322$ 1H NMR (CDCl$_3$): 5.50 (1H, dd), 5.17 (2H, broad s), 4.29 (2H, t), 4.12 (3H, s and 1H, m), 3.70 (1H, m), 2.77 (1H, m), 2.05 (1H, m), 1.82-1.63 (6H, overlapping m), 1.50 (2H, m), 0.97 (3H, t).

Intermediate 6

2-Butoxy-8-methoxy-9H-purin-6-amine trifluoroacetate salt

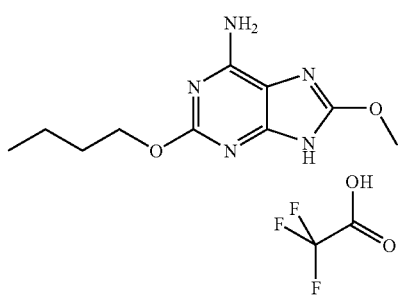

To a solution of 2-butoxy-8-methoxy-9-(tetrahydro-2H-pyran-2-yl)-9H-purin-6-amine (7.34 g) in methanol (100 mL) was added trifluoroacetic acid (10 mL). The mixture was stirred at ambient temperature over the weekend to give a suspension. The reaction mixture was concentrated to a small volume (thick slurry) before being diluted with ethyl acetate (50 mL). The resultant slurry was filtered and washed with a small volume of ethyl acetate until the filtrate was colourless. The solid remaining was dried by air and then in vacuo to give the title compound as a solid (6.20 g). The filtrate obtained previously was concentrated to give a slurry which was diluted with a small volume of ethyl acetate (10 mL) and then filtered and dried as above. This second crop was isolated as a white solid (0.276 g). Both crops were identical by NMR.

MS calcd for $(C_{10}H_{15}N_5O_2)^+=237$
MS found (electrospray): $(M+H)^+=238$ 1H NMR (CD$_3$OD): 4.47 (2H, t), 4.15 (3H, s), 1.80 (2H, m), 1.50 (2H, m), 0.99 (3H, t) (exchangeable NH$_2$, NH and COOH protons not observed).

Intermediate 7

2-Butoxy-8-methoxy-9-(tetrahydro-2H-pyran-4-ylmethyl)-9H-Purin-6-amine

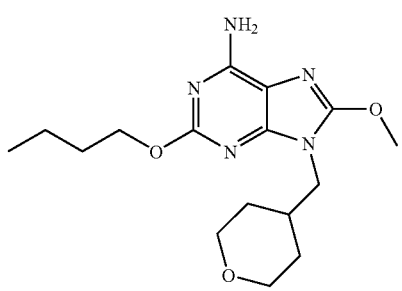

2-Butoxy-8-methoxy-9H-purin-6-amine trifluoroacetate salt (0.5 g) was heated to 60° C. for 1 hour with anhydrous potassium carbonate (0.79 g) in dry DMF (10 mL) and allowed to cool to room temperature before adding 4-(bromomethyl)tetrahydro-2H-pyran (0.26 g). The reaction was stirred at room temperature for 39 hours and heated for 2 hours at 50° C. The reaction was poured into water and extracted into ethyl acetate (twice). The combined ethyl acetate extracts were dried through a hydrophobic frit, stripped to dryness and purified first by silica chromatography (ISCO) (40 g) eluting with 0-100% ethyl acetate:cyclohexane then 0-20% methanol:ethyl acetate and then by reverse phase chromatography (43 g, C-18) (ISCO) eluting 20-60% acetonitrile (0.05% formic acid): water (0.1% formic acid) to give the title compound as a white solid.

MS calcd for $(C_{16}H_{25}N_5O_3)^+$=335
MS found (electrospray): $(M+H)^+$=336
1H NMR (CD$_3$OD): 4.29 (2H, t), 4.13 (3H, s), 3.92 (2H, m), 3.81 (2H, dd), 3.36 (2H, m), 2.12 (1H, m), 1.74 (2H, m), 1.52-1.47 (4H, m), 1.37 (2H, m), 0.98 (3H, t) (NH$_2$ exchanged).

Intermediate 8

2-Butoxy-8-methoxy-9-(tetrahydro-2H-pyran-2-ylmethyl)-9H-Purin-6-amine

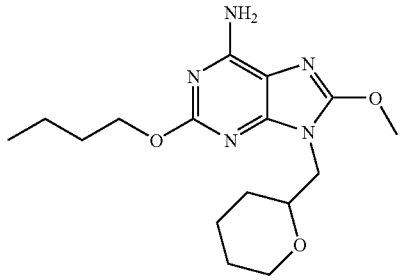

2-Butoxy-8-methoxy-9H-purin-6-amine trifluoroacetate salt (0.20 g) was heated with anhydrous potassium carbonate (0.315 g) in dry DMF (5 mL) at 60° C. for 1 hour and cooled to room temperature. 2-(Bromomethyl) tetrahydro-2H-pyran (73 uL) was added and the reaction mixture heated at 50° C., overnight. The reaction mixture was quenched into water (50 mL) and extracted into ethyl acetate (25 mL, 3 times). The combined organic layers were separated and passed through a hydrophobic frit to dry, then stripped to dryness and the pale yellow gum (145 mg), which turned to a white solid when triturated with methanol, was purified by MDAP to give the title compound (6 mg) (~85% pure).

MS calcd for $(C_{16}H_{25}N_5O_3)^+$=335
MS found (electrospray): $(M+H)^+$=336.

Intermediate 9

N$^2$-Butyl-9-(tetrahydro-2H-pyran-2-yl)-9H-purine-2,6-diamine

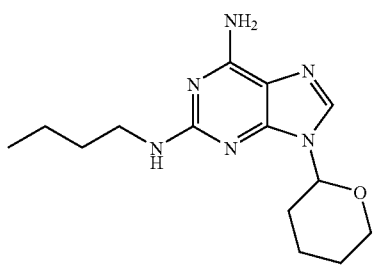

To a solution of 2-chloro-9-(tetrahydro-2H-pyran-2-yl)-9H-purin-6-amine (10 g) in dry ethylene glycol (50 ml) at room temperature and under nitrogen was added n-butylamine (16 ml) in one go. The reaction was heated at 120° C. overnight. The reaction was cooled to room temperature, diluted with ethyl acetate (150 ml) and washed with water (2×50 ml). The organic layer was dried over MgSO$_4$, filtered and concentrated in vacuo. This afforded the title compound as a viscous green oil (10.2 g) that was used in the next step without further purification.

MS calcd for $(C_{14}H_{22}N_6O)^+$=290
MS found (electrospray): $(M+H)^+$=291
$^1$H NMR((CD$_3$)$_2$SO): δ 7.8 (1H, s), 6.6 (2H, s), 6.2 (1H, t), 5.4 (1H, dd), 4.0 (1H, m), 3.6 (1H, m), 3.2 (2H, m), 2.2 (1H, m), 1.9 (1H, m), 1.8 (1H, m), 1.7 (1H, m), 1.5 (2H, m), 1.4 (2H, m), 1.3 (2H, m), 0.9 (3H, t).

Intermediate 10

N$^2$-Butyl-8-methoxy-9H-purine-2,6-diamine trifluoroacetic acid salt

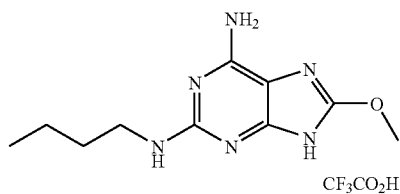

To a solution of crude N$^2$-butyl-9-(tetrahydro-2H-pyran-2-yl)-9H-purine-2,6-diamine (~10.2 g) in dry chloroform (100 ml) at room temperature was added N-bromosuccinimide (6.3 g) in portions over 5 minutes. The dark solution was allowed to stir at room temperature for 30 minutes. The reaction mixture was washed with water (20 ml). The organic phase was passed through a hydrophobic frit and concentrated in vacuo. This afforded a beige solid which was dissolved in dry methanol (100 ml) and at room temperature under nitrogen was added sodium methoxide solution (25 wt. % in methanol, 24 ml) in one go. The reaction was heated at 65° C., with a condenser attached, overnight. The reaction was cooled and concentrated in vacuo. The resultant orange residue was taken up in ethyl acetate (150 ml) and poured into saturated aqueous ammonium chloride (50 ml). The organic layer was separated and washed further with water (50 ml). The organic layer was dried over MgSO$_4$, filtered and concentrated in vacuo. To this material in dry methanol (70 ml) at room temperature was added trifluoroacetic acid (7 ml) in one go. The reaction was stirred for 30 hours and concentrated in vacuo to yield a dark brown solid. This was taken up in diethyl ether (20 ml) and triturated. The solid was filtered to afford the title compound as a beige solid (3.3 g, 35%, 4 steps).

MS calcd for $(C_{10}H_{16}N_6O)^+$=236
MS found (electrospray): $(M+H)^+$=237
$^1$H NMR((CD$_3$)$_2$SO): δ 13.3-12.3 (1H, br.m), 8.6-7.3 (2H, m), 4.05 (3H, s), 3.28 (2H, m), 1.52 (2H, m), 1.33 (2H, m), 0.89 (3H, t) (remaining exchangeable protons not clear).

Intermediate 11

N²-Butyl-8-methoxy-9-(tetrahydro-2H-pyran-4-ylmethyl)-9H-Purine-2,6-diamine

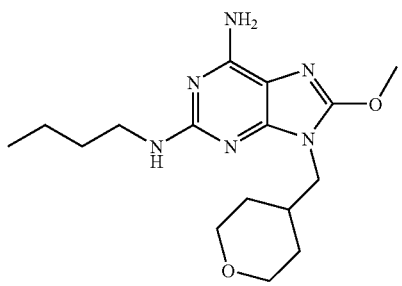

To a solution of N²-butyl-8-methoxy-9H-purine-2,6-diamine trifluoroacetic acid salt (500 mg) in dry N,N-dimethylformamide (8 ml) at room temperature and under nitrogen was added potassium carbonate (1.17 g) in one go. The reaction was stirred at 60° C. for 1.5 hours and then cooled to room temperature. 4-(bromomethyl)tetrahydro-2H-pyran (0.3 ml) was added in one go and the reaction heated at 50° C. overnight. The reaction was diluted with ethyl acetate (20 ml) and washed with water (10 ml). The organic layer was separated and concentrated in vacuo. The product was purified by $C_{18}$ reverse phase chromatography using water (containing 0.1% formic acid)-acetonitrile (containing 0.05% formic acid) as eluant (10-45%) to afford the title compound as a yellow viscous oil (315 mg, 90% clean).

MS calcd for $(C_{16}H_{26}N_6O_2)^+$=334
MS found (electrospray): $(M+H)^+$=335
$^1$H NMR((CD$_3$)$_2$SO): δ 6.29 (2H, s), 6.17 (1H, t), 4.00 (3H, s), 3.81 (2H, m), 3.66 (2H, d), 3.20 (4H, 2×m), 2.01 (1H, m), 1.47 (2H, m), 1.40 (2H, m), 1.31 (2H, m), 1.22 (2H, m), 0.89 (3H, t).

Intermediate 11, Alternative Procedure

N²-Butyl-8-(methoxy)-9-(tetrahydro-2H-pyran-4-ylmethyl)-9H-purine-2.6-diamine

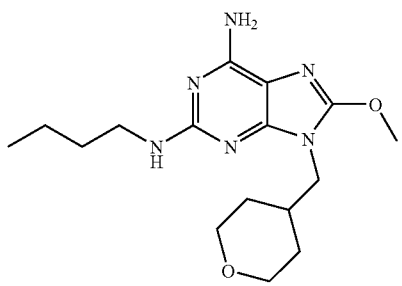

A mixture of N²-butyl-8-(methoxy)-3H-purine-2,6-diamine trifluoroacetate (12.89 g) and anhydrous potassium carbonate (20.58 g) in anhydrous DMF (175 mL) was heated to 60° C. (external) for 1.5 hours under nitrogen. The reaction mixture was cooled to room temperature before adding tetrahydro-2H-pyran-4-ylmethyl methanesulfonate (7.571 g) and then the reaction was heated to 90° C. for 2.5 hours. The reaction mixture was examined by LCMS and showed incomplete reaction and so the reaction temperature was reduced to 50° C. (external) and the reaction mixture was heated overnight under nitrogen.

The reaction mixture was then partitioned between water (300 mL) and ethyl acetate (300 mL). The organic was separated and the aqueous layer was re-extracted with further ethyl acetate (300 mL). The organic extracts were combined and washed with brine (500 mL). The organic was dried by passing through a hydrophobic frit (after separating the brine layer). The organic was evaporated under reduced pressure to give a crude brown mobile oil (16.01 g) that solidified to a wet solid (over 2 days). This material in ~3 g batches was purified using reverse phase chromatography {ISCO [column (C18) 330 g] (20-60% acetonitrile: water)}. The appropriate pure fractions from all purifications were combined and evaporated under reduced pressure to give clean title compound as a light-tan powdery solid (5.1530 g).

MS calcd for $(C_{16}H_{26}N_6O_2)^+$=334
MS found (electrospray): $(M+H)^+$=335
1H NMR (CDCl$_3$): 6.95 (2H, broad s), 6.52 (1H, broad s), 4.10 (3H, s), 4.01-3.92 (2H, m), 3.80-3.73 (2H, m), 3.44-3.29 (4H, overlapping m), 2.14-2.00 (1H, m), 1.65-1.34 (8H, overlapping m), 0.98-0.91 (3H, m).

Note: contains residual formic acid.

Intermediate 12

N²-Butyl-8-methoxy-9-(tetrahydro-2H-pyran-2-ylmethyl)-9H-purine-2,6-diamine

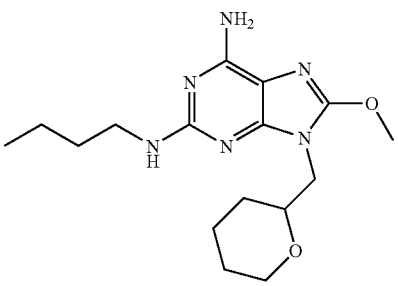

To a solution of N²-butyl-8-methoxy-9H-purine-2,6-diamine trifluoroacetic acid salt (400 mg) in dry N,N-dimethylformamide (6 ml) at room temperature and under nitrogen was added potassium carbonate (630 mg) in one go. The reaction was stirred at 60° C. for 1.5 hours and then cooled to 50° C. 2-(Bromomethyl)tetrahydro-2H-pyran (175 μl) was added in one go and the reaction heated to 50° C. overnight and then at 90° C. for 2 hours. The reaction was diluted with ethyl acetate (20 ml) and washed with water (10 ml). The organic layer was separated and concentrated in vacuo. The product was semi-purified by MDAP to afford a mixture of the title compound and an isomer. This mixture was taken on without further purification.

MS calcd for $(C_{16}H_{26}N_6O_2)^+$=334
MS found (electrospray): $(M+H)^+$=335.

Intermediate 13

3-(Bromomethyl)tetrahydro-2H-pyran

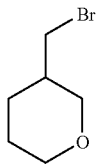

To tetrahydro-2H-pyran-3-ylmethanol (1 g) in dry dichloromethane (28 ml) at 0° C. and under nitrogen, was added triethylamine (2.7 ml) in one go, followed by methanesulphonyl chloride (0.87 ml) dropwise over 1 minute. The reaction was allowed to warm to room temperature and left at this temperature overnight. The reaction mixture was diluted with dichloromethane (20 ml) and washed with saturated aqueous sodium bicarbonate (20 ml). The organic layer was passed through a hydrophobic frit to dry and concentrated in vacuo to yield a yellow oil. To this oil in dry acetone (40 ml) and at room temperature was added lithium bromide (3 g) in one go. The reaction was heated to reflux for 1 hour. The reaction was allowed to cool to room temperature and taken up in dichloromethane (60 ml) and washed with water (20 ml). The organic layer was passed through a hydrophobic frit to dry and concentrated in vacuo. The product was purified by silica chromatography (40 g) (ISCO) using a gradient elution of 0-50% cyclohexane:ethyl acetate to afford the title compound as a yellow oil (340 mg).

$^1$H NMR (CDCl$_3$): δ 3.99 (2H, m), 3.84 (1H, m), 3.41 (1H, m), 3.35-3.21 (2H, m), 2.05-1.90 (2H, m), 1.71-1.59 (2H, m), 1.38 (1H, m).

Intermediate 14

N$^2$-Butyl-8-methoxy-9-(tetrahydro-2H-pyran-3-ylmethyl)-9H-purine-2,6-diamine

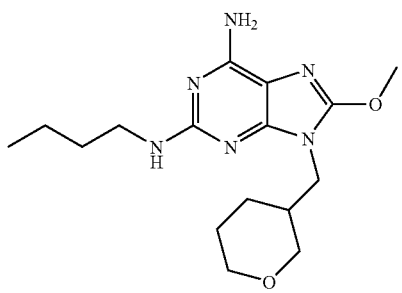

To a solution of N$^2$-butyl-8-methoxy-9H-purine-2,6-diamine trifluoroacetic acid salt (100 mg) in dry N,N-dimethylformamide (1 ml) at room temperature and under nitrogen was added potassium carbonate (158 mg) in one go. The reaction was stirred at 60° C. for 1.5 hours and then cooled to 50° C. A solution of 3-(bromomethyl)tetrahydro-2H-pyran (56 mg) in dry N,N-dimethylformamide (0.3 ml) was added in one go and the reaction heated at 50° C. for 16 hours. The reaction was diluted with ethyl acetate (15 ml) and washed with water (5 ml). The organic layer was separated, dried over magnesium sulphate, filtered, and concentrated in vacuo. The product was purified by C$_{18}$ reverse phase chromatography using water (containing 0.1% formic acid)-acetonitrile (containing 0.05% formic acid) as eluant (20-60%) to afford the title compound as a yellow oil (45 mg).

MS calcd for (C$_{16}$H$_{26}$N$_6$O$_2$)$^+$=334
MS found (electrospray): (M+H)$^+$=335.

Intermediate 15

3-(Bromomethyl)tetrahydrofuran

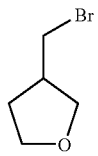

To tetrahydrofuran-3-ylmethanol (1 g) in dry dichloromethane (30 ml) at 0° C. and under nitrogen, was added triethylamine (2.7 ml) in one go, followed by methanesulphonyl chloride (1 ml) dropwise over 3 minutes. The reaction was stirred at 0° C. until the ice in the bath melted and then left at room temperature overnight. The reaction mixture was washed with saturated aqueous sodium bicarbonate (10 ml). The organic layer was passed through a hydrophobic frit to dry and concentrated in vacuo to yield a yellow oil (1.7 g). To this oil in dry acetone (50 ml) and at room temperature was added lithium bromide (3.3 g) in one go. The reaction was heated to reflux for 20 hours. The reaction was allowed to cool to room temperature and concentrated in vacuo. The residue was taken up in dichloromethane (50 ml) and washed with water (25 ml). The organic layer was passed through a hydrophobic frit to dry and concentrated in vacuo. The product was purified by silica chromatography (40 g) (ISCO) using a gradient elution of 0-50% cyclohexane:ethyl acetate to afford the title compound as a colourless oil (890 mg).

$^1$H NMR((CD$_3$)$_2$SO): δ 3.81-3.73 (2H, m), 3.66 (1H, m), 3.54 (2H, m), 3.42 (1H, m), 2.61 (1H, m), 2.02 (1H, m), 1.60 (1H, m).

Intermediate 16

2-Butoxy-8-methoxy-9-(tetrahydrofuran-3-ylmethyl)-9H-purin-6-amine

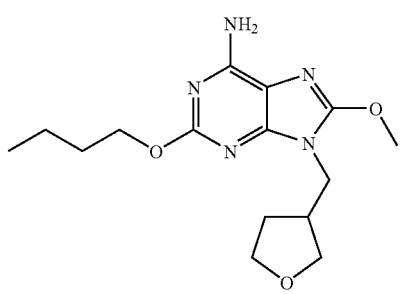

2-Butoxy-8-methoxy-9H-purin-6-amine trifluoroacetate salt (0.20 g) was dissolved in anhydrous N,N-dimethylformamide (5 mL) was treated with anhydrous potassium carbonate (0.315 g), heated to 60° C. for 1 hour and then cooled to room temperature. To the above was added 3-(bromomethyl)tetrahydrofuran (0.103 g) and the reaction mixture heated at 50° C., overnight. The reaction mixture was quenched with water (25 mL) and extracted into ethyl acetate (3 times, 100 mL combined total volume). The combined organic phase was separated and passed through a hydrophobic frit to dry. The organic phase was stripped to give a gum which was purified by $C_{18}$ reverse phase chromatography using water (containing 0.1% formic acid)-acetonitrile (containing 0.05% formic acid) as eluant (20-60%) to afford the title compound as a white solid (97 mg).

MS calcd for $(C_{15}H_{23}N_5O_3)^+=321$

MS found (electrospray): $(M+H)^+=322$

1H NMR (CDCl$_3$): 5.39 (2H, s), 4.24 (2H, t), 4.08 (3H, s), 3.96-3.85 (3H, overlapping m), 3.71 (2H, m), 3.60 (1H, m), 2.81 (1H, m), 1.93 (1H, m), 1.76-1.63 (3H, overlapping m), 1.46 (2H, m), 0.93 (3H, t).

Intermediate 16, Alternative Procedure 2-(Butyloxy)-8-(methyloxy)-9-(tetrahydro-3-furanylmethyl)-9H-purin-6-amine

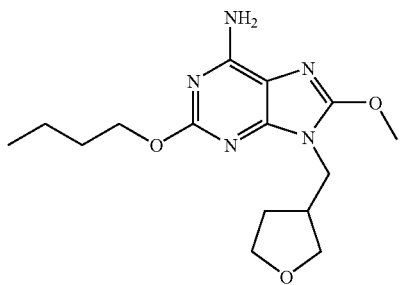

A solution of 2-butoxy-8-methoxy-9H-purin-6-amine trifluoroacetate salt (4.5 g), tetrahydro-3-furanylmethyl methanesulfonate (2.77 g) and potassium carbonate (5.31 g) in dimethyl sulfoxide (45 ml) was stirred and heated at 60° C. for 1.5 hours, followed by heating at 90° C. for 2.5 hours. The reaction was allowed to cool and the mixture diluted with water and brine, and shaken with ethyl acetate. The insoluble solid present was filtered (209 mg of product) and the organic layer separated. The aqueous layer was further extracted four times with ethyl acetate. The combined organic layers were washed with water and then brine. The organic layer was dried by passing through a hydrophobic frit and concentrated in vacuo to yield a light brown solid (4.18 g). This was recrystallised from acetonitrile (25 ml) to afford the product (2.28 g). This was further purified by dissolving in dichloromethane and washing with 1M hydrochloric acid, brine and saturated sodium hydrogencarbonate. The organic layer was dried through a hydrophobic frit and concentrated in vacuo to yield the product as a cream coloured solid (2.03 g).

MS calcd for $(C_{15}H_{23}N_5O_3)^+=321$

MS found (electrospray): $(M+H)^+=322$ $^1$H NMR (CDCl$_3$): δ 5.32 (2H, broad s), 4.27 (2H, t), 4.12 (3H, s), 4.00-3.88 (3H, m), 3.76 (2H, m), 3.63 (1H, m), 2.85 (1H, m), 1.97 (1H, m), 1.81-1.66 (3H, m), 1.49 (2H, m), 0.96 (3H, t).

Intermediate 17

2-Butoxy-8-methoxy-9-[2-(tetrahydro-2H-pyran-4-yl)ethyl]-9H-purin-6-amine

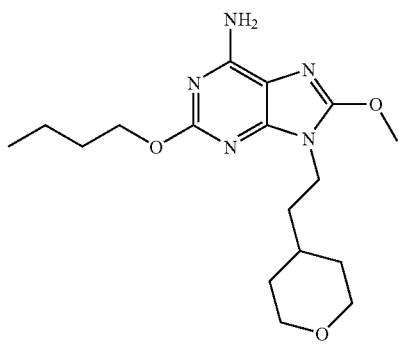

2-Butoxy-8-methoxy-9H-purin-6-amine trifluoroacetate salt (0.2 g) in anhydrous N,N-dimethylformamide (5 mL) was treated with anhydrous potassium carbonate (0.315 g) and then heated to 60° C. for 1 hour. On cooling to room temperature, to the above was added 4-(2-bromoethyl)tetrahydro-2H-pyran (0.110 g) and the reaction was warmed to 50° C., overnight. The reaction mixture was quenched with water (5 mL) and extracted into ethyl acetate (3 times, 100 mL combined total volume). The separated organic layers were combined and passed through a hydrophobic frit to dry. The organic phase was stripped to give a gum which was purified by $C_{18}$ reverse phase chromatography using water (containing 0.1% formic acid)-acetonitrile (containing 0.05% formic acid) as eluant (20-60%) to afford the title compound as a white solid (111 mg).

MS calcd for $(C_{17}H_{27}N_5O_3)^+=349$

MS found (electrospray): $(M+H)^+=350$

1H NMR (CDCl$_3$): 5.20 (2H, s), 4.24 (2H, t), 4.10 (3H, s), 3.94 (4H, overlapping m), 3.31 (2H, m), 1.78-1.65 (6H, overlapping m), 1.52-1.39 (3H, overlapping m), 1.30 (2H, m), 0.95 (3H, t).

Intermediate 18

2-Butoxy-8-methoxy-9-(tetrahydro-2H-pyran-3-ylmethyl)-9H-purin-6-amine

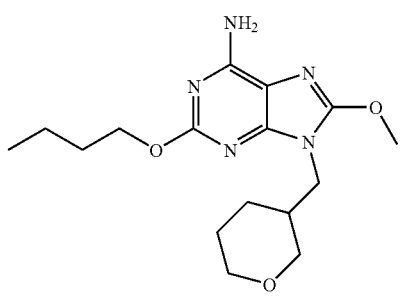

2-Butoxy-8-methoxy-9H-purin-6-amine trifluoroacetate salt (0.2 g) in dry N,N-dimethylformamide (5 mL) was heated at 60° C. with anhydrous potassium carbonate (0.315 g) for 1 hour and allowed to cool to room temperature before adding 3-(bromomethyl)tetrahydro-2H-pyran (0.112 g). The reaction mixture was heated at 50° C., overnight. The reaction mixture was quenched with water (20 mL) and extracted into ethyl acetate (3 times, 75 mL combined volume). The organic phase was separated, combined and passed through a hydrophobic frit to dry. The organic phase was evaporated under reduced pressure to give a yellow oil which was purified by $C_{18}$ reverse phase chromatography using water (containing 0.1% formic acid)-acetonitrile (containing 0.05% formic acid) as eluant (20-60%) to afford the title compound as a white solid (105.4 mg).

MS calcd for $(C_{16}H_{25}N_5O_3)^+$=335
MS found (electrospray): $(M+H)^+$=336
1H NMR (CDCl$_3$): 5.14 (2H, s), 4.26 (2H, t), 4.10 (3H, s), 3.88-3.72 (4H, overlapping m), 3.42 (1H, m), 3.27 (1H, dd), 2.18 (1H, m), 1.80-1.63 (4H, overlapping m), 1.61-1.42 (3H, overlapping m), 1.33-1.18 (1H, m), 0.95 (3H, t).

Intermediate 19

2-(Tetrahydrofuran-2-yl)ethanol

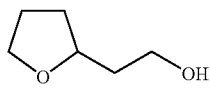

A stirring solution of ethyl tetrahydrofuran-2-ylacetate (2.5 g) in dry THF (25 ml) was cooled (ice bath) and 1M lithium aluminium hydride in tetrahydrofuran added dropwise under nitrogen below 15° C. The reaction was allowed to warm to ambient temperature and after 3 h re-cooled (ice bath) and 5N sodium hydroxide (5.5 ml) carefully added below 10° C. Diethyl ether (50 ml) was then added and after 10 min the resulting solid filtered and washed well with ether. The combined filtrate was evaporated to give the title compound as a clear oil, yield 1.9 g.

$^1$H NMR (CDCl$_3$): δ 4.03 (1H, m), 3.91 (1H, m), 3.79 (2H, m), 3.74 (1H, m), 2.82 (1H, s), 2.03 (1H, m), 1.98-1.84 (2H, m), 1.84-1.70 (2H, m), 1.63-1.50 (1H, m).

Intermediate 20

2-(Tetrahydrofuran-2-yl)ethyl methanesulfonate

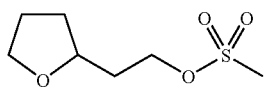

To an ice cooled stirring solution of 2-(tetrahydrofuran-2-yl)ethanol (1.9 g) and triethylamine (4.4 ml) in dry dichloromethane (30 ml) was added dropwise over 5 min methanesulphonyl chloride (1.59 ml). The mixture was allowed to warm slowly to ambient temperature over 16 h then washed with saturated sodium hydrogen carbonate. The aqueous layer was further extracted with dichloromethane and the combined extracts washed with brine, dried by passing through a phase separation cartridge and stripped to give the title compound as a light brown oil, yield 3.1 g.

$^1$H NMR (CDCl$_3$): δ 4.36 (2H, t), 3.96 (1H, m), 3.86 (1H, m), 3.74 (1H, m), 3.02 (3H, s), 2.01-1.84 (4H, m), 1.58-1.40 (2H, m).

Intermediate 21

2-(2-Bromoethyl)tetrahydrofuran

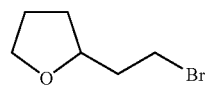

2-(Tetrahydrofuran-2-yl)ethyl methanesulfonate (3.1 g) and anhydrous lithium bromide (6.57 g) in acetone (50 ml) were refluxed with stirring for 3 h. After allowing to cool the solvent was stripped and the residue treated with water and extracted three times with dichloromethane. The combined extracts were washed with saturated sodium hydrogen carbonate, dried by passing through a phase separation cartridge and stripped to give the title compound as an orange oil, yield 1.99 g.

$^1$H NMR (CDCl$_3$): δ 3.98 (1H, m), 3.85 (1H, m), 3.74 (1H, m), 3.50 (2H, m), 2.12-1.96 (3H, m), 1.96-1.85 (2H, m), 1.54-1.43 (1H, m).

Intermediate 22

2-Butoxy-8-methoxy-9-[2-(tetrahydrofuran-2-yl)ethyl]-9H-Purin-6-amine

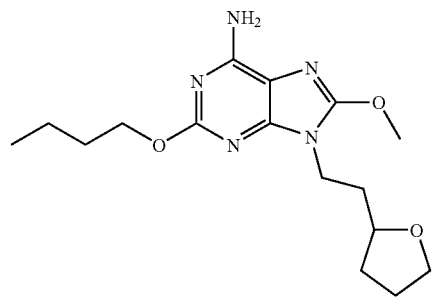

A stirring mixture of 2-butoxy-8-methoxy-1H-purin-6-amine trifluoroacetate salt (200 mg) and potassium carbonate (236 mg) in dry N,N-dimethylformamide (2 ml) was heated with stirring at 60° C. for 1 h. 2-(2-Bromoethyl)tetrahydrofuran (122 mg) was added and the stirring mixture heated at 50° C. for 4 h. After allowing to cool, water was added and the mixture extracted three times with ethyl acetate. The combined extracts were washed with water then brine, dried by passing through a phase separation cartridge and stripped to give a brown oil. This was purified by $C_{18}$ reverse phase chromatography using water (containing 0.1% formic acid)-acetonitrile (containing 0.05% formic acid) as eluent (20-60%) and the appropriate fractions combined and evaporated to remove acetonitrile. The remaining aqueous mixture was made basic with saturated sodium hydrogen carbonate, extracted three times with dichloromethane and the combined extracts dried by passing through a phase separation cartridge then evaporated to afford the title compound as a clear oil, yield 122 mg).

MS calcd for $(C_{16}H_{25}N_5O_3)^+$=335
MS found (electrospray): $(M+H)^+$=336
$^1$H NMR (CDCl$_3$): δ 5.10 (2H, s), 4.28 (2H, m), 4.12 (3H, s), 4.04 (2H, m), 3.85 (2H, m), 3.71 (1H, m), 1.98 (3H, m), 1.88 (2H, m), 1.77 (2H, m), 1.51 (3H, m), 0.97 (3H, t).

Intermediate 23

N$^2$-Butyl-8-methoxy-9-[2-(tetrahydrofuran-2-yl)ethyl]-9H-Purine-2,6-diamine

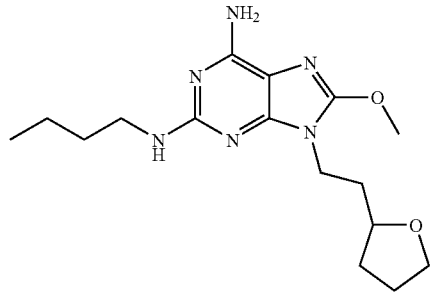

A stirring mixture of N$^2$-butyl-8-methoxy-9H-purine-2,6-diamine trifluoroacetic acid salt (200 mg) and potassium carbonate (236 mg) in dry N,N-dimethylformamide (2 ml) was heated with stirring at 60° C. for 1 h. 2-(2-Bromoethyl)tetrahydrofuran (122 mg) was added and the stirring mixture heated at 50° C. for 4 h. After allowing to cool, water was added and the mixture extracted three times with ethyl acetate. The combined extracts were washed with water then brine, dried by passing through a phase separation cartridge and stripped to give a brown oil. This was purified by C$_{18}$ reverse phase chromatography using water (containing 0.1% formic acid)-acetonitrile (containing 0.05% formic acid) as eluent (20-60%) and the appropriate fractions combined and evaporated to remove acetonitrile. The remaining aqueous mixture was made basic with saturated sodium hydrogen carbonate, extracted three times with dichloromethane and the combined extracts dried by passing through a phase separation cartridge then evaporated to afford the title compound, yield 107 mg.

MS calcd for $(C_{16}H_{26}N_6O_2)^+$=334
MS found (electrospray): $(M+H)^+$=335
$^1$H NMR (CDCl$_3$): δ 4.90 (2H, s), 4.58 (1H, br. t), 4.09 (3H, s), 3.98 (2H, m), 3.86 (2H, m), 3.72 (1H, m), 3.38 (2H, m), 1.99 (3H, m), 1.88 (2H, m), 1.57 (2H, m), 1.52-1.36 (3H, m), 0.95 (3H, t).

Intermediate 24

5,6-Dihydro-2H-Pyran-3-carbaldehyde

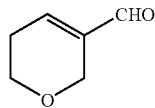

Conc. hydrochloric acid (5.5 ml) was added to water (28 ml) followed by acrolein (33.8 ml) and toluene (15 ml). The stirred mixture was heated under reflux at 75° C. for 1 h when reflux gradually abated. After allowing to cool, potassium carbonate was added until basic and the mixture extracted twice with ether. The combined extracts were washed with brine, dried (Na$_2$SO$_4$) and evaporated to a brown oil. Distillation at 6 mbar pressure gave the product as a pale yellow mobile liquid, bp 76-9° C., yield 4 g (14%).

$^1$H NMR (CDCl$_3$): δ 9.42 (1H, s), 6.94 (1H, m), 4.35 (2H, m), 3.82 (2H, m), 2.46 (2H, m).

Intermediate 25

Tetrahydro-2H-pyran-3-carbaldehyde

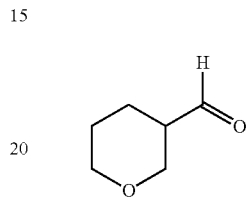

5,6-Dihydro-2H-pyran-3-carbaldehyde (2.98 gm) in ethanol (70 ml) was treated with 10% wetted palladium on carbon catalyst under nitrogen, then hydrogenated at ambient temperature and pressure for 30 min. The catalyst was filtered off through Celite and the filtrate evaporated, then re-evaporated from toluene to give the product as an oil, yield 2.58 g.

$^1$H NMR (CDCl$_3$): δ 9.72 (1H, s), 3.98 (1H, m), 3.82 (1H, m), 3.73 (1H, m), 3.58 (1H, m), 2.49 (1H, m), 1.95 (1H, m), 1.87 (1H, m), 1.70 (1H, m), 1.61 (1H, m).

Intermediate 26

3-[(E,Z)-2-(Methoxy)ethenyl]tetrahydro-2H-pyran

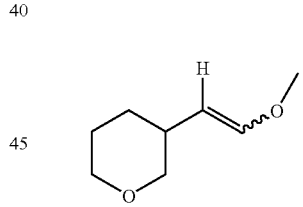

A suspension of methoxymethyltriphenylphosphonium chloride (15.5 gm) in dry THF (40 ml) was cooled to −40° C. and a solution of potassium tert-butoxide (5.08 gm) in dry THF (40 ml) added dropwise with stirring under nitrogen. After 45 min the mixture was further cooled to −65° C. and a solution of tetrahydro-2H-pyran-3-carbaldehyde (2.58 gm) in dry THF (15 ml) added dropwise. The cooling bath was removed and after allowing to warm to ambient temperature the reaction was stirred for a further 30 min. The mixture was then quenched onto ice, extracted three times with ether and the combined extracts washed with brine, dried (Na$_2$SO$_4$) and evaporated then re-evaporated with toluene. The crude product was purified by flash chromatography (silica, 0-20% ethyl acetate-cyclohexane) to give the title compound as a colourless oil, yield 2.22 g (69%).

$^1$H NMR (CDCl$_3$): δ 6.36+5.89 (1H, m), 4.53+4.12 (1H, m), 3.88 (1H, m), 3.78 (1H, m), 3.58+3.51 (3H, s), 3.34 (1H, m), 3.10 (1H, m), 2.73+2.20 (1H, m), 1.84 (1H, m), 1.63 (2H, m), 1.30 (1H, m).

Intermediate 27

Tetrahydro-2H-pyran-3-ylacetaldehyde

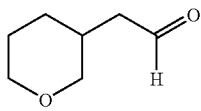

To a stirring solution of 3-[2-(methoxy)ethenyl]tetrahydro-2H-pyran (2.22 gm) in THF (15 ml) was added 2N hydrochloric acid (15 ml). After 1 h the mixture was diluted with water and extracted three times with ether. The combined extracts were washed with brine, dried (Na$_2$SO$_4$) and evaporated to give the title product as a pale yellow oil, yield 1.79 g.

$^1$H NMR (CDCl$_3$): δ 9.77 (1H, s), 3.85 (2H, m), 3.43 (1H, m), 3.17 (1H, m), 2.34 (2H, m), 2.23 (1H, m), 1.90 (1H, m), 1.64 (2H, m), 1.27 (1H, m).

Intermediate 28

2-(Tetrahydro-2H-pyran-3-yl)ethanol

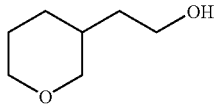

A suspension of sodium borohydride (554 mg) in ethanol (20 ml) was cooled (ice bath) and a solution of tetrahydro-2H-pyran-3-ylacetaldehyde (1.88 gm) in ethanol (8 ml) added dropwise with stirring over 10 min. After 15 min the ice bath was removed and after a further 3 h the mixture was heated at 50° C. for 1 h. After cooling the solvent was evaporated and the residue treated with water and extracted three times with dichloromethane. The combined extracts were washed with dilute brine, dried by passing through a hydrophobic frit and evaporated to give the title product as an oil. A further batch of product was obtained by acidifying the aqueous solution with 2N hydrochloric acid, saturating with sodium chloride and extracting three times with dichloromethane. These extracts were treated as above and the batches combined to give a total yield of 1.54 g (81%).

$^1$H NMR (CDCl$_3$): δ 3.88 (2H, m), 3.70 (2H, m), 3.38 (1H, m), 3.11 (1H, t), 1.89 (1H, m), 1.76 (1H, m), 1.61 (1H, m), 1.45 (2H, m), 1.22 (2H, m). OH not visible.

Intermediate 29

2-(Tetrahydro-2H-pyran-3-yl)ethyl methanesulfonate

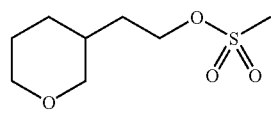

A solution of 2-(tetrahydro-2H-pyran-3-yl)ethanol (1.54 gm) and triethylamine (3.3 ml) in dichloromethane (25 ml) was cooled (ice bath) and methanesulphonyl chloride (1.19 ml) added dropwise with stirring over 5 min. The reaction slowly warmed to ambient temperature as the ice bath melted. After 16 h the mixture was washed with saturated aq. sodium hydrogen carbonate, the aqueous layer extracted twice with dichloromethane and the combined extracts washed with dilute brine, dried by passing through a hydrophobic frit and evaporated to give the title compound as a brown oil, yield 2.38 g.

$^1$H NMR (CDCl$_3$): δ 4.27 (2H, t), 3.86 (2H, m), 3.41 (1H, m), 3.14 (1H, m), 3.02 (3H, s), 1.91 (1H, m), 1.8 (1H, m), 1.71 (1H, m), 1.63 (3H, m), 1.23 (1H, m).

Intermediate 30

2-Butoxy-8-methoxy-9-[2-(tetrahydro-2H-pyran-3-yl)ethyl]-9H-purin-6-amine

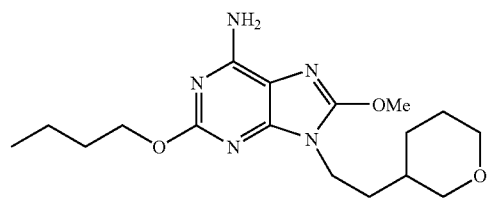

A stirring mixture of 2-butoxy-8-methoxy-9H-purin-6-amine trifluoroacetate salt (200 mg) and potassium carbonate (236 mg) in dry N,N-dimethylformamide (2 ml) was heated with stirring at 60° C. for 1 h. 2-(Tetrahydro-2H-pyran-3-yl)ethyl methanesulfonate (142 mg) was added and the stirring mixture heated at 60° C. for 3 h. Water was added and the mixture extracted three times with ethyl acetate. The combined extracts were washed with water then brine, dried by passing through a phase separation cartridge and stripped to give a brown oil. This was purified by C$_{18}$ reverse phase chromatography using water (0.1% formic acid)-acetonitrile (0.05% formic acid) as eluent (20-70%) and the appropriate fractions combined and evaporated to remove acetonitrile. The remaining aqueous mixture was made basic with saturated sodium hydrogen carbonate, extracted three times with dichloromethane and the combined extracts dried by passing through a phase separation cartridge then evaporated to afford the title compound as a brown oil, yield 108 mg.

MS calcd for (C$_{17}$H$_{27}$N$_5$O$_3$)$^+$=349

MS found (electrospray): (M+H)$^+$=350

$^1$H NMR (CDCl$_3$): δ 5.10 (2H, s), 4.28 (2H, t), 4.12 (3H, s), 3.96 (2H, t), 3.87 (2H, m), 3.38 (1H, m), 3.12 (1H, m), 1.96 (1H, m), 1.77 (2H, m), 1.71-1.44 (6H, m), 1.21 (2H, m), 0.97 (3H, t).

Intermediate 31

N$^2$-Butyl-8-methoxy-9-[2-(tetrahydro-2H-pyran-3-yl)ethyl]-9H-purine-2,6-diamine

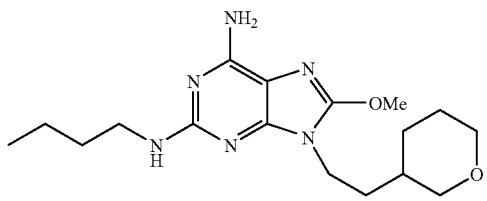

A stirring mixture of N$^2$-butyl-8-methoxy-9H-purine-2,6-diamine trifluoroacetic acid salt (200 mg) and potassium carbonate (236 mg) in dry N,N-dimethylformamide (2 ml) was heated with stirring at 60° C. for 1 h. 2-(Tetrahydro-2H-pyran-3-yl)ethyl methanesulfonate (142 mg) was added and the stirring mixture heated at 60° C. for 3 h. Water was added and the mixture extracted three times with ethyl acetate. The combined extracts were washed with water then brine, dried by passing through a phase separation cartridge and stripped to give a brown oil. This was purified by C$_{18}$ reverse phase chromatography using water (0.1% formic acid)-acetonitrile (0.05% formic acid) as eluent (20-60%) and the appropriate fractions combined and evaporated to remove acetonitrile. The remaining aqueous mixture was made basic with saturated sodium hydrogen carbonate, extracted three times with dichloromethane and the combined extracts dried by passing through a phase separation cartridge then evaporated to afford the title compound as a brown solid, yield 138 mg.

MS calcd for (C$_{17}$H$_{28}$N$_6$O$_2$)$^+$=348
MS found (electrospray): (M+H)$^+$=349
$^1$H NMR (CDCl$_3$): δ 4.89 (2H, br. s), 4.57 (1H, br. t), 4.08 (3H, s), 3.88 (4H, m), 3.36 (3H, m), 3.12 (1H, m), 1.97 (1H, m), 1.68-1.52 (7H, m), 1.40 (2H, m), 1.20 (1H, m), 0.94 (3H, t).

Intermediate 32

2-(Tetrahydro-2H-pyran-4-yl)ethanol

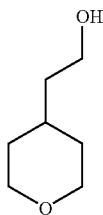

To an ice-cold solution of lithium aluminium hydride (12.6 ml, 2.3M solution in tetrahydrofuran) in dry tetrahydrofuran (20 ml) and under nitrogen, was added a solution of ethyl tetrahydro-2H-pyran-4-yl acetate (5 g) in dry tetrahydrofuran dropwise over 10 minutes. Following the addition the reaction was heated to reflux, overnight. The reaction was cooled and diluted with diethyl ether (100 ml). A 5M aqueous solution of sodium hydroxide (~10 ml) was added cautiously to the reaction mixture until the effervescence ceased. The formed white precipitate was filtered off. The resulting filtrate was dried over potassium carbonate, filtered and concentrated in vacuo. This yielded the title compound as a colourless oil (3.3 g).

MS calcd for (C$_7$H$_{14}$O$_2$)$^+$=130
MS found (electrospray): (M+H)$^+$=131
1H NMR (DMSO): 4.35 (1H, t), 3.80 (2H, m), 3.43 (2H, m), 3.25 (2H, m), 1.60 (1H, m), 1.54 (2H, m), 1.35 (2H, m), 1.13 (2H, m).

Intermediate 33

2-(Tetrahydro-2H-pyran-4-yl)ethyl methanesulfonate

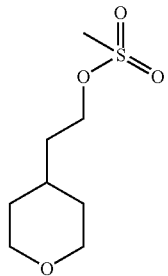

To 2-(tetrahydro-2H-pyran-4-yl)ethanol (3,3 g) in dry dichloromethane (100 ml) at 0° C. and under nitrogen was added triethylamine (4.6 ml), followed by methanesulphonyl chloride (2.6 ml) dropwise over 5 minutes. The reaction was stirred until the ice in the bath melted and left overnight at room temperature. The reaction was washed with saturated aqueous sodium bicarbonate (40 ml). The organic layer was dried by passing through a hydrophobic frit and concentrated in vacuo to yield the title compound as a yellow oil (5.4 g).

$^1$H NMR (DMSO): 4.24 (2H, t), 3.82 (2H, m), 3.80 (3H, s), 3.27 (2H, m), 2.50 (5H, m), 1.60 (2H, m).

Intermediate 34

4-(2-Bromoethyl)tetrahydro-2H-pyran

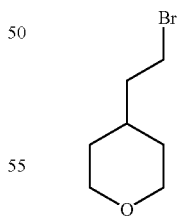

To 2-(tetrahydro-2H-pyran-4-yl)ethyl methanesulfonate (5.4 g) in dry acetone at room temperature was added lithium bromide (9 g) in one go. The reaction was heated to reflux for 4 hours, under nitrogen. The reaction was cooled to room temperature and concentrated in vacuo. The residue was taken up in dichloromethane (100 ml) and washed with water (50 ml). The organic layer was dried by passing through a hydrophobic frit, and concentrated in vacuo. The product was purified by silica chromatography (40 g) (ISCO) using a gradient elution of 0-50% cyclohexane:ethyl acetate to afford the title compound as a colourless oil (3.5 g).

¹H NMR (DMSO): 3.82 (2H, m), 3.56 (2H, t), 3.26 (2H, m), 1.75 (2H, m), 1.65 (1H, m), 1.57 (2H, m), 1.16 (2H, m).

Intermediate 35

2-[(2,2-Dimethylpentyl)oxy]-9-(tetrahydro-2H-pyran-2-yl)-9H-purin-6-amine

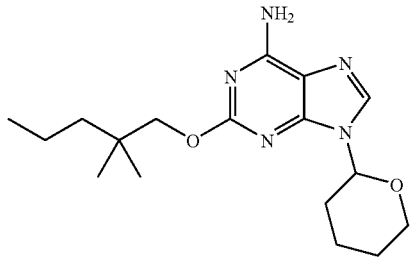

To a suspension of 2-chloro-9-(tetrahydro-2H-pyran-2-yl)-9H-purin-6-amine (500 mg) and 2,2-dimethylpentanol (3.8 mL) at 50° C. was added sodium hydride (396 mg, 60% dispersion) in portions. To the resultant viscous foam was added a further portion of 2,2-dimethylpentanol (1.5 mL). The reaction was stirred at 50° C. for 72 h. The reaction mixture was cooled then carefully quenched with water (10 mL) and extracted with EtOAc (3×25 mL). The organics were combined, washed with brine (30 mL), dried over MgSO₄, filtered and concentrated in vacuo to give a yellow oil. This was azeotroped with toluene (×3) and the resulting viscous yellow oil was purified by C₁₈ reverse phase chromatography (ISCO) using water (0.1% formic acid)-acetonitrile (0.05% formic acid) as eluent (30-80%) to afford the title compound as a brown solid (372 mg).

MS calcd for $(C_{17}H_{27}N_5O_2)^+$=333
MS found (electrospray): $(M+H)^+$=334

Intermediate 36

8-Bromo-2-[(2,2-dimethylpentyl)oxy]-9-(tetrahydro-2H-pyran-2-yl)-9H-purin-6-amine

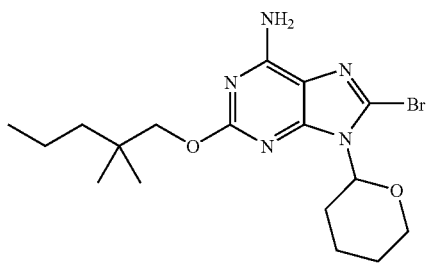

To 2-[(2,2-dimethylpentyl)oxy]-9-(tetrahydro-2H-pyran-2-yl)-9H-purin-6-amine (372 mg) in dry chloroform (4.05 mL) at 0° C. was added NBS (209 mg) in a single portion. The reaction was warmed to room temperature and was stirred for 5 h. The mixture was taken up into DCM (20 mL) and washed with water (30 mL). The organics were separated and dried using a hydrophobic frit then concentrated in vacuo to afford the title compound as a green/brown viscous foam (475 mg).

MS calcd for $(C_{17}H_{26}BrN_5O_2)^+$=411/413
MS found (electrospray): $(M+H)^+$=412/414

¹H NMR((CD₃)₂SO): δ 7.48 (2H, br, s), 5.52 (1H, dd), 4.08-3.89 (3H, m), 3.70 (1H, m), 2.97-2.83 (1H, m), 2.04-1.94 (1H, m), 1.89-1.51 (4H, m), 1.35-1.21 (4H, m), 0.99-0.91 (6H, s), 0.90-0.84 (3H, m).

Intermediate 37

2-[(2,2-Dimethylpentyl)oxy]-8-methoxy-9-(tetrahydro-2H-pyran-2-yl)-9H-Purin-6-amine

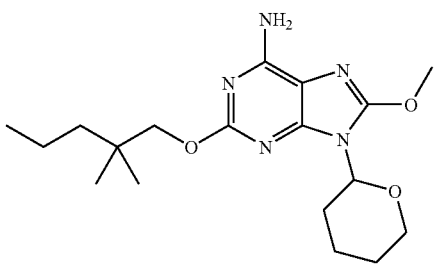

To a solution of 8-bromo-2-[(2,2-dimethylpentyl)oxy]-9-(tetrahydro-2H-pyran-2-yl)-9H-purin-6-amine (475 mg) in dry MeOH (3.92 mL) was added sodium methoxide solution (0.649 mL, 30% wt. in MeOH). The reaction mixture was stirred at reflux for 5 h. The reaction was cooled and concentrated in vacuo to give an orange residue. The residue was taken up in saturated ammonium chloride solution (25 mL) and was extracted with EtOAc (25 mL). The organic layer was separated and washed with water (15 mL). The organics were separated, dried over MgSO₄, filtered and concentrated in vacuo to give the title compound as an orange solid (323 mg).

MS calcd for $(C_{18}H_{29}N_5O_3)^+$=363
MS found (electrospray): $(M+H)^+$=364

¹H NMR((CD₃)₂SO): δ 6.85 (2H, s), 5.37 (1H, dd), 4.05 (3H, s), 4.02-3.83 (3H, m), 3.63-3.54 (1H, m), 2.72-2.58 (1H, m), 1.97-1.91 (1H, m), 1.77-1.46 (4H, m), 1.31-1.23 (4H, m), 0.93 (6H, s), 0.89-0.83 (3H, m).

Intermediate 38

2-[(2,2-Dimethylpentyl)oxy]-8-methoxy-9H-purin-6-amine trifluoroacetic acid salt

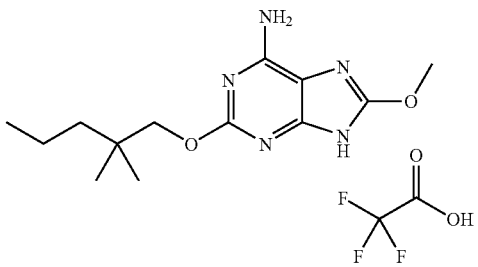

To a solution of 2-[(2,2-dimethylpentyl)oxy]-8-methoxy-9-(tetrahydro-2H-pyran-2-yl)-9H-purin-6-amine (323 mg) in dry MeOH (3.23 mL) was added TFA (0.323 mL) and the reaction was stirred at room temperature for 48 h. The reaction was concentrated in vacuo to give a yellow residue. The residue was triturated with Et$_2$O and was filtered to give the title compound as an off-white solid (252 mg).

MS calcd for $(C_{13}H_{21}N_5O_2)^+$=279
MS found (electrospray): (M+H)$^+$=280

Intermediate 39

2-[(2,2-Dimethylpentyl)oxy]-8-methoxy-9-(tetrahydro-2H-pyran-4-ylmethyl)-9H-Purin-6-amine

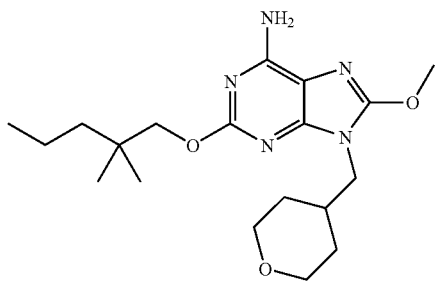

To a solution of 2-[(2,2-dimethylpentyl)oxy]-8-methoxy-9H-purin-6-amine trifluoroacetic acid salt (252 mg) in dry DMF (3.97 mL) was added potassium carbonate (356 mg). The mixture was stirred at 60° C. for 90 mins. The reaction was cooled and 4-(bromomethyl)tetrahydro-2H-pyran (127 mg) was added. The mixture was stirred at 50° C. for 6 h. The reaction was cooled and taken up in EtOAc (40 mL). The mixture was washed with water (2×20 mL) and the organics were separated, dried over MgSO$_4$ and concentrated in vacuo to give a viscous oil. The crude material was purified by C$_{18}$ reverse phase chromatography (ISCO) using water (0.1% formic acid)-acetonitrile (0.05% formic acid) as eluent (30-80%) to afford the title compound as an off-white solid (116 mg).

MS calcd for $(C_{19}H_{31}N_5O_3)^+$=377
MS found (electrospray): (M+H)$^+$=378

Intermediate 40

N$^2$-Pentyl-9-(tetrahydro-2H-pyran-2-yl)-9H-purine-2,6-diamine

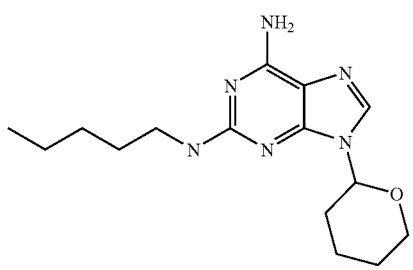

To a solution of 2-chloro-9-(tetrahydro-2H-pyran-2-yl)-9H-purin-6-amine (500 mg) in dry ethylene glycol (2.3 mL) was added 1-pentylamine (689 mg). The solution was stirred at reflux (120° C.) overnight. The reaction was cooled, taken up in EtOAc (30 mL) and washed with water (2×20 mL). The organics were separated, dried over MgSO$_4$, filtered and concentrated in vacuo to give the title compound as a viscous brown oil (561 mg).

MS calcd for $(C_{15}H_{24}N_6O)^+$=304
MS found (electrospray): (M+H)$^+$=305
$^1$H NMR((CD$_3$)$_2$SO): δ 7.85 (1H, s), 6.62 (2H, s), 6.22 (1H, t), 5.40 (1H, dd), 4.01-3.95 (1H, m), 3.63-3.55 (1H, m), 3.26-3.19 (2H, m), 2.25-2.13 (1H, m), 1.95 (1H, m), 1.85 (1H, m), 1.66 (1H, m), 1.60-1.15 (8H, m), 0.87 (3H, m). Evidence of additional protons between 0.8-1,6-grease or hydrocarbon fragments.

Intermediate 41

8-Bromo-N$^2$-pentyl-9-(tetrahydro-2H-pyran-2-yl)-9H-purine-2,6-diamine

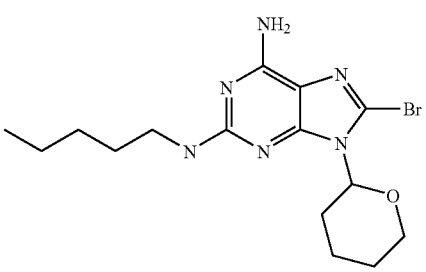

A solution of N$^2$-pentyl-9-(tetrahydro-2H-pyran-2-yl)-9H-purine-2,6-diamine (543 mg) in dry chloroform (4.6 mL) was cooled to 0° C. and NBS (334 mg) was added. The mixture was stirred at room temperature for 10 mins. The reaction was taken up in DCM (30 mL) and was washed with water (30 mL). The organics were separated, dried using a hydrophobic frit and concentrated in vacuo to give the title compound as a viscous brown residue (627 mg) which was used crude in the next step.

MS calcd for $(C_{15}H_{23}BrN_6O)^+$=382/384
MS found (electrospray): (M+H)$^+$=383/385

Intermediate 42

8-Methoxy-N$^2$-Pentyl-9-(tetrahydro-2H-pyran-2-yl)-9H-purine-2,6-diamine

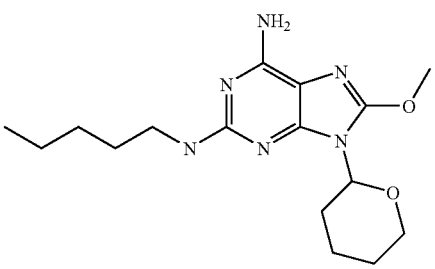

To a solution of 8-bromo-N$^2$-pentyl-9-(tetrahydro-2H-pyran-2-yl)-9H-purine-2,6-diamine (607 mg) in dry MeOH (4.75 mL) was added sodium methoxide solution (0.906 mL, 30% wt. MeOH) and the mixture was stirred at 60° C. for 48 h. The reaction was concentrated in vacuo. The residue was taken up in EtOAc (25 mL) and washed with saturated ammonium chloride (25 mL). The organics were separated, dried over MgSO$_4$, filtered and concentrated in vacuo to give the title compound as a red/brown viscous oil (520 mg) which was used crude in the next step.

MS calcd for $(C_{16}H_{26}N_6O_2)^+$=334
MS found (electrospray): (M+H)$^+$=335

Intermediate 43

8-Methoxy-N$^2$-Pentyl-9H-purine-2,6-diamine trifluoroacetic acid salt

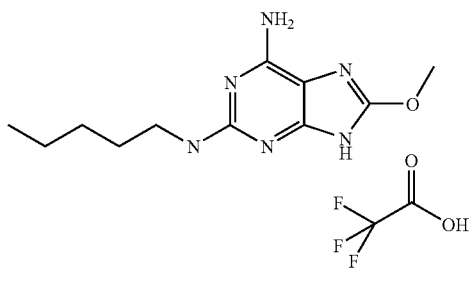

To a solution of 8-methoxy-N$^2$-pentyl-9-(tetrahydro-2H-pyran-2-yl)-9H-purine-2,6-diamine (520 mg) in dry MeOH (5.2 mL) was added TFA (0.52 mL) and the mixture was stirred at room temperature for 48 h. The reaction was concentrated in vacuo to give an orange residue which was triturated with Et$_2$O and filtered to give the title compound as an off-white solid (223 mg).

MS calcd for $(C_{11}H_{18}N_6O)^+$=250
MS found (electrospray): (M+H)$^+$=251
$^1$H NMR((CD$_3$)$_2$SO): δ 13.02-12.15 (1H, br.d), 8.33-7.18 (2H, br.m), 4.04 (3H, s), 3.32-3.17 (2H, m), 1.59-1.47 (2H, m), 1.38-1.20 (4H, m), 0.88 (3H, t), one exchangeable proton not seen.

Intermediate 44

8-Methoxy-N$^2$-Pentyl-9-(tetrahydro-2H-pyran-4-ylmethyl)-9H-purine-2,6-diamine

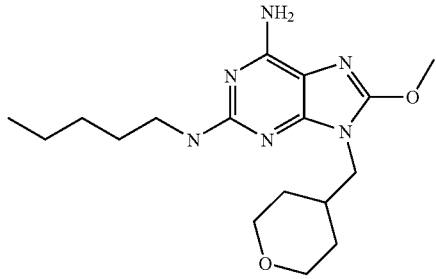

To a solution of 8-methoxy-N$^2$-pentyl-9H-purine-2,6-diamine trifluoroacetic acid salt (223 mg) in dry DMF (3.85 mL) was added potassium carbonate (339 mg) at 60° C. and the mixture was stirred for 90 mins. The mixture was cooled to room temperature and 4-(bromomethyl)tetrahydro-2H-pyran (121 mg) was added in one portion. The reaction was stirred at 50° C. overnight and was then cooled and taken up in EtOAc (20 mL). The organics were washed with water (2×10 mL), separated, dried over MgSO$_4$, filtered and concentrated in vacuo to give an off-white solid. The crude material was purified by C$_{18}$ reverse phase chromatography (ISCO) using water (0.1% formic acid)-acetonitrile (0.05% formic acid) as eluent (20-60%) to afford the title compound as an off-white solid (140 mg).

MS calcd for $(C_{17}H_{28}N_6O_2)^+$=348
MS found (electrospray): (M+H)$^+$=349

Intermediate 45

2-[(3-Methylbutyl)oxy]-9-(tetrahydro-2H-pyran-2-yl)-9H-Purin-6-amine

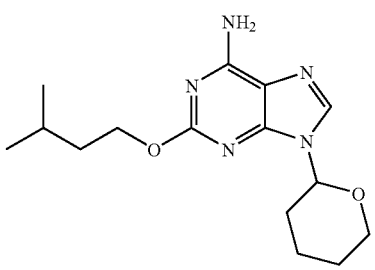

To 3-methyl-1-butanol (1.03 mL) in DME (5 mL) was added sodium tert-butoxide (912 mg) in portions over 5 mins with stirring. The mixture was stirred at room temperature until homogeneous. 2-Chloro-9-(tetrahydro-2H-pyran-2-yl)-9H-purin-6-amine (600 mg) was added followed by DME (4.6 mL). The reaction was heated at 110° C. overnight. The reaction was allowed to cool, was taken up in water (20 mL) and washed with EtOAc (2×20 mL). The organics were extracted with brine, separated, dried over MgSO$_4$, filtered and concentrated in vacuo to give a viscous yellow oil. The crude material was purified by C$_{18}$ reverse phase chromatography (ISCO) using water (0.1% formic acid)-acetonitrile (0.05% formic acid) as eluent (30-80%) to afford the title compound as a yellow residue (266 mg).

MS calcd for $(C_{15}H_{23}N_5O_2)^+$=305
MS found (electrospray): (M+H)$^+$=306

Intermediate 46

8-Bromo-2-[(3-methylbutyl)oxy]-9-(tetrahydro-2H-Pyran-2-yl)-9H-Purin-6-amine

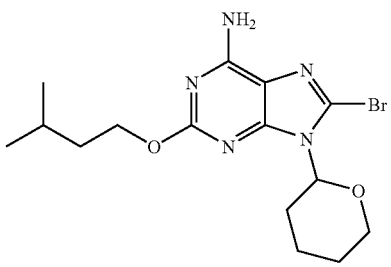

To a solution of 2-[(3-methylbutyl)oxy]-9-(tetrahydro-2H-pyran-2-yl)-9H-purin-6-amine (266 mg) in dry chloroform (3.15 mL) at 0° C. was added NBS (163 mg). The reaction was warmed to room temperature and was stirred for 5 h. The reaction was taken up into DCM (20 mL) and extracted with water (20 mL). The organics were separated, dried using a hydrophobic frit and concentrated in vacuo to give the title compound as a green/brown solid (314 mg).

MS calcd for $(C_{15}H_{22}BrN_5O_2)^+$=383/385
MS found (electrospray): $(M+H)^+$=384/386
$^1H$ NMR$((CD_3)_2SO)$: δ 7.38 (2H, br.s), 5.49 (1H, dd), 4.24 (2H, t), 4.03 (1H, d), 3.68-3.57 (1H, m), 3.03-2.90 (1H, m), 2.03-1.50 (8H, m), 0.92 (6H, d).

Intermediate 47

2-[(3-Methyl butyl)oxy]-8-methoxy-9-(tetrahydro-2H-pyran-2-yl)-9H-Purin-6-amine

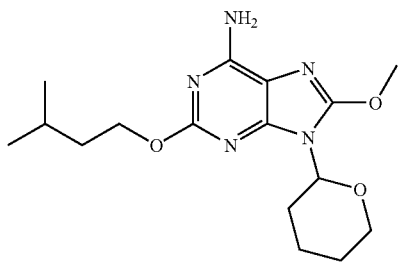

To a solution of 8-bromo-2-[(3-methylbutyl)oxy]-9-(tetrahydro-2H-pyran-2-yl)-9H-purin-6-amine (314 mg) was added sodium methoxide solution (0.460 mL, 30% wt. MeOH) and the mixture was stirred at reflux for 4 h. The reaction was allowed to cool and was concentrated in vacuo to give an orange residue. The residue was taken up in EtOAc (20 mL) and was extracted with saturated ammonium chloride solution (20 mL), followed by water (20 mL). The organics were separated, dried over MgSO$_4$, filtered and concentrated in vacuo to give the title compound as a light orange solid (210 mg).

MS calcd for $(C_{16}H_{25}N_5O_3)^+$=335
MS found (electrospray): $(M+H)^+$=336
$^1H$ NMR$((CD_3)_2SO)$: δ 6.81 (2H, br.s), 5.34 (1H, dd), 4.26-4.15 (2H, m), 4.05 (3H, s), 3.96 (1H, d), 3.61-3.52 (1H, m), 2.77-2.66 (1H, m), 1.98-1.90 (1H, m), 1.79-1.46 (7H, m), 0.92 (6H, d).

Intermediate 48

2-[(3-Methylbutyl)oxy]-8-methoxy-9H-purin-6-amine trifluoroacetic acid salt

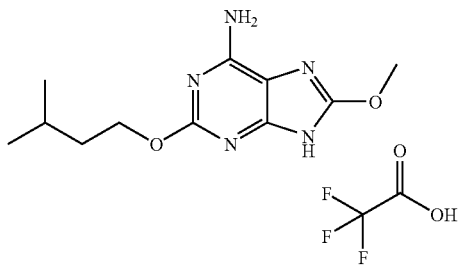

To a solution of 2-[(3-methylbutyl)oxy]-8-methoxy-9-(tetrahydro-2H-pyran-2-yl)-9H-purin-6-amine (210 mg) in dry MeOH (2.1 mL) was added TFA (0.21 ml) and the mixture was stirred at room temperature for 24 h. The reaction was concentrated in vacuo to give a yellow residue which was triturated with Et$_2$O (15 mL) and filtered under reduced pressure to give the title compound as an off-white solid (143 mg).

MS calcd for $(C_{11}H_{17}N_5O_2)^+$=251
MS found (electrospray): $(M+H)^+$=252
$^1H$ NMR$((CD_3)_2SO)$: δ 7.90 (1H, br), 4.38-4.30 (2H, m), 4.05 (3H, s), 1.79-1.68 (1H, m), 1.65-1.56 (2H, m), 0.93 (6H, d) two exchangeable protons not seen.

Intermediate 49

2-[(3-Methylbutyl)oxy]-8-(methoxy)-9-(tetrahydro-2H-pyran-4-ylmethyl)-9H-Purin-6-amine

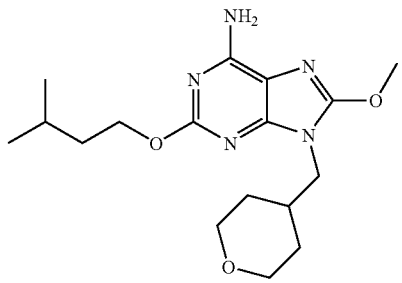

To a solution of 2-[(3-methylbutyl)oxy]-8-methoxy-9H-purin-6-amine trifluoroacetic acid salt (143 mg) in dry DMF (2.42 mL) was added potassium carbonate (217 mg) and the mixture was stirred at 60° C. for 90 mins. The reaction was cooled and 4-(bromomethyl)tetrahydro-2H-pyran (77 mg) was added. The reaction was stirred at 50° C. overnight and was cooled to room temperature. The mixture was taken up in EtOAc (30 mL) and extracted with water (2×15 mL). The organics were separated, dried over MgSO$_4$ and concentrated in vacuo to give a viscous yellow oil. The crude material was purified by C$_{18}$ reverse phase chromatography (ISCO) using water (0.1% formic acid)-acetonitrile (0.05% formic acid) as eluent (20-60%) to afford the title compound as a clear viscous oil (52 mg).

MS calcd for $(C_{17}H_{27}N_5O_3)^+$=349
MS found (electrospray): $(M+H)^+$=350

Intermediate 50

2-[(2-Methylbutyl)oxy]-9-(tetrahydro-2H-pyran-2-yl)-9H-purin-6-amine

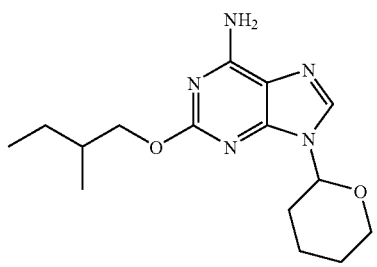

To 2-methyl-1-butanol (0.855 mL) in DME (4 mL) was added sodium tert-butoxide (760 mg). The mixture was stirred at room temperature until homogeneous. 2-Chloro-9-(tetrahydro-2H-pyran-2-yl)-9H-purin-6-amine (500 mg) was added followed by DME (4 mL). The reaction was heated at 110° C. overnight. The mixture was cooled and concentrated in vacuo to give a yellow residue. The residue was taken up in water (30 mL) and extracted with EtOAc (2×30 mL). The organics were separated and washed with brine (30 mL). The organics were separated, dried over MgSO$_4$, filtered and concentrated in vacuo to give the title compound as a yellow/brown residue. This material was taken on to the next step without further purification.

MS calcd for $(C_{15}H_{23}N_5O_2)^+$=305
MS found (electrospray): (M+H)$^+$=306

Intermediate 51

8-Bromo-2-[(2-methylbutyl)oxy]-9-(tetrahydro-2H-Pyran-2-yl)-9H-Purin-6-amine

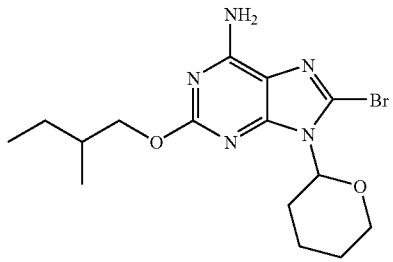

A solution of 2-[(2-methylbutyl)oxy]-9-(tetrahydro-2H-pyran-2-yl)-9H-purin-6-amine (245 mg) in dry chloroform (2.9 mL) was cooled to 0° C. and NBS (150 mg) was added to give a green/brown solution. The reaction mixture was stirred at room temperature for 6 h. The mixture was taken up into DCM (20 mL) and was washed with water (20 mL). The organics were separated, dried by passing through a hydrophobic frit and concentrated in vacuo to give the title compound as green solid (292 mg).

MS calcd for $(C_{15}H_{22}BrN_5O_2)^+$=383/385
MS found (electrospray): (M+H)$^+$=384/386
$^1$H NMR((CD$_3$)$_2$SO): δ 7.39 (2H, br), 5.50 (1H, dd), 4.15-4.07 (1H, m), 4.06-3.95 (2H, m), 3.70-3.57 (1H, m), 3.02-2.88 (1H, m), 2.03-1.40 (7H, m), 1.27-1.13 (1H, m), 0.99-0.84 (6H, m).

Intermediate 52

2-[(2-Methyl butyl)oxy]-8-methoxy-9-(tetrahydro-2H-pyran-2-yl)-9H-Purin-6-amine

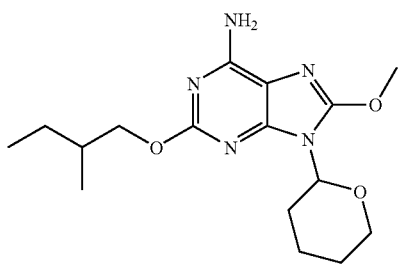

To a solution of 8-bromo-2-[(2-methylbutyl)oxy]-9-(tetrahydro-2H-pyran-2-yl)-9H-purin-6-amine (284 mg) in dry MeOH (2.54 mL) was added sodium methoxide solution (0.416 mL, 30% wt. MeOH) and the mixture was stirred at reflux for 1 h. The reaction was allowed to cool and was concentrated in vacuo. The resulting residue was dissolved in EtOAc (15 mL) and was poured into saturated ammonium chloride solution (15 mL). The organics were separated, dried over MgSO$_4$, filtered and concentrated in vacuo to give the title compound as an orange foam (199 mg).

MS calcd for $(C_{16}H_{25}N_5O_3)^+$=335
MS found (electrospray): (M+H)$^+$=336
$^1$H NMR((CD$_3$)$_2$SO): δ 6.87 (2H, s), 5.35 (1H, dd), 4.13-3.91 (6H, m), 3.66-3.50 (1H, m), 2.77-2.62 (1H, m), 1.98-1.42 (7H, m), 1.26-1.13 (1H, m), 0.98-0.85 (6H, m).

Intermediate 53

2-[(2-Methylbutyl)oxy]-8-(methoxy)-9H-purin-6-amine trifluoroacetic acid salt

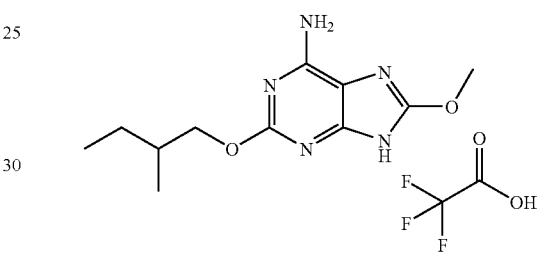

To a solution of 2-[(2-methylbutyl)oxy]-8-methoxy-9-(tetrahydro-2H-pyran-2-yl)-9H-purin-6-amine (199 mg) in dry MeOH (1.99 mL) was added TFA (0.199 mL). The mixture was stirred at room temperature for 24 h. The reaction was concentrated in vacuo to give a yellow residue. The residue was triturated with Et$_2$O and was filtered to give the title compound as an off-white solid (111 mg).

MS calcd for $(C_{11}H_{17}N_5O_2)^+$=251
MS found (electrospray): (M+H)$^+$=252
$^1$H NMR((CD$_3$)$_2$SO): δ 8.01-7.46 (2H, br), 4.20-4.00 (6H, m), 1.88-1.73 (1H, m), 1.54-1.40 (1H, m), 1.28-1.12 (1H, m), 0.99-0.84 (6H, m).

Intermediate 54

2-[(2-Methyl butyl)oxy]-8-methoxy-9-(tetrahydro-2H-pyran-4-ylmethyl)-9H-Purin-6-amine

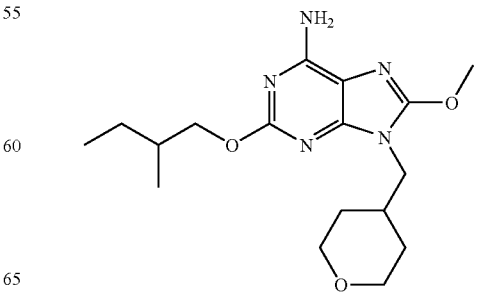

To a solution of 2-[(2-methylbutyl)oxy]-8-methoxy-9H-purin-6-amine (109 mg) in dry DMF (1.86 mL) was added potassium carbonate (165 mg) and the mixture was stirred at 60° C. for 90 mins. The mixture was cooled to room temperature and 4-(bromomethyl)tetrahydro-2H-pyran (59 mg) was added. The reaction was stirred at 50° C. overnight and was cooled to room temperature. The mixture was taken up in EtOAc (15 mL) and washed with water (2×10 mL). The organics were separated, dried over MgSO$_4$, filtered and concentrated in vacuo to give a yellow viscous oil. The material was purified by C$_{18}$ reverse phase chromatography (ISCO) using water (0.1% formic acid)-acetonitrile (0.05% formic acid) as eluent (20-60%) to afford the title compound as a yellow oil (41 mg).

MS calcd for $(C_{17}H_{27}N_5O_3)^+=349$

MS found (electrospray): $(M+H)^+=350$

Intermediate 55

2-[(1-Methylbutyl)oxy]-9-(tetrahydro-2H-pyran-2-yl)-9H-purin-6-amine

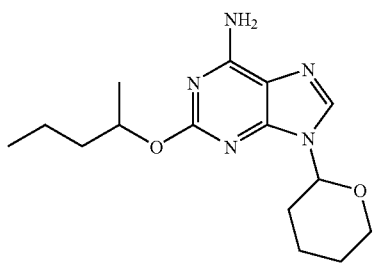

To 2-pentanol (3.65 mL) was added sodium tert-butoxide (760 mg) in portions over 5 mins. The mixture was stirred at room temperature until homogeneous. 2-Chloro-9-(tetrahydro-2H-pyran-2-yl)-9H-purin-6-amine (500 mg) was added and the reaction was heated at 50° C. overnight, then for a further 72 h. The reaction mixture was cooled and quenched with water (10 mL) and was extracted with EtOAc (3×25 mL). The organics were combined, washed with brine (30 mL), dried over MgSO$_4$, filtered and concentrated in vacuo to give crude title compound as a viscous yellow oil.

In a separate flask, a suspension of 2-chloro-9-(tetrahydro-2H-pyran-2-yl)-9H-purin-6-amine (500 mg) and 2-pentanol (3.8 mL) was heated to 50° C. Sodium hydride (396 mg, 60% dispersion) was added in portions and the reaction was stirred at 50° C. for 72 h. The reaction was cooled and quenched with water (10 mL) and was extracted with EtOAc (3×25 mL). The combined organics were washed with brine (30 mL), dried over MgSO$_4$, filtered and concentrated in vacuo to give crude title compound as a yellow oil.

The two crude reaction products were combined and purified by C$_{18}$ reverse phase chromatography (ISCO) using water (0.1% formic acid)-acetonitrile (0.05% formic acid) as eluent (20-60%) to afford the title compound as a brown oil (382 mg).

MS calcd for $(C_{15}H_{23}N_5O_2)^+=305$

MS found (electrospray): $(M+H)^+=306$

Intermediate 56

8-Bromo-2-[(1-methylbutyl)oxy]-9-(tetrahydro-2H-pyran-2-yl)-9H-purin-6-amine

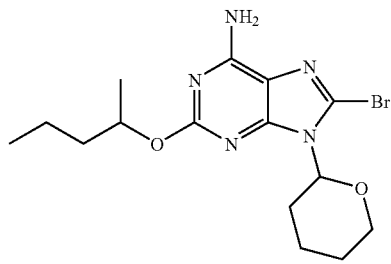

To a solution of 2-[(1-methylbutyl)oxy]-9-(tetrahydro-2H-pyran-2-yl)-9H-purin-6-amine (382 mg) in dry chloroform (4.52 mL) at 0° C. was added NBS (234 mg) in a single portion. The reaction was warmed to room temperature and stirred for 5 h. The reaction mixture was taken up in DCM (20 mL) and was washed with water (30 mL). The organics were separated, dried by passing through a hydrophobic frit and concentrated in vacuo to give a green/brown foam (493 mg).

MS calcd for $(C_{15}H_{22}BrN_5O_2)^+=383/385$

MS found (electrospray): $(M+H)^+=384/386$ $^1$H NMR((CD$_3$)$_2$SO): δ 7.44 (2H, br), 5.48 (1H, dd), 5.09-4.98 (1H, m), 4.07-3.98 (1H, m), 3.68-3.57 (1H, m), 3.02-2.88 (1H, m), 2.03-1.91 (1H, m), 1.87-1.79 (1H, m), 1.74-1.45 (5H, m), 1.44-1.20 (5H, m), 0.95-0.85 (3H, m).

Intermediate 57

2-[(1-Methylbutyl)oxy]-8-methoxy-9-(tetrahydro-2H-pyran-2-yl)-9H-Purin-6-amine

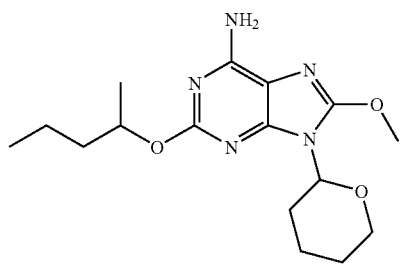

To a solution of 8-bromo-2-[(1-methylbutyl)oxy]-9-(tetrahydro-2H-pyran-2-yl)-9H-purin-6-amine (493 mg) in dry MeOH (4.37 mL) was added sodium methoxide solution (0.722 mL, 30% wt. in MeOH) and the mixture was stirred at reflux for 6 h. A further portion of sodium methoxide solution (0.120 mL, 30% wt. in MeOH) was added and the reaction was continued for 90 mins. The reaction was cooled and concentrated in vacuo to give an orange residue. The residue was taken up in saturated ammonium chloride (25 mL) and washed with EtOAc (25 mL). The organics were separated and washed with water (15 mL). The organics were separated, dried over MgSO₄, filtered and concentrated in vacuo to give the title compound as an orange foam (313 mg).

MS calcd for $(C_{16}H_{25}N_5O_3)^+=335$
MS found (electrospray): $(M+H)^+=336$
¹H NMR((CD₃)₂SO): δ 6.78 (2H, s), 5.33 (1H, d), 5.07-4.96 (1H, m), 4.09-3.92 (4H, m), 3.62-3.49 (1H, m), 2.80-2.64 (1H, m), 1.97-1.88 (1H, m), 1.77-1.43 (6H, m), 1.42-1.19 (5H, m), 0.95-0.84 (3H, m).

Intermediate 58

2-[(1-Methylbutyl)oxy]-8-methoxy-9H-purin-6-amine trifluoroacetic acid salt

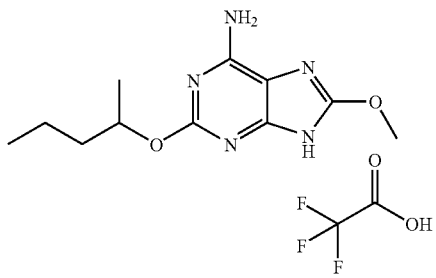

To a solution of 2-[(1-methylbutyl)oxy]-8-methoxy-9-(tetrahydro-2H-pyran-2-yl)-9H-purin-6-amine (313 mg) in dry MeOH (3.13 mL) was added TFA (0.313 mL) and the mixture was stirred at room temperature for 48 h. The reaction mixture was concentrated in vacuo to give a yellow residue which was triturated with Et₂O and filtered to give the title compound as an off-white solid (218 mg).

MS calcd for $(C_{11}H_{17}N_5O_2)^+=251$
MS found (electrospray): $(M+H)^+=252$
¹H NMR((CD₃)₂SO): δ 8.12 (2H, br), 5.20-5.09 (1H, m), 4.05 (3H, s), 1.74-1.52 (2H, m), 1.45-1.27 (5H, m), 0.94-0.85 (3H, m), one exchangeable proton not seen.

Intermediate 59

2-[(1-Methylbutyl)oxy]-8-methoxy-9-(tetrahydro-2H-pyran-4-ylmethyl)-9H-Purin-6-amine

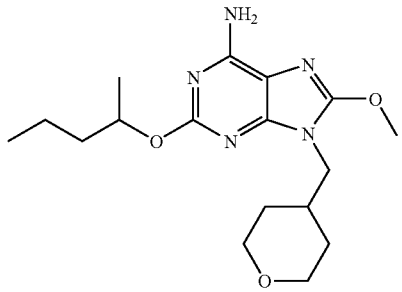

To a solution of 2-[(1-methylbutyl)oxy]-8-methoxy-9H-purin-6-amine trifluoroacetic acid salt (218 mg) in dry DMF (3.71 mL) was added potassium carbonate (330 mg). The mixture was stirred at 60° C. for 90 mins. The reaction was cooled and 4-(bromomethyl)tetrahydro-2H-pyran (118 mg) was added. The reaction was stirred at 50° C. for 6 h and was cooled to room temperature. The mixture was taken up in EtOAc (40 mL) and washed with water (2×20 mL). The organics were separated, dried over MgSO₄ and concentrated in vacuo to give a viscous yellow oil. The material was purified by $C_{18}$ reverse phase chromatography (ISCO) using water (0.1% formic acid)-acetonitrile (0.05% formic acid) as eluent (20-60%) to afford the title compound as a clear oil (92 mg).

MS calcd for $(C_{17}H_{27}N_5O_3)^+=349$
MS found (electrospray): $(M+H)^+=350$ Intermediate 60

2-Chloro-1H-purin-6-amine

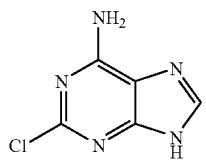

A mixture of 2,6-dichloro-1H-purine (5 g) and ammonia solution (79.2 mL, 2M in (isopropanol) was stirred and heated at 120° C. in an autoclave overnight. The reaction was cooled and concentrated in vacuo to give the title compound as an off-white solid in quantitative yield.

MS calcd for $(C_5H_4ClN_5)^+=169/171$
MS found (electrospray): $(M+H)^+=170/172$
¹H NMR((CD₃)₂SO): δ 8.14 (1H, s), 7.66 (2H, s), one exchangeable proton not seen.

Intermediate 61

2-Chloro-9-(tetrahydro-2H-pyran-4-ylmethyl)-9H-purin-6-amine

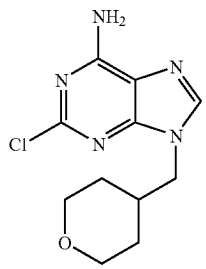

To a suspension of 2-chloro-1H-purin-6-amine (1.57 g) and potassium carbonate (2.57 g) in DMF (55 mL) was added 4-(bromomethyl)tetrahydro-2H-pyran (2.0 g) in one portion. The mixture was stirred at 90° C. overnight. The reaction mixture was taken up in chloroform/isopropanol (3:1, 100 mL) and was extracted with water (100 mL). The organics were separated and the aqueous was extracted with chloroform/isopropanol (3:1, 2×50 mL). The organics were combined, dried by passing through a hydrophobic frit and concentrated in vacuo to give the title compound as an off-white solid (1.30 g, 52%).

MS calcd for $(C_{11}H_{14}ClN_5O)^+=267/269$
MS found (electrospray): $(M+H)^+=268/270$ ¹H NMR((CD₃)₂SO): δ 8.13 (1H, s), 7.73 (2H, br.s), 4.00 (2H, d), 3.81 (2H, dd), 3.28-3.17 (2H, m), 2.14-1.99 (1H, m), 1.43-1.33 (2H, m), 1.33-1.17 (2H, m).

Intermediate 62

8-Bromo-2-chloro-9-(tetrahydro-2H-pyran-4-ylmethyl)-9H-Purin-6-amine

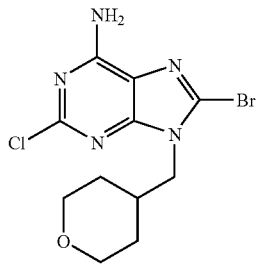

To a solution of 2-chloro-9-(tetrahydro-2H-pyran-4-ylmethyl)-9H-purin-6-amine (1.30 g) in dry chloroform (32 mL) at room temperature was added NBS (2.16 g). The reaction was stirred at 60° C. for 6 h. the mixture was cooled, taken up in DCM (50 mL) and washed with water (50 mL). The organics were passed through a hydrophobic frit and concentrated in vacuo to give the title compound as a brown solid (1.36 g).
MS calcd for (C₁₁H₁₃BrClN₅O)⁺=345/347/349
MS found (electrospray): (M+H)⁺=346/348/350
¹H NMR((CD₃)₂SO): δ 7.91 (2H, br), 4.04-3.94 (1H, m), 3.82 (2H, dd), 3.31-3.15 (2H, m), 2.19-2.01 (1H, m), 1.48-1.15 (5H, m).

Intermediate 63

2-Chloro-8-methoxy-9-(tetrahydro-2H-pyran-4-ylmethyl)-9H-Purin-6-amine

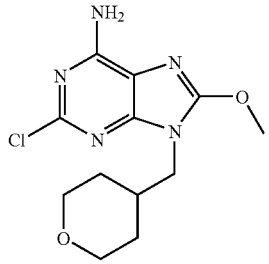

To a solution of 8-bromo-2-chloro-9-(tetrahydro-2H-pyran-4-ylmethyl)-9H-purin-6-amine (1.36 g) in dry MeOH (27.5 mL) was added 1M sodium hydroxide solution (27.5 mL) and the mixture was stirred at reflux for 30 mins. The reaction was cooled to room temperature and concentrated in vacuo. The residue obtained was triturated with water (60 mL) and extracted with EtOAc (120 mL). The organic layer was washed with brine (60 mL), dried over MgSO₄, filtered and concentrated in vacuo to give a pink/white solid. The material was taken up in MeOH/DMSO (1:1) and a precipitate crashed out of solution. The solid was filtered off and the filtrate was purified by C₁₈ reverse phase chromatography (ISCO) using water (0.1% formic acid)-acetonitrile (0.05% formic acid) as eluent (10-45%). The filtered solid was combined with the material obtained from the purification to give the title compound (192 mg).
MS calcd for (C₁₂H₁₆ClN₅O₂)⁺=297/299
MS found (electrospray): (M+H)⁺=298/300
¹H NMR((CD₃)₂SO): δ 7.45-7.28 (2H, m), 4.10 (3H, s), 3.87-3.73 (3H, m), 3.22 (3H, t), 2.07-1.93 (1H, m), 1.46-1.36 (2H, m), 1.33-1.14 (2H, m).

Intermediate 64

2-[(2-Cyclopropylethyl)oxy]-9-(tetrahydro-2H-pyran-2-yl)-9H-purin-6-amine

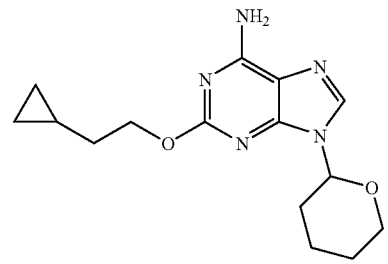

To a mixture of 2-cyclopropylethanol (3.45 g) in DME (20 mL) was added sodium tert-butoxide (3.86 g) gradually. The reaction was stirred under nitrogen for 30 mins, then 2-chloro-9-(tetrahydro-2H-pyran-2-yl)-9H-purin-6-amine (2.54 g) and DME (20 mL) were added. The reaction was heated to reflux (110° C.) overnight, then for another 8 h. The reaction was quenched into water (100 mL) and extracted with EtOAc (2×100 mL). The organics were combined and washed with brine (100 mL) and dried using a hydrophobic frit. The resultant oil was azeotroped with toluene (×2) to give a gum. This was triturated with Et₂O (cooled CO₂/acetone bath) until the title compound was obtained as a yellow powder (1.579 g) which was placed under high vacuum for 24 h.
MS calcd for (C₁₅H₂₁N₅O₂)⁺=303
MS found (electrospray): (M+H)⁺=304
¹H NMR (CDCl₃): δ 7.85 (1H, s), 5.64 (1H, dd), 5.51 (2H, br), 4.39 (2H, dt), 4.19-4.11 (1H, m), 3.80-3.71 (1H, m), 2.13-1.94 (3H, m), 1.83-1.59 (5H, m), 0.94-0.82 (1H, m), 0.53-0.43 (2H, m), 0.16-0.09 (2H, m).

Intermediate 65

8-Bromo-2-[(2-cyclopropylethyl)oxy]-9-(tetrahydro-2H-pyran-2-yl)-9H-purin-6-amine

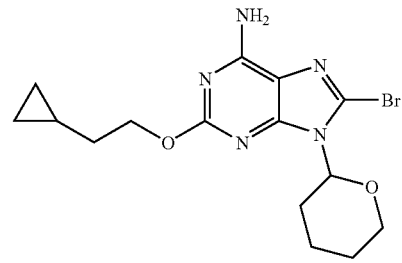

2-[(2-Cyclopropylethyl)oxy]-9-(tetrahydro-2H-pyran-2-yl)-9H-purin-6-amine (1.579 g) was dissolved in chloroform (15 mL) and was cooled in an ice bath to 1° C. NBS (1.02 g) was added gradually, keeping the reaction temperature below 2° C. The reaction was stirred for 30 mins (with cooling in an ice bath) before being allowed to warm to room temperature. The reaction was then stirred for 6 h. Chloroform (50 mL) was added and the mixture was partitioned with water (50 mL) and was separated using a hydrophobic frit. The organics were evaporated under reduced pressure to give the title compound as a brown foam (1.867 g).

MS calcd for $(C_{15}H_{20}BrN_5O_2)^+$=381/383
MS found (electrospray): $(M+H)^+$=382/384
$^1$H NMR (CDCl$_3$): δ 5.62 (1H, dd), 5.45 (2H, br), 4.44-4.34 (2H, m), 4.22-4.14 (1H, m), 3,72 (1H, dt), 3.11-2.99 (1H, m), 2.16-2.07 (1H, m), 1.90-1.58 (6H, m), 0.93-0.82 (1H, m), 0.53-0.46 (2H, m), 0.16-0.10 (2H, m).

Intermediate 66

2-[(2-Cyclopropylethyl)oxy]-8-methoxy-9-(tetrahydro-2H-pyran-2-yl)-9H-purin-6-amine

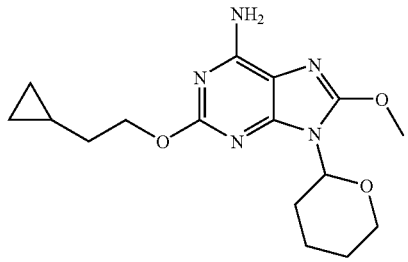

A solution of 8-bromo-2-[(2-cyclopropylethyl)oxy]-9-(tetrahydro-2H-pyran-2-yl)-9H-purin-6-amine (1.867 g) in dry MeOH (14 mL) was treated with sodium methoxide solution (3.1 mL, 25 wt. MeOH) and was heated to reflux for 5 h. The reaction was concentrated under reduced pressure before being partitioned between EtOAc (100 mL) and ammonium chloride (100 mL). The organics were separated and aqueous was re-extracted with EtOAc (100 mL). The combined organics were washed with brine (100 mL), separated and dried using a hydrophobic frit. The organics were evaporated under reduced pressure to give the title compound as a brown foam (845 mg).

MS calcd for $(C_{16}H_{23}N_5O_3)^+$=333
MS found (electrospray): $(M+H)^+$=334
$^1$H NMR (CDCl$_3$): δ 5.51 (1H, dd), 5.13 (2H, br), 4.36 (2H, t), 4.13 (3H, t), 3.70 (1H, dt), 2.84-2.72 (1H, m), 2.10-2.01 (1H, m), 1.82-1.53 (7H, m), 0.93-0.82 (1H, m), 0.52-0.45 (2H, m), 0.16-0.09 (2H, m).

Intermediate 67

2-[(2-Cyclopropylethyl)oxy]-8-methoxy-9H-purin-6-amine trifluoroacetic acid salt

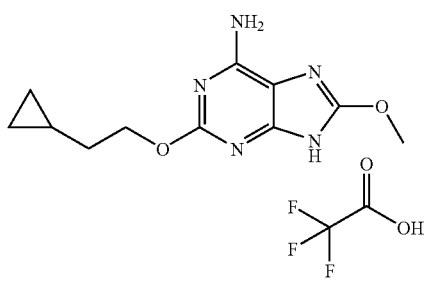

2-[(2-Cyclopropylethyl)oxy]-8-methoxy-9-(tetrahydro-2H-pyran-2-yl)-9H-purin-6-amine (845 mg) was dissolved in MeOH (10 mL) and TFA (1 mL) was added. The reaction was stirred over a weekend and was evaporated to dryness under reduced pressure to give a brown solid. EtOAc was added and the solid was filtered off and washed with more EtOAc (15 mL EtOAc used in total). The solid was then washed with Et$_2$O (5 mL) and air-dried under suction to give the title compound as an off-white solid (937 mg).

MS calcd for $(C_{11}H_{15}N_5O_2)^+$=249
MS found (electrospray): $(M+H)^+$=250
$^1$H NMR (CDCl$_3$): δ 7.91 (2H, br), 4.24 (2H, t), 3.93 (3H, s), 1.53-1.45 (2H, m), 0.71-0.60 (1H, m), 0.34-0.27 (2H, m), 0.02-0.04 (2H, m), one exchangeable proton not seen, trace of ammonium ion present.

Intermediate 68

Tetrahydro-3-furanylmethyl methanesulfonate

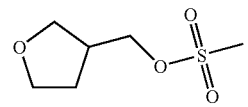

To tetrahydro-3-furanmethanol (25 g) in dry DCM (250 mL) at 0° C. under nitrogen was added triethylamine (68 mL) in a single portion. Methanesulphonyl chloride (24.7 mL) was added dropwise over 15 mins. The reaction was warmed to room temperature and was left over a weekend. The mixture was taken up in DCM (50 mL) and washed with saturated sodium bicarbonate solution (100 mL). The organics were dried using a hydrophobic frit and concentrated in vacuo to give the title compound as a brown oil in quantitative yield.

$^1$H NMR((CD$_3$)$_2$SO): δ 4.19-4.08 (2H, m), 3.77-3.69 (2H, m), 3.66-3.59 (1H, m), 3.46 (1H, dd), 3.19 (3H, s), 2.64-2.53 (1H, m), 2.03-1.92 (1H, m), 1.63-1.53 (1H, m).

Intermediate 69

2-[(2-Cyclopropylethyl)oxy]-8-methoxy-9-(tetrahydro-3-furanylmethyl)-9H-purin-6-amine

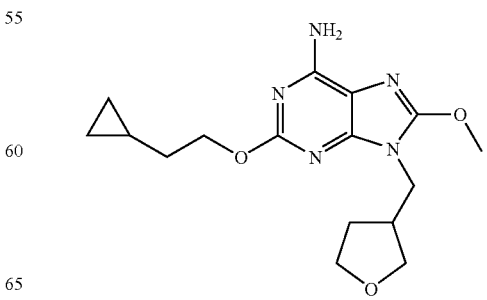

To a solution of 2-[(2-Cyclopropylethyl)oxy]-8-methoxy-9H-purin-6-amine trifluoroacetic acid salt (300 mg) in dry DMF (5 mL) was added anhydrous potassium carbonate (457 mg) and the mixture was heated at 60° C. for 1.5 h. The reaction was cooled to room temperature and tetrahydro-3-furanylmethyl methanesulfonate (164 mg) was added. The reaction was heated at 90° C. for 3.5 h and was then quenched into water (50 mL) and extracted with EtOAc (3×50 mL). The organics were separated, dried by passing through a hydrophobic frit and evaporated under reduced pressure to give a glassy solid. The material was purified by $C_{18}$ reverse phase chromatography (ISCO) using water (0.1% formic acid)-acetonitrile (0.05% formic acid) as eluent (20-60%) to give the title compound (103.8 mg).

MS calcd for $(C_{16}H_{23}N_5O_3)^+$=333
MS found (electrospray): $(M+H)^+$=334
$^1$H NMR (CDCl$_3$): δ 5.37 (2H, br), 4.22 (2H, t), 4.00 (3H, s), 3.89-3.77 (3H, m), 3.69-3.61 (2H, m), 3.52 (1H, dd), 2.80-2.67 (1H, m), 1.91-1.81 (1H, m), 1.65-1.53 (3H, m), 0.80-0.69 (1H, m), 0.39-0.32 (2H, m), 0.02-0.04 (2H, m).

Intermediate 70

2-[(E/Z)-2-methoxyethenyl]tetrahydro-2H-pyran

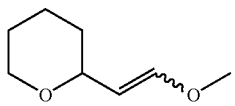

A solution of oxalyl chloride (5.33 mL) in DCM (30 mL) was cooled to −60° C. and a solution of DMSO (7.4 mL) in DCM (100 mL) was added dropwise with stirring, keeping the temperature between −55° C. and −60° C. After 20 mins tetrahydro-2H-pyran-2-ylmethanol (6 g) was added dropwise. After 30 mins, triethylamine (36 mL) was added dropwise and after a further 30 mins the mixture was allowed to warm to room temperature. After 30 mins the mixture was treated with water, the mixture was shaken and the layers separated. The aqueous layer was extracted with DCM (×2) and the combined extracts were washed with dilute brine, dried using a hydrophobic frit and evaporated to a pale oil (3.8 g). The material was purified by normal phase chromatography (ISCO) using cyclohexane/EtOAc as eluent (0-40%) to give a clear oil (780 mg).

A suspension of (methoxymethyl)triphenylphosphonium chloride (4.69 g) in dry THF was cooled to −40° C. and a solution of potassium tert-butoxide (1.54 g) in dry THF was added dropwise with stirring. After 45 mins, the reaction was cooled to −65° C. and the clear oil (780 mg, prepared above) was added in dry THF dropwise, keeping the temperature between −60° C. and −65° C. The mixture was allowed to warm to room temperature and after a further 30 mins was quenched with ice/water. The mixture was extracted with Et$_2$O (×3) and the combined extracted were washed with brine, dried over sodium sulphate, evaporated in vacuo, then re-evaporated in vacuo with toluene to give crude material (3.71 g). The material was purified by normal phase chromatography (ISCO) using cyclohexane/EtOAc as eluent (0-20%) to give the title compound as a clear oil (581 mg).

$^1$H NMR (CDCl$_3$): δ 6.58+5.91 (1H d+d), 4.81+4.45 (1H, dd+dd), 4.31-4.23+3.76-3.69+3.52-3.44 (2H, m+m+m), 4.04-3.95 (1H, m), 3.61+3.56 (3H, s+s), 1.89-1.77 (1H, m), 1.67-1/32 (5H, m), mixture of isomers in approx. 60:40 ratio.

Intermediate 71

Tetrahydro-2H-pyran-2-ylacetaldehyde

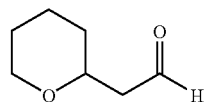

To a solution of 2-[(E/Z)-2-(Methoxy)ethenyl]tetrahydro-2H-pyran (581 mg) in THF (4 mL) was added 2N HCl (4 mL) with stirring. After 2 h the mixture was diluted with water and was extracted with DCM (×3). The combined organics were washed with dilute brine, dried through a hydrophobic frit and evaporated to give the title compound as a clear oil (528 mg).

$^1$H NMR (CDCl$_3$): δ 9.80 (1H, t), 4.01-3.93 (1H, m), 3.88-3.79 (1H, m), 3.51-3.43 (1H, m), 2.63-2.54 (1H, m), 2.50-2.42 (1H, m), 1.91-1.80 (1H, m), 1.68-1.48 (4H, m), 1.44-1.31 (1H, m).

Intermediate 72

2-(Tetrahydro-2H-pyran-2-yl)ethanol

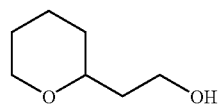

To a stirred solution of tetrahydro-2H-pyran-2-ylacetaldehyde (528 mg) in ethanol (5 mL) was added sodium borohydride granules (156 mg). The mixture was heated at 50° C. for 2 h under nitrogen. After cooling, the solvent was evaporated and the residue treated with brine. The mixture was acidified by careful addition of 2N HCl and this mixture was extracted with DCM (×3). The combined organics were washed with brine, dried using a hydrophobic frit and evaporated to give the title compound as a clear oil (465 mg).

$^1$H NMR (CDCl$_3$): δ 4.02-3.93 (1H, m), 3.83-3.73 (2H, m), 3.57-3.38 (2H, m), 2.83-2.74 (1H, m), 1.88-1.32 (7H, m), hydroxyl proton not seen.

Intermediate 73

2-(Tetrahydro-2H-pyran-2-yl)ethyl methanesulfonate

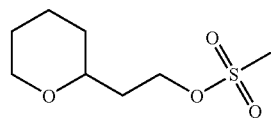

2-(Tetrahydro-2H-pyran-2-yl)ethanol (465 mg) was dissolved in dry DCM (10 mL) and triethylamine (996 mg) was added. The stirred solution was cooled in an ice bath under nitrogen and methanesulphonyl chloride (359 mg) was added dropwise over 5 mins. The reaction was allowed to warm to room temperature as the ice bath melted and was left for 16 h.

The mixture was then shaken with saturated sodium bicarbonate solution and the aqueous layer was extracted with DCM (×2). The combined organic extracts were washed with brine, dried using a hydrophobic frit and evaporated to give the title compound as a brown oil (718 mg).

¹H NMR (CDCl₃): δ 4.43-4.27 (2H, m), 4.00-3.92 (1H, m), 3.47-3.35 (2H, m), 3.01 (3H, s), 1.93-1.78 (3H, m), 1.64-1.44 (4H, m), 1.37-1.24 (1H, m).

Intermediate 74

2-Butyloxy-8-methoxy-9-[2-(tetrahydro-2H-pyran-2-yl)ethyl]-9H-Purin-6-amine

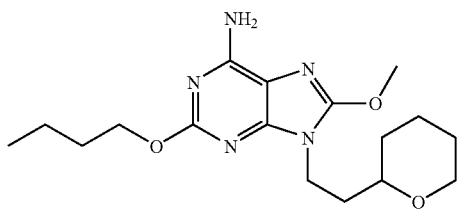

A mixture of 2-butoxy-8-methoxy-9H-purin-6-amine trifluoroacetate salt (200 mg) and potassium carbonate (236 mg) in dry DMF (2 mL) were heated at 60° C. with stirring for 1 h. 2-(Tetrahydro-2H-pyran-2-yl)ethyl methanesulfonate (142 mg) was added and the reaction was continued for 16 h at 60° C. The mixture was quenched with water and extracted with EtOAc (×3). The combined organics were washed with water and brine, dried using a hydrophobic frit and evaporated to give crude material (540 mg). The material was purified by normal phase chromatography (ISCO) using 0-20% methanol/EtOAc as eluent to give the title compound as a white solid (88 mg).

MS calcd for $(C_{17}H_{27}N_5O_3)^+$=349
MS found (electrospray): $(M+H)^+$=350
¹H NMR (CDCl₃): δ 5.12 (2H, s), 4.29 (2H, t), 4.12 (3H, s), 4.05 (2H, dt), 3.99-3.92 (1H, m), 3.36 (1H, dt), 3.27-3.19 (1H, m), 1.88 (2H, quartet), 1.84-1.66 (5H, m), 1.63-1.37 (4H, m), 1.36-1.23 (1H, m), 0.97 (3H, t).

Intermediate 75

(2,2-Dimethyltetrahydro-2H-pyran-4-yl)methanol

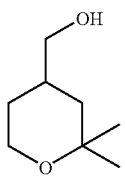

A solution of 2,2-dimethyltetrahydro-2H-pyran-4-carbaldehyde (2.5 g) in ethanol (30 mL) was cooled (ice bath) and sodium borohydride (665 mg) was added with stirring. The ice bath was removed and the mixture was allowed to warm to room temperature. After 2 h the reaction was heated to 50° C. for 1 h, then allowed to cool to room temperature. The solvent was evaporated and the residue was treated with brine, acidified and extracted into DCM (×3). The combined organics were dried through a hydrophobic frit and evaporated to give a clear oil (2.54 g).

¹H NMR (CDCl₃): δ 3.87-3.62 (2H, m), 3.47 (2H, d), 1.99-1.87 (1H, m), 1.67-1.55 (3H, m), 1.28-1.06 (8H, m).

Intermediate 76

(2,2-Dimethyltetrahydro-2H-pyran-4-yl)methyl methanesulfonate

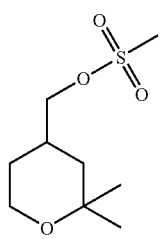

(2,2-Dimethyltetrahydro-2H-pyran-4-yl)methanol (2.54 g) was dissolved in dry DCM (40 mL) and triethylamine (4.9 mL) was added with stirring. The solution was cooled (ice bath) under nitrogen and methanesulphonyl chloride (1.77 mL) was added dropwise over 5 mins. The mixture was allowed to warm slowly to room temperature as the ice bath melted and was left for 16 h. The mixture was shaken with saturated sodium bicarbonate solution and the aqueous layer was extracted with DCM (×2). The combined organics were washed with brine, dried using a hydrophobic frit and evaporated to give the title compound (3.93 g).

¹H NMR (CDCl₃): δ 4.03 (2H, d), 3.82-3.75 (1H, m), 3.68 (1H, dt), 3.02 (3H, s), 2.25-2.12 (1H, m), 1.70-1.55 (3H, m), 1.33-1.13 (7H, m).

Intermediate 77

4-(Bromomethyl)-2,2-dimethyltetrahydro-2H-pyran

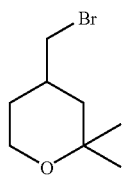

A mixture of (2,2-dimethyltetrahydro-2H-pyran-4-yl)methyl methanesulfonate (1.5 g) and anhydrous lithium bromide (2.72 g) in acetone (40 mL) was refluxed under nitrogen for 4 h. The reaction was allowed to cool and the solvent was evaporated. The residue was treated with saturated sodium bicarbonate solution and was extracted with DCM (×3). The combined organics were washed with dilute brine, dried by passing through a hydrophobic frit and evaporated to give the title compound as a brown oil (1.23 g).

¹H NMR (CDCl₃): δ 3.82-3.75 (1H, m), 3.71-3.62 (1H, m), 3.26 (2H, d), 2.11-1.98 (1H, m), 1.80-1.66 (2H, m), 1.29-1.08 (8H, m).

Intermediate 78

2-Butyloxy-9-[(2,2-dimethyltetrahydro-2H-pyran-4-yl)methyl]-8-methoxy-9H-purin-6-amine

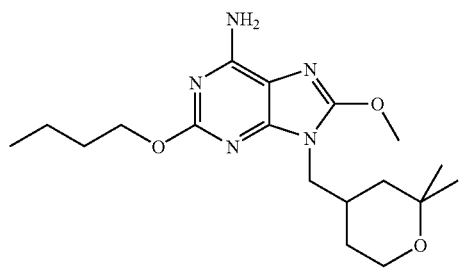

A mixture of 2-butoxy-8-methoxy-9H-purin-6-amine trifluoroacetate salt (223 mg) and potassium carbonate (264 mg) in dry DMF (2 mL) were heated at 60° C. under nitrogen with stirring for 1 h. 4-(Bromomethyl)-2,2-dimethyltetrahydro-2H-pyran (158 mg) was added and the reaction was stirred for 16 h at 60° C. The mixture was quenched with water and extracted with EtOAc (×3). The combined organics were washed with water and brine, dried using a hydrophobic frit and evaporated to give a brown oil. The crude material was purified by normal phase chromatography (ISCO) using 5-20% methanol/EtOAc as eluent to give a pale oil (181 mg). The material was re-purified by normal phase chromatography (ISCO) using 0-15% methanol/EtOAc as eluent to give the title compound (161 mg).

MS calcd for $(C_{18}H_{29}N_5O_3)^+=363$
MS found (electrospray): $(M+H)^+=364$ Intermediate 79

N²-Butyl-9-[(2,2-dimethyltetrahydro-2H-pyran-4-yl)methyl]-8-methoxy-9H-purine-2,6-diamine

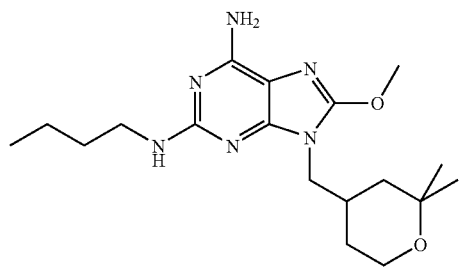

A mixture of N²-Butyl-8-methoxy-9H-purine-2,6-diamine trifluoroacetic acid salt (200 mg) and potassium carbonate (236 mg) in dry DMF (2 mL) were heated at 60° C. under nitrogen with stirring for 1 h. (2,2-Dimethyltetrahydro-2H-pyran-4-yl)methyl methanesulfonate (152 mg) was added and stirring was continued for 5 h at 50° C. The reaction was cooled to room temperature and stirred for 16 h. Lithium bromide (50 mg) was added and heating was continued for 5 h at 50° C., then 8 h at 90° C. The mixture was quenched with water and extracted with EtOAc (×3). The combined organics were washed with water and brine, dried using a hydrophobic frit and evaporated to give crude material (210 mg). This was purified by $C_{18}$ reverse phase chromatography (ISCO) using water (0.1% formic acid)-acetonitrile (0.05% formic acid) as eluent (20-60%) to give the title compound (75 mg).

MS calcd for $(C_{18}H_{30}N_6O_2)^+=362$
MS found (electrospray): $(M+H)^+=363$
¹H NMR (CDCl₃): δ 4.92 (2H, br), 4.60 (1H, t), 4.09 (3H, s), 3.79-3.68 (3H, m), 3.65-3.55 (1H, m), 3.43-3.33 (2H, m), 2.36-2.23 (1H, m), 1.62-1.53 (2H, m), 1.51-1.13 (12H, m), 0.99-0.91 (3H, m).

Intermediate 80

3-[(E/Z)-2-methoxyethenyl]tetrahydrofuran

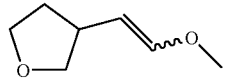

A suspension of (methoxymethyl)triphenylphosphonium chloride (13.71 g) in dry THF (40 mL) was cooled to −40° C. and a solution of potassium tert-butoxide (4.94 g) in dry THF (40 mL) was added dropwise with stirring. After 45 mins the reaction was cooled to −65° C. Meanwhile, a solution of tetrahydro-3-furancarbaldehyde (8 mL, 50% in water) was treated with brine to give a cloudy suspension. This was extracted with Et₂O (×3), and the combined organics were dried over sodium sulphate and the solution was added dropwise to the reaction at −60° C. to −65° C. The mixture was then allowed to warm to room temperature. After 30 mins the mixture was poured into water and was extracted with Et₂O (×3). The combined extracts were washed with brine, dried over sodium sulphate and stripped to give an oil. This was dissolved in a small amount of DCM and was loaded onto a silica ISCO Cartridge, and solvent was removed under reduced pressure. The crude material was purified by normal phase chromatography (ISCO) using 0-20% EtOAc/cyclohexane as eluent to give the title compound (460 mg).

¹H NMR (CDCl₃): δ 6.37 (0.75H, d), 5.92 (0.25H, d), 4.67 (0.75H, dd), 4.32 (0.25H, dd), 3.97-3.85 (2H, m), 3.84-3.75 (1H, m), 3.60 (0.75H, s), 3.52 (2.25H, s), 3.38-3.31 (1H, m), 3.28-3.19 (0.25H, m), 2.81-2.69 (0.75H, m), 2.16-2.03 (1H, m), 1.71-1.58 (1H, m), mixture of isomers in approx. 1:3 ratio.

Intermediate 81

2-(Tetrahydro-3-furanyl)ethanol

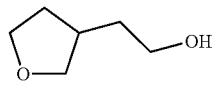

3-[(E/Z)-2-methoxyethenyl]tetrahydrofuran (460 mg) was treated with ethanol (2 mL) and 2N HCl (2 mL), and the clear solution was stirred for 4 h. The solution was heated at 50° C. for 1 h, then left at room temperature for 16 h. The acid was neutralised by adding 2N sodium hydroxide solution (2 mL) and was diluted with ethanol (3 mL). Sodium borohydride (136 mg) was added with stirring. After 3 h the solvent was stripped off and the residue was treated with brine and carefully acidified with 2N HCl. The mixture was extracted with DCM (×3), was washed with brine, dried using a hydrophobic frit and evaporated to a clear oil (200 mg). The aqueous layers were combined, saturated with solid NaCl, extracted with DCM (×3), dried using a hydrophobic frit and evaporated to give a second crop of material (100 mg). This was combined with the first crop of clear oil (200 mg), and was purified by normal phase chromatography (ISCO) using 0-20% MeOH/EtOAc as eluent to give the title compound (230 mg).

$^1$H NMR (CDCl$_3$): δ 3.98-3.83 (2H, m), 3.82-3.64 (3H, m), 3.42-3.35 (1H, m), 2.39-2.27 (1H, m), 2.14-2.03 (1H, m), 1.72-1.64 (2H, m), 1.58-1.51 (1H, m), hydroxyl proton not seen.

Intermediate 82

2-(Tetrahydro-3-furanyl)ethyl methanesulfonate

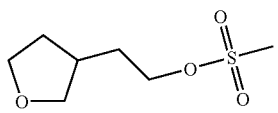

2-(Tetrahydro-3-furanyl)ethanol (230 mg) was dissolved in dry DCM (5 mL) and triethylamine (0.552 mL) was added. The stirred solution was cooled (ice bath) under nitrogen and methanesulphonyl chloride (0.199 mL) was added dropwise over 5 mins. The mixture was allowed to warm slowly to room temperature as the ice bath melted and was left for 16 h. The mixture was shaken with saturated sodium bicarbonate solution and the aqueous layer was extracted with DCM (×2). The combined organics were washed with brine, dried using a hydrophobic frit and evaporated to give the title compound (364 mg).

$^1$H NMR (CDCl$_3$): δ 4.32-4.22 (2H, m), 3.98-3.73 (4H, m), 3.44-3.37 (1H, m), 3.03 (3H, s), 2.40-2.30 (1H, m), 2.18-2.06 (1H, m), 1.95-1.79 (2H, m).

Intermediate 83

3-(2-Bromoethyl)tetrahydrofuran

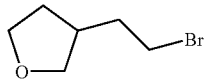

A mixture of 2-(tetrahydro-3-furanyl)ethyl methanesulfonate (364 mg) and anhydrous lithium bromide (780 mg) were refluxed with stirring in acetone (10 mL) under nitrogen for 4 h. The mixture was allowed to cool and the solvent was evaporated. The residue was treated with saturated sodium bicarbonate solution and was extracted with DCM (×3). The combined organics were washed with dilute brine, dried using a hydrophobic frit and evaporated to give the title compound (308 mg).

$^1$H NMR (CDCl$_3$): δ 3.97-3.84 (2H, m), 3.81-3.74 (1H, m), 3.46-3.36 (3H, m), 2.47-2.36 (1H, m), 2.16-2.06 (1H, m), 2.01-1.92 (2H, m), 1.56-1.49 (1H, m).

Intermediate 84

2-Butyloxy-8-methoxy-9-[2-(tetrahydro-3-furanyl)ethyl]-9H-Purin-6-amine

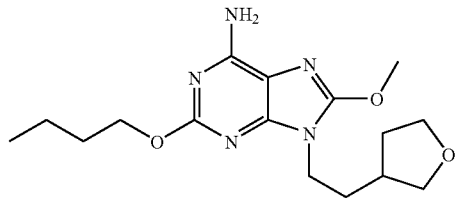

A mixture of 2-butoxy-8-methoxy-9H-purin-6-amine trifluoroacetate salt (200 mg) and potassium carbonate (236 mg) in dry DMF (2 mL) was heated at 60° C. with stirring for 1 h. 3-(2-Bromoethyl)tetrahydrofuran (123 mg) was added and the reaction was continued for 2 h. The mixture was quenched with water and extracted with EtOAc (×3). The combined organics were washed with water and brine, dried using a hydrophobic frit and evaporated to give an oil (265 mg). The crude material was purified by normal phase chromatography (ISCO) using 0-15% MeOH/EtOAc as eluent to give the title compound (102 mg).

MS calcd for (C$_{16}$H$_{25}$N$_5$O$_3$)$^+$=335

MS found (electrospray): (M+H)$^+$=336

$^1$H NMR (CDCl$_3$): δ 5.15 (2H, br), 4.32-4.24 (2H, m), 4.12 (3H, s), 3.99-3.94 (2H, m), 3.93-3.82 (2H, m), 3.77-3.69 (1H, m), 3.39 (1H, dd), 2.19-2.06 (2H, m), 1.90-1.72 (4H, m), 1.59-1.45 (3H, m), 0.97 (3H, t).

Intermediate 85

Tetrahydro-2H-pyran-3-ylmethyl methanesulfonate

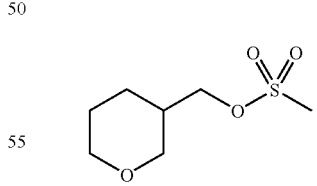

To tetrahydro-2H-pyran-3-ylmethanol (4.92 g) in dry dichloromethane (140 ml) at 0° C. and under nitrogen, was added anhydrous triethylamine (13.6 ml) in one go, followed by mesyl chloride (4.3 ml) dropwise over 5 minutes. The reaction was allowed to warm to room temperature and stirred at this temperature overnight. The reaction was quenched with saturated aqueous sodium bicarbonate (50 ml). The organic layer was separated, passed through a hydrophobic frit to dry and concentrated in vacuo to yield a red oil (8.8 g).

¹H NMR (CDCl₃): δ 4.18-4.08 (2H, m), 3.94-3.88 (1H, m), 3.81 (1H, m), 3.51-3.43 (1H, m), 3.37-3.31 (1H, m), 3.01 (3H, s), 2.07 (1H, m), 1.85 (1H, m), 1.72-1.56 (2H, m), 1.47-1.36 (1H, m).

Intermediate 86

Tetrahydro-2H-pyran-4-ylmethyl methanesulfonate

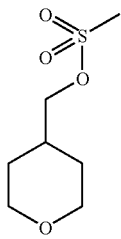

To tetrahydro-2H-pyran-4-ylmethanol (6.2 g) in dry dichloromethane (226.3 ml) at 0° C. and under nitrogen, was added triethylamine (18.1 ml), followed by mesyl chloride (5.4 ml). The reaction was allowed to warm to room temperature and left at this temperature overnight. The reaction mixture was washed with saturated aqueous sodium bicarbonate (200 ml). The organic layer was separated, passed through a hydrophobic frit to dry and concentrated in vacuo to yield a light brown lumpy solid (10.17 g).

¹H NMR (DMSO): δ 4.06 (2H, d), 3.85 (2H, m), 3.35-3.25 (1H, m), 3.17 (3H, s), 2.50 (1H, m), 2.00-1.87 (1H, m), 1.58 (2H, m), 1.32-1.20 (2H, m).

Intermediate 87

N²-Butyl-8-(methoxy)-9-[2-(tetrahydro-2H-pyran-2-yl)ethyl]-9H-Purine-2,6-diamine

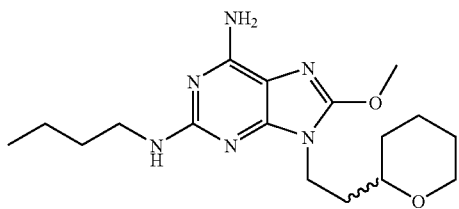

A mixture of N²-butyl-8-methoxy-9H-purine-2,6-diamine trifluoroacetic acid salt (200 mg) and potassium carbonate (236 mg) in dry DMF (2 mL) were heated at 60° C. with stirring for 1 h. 2-(Tetrahydro-2H-pyran-2-yl)ethyl methanesulfonate (142 mg) was added and the reaction was continued for 3 h at 60° C. The mixture was quenched with water and extracted with EtOAc (×3). The combined organics were washed with water and brine, dried using a hydrophobic frit and evaporated to give crude material (250 mg). The material was purified by C₁₈ reverse phase chromatography using water (containing 0.1% formic acid)-acetonitrile (containing 0.05% formic acid) as eluent (20-60%) and the appropriate fractions combined and evaporated to remove acetonitrile. The remaining aqueous mixture was made basic with saturated sodium hydrogen carbonate, extracted three times with dichloromethane and the combined extracts dried by passing through a phase separation cartridge then evaporated to give 75 mg of material which was recrystallised from ether/light petrol yielding the title compound as a solid, 54 mg.

¹H NMR (CDCl₃): δ 4.92 (2H, s), 4.59 (1H, m), 4.10 (3H, s), 3.99 (3H, m), 3.38 (3H, m), 3.25 (1H, m), 1.93-1.37 (11H, m), 1.37-1.23 (1H, m), 0.96 (3H, t).

Intermediate 88

N²-Butyl-8-(methoxy)-9-[2-(tetrahydro-3-furanyl)ethyl]-9H-Purine-2,6-diamine

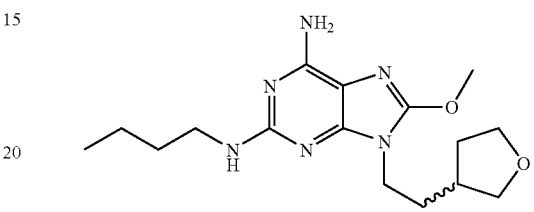

A mixture of N²-butyl-8-methoxy-9H-purine-2,6-diamine trifluoroacetic acid salt, (200 mg) and potassium carbonate (236 mg) in dry DMF (2 mL) were heated at 60° C. with stirring for 1 h. 3-(2-Bromoethyl)tetrahydrofuran, Intermediate 83 (123 mg) was added and the reaction was continued for 2 h at 60° C. The mixture was quenched with water and extracted with EtOAc (×3). The combined organics were washed with water and brine, dried using a hydrophobic frit and evaporated to an oil (261 mg). This material was purified by flash chromatography (silica, 5-20% methanol:ethyl acetate) and the appropriate fractions combined and evaporated to give the title compound, yield 181 mg.

MS calcd for (C₁₆H₂₆N₆O₂)=334
MS found (electrospray): (M+H)⁺=335
¹H NMR (CDCl₃): δ 4.96 (2H, s), 4.60 (1H, br.t), 4.10 (3H, s), 3.88 (4H, m), 3.73 (1H, m), 3.38 (3H, m), 2.12 (1H, m), 1.85 (3H, m), 1.57 (3H, m), 1.41 (2H, m), 0.95 (3H, t).

Intermediate 89 and Intermediate 90

2-Butoxy-8-methoxy-9-(tetrahydrofuran-3-ylmethyl)-9H-purin-6-amine enantiomers

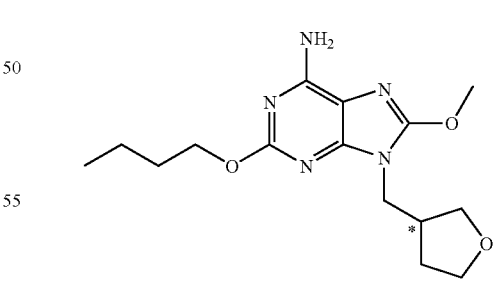

2-Butoxy-8-methoxy-9-(tetrahydrofuran-3-ylmethyl)-9H-purin-6-amine (0.5 gm) was separated into its respective enantiomers using a Chiralpak AD 1"×25 cm column, eluting with heptane:IPA 90:10. Fractions containing the faster eluting material were combined and evaporated to a solid to yield isomer 1, Intermediate 89, 176 mg.

MS calcd for (C₁₅H₂₃N₅O₃)⁺=321
MS found (electrospray): (M+H)⁺=322

1H NMR (CDCl$_3$): 5.20 (2H, s), 4.28 (2H, t), 4.13 (3H, s), 4.01-3.89 (3H, overlapping m), 3.77 (2H, m), 3.64 (1H, m), 2.85 (1H, m), 1.97 (1H, m), 1.81-1.67 (3H, overlapping m), 1.50 (2H, m), 0.96 (3H, t). Fractions containing the slower eluting material were combined and evaporated to a solid to yield isomer 2, Intermediate 90 178 mg.

MS calcd for $(C_{15}H_{23}N_5O_3)^+$=321
MS found (electrospray): (M+H)$^+$=322 1H NMR (CDCl$_3$): 5.15 (2H, s), 4.27 (2H, t), 4.13 (3H, s), 4.01-3.89 (3H, overlapping m), 3.77 (2H, m), 3.64 (1H, m), 2.85 (1H, m), 1.97 (1H, m), 1.81-1.67 (3H, overlapping m), 1.50 (2H, m), 0.96 (3H, t).

Intermediate 89, Alternative Procedure 2-(Butyloxy)-8-(methyloxy)-9-(tetrahydro-3-furanylmethyl)-9H-purin-6-amine (Isomer 1)

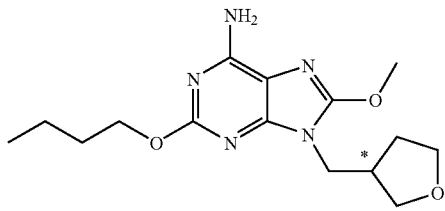

A stirring mixture of N$^2$-butyl-8-methoxy-9H-purine-2,6-diamine trifluoroacetic acid salt (3.25 gm) and potassium carbonate (3.83 gm) in dry N,N-dimethylformamide (30 ml) was heated with stirring at 60° C. for 1 h. Tetrahydro-3-furanylmethyl methanesulfonate (2 gm, Isomer 1) was added and the stirring mixture heated at 90° C. for 3 h. The solvent was evaporated, water was added and the mixture extracted three times with ethyl acetate. The combined extracts were washed with water then brine, dried by passing through a hydrophobic frit and stripped to give an orange solid. This was purified by C$_{18}$ reverse phase chromatography using water (0.1% formic acid)-acetonitrile (0.05% formic acid) as eluent (20-60%) and the appropriate fractions combined and evaporated to give the title compound as a light orange solid, yield 1.56 gm.

MS calcd for $(C_{15}H_{23}N_5O_3)^+$=321
MS found (electrospray): (M+H)$^+$=322

Intermediate 90, Alternative Procedure 2-(Butyloxy)-8-(methoxy)-9-(tetrahydro-3-furanylmethyl)-9H-purin-6-amine (Isomer 2)

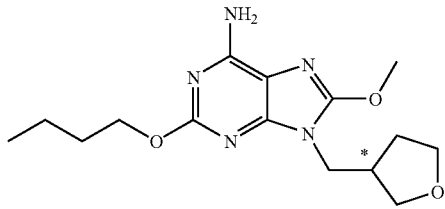

A stirring mixture of N$^2$-butyl-8-methoxy-9H-purine-2,6-diamine trifluoroacetic acid salt (3.25 gm) and potassium carbonate (3.83 gm) in dry N,N-dimethylformamide (30 ml) was heated with stirring at 60° C. for 1 h. Tetrahydro-3-furanylmethyl methanesulfonate (2 gm, Isomer 2) was added and the stirring mixture heated at 90° C. for 3 h. The solvent was evaporated, water was added and the mixture extracted three times with ethyl acetate. The combined extracts were washed with water then brine, dried by passing through a hydrophobic frit and stripped to give an orange solid. This was purified by C$_{18}$ reverse phase chromatography using water (0.1% formic acid)-acetonitrile (0.05% formic acid) as eluent (20-60%) and the appropriate fractions combined and evaporated to give the title compound as a light orange solid, yield 2.2 gm.

MS calcd for $(C_{15}H_{23}N_5O_3)^+$=321
MS found (electrospray): (M+H)$^+$=322

Intermediate 91

2-{[2-(Ethyloxy)ethyl]oxy}-9-(tetrahydro-2H-pyran-2-yl)-9H-purin-6-amine

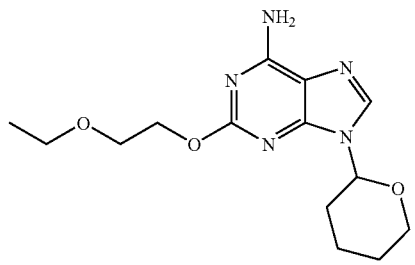

To a stirred solution of potassium t.butoxide (9.3 g, 82.8 mmol) in 1-ethoxy-2-ethanol (70 ml) was added 2-chloro-9-(tetrahydro-2H-pyran-2-yl)-9H-purin-6-amine (7 g, 27.6 mmol). The mixture was heated to 80-90° C. for 2 h. Then most of the solvent was removed by evaporation under reduced pressure. The residue was partitioned between water and dichloromethane. The dichloromethane layer was separated, concentrated to give a light brown solid, which was washed with petroleum ether, dried in vacuo (7.8 g, 92%).

1H NMR (CDCl$_3$): 7.86 (1H, s), 6.0-5.8 (2H, br.s), 5.61 (1H, d), 4.49 (2H, m), 4.3-4.1 (1H, m), 3.80 (2H, t), 3.8-3.7 (1H, m), 3.60 (2H, t), 2.15-1.9 (3H, m), 1.85-1.55 (3H, m), 1.23 (3H, t). Impurity peaks at 3.75, 3.55, 1.2, 0.85.

Intermediate 92

8-Bromo-2-{[2-(ethyoxy)ethyl]oxy}-9-(tetrahydro-2H-pyran-2-yl)-9H-purin-6-amine

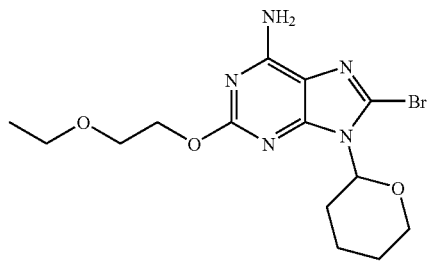

To a stirred solution of 2-{[2-(ethyloxy)ethyl]oxy}-9-(tetrahydro-2H-pyran-2-yl)-9H-purin-6-amine (7.8 g, 25.4 mmol) in dichloromethane (100 ml) and NBS (5 g, 27.9 mmol) added with stirring. After 2 h, the solvent was removed. The product was purified through a silica column using petroleum ether: ethyl acetate 2:1 as eluent, which was a pale yellow solid (7.8 g, 79.6%).

1H NMR (CDCl$_3$): 5.9-5.7 (2H, br.s), 5.57 (1H, d), 4.55-4.4 (2H, m), 4.2-4.1 (1H, m), 3.78 (2H, t), 3.75-3.6 (1H, m), 3.58 (2H, q), 2.9-3.1 (1H, m), 2.15-2.0 (1H, m), 1.9-1.5 (4H, m), 1.21 (3H, t).

Intermediate 93

2-{[2-(Ethyloxy)ethyl]oxy}-8-(methyloxy)-9-(tetrahydro-2H-pyran-2-yl)-9H-Purin-6-amine

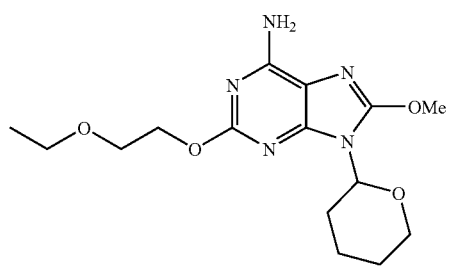

Sodium (1.25 g, 54.4 mmol) was dissolved in methanol (40 ml). After 10 min, 8-bromo-2-{[2-(ethyloxy)ethyl]oxy}-9-(tetrahydro-2H-pyran-2-yl)-9H-purin-6-amine (7 g, 18 mmol) was added with stirring. The mixture was heated to reflux for 2 h. The solvent was removed. The residue on a silica column using DCM: MeOH 100:1 as eluent to give the product as a yellow solid (4.78 g, 78.4%).

1H NMR (CD$_3$OD): 5.6-5.5 (1H, m), 4.55-4.4 (2H, m), 4.18 (3H, s), 4.15-4.05 (1H, m), 3.9-3.8 (2H, 2×m), 3.8-3.7 (1H, m), 3.7-3.6 (2H, q), 2.9-2.75 (1H, m), 2.15-2.05 (1H, m), 1.9-1.55 (4H, m), 1.25 (3H, t). Exchangeable protons not observed.

Intermediate 94

2-{[2-(Ethyloxy)ethyl]oxy}-8-(methyloxy)-1H-Purin-6-amine trifluoroacetic acid salt

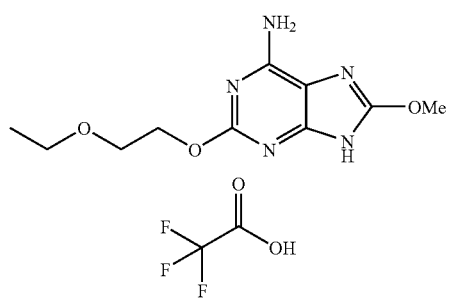

2-{[2-(Ethyloxy)ethyl]oxy}-8-(methyloxy)-9-(tetrahydro-2H-pyran-2-yl)-9H-purin-6-amine (4.78 g, 14.2 mmol) was dissolved in MeOH (30 ml) and TFA (7.5 ml) was added with stirring at 0° C. The mixture was left standing at room temperature for 1 day. A white solid was formed. The solid was filtered off and washed with ethyl acetate and dried in vacuo. This gave product (4 g, 80.5%).

1H NMR (CD$_3$OD): 4.6-4.55 (2H, m), 4.15 (3H, s), 3.85-3.75 (2H, m), 3.37 (2H, q), 1.18 (3H, d). Exchangeable protons not observed.

Intermediate 95

2-(2-Ethoxyethoxy)-8-methoxy-9-(tetrahydro-2H-pyran-4-ylmethyl)-9H-purin-6-amine

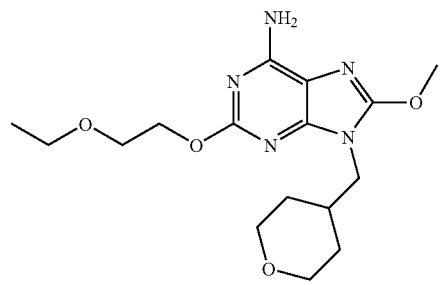

To a solution of 2-[2-(ethyloxy)ethyl]oxy-8-(methoxy)-9H-purin-6-amine trifluoroacetic acid salt (500 mg) in dry N,N-dimethylformamide (4.5 ml) at room temperature and under nitrogen was added potassium carbonate (0.75 g) in one go. The reaction was stirred at 60° C. for 1.5 hours. Tetrahydro-2H-pyran-4-ylmethyl methanesulfonate (0.29 g) was added in one portion and the reaction heated at 90° C. for 3 hours. The reaction was cooled to room temperature and then diluted with ethyl acetate (20 ml) and washed with water (15 ml). The organic layer was dried over magnesium sulphate, filtered and concentrated in vacuo. The product was purified by C$_{18}$ reverse phase chromatography using water (containing 0.1% formic acid)-acetonitrile (containing 0.05% formic acid) as eluent (10-45%) to afford the title compound as a white solid (240 mg).

MS calcd for (C$_{16}$H$_{25}$N$_5$O$_4$)$^+$=351
MS found (electrospray): (M+H)$^+$=352
$^1$H NMR((CD$_3$)$_2$SO): δ 6.81 (2H, s), 4.27 (2H, m), 4.05 (3H, s), 3.81 (2H, m), 3.73 (2H, d), 3.64 (2H, m), 3.48 (2H, q), 3.22 (2H, m), 2.01 (1H, m), 1.41 (2H, m), 1.23 (2H, m), 1.12 (3H, t).

Intermediate 96

2-{[2-(Ethyloxy)ethyl]oxy}-8-(methoxy)-9-(tetrahydro-2H-pyran-3-ylmethyl)-9H-Purin-6-amine

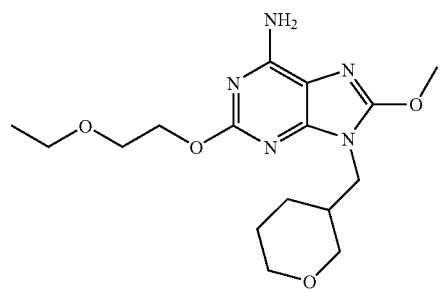

To a solution of 2-{[2-(ethyloxy)ethyl]oxy}-8-(methoxy)-9H-purin-6-amine trifluoroacetic acid salt (500 mg) in dry N,N-dimethylformamide (6.0 ml) at room temperature and under nitrogen was added potassium carbonate (0.75 g) in one go. The reaction was stirred at 60° C. for 1.5 hours. A solution of tetrahydro-2H-pyran-3-ylmethyl methanesulfonate (0.29 g) in dry N,N-dimethylformamide (1.0 ml) was added in one go and the reaction heated at 90° C. for 2 hours. The reaction was cooled to room temperature and then diluted with ethyl acetate (20 ml) and washed with water (10 ml). The organic layer was concentrated in vacuo. The product was purified by $C_{18}$ reverse phase chromatography using water (containing 0.1% formic acid)-acetonitrile (containing 0.05% formic acid) as eluant (10-60%) to afford the title compound as a clear viscous oil that crystallises at room temperature (245 mg).

MS calcd for $(C_{16}H_{25}N_5O_4)^+=351$
MS found (electrospray): $(M+H)^+=352$ Intermediate 97

2-{[1-Methyl-2-(methoxy)ethyl]oxy}-9-(tetrahydro-2H-pyran-2-yl)-9H-purin-6-amine

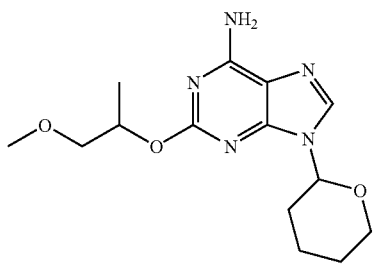

To a stirred solution of potassium t.butoxide (9.3 g, 82.8 mmol) in 1-methoxy-2-propanol (70 ml) was added 2-chloro-9-(tetrahydro-2H-pyran-2-yl)-9H-purin-6-amine (7 g, 27.6 mmol). The mixture was heated to 80-90° C. for 4 h. Then most of the solvent was removed by evaporation under reduced pressure. The residue was partitioned between water and dichloromethane. The dichloromethane layer was separated, concentrated to give a brown oil (7.2 g, 84.7%).

1H NMR (CDCl$_3$): 7.84 (1H, s), 5.8-5.55 (2H, br.s+1H, m), 5.45-5.3 (1H, m), 4.2-4.05 (1H, m), 3.8-3.6 (2H, 2×m), 3.5-3.42 (1H, m), 3.40 (3H, s), 2.1-1.9 (3H, m), 1.8-1.55 (3H, m), 1.35 (3H, dd). Impurity peaks at 5.05, 3.38, 1.21, 1.12.

Intermediate 98

8-Bromo-2-{[1-methyl-2-(methoxy)ethyl]oxy}-9-(tetrahydro-2H-Pyran-2-yl)-9H-purin-6-amine

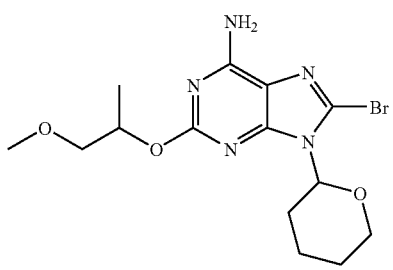

To a stirred solution of 2-{[1-methyl-2-(methoxy)ethyl]oxy}-9-(tetrahydro-2H-pyran-2-yl)-9H-purin-6-amine (7.2 g, 23.4 mmol) in dichloromethane (100 ml) was added NBS (4.6 g, 25.8 mmol). After 4 h, the solvent was removed. The product was purified on a silica column using petroleum ether: ethyl acetate 2:1 as eluent. This gave the product (7.3 g, 81.1%).

1H NMR (CDCl$_3$): 5.9-5.65 (2H, br.s), 5.65-5.55 (1H, m), 5.4-5.2 (1H, m), 4.2-4.05 (1H, m), 3.8-3.6 (2H, m), 3.55-3.42 (1H, m), 3.40 (3H, 2×s), 2.9-3.1 (1H, m), 2.15-2.0 (1H, m), 1.9-1.5 (4H, m), 1.37 (3H, dd).

Intermediate 99

2-{[1-Methyl-2-(methoxy)ethyl]oxy}-8-(methoxy)-9-(tetra hydro-2H-Pyran-2-yl)-9H-purin-6-amine

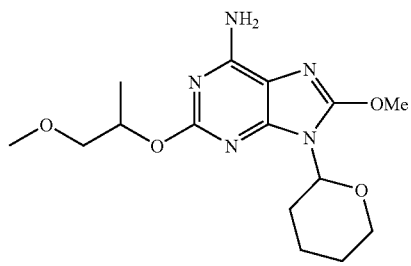

Sodium (1.16 g, 50.5 mmol) was dissolved in methanol (40 ml) and 8-bromo-2-{[1-methyl-2-(methoxy)ethyl]oxy}-9-(tetrahydro-2H-pyran-2-yl)-9H-purin-6-amine (6.5 g, 16.8 mmol) added with stirring. The mixture was heated to reflux for 2 h. The solvent was removed by evaporation. The residue was purified on a silica column using DCM: MeOH 150:1 as eluent. This gave product (4.7 g, 82.9%).

1H NMR (CD$_3$OD): 5.6-5.5 (1H, m), 5.4-5.3 (1H, m), 4.20 (3H, s), 4.2-4.1 (1H, m), 3.8-3.6 (2H, 2×m), 3.6-3.5 (1H, m), 3.45 (3H, 2×s), 2.95-2.8 (1H, m), 2.2-2.05 (1H, m), 1.9-1.6 (4H, m), 1.40 (3H, dd). Exchangeable protons not observed.

Intermediate 100

2-{[1-Methyl-2-(methoxy)ethyl]oxy}-8-(methoxy)-9H-purin-6-amine trifluoroacetic acid salt

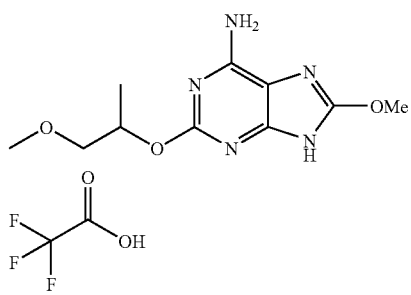

TFA (7.5 ml) was added to a solution of 2-{[1-methyl-2-(methoxy)ethyl]oxy}-8-(methoxy)-9-(tetrahydro-2H-pyran-2-yl)-9H-purin-6-amine (4.7 g, 13.9 mmol) in MeOH (30 ml) with stirring. The mixture was left to stand at room temperature for 1 day. A white solid formed which was filtered off and washed with ethyl acetate. This gave product (3.7 g, 76.1%)

1H NMR (CD$_3$OD): 5.55-5.4 (1H, m), 4.16 (3H, s), 3.7-3.55 (2H, m), 3.39 (3H, s), 1.40 (3H, d). Exchangeable protons not observed.

Intermediate 101

2-{[1-Methyl-2-(methoxy)ethyl]oxy}-8-(methoxy)-9-(tetrahydro-2H-Pyran-4-ylmethyl)-9H-purin-6-amine

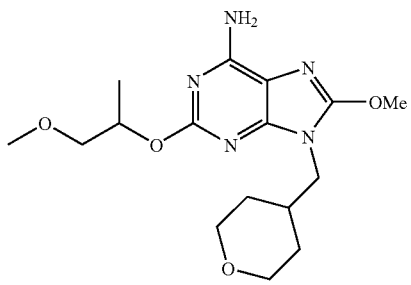

To a solution of 2-{[1-methyl-2-(methoxy)ethyl]oxy}-8-(methoxy)-9H-purin-6-amine trifluoroacetic acid salt (500 mg) in dry N,N-dimethylformamide (4.5 ml) at room temperature and under nitrogen was added potassium carbonate (0.75 g) in one go. The reaction was stirred at 60° C. for 1.5 hours. Tetrahydro-2H-pyran-4-ylmethyl methanesulfonate (0.29 g) was added in one go and the reaction heated at 90° C. for 3 hours. The reaction was cooled to room temperature and then diluted with ethyl acetate (20 ml) and washed with water (15 ml). The organic layer was dried over magnesium sulphate, filtered and concentrated in vacuo. The product was purified by C$_{18}$ reverse phase chromatography using water (containing 0.1% formic acid)-acetonitrile (containing 0.05% formic acid) as eluant (10-45%) to afford the title compound as a viscous clear oil (260 mg).

MS calcd for (C$_{16}$H$_{25}$N$_5$O$_4$)$^+$=351
MS found (electrospray): (M+H)$^+$=352.

1H NMR((CD$_3$)$_2$SO): δ 6.77 (2H, s), 5.16 (1H, m), 4.05 (3H, s), 3.81 (2H, m), 3.72 (2H, d), 3.48 (2H, m), 3.28 (3H, s), 3.22 (2H, m), 2.01 (1H, m), 1.41 (2H, m), 1.24 (2H, m), 1.21 (3H, d).

Intermediate 102

2-{[1-Methyl-2-(methyloxy)ethyl]oxy}-8-(methoxy)-9-(tetrahydro-2H-pyran-3-ylmethyl)-9H-purin-6-amine

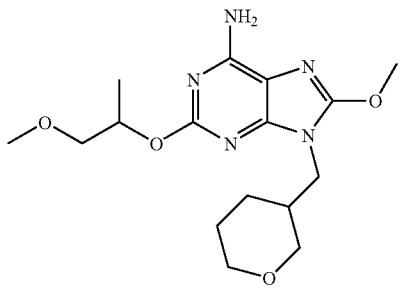

To a solution of 2-{[1-methyl-2-(methoxy)ethyl]oxy}-8-(methoxy)-9H-purin-6-amine trifluoroacetic acid salt (500 mg) in dry N,N-dimethylformamide (6.0 ml) at room temperature and under nitrogen was added potassium carbonate (0.75 g) in one go. The reaction was stirred at 60° C. for 1.5 hours. A solution of tetrahydro-2H-pyran-3-ylmethyl methanesulfonate (0.29 g) in dry N,N-dimethylformamide (1.0 ml) was added in one go and the reaction heated at 90° C. for 2 hours. The reaction was cooled to room temperature and then diluted with ethyl acetate (20 ml) and washed with water (10 ml). The organic layer was concentrated in vacuo. The product was purified by C$_{18}$ reverse phase chromatography using water (containing 0.1% formic acid)-acetonitrile (containing 0.05% formic acid) as eluant (10-60%) to afford the title compound as a clear viscous oil (300 mg).

MS calcd for (C$_{16}$H$_{25}$N$_5$O$_4$)$^+$=351
MS found (electrospray): (M+H)$^+$=352

Intermediate 103

(2-Cyclopropylethyl)amine

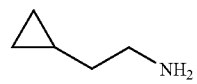

To a 1.0M solution of lithium aluminium hydride in diethyl ether (40 ml) at 0° C. was added dropwise concentrated sulphuric acid (1.09 ml) over 12 minutes. The reaction was warmed to RT and stirred for 1 hour. A solution of cyclopropylacetonitrile (1.06 g) in diethyl ether (5 ml) was added to dropwise to the reaction over 10 minutes. The reaction was heated to reflux for 2 hours, cooled to 0° C. and quenched with slow addition of water. A solution of sodium hydroxide (2 g) in water (18 ml) was added and the organic phase decanted from the resulting white precipitate. The precipitate was rinsed with diethyl ether (2×20 ml). The combined organics were concentrated in vacuo (30° C., 300 mbar) to afford the title compound as a colourless oil (1.10 g).

$^1$H NMR((CD$_3$)$_2$SO): δ 2.58 (2H, t), 1.23 (2H, q), 0.68 (1H, m), 0.36 (2H, m), −0.01 (2H, m). NH$_2$ protons not observed.

Intermediate 104

Cyclopentylmethylamine

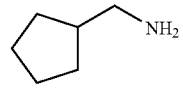

To a 1.0M solution of lithium aluminium hydride in dry diethyl ether (27 ml) at RT was added a solution of cyclopentanecarbonitrile (2 g) in dry diethyl ether (10 ml) dropwise over 10 minutes. The purple solution was stirred at RT for 24 hours. The resulting pink solution was cooled to 0° C. and 5.0M sodium hydroxide solution (10 ml) was added slowly until effervescence ceased. The reaction was filtered from the white precipitate that had formed. The filtrate was dried over magnesium sulphate, filtered and concentrated in vacuo (RT, 200 mbar) to afford the title compound as a clear oil (1.6 g).

$^1$H NMR((CD$_3$)$_2$SO): δ 2.63 (2H, d), 1.92 (1H, m), 1.77 (2H, m), 1.57 (4H, m), 1.18 (2H, m). NH$_2$ protons not observed.

Intermediate 105

8-Bromo-N$^2$-(cyclopentylmethyl)-9-(tetrahydro-2H-pyran-4-ylmethyl)-9H-Purine-2,6-diamine

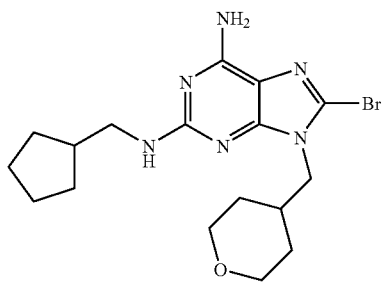

A solution of 2-chloro-9-(tetrahydro-2H-pyran-4-ylmethyl)-9H-purin-6-amine (150 mg) in cyclopentylamine (276 mg) was heated in the microwave at 170° C. for two minutes. The reaction mixture was concentrated in vacuo. To the resulting yellow residue in dry chloroform (2 mL) at room temperature, was added NBS (120 mg) in one go. The reaction was stirred at RT for 10 minutes. More NBS (150 mg) was added and the reaction stirred for an additional 30 minutes at RT. The reaction was concentrated in vacuo and the product was purified by C$_{18}$ reverse phase chromatography using water (containing 0.1% formic acid)-acetonitrile (containing 0.05% formic acid) as eluant (20-60%) to afford the title compound as a white solid (40 mg).

MS calcd for (C$_{17}$H$_{25}$BrN$_6$O)$^+$=409/410
MS found (electrospray): (M+H)$^+$=410/411

Intermediate 106

N$^2$-(Cyclohexylmethyl)-9-(tetrahydro-2H-pyran-4-ylmethyl)-9H-Purine-2,6-diamine

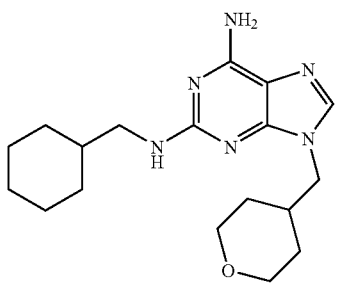

A solution of 2-chloro-9-(tetrahydro-2H-pyran-4-ylmethyl)-9H-purin-6-amine (150 mg) in cyclohexylamine (363 ul) was heated in the microwave at 170° C. for five minutes. The crude reaction mixture was subjected to C$_{18}$ reverse phase chromatography using water (containing 0.1% formic acid)-acetonitrile (containing 0.05% formic acid) as eluant (20-60%) to afford a white solid (98 mg).

MS calcd for (C$_{18}$H$_{28}$N$_6$O)$^+$=344
MS found (electrospray): (M+H)$^+$=345

$^1$H NMR((CD$_3$)$_2$SO): δ 7.64 (1H, s), 6.54 (2H, s), 6.20 (1H, m), 3.84 (4H, m), 3.21 (2H, m), 3.08 (2H, m), 2.09 (1H, m), 1.78-1.52 (6H, m), 1.40 (2H, m), 1.30-1.10 (5H, m), 0.89 (2H, m).

Intermediate 107

8-Bromo-N$^2$-(cyclohexylmethyl)-9-(tetrahydro-2H-Pyran-4-ylmethyl)-9H-Purine-2,6-diamine

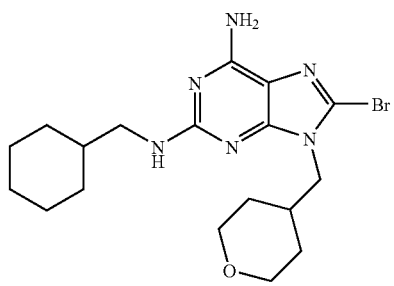

To a solution of N$^2$-(cyclohexylmethyl)-9-(tetrahydro-2H-pyran-4-ylmethyl)-9H-purine-2,6-diamine (90 mg) in dry chloroform (1 mL) at room temperature was added NBS (46 mg) in one go. The dark brown reaction was stirred at RT for 1 hour. The reaction was diluted with DCM (15 mL) and washed with water (5 mL). The organics were passed through a hydrophobic frit and concentrated in vacuo.

MS calcd for (C$_{18}$H$_{27}$BrN$_6$O)$^+$=422/424
MS found (electrospray): (M+H)$^+$=423/425

Intermediate 108

Tetrahydro-2H-pyran-4-ylmethanol

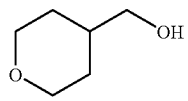

Methyl tetrahydro-2H-pyran carboxylate (SC/143233, Aldrich) (5.0 g) in dry THF (10 mL) was added drop wise to a cooled solution of 1M lithium aluminium hydride in THF (32 mL), keeping the temperature below 10° C. On completion of the addition, the exotherm was allowed to subside before allowing the reaction mixture to warm to room temperature. The reaction was then stirred for 2 hours. The reaction was quenched with water (2 mL) added very carefully and with cooling, followed by 2N sodium hydroxide (2 mL). To resultant suspension was then added water (100 mL) and then extracted with dichloromethane (100 mL, 3 times). The organic layer was separated, combined and dried by passing through a hydrophobic frit. The organic was evaporated under reduced pressure to give colourless mobile oil that was then placed under high vacuo for 30 minutes at room temperature.

This gave the title compound as colourless mobile oil (2.4367 g).

1H NMR (CDCl$_3$): 4.04-3.96 (2H, m), 3.54-3.47 (2H, m), 3.46-3.36 (2H, m), 1.82-1.61 (3H, m), 1.57-1.50 (1H, m), 1.40-1.27 (2H, m)

Intermediate 109

2,6-Dichloro-9-(tetrahydro-2H-pyran-4-ylmethyl)-9H-purine

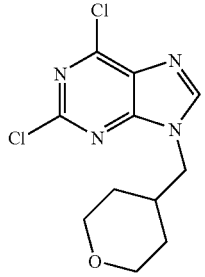

A mixture of tetrahydro-2H-pyran-4-ylmethanol (2.44 g) and 2,6-dichloropurine (1.97 g) was dissolved in dry THF (25 mL). To this solution was added triphenylphosphine (5.51 g), followed by diisopropyl azodicarboxylate (4.14 mL) added drop wise. The temperature of the reaction was kept below 43° C. (some cooling with a water bath was required). The reaction was stirred overnight at ambient temperature before being quenched with water (100 mL) and extracted into ethyl acetate (50 mL, twice). The separated and combined organic layer was then washed with water (100 mL). The organic layer was separated and then dried by passing through a hydrophobic frit before evaporation under reduced pressure to give pale yellow viscous oil. The material was partially purified by silica chromatography (ISCO) using 0-100% ethyl acetate: cyclohexane.

The desired product eluted as two peaks. Peak 1 eluted at 70% ethyl acetate: cyclohexane. Peak 2 eluted with 100% ethyl acetate.

NMR (CD$_3$OD) showed both batches were identical with the exception that the second peak contained marginally more triphenylphosphine oxide as impurity.

Peak 1: 1H NMR (CD$_3$OD): 8.56 (1H, s), 4.24-4.20 (2H, m), 3.96-3.90 (2H, m), 3.42-3.33 (2H, m), 2.30-2.17 (1H, m), 1.55-1.34 (5H, overlapping m). [7.69-7.52 (15H, overlapping m)-triphenylphosphine oxide impurity]. Title compound:triphenylphosphine oxide impurity (1:0.92).

Peak 2: 1H NMR (CD$_3$OD): $^1$H NMR (CD$_3$OD): 8.56 (1H, s), 4.24-4.20 (2H, m), 3.96-3.90 (2H, m), 3.42-3.33 (2H, m), 2.30-2.17 (1H, m), 1.55-1.34 (5H, overlapping m). [7.69-7.52 (15H, overlapping m)—triphenylphosphine oxide impurity]. Title compound:triphenylphosphine oxide impurity (1:0.54).

Both batches were combined to give the title compound (3.0833 g, crude) and triphenylphosphine as impurity MS calcd for (C$_{11}$H$_{12}$Cl$_2$N$_4$O)$^+$=286, 288, 290
MS found (electrospray): (M+H)$^+$=287, 289, 291

Intermediate 110

2-Chloro-9-(tetrahydro-2H-pyran-4-ylmethyl)-9H-purin-6-amine

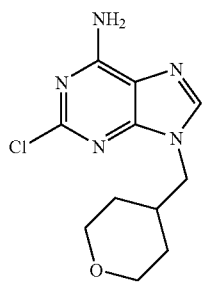

2,6-dichloro-9-(tetrahydro-2H-pyran-4-ylmethyl)-9H-purine (3.08 g, containing triphenylphosphine oxide) was heated with 2M ammonia in IPA (50 mL) at 50° C., overnight. The reaction mixture was then evaporated to dryness to give a yellow solid. This material (3.2089 g) was recrystallised using methanol (50 mL) and after cooling the resultant solid was filtered and washed with methanol (5 mL) to give the title compound (1.5554 g). The filtrate was evaporated and recrystallised from methanol (25 mL) and after cooling the resultant solid was filtered to give a second crop (0.2324 g) and was consistent with first batch by NMR and LCMS.

1H NMR (CD$_3$OD): 8.06 (1H, s), 4.10-4.05 (2H, m), 3.96-3.88 (2H, m), 3.41-3.32 (2H, m), 2.23-2.10 (1H, m), 1.53-1.45 (2H, m), 1.43-1.30 (2H, m) (NH$_2$ exchanged).
MS calcd for (C$_{11}$H$_{14}$ClN$_5$O)$^+$=267, 269
MS found (electrospray): (M+H)$^+$=268, 270

Intermediate 111

2-[(2-Methylpropyl)oxy]-9-(tetrahydro-2H-pyran-4-ylmethyl)-9H-Purin-6-amine

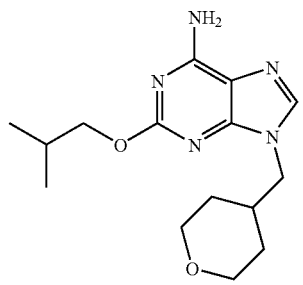

2-Chloro-9-(tetrahydro-2H-pyran-4-ylmethyl)-9H-purin-6-amine (0.20 g) was added to a suspension of 2-methyl-1-propanol (2 mL) and sodium tert-butoxide (0.288 g). The mixture was heated in a microwave for 30 minutes at 105° C. The reaction mixture was washed with water after diluting with ethyl acetate (50 mL). The organic was separated and dried by passing through a hydrophobic frit before volatiles were stripped off under reduced pressure to give a pinkish solid. This material was triturated with diethyl ether and filtered to give the title compound as a pinkish solid (91.1 mg).

1H NMR((CD$_3$)$_2$SO): 7.89 (1H, s), 7.14 (2H, broad s), 4.02-3.90 (4H, m), 3.85-3.76 (2H, m), 3.31-3.13 (2H, m), 2.15-1.92 (2H, slightly overlapping m's), 1.43-1.35 (2H, m), 1.29-1.16 (2H, m), 1.00-0.92 (6H, m).

MS calcd for (C$_{15}$H$_{23}$N$_5$O$_2$)$^+$=305
MS found (electrospray): (M+H)$^+$=306

Intermediate 112

8-Bromo-2-[(2-methylpropyl)oxy]-9-(tetrahydro-2H-pyran-4-ylmethyl)-9H-Purin-6-amine

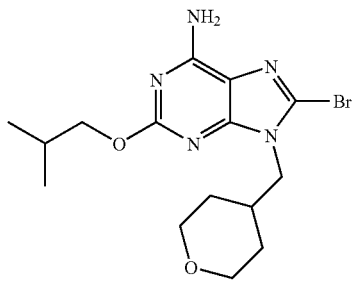

2-[(2-Methylpropyl)oxy]-9-(tetrahydro-2H-pyran-4-ylmethyl)-9H-purin-6-amine (88 mg) was dissolved in glacial acetic acid (1.5 mL) before adding sodium acetate (355 mg). The above was then cooled in an ice-bath before bromine (0.2 mL) which was added gradually. The reaction mixture was warmed to room temperature before being heated to 70° C. (external temperature) for 4 hours. The reaction mixture was quenched with 10% (w/v) sodium thiosulphate solution (to a pale yellow colour with no further change) and then the pH was adjusted to 6-7 by the addition of 2M sodium hydroxide. This was then extracted into ethyl acetate (20 mL, 3 times). The organic layer was separated, combined and dried by passing through a hydrophobic frit. The organic layer was evaporated under reduced pressure and then azeotroped with toluene to give the title compound as a pale yellow solid (0.10 g). This material then used in the next stage without the need for purification 1H NMR (CD$_3$OD): 4.11-4.07 (2H, m), 4.05-4.01 (2H, m), 3.96-3.86 (2H, m), 3.40-3.25 (2H, m) (slightly obscured by residual protons CHD$_2$OD), 2.29-2.16 (1H, m), 2.14-2.00 (1H, m), 1.55-1.37 (4H, m), 1.06-0.90 (6H, m) (NH2 exchanged).

MS calcd for (C$_{15}$H$_{22}$BrN$_5$O$_2$)$^+$=383, 385
MS found (electrospray): (M+H)$^+$=384, 386

Intermediate 113

2-[(2-Cyclopropylethyl)oxy]-8-(methyloxy)-9-(tetrahydro-2H-pyran-4-ylmethyl)-9H-Purin-6-amine

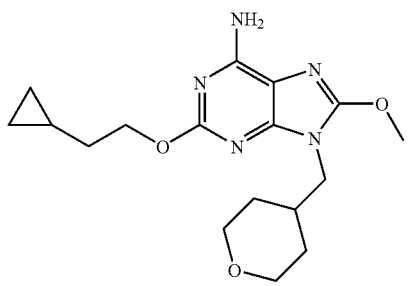

2-[(2-Cyclopropylethyl)oxy]-8-methoxy-9H-purin-6-amine trifluoroacetic acid salt (0.30 g) was heated with potassium carbonate (anhydrous, 0.46 g) in anhydrous DMF (5 mL) at 60° C. for 1 hour. The reaction was cooled to room temperature before 4-(bromomethyl) tetrahydro-2H-pyran (0.16 g) in anhydrous DMF (1 mL) was added. The reaction mixture was then heated to 50° C. overnight. The reaction was quenched into water (50 mL) and extracted with ethyl acetate (50 mL, 3 times). The organic layer was combined and washed with brine (50 mL). The organic layer was separated and dried by passing through a hydrophobic frit before being evaporated under reduced pressure to give oil). This material was purified by C$_{18}$ reverse phase chromatography using water (containing 0.1% formic acid)-acetonitrile (containing 0.05% formic acid) as eluent (20-60%). This material was purified by reverse phase chromatography (20-60% acetonitrile: water). This gave the title compound as a white solid (0.1279 g).

1H NMR (CDCl$_3$): 5.14 (2H, broad s), 4.39-4.32 (2H, m), 4.12 (3H, m), 4.00-3.92 (2H, m), 3.85-3.79 (2H, m), 2.19-2.07 (1H, m), 1.80-1.62 (representing 2H, m [water underlying]), 1.54-1.34 (4H, m), 0.91-0.81 (1H, m), 0.91-0.81 (2H, m), 0.50-0.08 (2H, m), 0.14-0.08 (2H, m).

MS calcd for (C$_{17}$H$_{25}$N$_5$O$_3$)$^+$=347 MS found (electrospray): (M+H)$^+$=348

Intermediate 114

2-[(Cyclohexylmethyl)oxy]-9-(tetrahydro-2H-pyran-2-yl)-9H-purin-6-amine

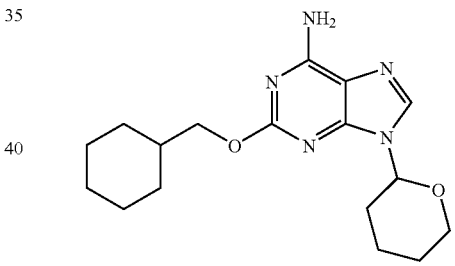

Cyclohexylmethanol (4.5784 g) was diluted with 1,2-dimethoxyethane (99%+) (20 mL) before sodium tert-butoxide (3.853 g) was added gradually with stirring under nitrogen. An exotherm was observed on addition of sodium tert-butoxide. 2-Chloro-9-(tetrahydro-2H-pyran-2-yl)-9H-purin-6-amine (2.5428 g) was added and the resultant mixture was heated to reflux at 93° C. (internal). A further quantity of 1,2-dimethoxyethane (99%+) (20 mL) was added to help dissolution and refluxed overnight. The reaction mixture was dissolved in water (100 mL) and extracted with ethyl acetate (100 mL, twice). The combined organic extracts were washed with brine (100 mL) before the organic layer was separated and dried by passing through a hydrophobic frit. Evaporated volatiles under reduced pressure and then azeotroped with toluene (50 mL, twice) to give mobile amber oil. This material was purified by silica chromatography (ISCO) eluting with 0-100% ethyl acetate: cyclohexane). This gave the title compound after placing under vacuo as pale yellow foam (1.0364 g) (94% purity by LCMS, 6% 2-chloro-9-(tetrahydro-2H-pyran-2-yl)-9H-purin-6-amine) and was used in next step without further purification.

1H NMR (CDCl₃): 7.85 (1H, s), 5.69-5.61 (1H, m), 5.45 (2H, broad s), 4.20-4.07 (3H, overlapping m), 3.82-3.72 (1H, m), 2.14-1.59 (12H, overlapping m), 1.36-1.01 (5H, overlapping m).
MS calcd for $(C_{17}H_{25}N_5O_2)^+$=331
MS found (electrospray): $(M+H)^+$=332

Intermediate 115

8-Bromo-2-[(cyclohexylmethyl)oxy]-9-(tetrahydro-2H-pyran-2-yl)-9H-purin-6-amine

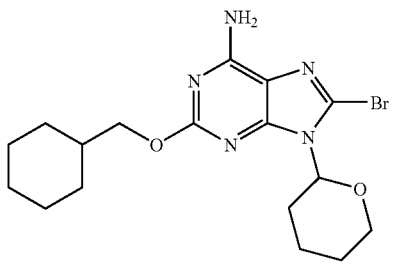

2-[(Cyclohexylmethyl)oxy]-9-(tetrahydro-2H-pyran-2-yl)-9H-purin-6-amine (1.0364 g) was dissolved in chloroform (20 mL) and cooled to 0° C. before N-bromosuccinimide (0.5852 g) was added gradually (the reaction temperature not exceeding 1.9° C. during the addition of N-bromosuccinimide). The reaction mixture was stirred at ~2° C. for 15 minutes before being warmed to room temperature at which it was stirred for 6 hours (under nitrogen). Water (100 mL) was added to the reaction mixture and stirred rapidly before the organic layer was separated using a hydrophobic frit. The organic phase was evaporated under reduced pressure to give dark brown oil. This material was purified by silica chromatography eluting with 0-50% ethyl acetate: cyclohexane to give the title compound as a pale yellow solid (0.8200 g).
1H NMR (CDCl₃): 5.64-5.58 (1H, m), 5.50-5.37 (2H, broad s), 4.20-4.06 (3H, overlapping m), 3.75-3.66 (1H, m), 3.09-2.97 (1H, m), 2.15-2.06 (1H, m), 1.93-1.57 (10H, overlapping m), 1.35-1.01 (5H, overlapping m).
MS calcd for $(C_{17}H_{24}BrN_5O_2)^+$=409, 411
MS found (electrospray): $(M+H)^+$=410, 412

Intermediate 116

2-[(Cyclohexylmethyl)oxy]-8-(methoxy)-9-(tetrahydro-2H-pyran-2-yl)-9H-purin-6-amine

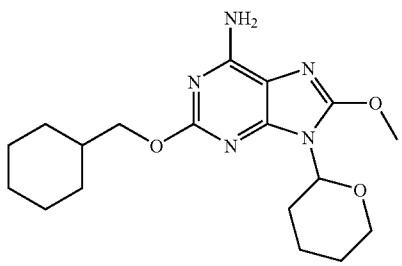

8-Bromo-2-[(cyclohexylmethyl)oxy]-9-(tetrahydro-2H-pyran-2-yl)-9H-purin-6-amine (0.8151 g) was refluxed with 30% (w/v) sodium methoxide in methanol (1.1 mL) diluted with anhydrous methanol (6.0 mL). The suspension was refluxed (70° C. external) overnight. The reaction was partitioned between ethyl acetate (50 mL) and saturated aqueous ammonium chloride solution (50 mL). The organic layer was separated and the aqueous layer was re-extracted with ethyl acetate (50 mL). The organic layers were combined and washed with brine (50 mL) and separated before then being dried by passing through a hydrophobic frit. Evaporation under reduced pressure gave crude title compound as foam (0.7132 g) used without purification.
NMR (CDCl₃) consistent but mixture of more than one compound.
MS calcd for $(C_{18}H_{27}N_5O_3)^+$=361 observed with other parent ions (e.g. 404)
MS found (electrospray): $(M+H)^+$=362

Intermediate 117

2-[(Cyclohexylmethyl)oxy]-8-(methyloxy)-9H-purin-6-amine trifluoroacetate salt

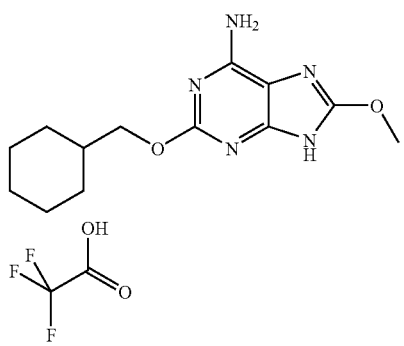

2-[(Cyclohexylmethyl)oxy]-8-methoxy-9-(tetrahydro-2H-pyran-2-yl)-9H-purin-6-amine (0.7132 g, crude) was dissolved in methanol (5 mL). To this solution was added neat trifluoroacetic acid (0.5 mL). The reaction mixture was stirred at ambient room temperature for 18 hours. The solvent was evaporated under reduced pressure and residue triturated with ethyl acetate (50 mL). The white resultant solid was filtered, washed using diethyl ether (10 mL) and then dried under suction. This gave clean title compound as a white solid (0.2799 g).
1H NMR (CD₃OD): 4.29-4.24 (2H, m), 4.14 (3H, s), 1.89-1.66 (6H, overlapping m), 1.39-1.03 (5H, overlapping m) [NH₂ and N-9 NH are exchanged].
MS calcd for $(C_{13}H_{19}N_5O_2)^+$=277
MS found (electrospray): $(M+H)^+$=278

Intermediate 118

2-[(Cyclohexylmethyl)oxy]-8-(methoxy)-9-(tetrahydro-2H-pyran-4-ylmethyl)-9H-purin-6-amine

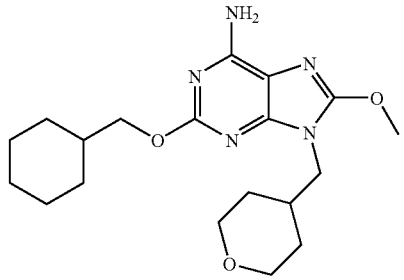

2-[(Cyclohexylmethyl)oxy]-8-(methoxy)-9H-purin-6-amine trifluoroacetate salt (0.28 g) was heated with anhydrous potassium carbonate (0.3957 g) in anhydrous DMF (5 mL) under nitrogen for 1 hour at 60° C. (external). The reaction mixture was cooled to room temperature before adding 4-(bromomethyl) tetrahydro-2H-pyran (0.14 g) in anhydrous DMF (1 mL). The reaction mixture was heated to 50° C., overnight. The reaction mixture was quenched into water (20 mL) and extracted into ethyl acetate (20 mL, 3 times). The organic layers was separated, combined and then washed with brine (20 mL). The organic layer was separated and then dried by passing through a hydrophobic frit. Evaporation under reduced pressure gave pale yellow oil that solidified on standing. This was purified by $C_{18}$ reverse phase chromatography using water (containing 0.1% formic acid)-acetonitrile (containing 0.05% formic acid) as eluent (30-80%) to give the title compound as a white solid (0.1677 g).

1H NMR (CDCl$_3$): 5.11 (2H, s), 4.11 (3H, s), 4.10-4.06 (2H, m), 3.99-3.91 (2H, m), 3.85-3.79 (2H, m), 3.38-3.29 (2H, m), 2.19-2.06 (1H, m), 1.94-1.63 (representing 5H, overlapping water), 1.54-1.00 (10H, overlapping m).

MS calcd for $(C_{19}H_{29}N_5O_3)^+$=375
MS found (electrospray): $(M+H)^+$=376

Intermediate 119

2-{[2-(Methoxy)ethyl]oxy}-9-(tetrahydro-2H-pyran-2-yl)-9H-Purin-6-amine (Method A)

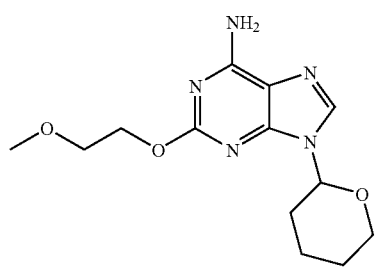

2-Methoxyethanol (3.2 mL) was diluted with 1,2-dimethoxyethane (20 mL). To this was added sodium tert-butoxide (3.9 g) gradually and the reaction mixture was stirred under nitrogen until it was homogenous. 2-Chloro-9-(tetrahydro-2H-pyran-2-yl)-9H-purin-6-amine (2.5376 g) was then added to the reaction mixture, followed by 1,2-dimethoxyethane (20 mL). The reaction mixture was then heated to reflux (110° C., external) overnight. The reaction was quenched with water (100 mL) and extracted with ethyl acetate (100 mL, twice). The combined organic layers were then washed with brine (100 mL). The organic layer was then dried by passing through a hydrophobic frit and then evaporated under reduced pressure (followed by azeotroping with toluene (100 mL, twice)). This gave an amber oil that under high vacuo gave gummy foam. This material was triturated with diethyl ether (with cooling) until this gave the title compound, a pale yellow solid.

1H NMR (CDCl$_3$): 7.86 (1H, s), 5.66-5.59 (1H, m), 5.47 (2H, broad s), 4.54-4.46 (2H, m), 4.19-4.10 (1H, m), 3.80-3.65 (3H, overlapping m), 3.43 (3H, s), 2.13-1.93 (3H, overlapping m), 1.81-1.58 (representing 3H, overlapping m, [overlapping water]).

MS calcd for $(C_{13}H_{19}N_5O_3)^+$=293
MS found (electrospray): $(M+H)^+$=294

Intermediate 119

2-{[2-(Methoxy)ethyl]oxy}-9-(tetrahydro-2H-pyran-2-yl)-9H-Purin-6-amine (Method B)

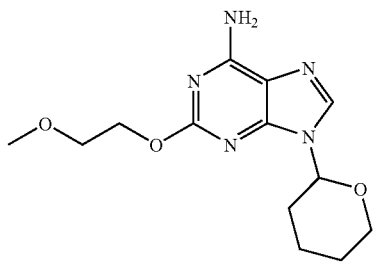

Potassium tert.-butoxide (46.5 g, 475 mmol) was added to 2-methoxyethanol (200 mL) in 20 min at room temperature, then 2-chloro-9-(tetrahydro-2H-pyran-2-yl)-9H-purin-6-amine (30 g) was added and the resulted mixture was heated at 80-90° C. for about 3 h. Evaporation of most of the solvent, to the residue was added 100 ml of water, stirred for 1 h at 0° C., filtered and dried. This gave product (30 g, 87%) that was almost identical to that from Intermediate 119, method A.

1H NMR (CDCl$_3$): 7.84 (1H, s), 5.66-5.59 (1H, m), 4.48 (2H, t), 4.18-4.08 (1H, m), 3.80-3.65 (3H, overlapping m), 3.43 (3H, s), 2.1-1.85 (3H, m), 1.80-1.55 (3H, m).

Intermediate 120

8-Bromo-2-{[2-(methoxy)ethyl]oxy}-9-(tetrahydro-2H-pyran-2-yl)-9H-purin-6-amine

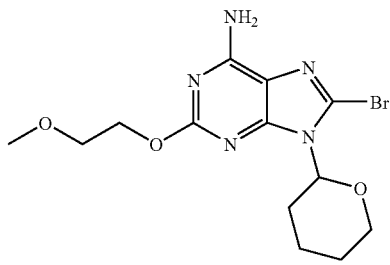

2-{[2-(Methoxy)ethyl]oxy}-9-(tetrahydro-2H-pyran-2-yl)-9H-purin-6-amine (1.61 g) was dissolved in chloroform (20 mL) and cooled to 0° C. To this solution was then added N-bromosuccinimide (1.02 g) gradually, keeping the temperature at ~2° C. The reaction was stirred at 2° C. for around 15 minutes before being allowed to warm to room temperature. The reaction mixture was then stirred under nitrogen for 5 hours. The reaction mixture was quenched with water (100 mL) and stirred rapidly before the organic layer was separated using a hydrophobic frit. The organic was evaporated under reduced pressure to give a dark brown gum. This material was purified by silica chromatography (ISCO) eluting initially with 0-70% ethyl acetate: cyclohexane holding isocratic at 70% ethyl acetate; cyclohexane until a minor impurity was eluted. The gradient was then resumed from 70%-95% ethyl acetate: cyclohexane. This gave the title compound as a white solid (1.4489 g)

1H NMR (CDCl₃): 5.65-5.56 (1H, m) 5.44 (2H, broad s), 4.52-4.43 (2H, m), 4.20-4.12 (1H, m), 3.79-3.65 (3H, overlapping m), 3.43 (3H, s), 3.09-2.96 (1H, m), 2.14-2.03 (1H, m), 1.89-1.56 (representing 4H, overlapping m, [underlying water]).

MS calcd for $(C_{13}H_{18}BrN_5O_3)^+$=371, 373
MS found (electrospray): $(M+H)^+$=372, 374

Intermediate 121

8-(Methoxy)-2-{[2-(methyloxy)ethyl]oxy}-9-(tetrahydro-2H-pyran-2-yl)-9H-Purin-6-amine

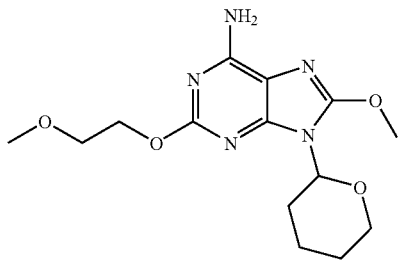

8-Bromo-2-{[2-(methoxy)ethyl]oxy}-9-(tetrahydro-2H-pyran-2-yl)-9H-purin-6-amine (1.4489 g) was suspended in dry methanol (11.5 mL) and then treated with 25% (w/v) sodium methoxide in methanol (2.5 mL). The reaction mixture was heated to reflux (65° C., externally) were upon a solution was obtained. After 4 hours the reaction mixture was concentrated under reduced pressure and saturated aqueous ammonium chloride (100 mL) was added. This was then extracted with ethyl acetate (100 mL, twice). The organic layers was separated, combined and washed with brine (100 mL). The organic layer was separated and then dried by passing through a hydrophobic frit. This was then evaporated under reduced pressure to give the title compound as a white solid (1.2032 g) after placing under high vacuo, overnight.

1H NMR (CDCl₃): 5.53-5.45 (1H, m), 5.16 (2H, broad s), 4.50-4.40 (2H, m), 4.16-4.40 (1H, m) overlapping 4.12 (3H, s), 3.80-3.62 (3H, overlapping m), 3.43 (3H, s), 2.83-2.69 (1H, m), 2.05-1.99 (1H, m), 1.82-1.51 (4H, overlapping m).

MS calcd for $(C_{14}H_{21}N_5O_4)^+$=323
MS found (electrospray): $(M+H)^+$=324

Intermediate 122

8-(Methoxy)-2-{[2-(methoxy)ethyl]oxy}-9H-purin-6-amine trifluoroacetate salt

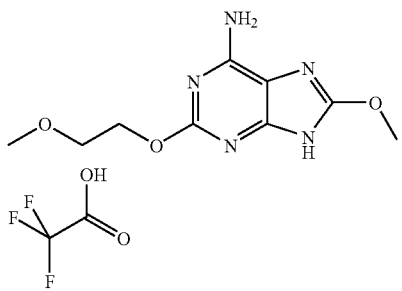

8-(Methoxy)-2-{[2-(methyloxy)ethyl]oxy}-9-(tetrahydro-2H-pyran-2-yl)-9H-purin-6-amine (1.2032 g) was dissolved in methanol (10 mL) which was treated with neat trifluoroacetic acid (1 mL) and then stirred for 2 days. The reaction mixture was evaporated under reduced pressure and the resultant solid suspended in ethyl acetate (25 mL) before being filtered to give the title compound (1.1310 g) as a white solid.

1H NMR((CD₃)₂SO): 7.50 (2H, broad s), 4.42-4.34 (2H, m), 4.04 (3H, s) 3.67-3.61 (2H, m), 3.30 (3H, s) (N9 proton not observed).

MS calcd for $(C_9H_{13}N_5O_3)^+$=239
MS found (electrospray): $(M+H)^+$=240

Intermediate 123

8-(Methoxy)-2-{[2-(methyloxy)ethyl]oxy}-9-(tetrahydro-2H-pyran-4-ylmethyl)-9H-Purin-6-amine

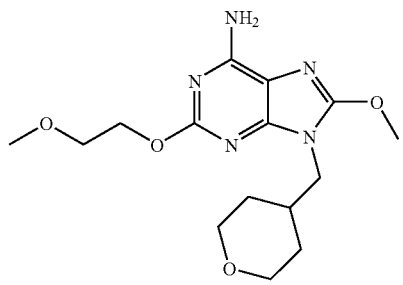

8-(Methoxy)-2-{[2-(methoxy)ethyl]oxy}-9H-purin-6-amine trifluoroacetate salt (0.30 g) was heated with anhydrous potassium carbonate (0.4698 g) in anhydrous DMF (5 mL) at 60° C. for 1 hour. The reaction mixture was cooled to room temperature before 4-(bromomethyl) tetrahydro-2H-pyran (0.1669 g) was added in anhydrous DMF (1 mL). The reaction mixture was then stirred overnight at 50° C. The reaction mixture was quenched into water (20 mL) and extracted into ethyl acetate (20 mL, 3 times).

The separated, combined organic layers were then washed with brine (20 mL). The separated organic layer was dried by passing through a hydrophobic frit before being evaporated under reduced pressure to give pale yellow oil which solidified on standing. This was purified by $C_{18}$ reverse phase chromatography using water (containing 0.1% formic acid)-acetonitrile (containing 0.05% formic acid) as eluent (10-45%) to give the title compound as a white solid (0.1454 g).

1H NMR (CDCl₃): 5.12 (2H, broad s), 4.47-4.41 (2H, m), 4.12 (3H, s), 4.00-3.91 (2H, m), 3.85-3.73 (4H, partially overlapping m), 3.43 (3H, s), 3.38-3.28 (2H, m), 2.18-2.06 (1H, m), 1.53-1.33 (4H, overlapping m).

MS calcd for $(C_{15}H_{23}N_5O_4)^+$=337
MS found (electrospray): $(M+H)^+$=338

Intermediate 124

8-(Methoxy)-2-{[2-(methyloxy)ethyl]oxy}-9-(tetrahydro-3-furanylmethyl)-9H-purin-6-amine

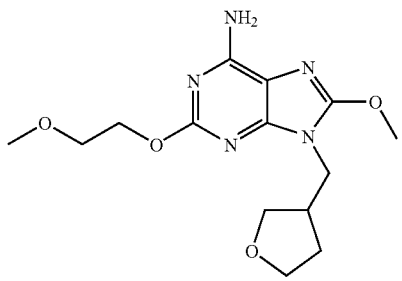

8-(Methoxy)-2-{[2-(methoxy)ethyl]oxy}-9H-purin-6-amine trifluoroacetate salt (0.30 g) was dissolved in dry DMF (5 mL). To this was added anhydrous potassium carbonate (0.47 g) and then heated to 60° C. for 1.5 hours. The reaction mixture was cooled to room temperature and tetrahydro-3-furanylmethyl methanesulfonate (0.168 g) was added. The reaction mixture was then heated to 90° C. for 3.5 hours. The reaction mixture was then quenched into water (100 mL) and extracted into ethyl acetate (50 mL, 3 times). The organic was separated and dried by passing through a hydrophobic frit and then evaporated under reduced pressure to give a glassy solid. This was purified by $C_{18}$ reverse phase chromatography using water (containing 0.1% formic acid)-acetonitrile (containing 0.05% formic acid) as eluent (10-45%). This gave the title compound as a white solid (0.1233 g).

1H NMR (CDCl$_3$): 5.46 (2H, broad s), 4.48-4.39 (2H, m), 4.12 (3H, s), 4.01-3.87 (3H, overlapping m), 3.79-3.70 (4H, overlapping m), 3.65-3.59 (1H, m), 3.43 (3H, s), 2.91-2.78 (1H, m), 2.02-1.90 (1H, m), 1.76-1.64 (1H, m).

MS calcd for $(C_{14}H_{21}N_5O_4)^+$=323
MS found (electrospray): $(M+H)^+$=324

Intermediate 125

2-[(Tetrahydro-2-furanylmethyl)oxy]-9-(tetrahydro-2H-pyran-2-yl)-9H-purin-6-amine

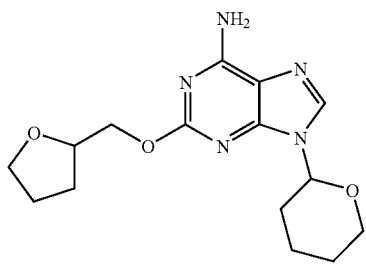

Tetrahydrofurfuryl alcohol (4.09 g) was diluted with 1,2-dimethoxyethane (20 mL). To this solution was added sodium tert-butoxide (3.84 g) gradually. The resultant reaction mixture was stirred until homogeneous (orange solution) before 2-chloro-9-(tetrahydro-2H-pyran-2-yl)-9H-purin-6-amine (2.53 g) was added. The reaction mixture was then heated to 110° C. (external) overnight under nitrogen. The reaction mixture was quenched with water (100 mL) and extracted with ethyl acetate (100 mL, 3 times). The organic layer was separated, combined and then dried by passing through a hydrophobic frit. This was evaporated under reduced pressure and the resultant material was then purified by silica chromatography eluting with 0-100% ethyl acetate: cyclohexane followed by methanol. An ISCO pump fault was detected whilst eluting with methanol, this line carried ethyl acetate previously and it was not known if the fault existed when eluting with ethyl acetate: cyclohexane. The appropriate fractions were evaporated to give the title compound as a solid (1.7258 g). This material was used in the next stage without further purification.

1H NMR (CDCl$_3$): 7.87 (1H, m), 6.69 (2H, broad m), 5.68-5.54 (1H, m), 4.45-4.36 (1H, m), 4.35-4.21 (2H, overlapping m), 4.17-4.08 (1H, m), 3.98-3.89 (1H, m), 3.85-3.68 (2H, overlapping m), 2.15-1.55 (10H, overlapping m).

Intermediate 126

8-Bromo-2-[(tetrahydro-2-furanylmethyl)oxy]-9-(tetrahydro-2H-Pyran-2-yl)-9H-purin-6-amine

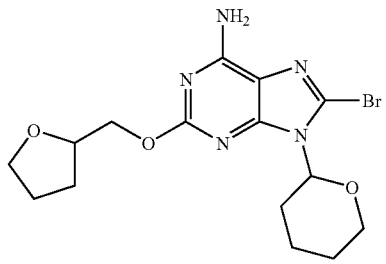

2-[(Tetrahydro-2-furanylmethyl)oxy]-9-(tetrahydro-2H-pyran-2-yl)-9H-purin-6-amine (1.7202 g) was dissolved in chloroform (15 mL) and cooled to ~1° C. before N-bromosuccinimide (1.056 g) was added keeping the reaction temperature below 2° C. The reaction mixture was then stirred at ~1° C. for 30 minutes before allowing to warm to room temperature were upon the reaction mixture was stirred for 3 hours. The reaction mixture was then stood overnight at room temperature before being partitioned between water (50 mL) and the organic phase separated using a hydrophobic frit. The organic phase was evaporated under reduced pressure to give a brown gum which was purified using silica chromatography (ISCO) eluting with 0-100% ethyl acetate: cyclohexane. This gave the title compound as a white foam solid (1.3748 g).

1H NMR (CDCl$_3$): 5.63-5.56 (1H, m), 5.43 (2H, broad s), 4.45-4.36 (1H, m), 4.34-4.10 (3H, overlapping m), 4.98-3.89 (1H, m), 3.85-3.77 (1H, m), 3.74-3.66 (1H, m), 3.09-2.97 (1H, m), 2.15-1.56 (representing 9H [overlapping water])

MS calcd for $(C_{15}H_{20}BrN_5O_3)^+$=397, 399
MS found (electrospray): $(M+H)^+$=398, 400

Intermediate 127

8-(Methoxy)-2-[(tetrahydro-2-furanylmethyl)oxy]-9-(tetrahydro-2H-Pyran-2-yl)-9H-purin-6-amine

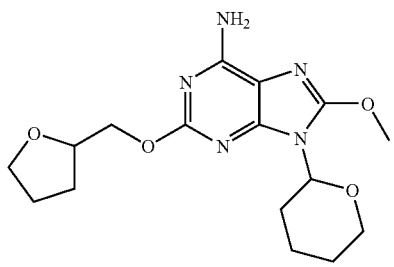

8-Bromo-2-[(tetrahydro-2-furanylmethyl)oxy]-9-(tetrahydro-2H-pyran-2-yl)-9H-purin-6-amine (1.3748 g) was dissolved in methanol (10.2 mL) and treated with 25% (w/v) sodium methoxide in methanol (2.2 mL). This was heated to reflux under nitrogen for 3.5 hours. The reaction mixture was evaporated under reduced pressure to dryness and saturated ammonium chloride solution was added (100 mL). This was then extracted with ethyl acetate (100 mL, 3 times). The organic layers were combined and washed with brine (100 mL) and then dried by passing through a hydrophobic frit after separating the aqueous layer. The organic was evaporated under reduced pressure to give the title compound as white foam (1.1614 g) and used in the next stage without requiring purification.

1H NMR (CDCl$_3$): 5.52-5.46 (1H, m), 5.15 (2H, broad s), 4.43-4.36 (1H, m), 4.33-4.26 (1H, m), 4.23-4.17 (1H, m), 4.16-4.09 (1H, m overlapping 4.13 (3H, s)), 3.97-3.90 (1H, m), 3.84-3.76 (1H, m), 3.73-3.65 (1H, m), 2.83-2.71 (1H, m), 2.13-1.53 (representing 9H, overlapping m [overlapping water]).

MS calcd for $(C_{16}H_{23}N_5O_4)^+$=349
MS found (electrospray): $(M+H)^+$=350

Intermediate 128

8-(Methoxy)-2-[(tetrahydro-2-furanylmethyl)oxy]-9H-Purin-6-amine trifluoroacetate salt

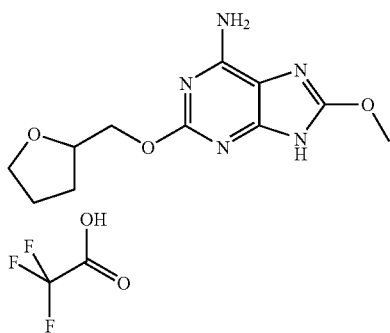

8-(Methoxy)-2-[(tetrahydro-2-furanyl methyl)oxy]-9-(tetrahydro-2H-pyran-2-yl)-9H-purin-6-amine (1.1614 g) was dissolved in methanol (20 mL) and treated with neat trifluoroacetic acid (2 mL). The reaction mixture was stirred for 24 hours to give a white suspension. The reaction mixture was then evaporated to dryness under reduced pressure. The resultant white solid was suspended using ethyl acetate (10 mL) and then isolated by filtration, washing with ethyl acetate (2 mL). The solid was air-dried under suction and then dried further under vacuo at 50° C. This gave the title compound as a white solid (1.0602 g).

1H NMR((CD$_3$)$_2$SO): 7.76 (2H, broad s), 4.35-4.11 (3H, overlapping m), 4.05 (3H, s), 3.82-3.73 (1H, m), 3.73-3.63 (1H, m), 2.05-1.77 (3H, overlapping m), 1.70-1.59 (1H, m) (N-9 NH not apparent from spectrum—indication of extremely broad signal at 12.7 ppm (but could be artefact of FT)).

MS calcd for $(C_{11}H_{15}N_5O_3)^+$=265
MS found (electrospray): $(M+H)^+$=266

Intermediate 129

8-(Methoxy)-2-[(tetrahydro-2-furanylmethyl)oxy]-9-(tetrahydro-2H-Pyran-4-ylmethyl)-9H-purin-6-amine

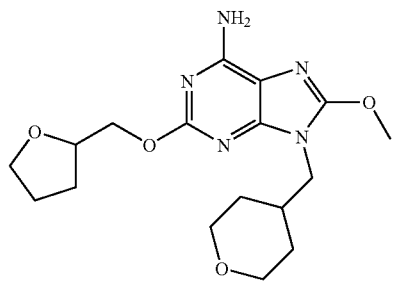

8-(Methoxy)-2-[(tetrahydro-2-furanylmethyl)oxy]-9H-purin-6-amine trifluoroacetate salt (0.30 g) was dissolved in dry DMF (5 mL). To this solution was added anhydrous potassium carbonate (0.4376 g) and then the reaction mixture was heated to 60° C. under nitrogen for 1 hour. The reaction mixture was then cooled to room temperature before adding tetrahydro-2H-pyran-4-ylmethyl methanesulfonate (0.1690 g) and then the resultant reaction mixture was heated to 90° C. for 2.5 hours. The reaction mixture was cooled and then quenched with water (50 mL), followed by extraction into ethyl acetate (50 mL, 3 times). After separating, the organic layers were combined and dried by passing through a hydrophobic frit. Evaporation under reduced pressure gave mobile oil which was then purified by C$_{18}$ reverse phase chromatography using water (containing 0.1% formic acid)-acetonitrile (containing 0.05% formic acid) as eluent (10-45%). This gave the title compound as a white solid (0.1560 g).

1H NMR (CDCl$_3$): 5.17 (2H, broad s), 4.40-4.26 (2H, close m), 4.23-4.17 (1H, m), 4.11 (3H, s), 3.99-3.89 (3H, overlapping m), 3.84-3.76 (3H, overlapping m), 3.37-3.29 (2H, m), 2.18-1.66 (representing 5H [underlying water peak]), 1.52-1.33 (4H, overlapping m).

MS calcd for $(C_{17}H_{25}N_5O_4)^+$=363
MS found (electrospray): $(M+H)^+$=364

Intermediate 130

Ethyl (2E)-3-(5,6-dihydro-2H-pyran-3-yl)-2-propenoate

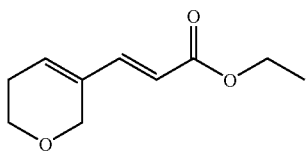

To 5,6-dihydro-2H-pyran-3-carbaldehyde (5.0 g) in dry dichloromethane (150 ml) at 0° C., was added carbethoxymethylene-triphenylphosphorane (15.53 g). The reaction was allowed to warm to room temperature and stirred overnight. The reaction was diluted with dichloromethane (150 ml) and washed with water (150 ml) and a saturated aqueous solution of brine (150 ml). The organic layer was dried by passing through a hydrophobic frit and concentrated in vacuo. to afford a yellow oil. The product was purified by silica chromatography (120 g) (ISCO) using a gradient elution of 0-10% cyclohexane:ethyl acetate to afford the title compound as a clear oil (5.59 g).

$^1$H NMR (CDCl$_3$): δ 7.27 (1H, t), 6.33 (1H, m), 5.67 (1H, d), 4.35 (2H, m), 4.26 (2H, q), 3.84 (2H, t), 2.39 (2H, m), 1.35 (3H, t).

Intermediate 131

Ethyl 3-(tetrahydro-2H-pyran-3-yl)propanoate

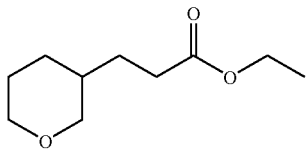

A solution of ethyl (2E)-3-(5,6-dihydro-2H-pyran-3-yl)-2-propenoate (3 g) and palladium on carbon (170 mg, 10%, wet) in ethyl acetate (75 ml) was hydrogenated at atmospheric pressure and room temperature. The hydrogen uptake (~825 ml) was complete after 30 minutes. The catalyst was filtered through celite and the filtrate concentrated in vacuo. to afford a pale yellow oil (2.90 g).

The above was repeated in the exact same fashion with a second batch. Hence a solution of ethyl (2E)-3-(5,6-dihydro-2H-pyran-3-yl)-2-propenoate (2.59 g) and palladium on carbon (147 mg, 10% wet) in ethyl acetate (65 ml) was hydrogenated at atmospheric pressure and room temperature. The hydrogen uptake (~715 ml) was complete after 15 minutes. The catalyst was filtered through celite and the filtrate concentrated in vacuo. to afford a pale yellow oil which was combined with that of the first batch (5.34 g). This was purified by silica chromatography (120 g) (ISCO) using a gradient elution of 0-10% cyclohexane:ethyl acetate to afford the title compound as a clear oil (4.61 g).

$^1$H NMR (CDCl$_3$): δ 4.13 (2H, q), 3.86 (2H, m), 3.35 (1H, m), 3.06 (1H, m), 2.31 (2H, m), 1.87 (1H, m), 1.64-1.41 (5H, m), 1.26 (3H, t), 1.15 (1H, m).

Intermediate 132

3-(Tetrahydro-2H-pyran-3-yl)-1-propanol

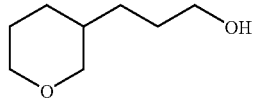

To a stirred solution of lithium aluminium hydride (24.8 ml, 1.0M in diethyl ether) in dry diethyl ether (77 ml) at 0° C. was added a solution of ethyl 3-(tetrahydro-2H-pyran-3-yl) propanoate (4.61 g) in dry diethyl ether (77 ml) dropwise over 20 minutes. After 15 minutes at 0° C. the reaction mixture was warmed to room temperature and stirred for a further nine hours. The reaction was quenched by the dropwise addition of water over a period of one hour, whilst cooled over ice. The resulting solids were filtered from the mixture and washed with diethyl ether. The organic layer was decanted off from the aqueous layer, dried over magnesium sulphate, filtered and concentrated in vacuo. to give a clear oil (3.33 g). The product was purified by silica chromatography (40 g) (ISCO) using a gradient elution of 0-50% cyclohexane:ethyl acetate to afford the title compound as a clear oil (2.64 g).

$^1$H NMR (CDCl$_3$): δ 3.87 (2H, m), 3.64 (2H, m), 3.35 (1H, m), 3.05 (1H, m), 1.88 (1H, m), 1.66-1.51 (5H, m), 1.39 (1H, t), 1.31-1.08 (3H, m).

Intermediate 133

3-(Tetrahydro-2H-pyran-3-yl)propyl methanesulfonate

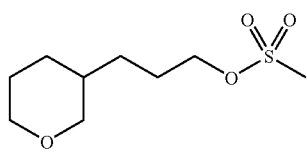

To a solution of 3-(tetrahydro-2H-pyran-3-yl)-1-propanol (2.64 g) in dry dichloromethane (78 ml) at 0° C. was added triethylamine (6.21 ml) followed by mesyl chloride (1.85 ml). The reaction mixture was allowed to warm to room temperature as the ice melted and allowed to stir for three hours. The reaction mixture was washed with sodium hydrogen carbonate. The organic layer was separated, dried by passing through a hydrophobic frit and concentrated in vacuo. to give a yellow oil (4.42 g). The product was purified by silica chromatography (80 g) (ISCO) using a gradient elution of 0-50% cyclohexane:ethyl acetate to afford the title compound as a clear oil (3.79 g).

¹H NMR (CDCl₃): δ 4.22 (2H, t), 3.86 (2H, m), 3.36 (1H, m), 3.07 (1H, m), 3.01 (3H, s), 1.87 (1H, m), 1.82-1.69 (2H, m), 1.65-1.54 (3H, m), 1.36-1.10 (3H, m).

Intermediate 134

N²-Butyl-8-(methoxy)-9-[3-(tetrahydro-2H-pyran-3-yl)propyl]-9H-Purine-2,6-diamine

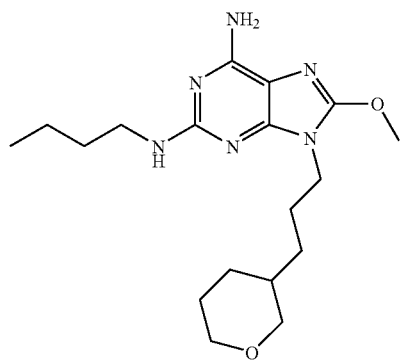

To a solution of N²-butyl-8-methoxy-9H-purine-2,6-diamine trifluoroacetic acid salt (300 mg) in dry N,N-dimethylformamide (5.3 ml) was added potassium carbonate (474 mg). The reaction was stirred at 60° C. for ninety minutes. The reaction was cooled and 3-(tetrahydro-2H-pyran-3-yl)propyl methanesulfonate (209 mg) was added and the reaction heated at 90° C. for three hours. The reaction was cooled, diluted with ethyl acetate and washed with water (2×). The organic layer was separated, dried over magnesium sulphate, filtered and concentrated in vacuo. to afford a yellow oil. The product was purified by C₁₈ reverse phase chromatography (43 g) (ISCO) using water (0.1% formic acid)-acetonitrile (0.05% formic acid) as eluant (30-80%) to afford the title compound as a yellow oily residue (198 mg).

MS calcd for $(C_{18}H_{30}N_6O_2)^+=362$
MS found (electrospray): $(M+H)^+=363$
¹H NMR (DMSO): δ 6.23 (2H, s), 6.01 (1H, t), 3.99 (3H, s), 3.77-3.67 (4H, m), 3.26-3.15 (3H, m), 2.91 (1H, m), 1.76 (1H, m), 1.71-1.60 (2H, m), 1.54-1.40 (5H, m), 1.36-1.26 (2H, m), 1.16-0.96 (3H, m), 0.88 (3H, m).

Intermediate 135

9-(Tetrahydro-2H-pyran-2-yl)-2-[(tetrahydro-2H-pyran-2-ylmethoxy]-9H-purin-6-amine

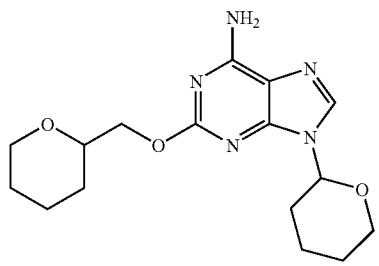

Tetrahydropyran-2-methanol (ex. Aldrich) (4.66 g) was diluted with 1,2-dimethoxyethane (20 mL). Added gradually sodium tert-butoxide (3.85 g) to the above and stirred until homogeneous (orange solution). 2-chloro-9-(tetrahydro-2H-pyran-2-yl)-9H-purin-6-amine (2.54 g) was added to the above and then heated to reflux (110° C., external), overnight and under nitrogen. The reaction mixture was quenched into water (100 mL) and extracted using ethyl acetate (100 mL, 3 times). The organic phase was separated and then passed through a hydrophobic frit. Evaporation under reduced pressure gave a gum that was then purified by ISCO (120 g, SiO₂) eluting with 0-50% methanol: DCM to give the title compound as a pale yellow foam (2.1732 g).

MS calcd for $(C_{16}H_{23}N_5O_3)^+=333$
MS found (electrospray): $(M+H)^+=334$
¹H NMR (CDCl₃): 7.85 (1H, s), 5.66-5.49 (overlapping 1H, m and 2H, broad s), 4.41-4.34 (1H, m), 4.25-4.19 (1H, m), 4.18-4.11 (1H, m), 4.06-4.00 (1H, m), 3.78-3.69 (2H, m), 3.54-3.45 (1H, m), 2.12-1.83 (4H, overlapping m), 1.83-1.36 (8H, overlapping m).

Intermediate 136

8-Bromo-9-(tetrahydro-2H-pyran-2-yl)-2-[(tetrahydro-2H-pyran-2-ylmethoxy]-9H-Purin-6-amine

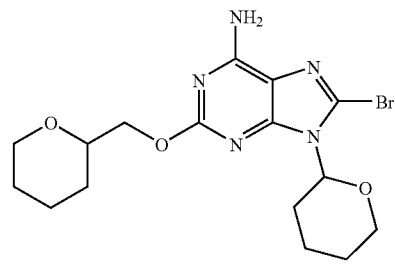

To a solution of 9-(tetrahydro-2H-pyran-2-yl)-2-[(tetrahydro-2H-pyran-2-yl methoxy]-9H-purin-6-amine (2.17 g) in dry chloroform (23.5 ml), cooled to 0° C., was added N-bromosuccinimide (1.22 g). The reaction was allowed to return to room temperature and stirred for 4 hours. The reaction was diluted with DCM (50 ml) and washed with water (50 ml) and then brine (50 ml). The organic layer was separated, dried by passing through a hydrophobic frit, and concentrated in vacuo. This afforded the title product as a brown foamy solid (2.76 g).

MS calcd for $(C_{16}H_{22}BrN_5O_3)^+=412, 413$
MS found (electrospray): $(M+H)^+=413, 414$ Intermediate 137

8-(Methoxy)-9-(tetrahydro-2H-pyran-2-yl)-2-[(tetrahydro-2H-pyran-2-ylmethoxy]-9H-purin-6-amine

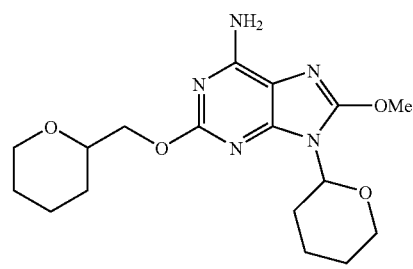

To a solution of 8-bromo-9-(tetrahydro-2H-pyran-2-yl)-2-[(tetrahydro-2H-pyran-2-ylmethoxy]-9H-purin-6-amine (2.76 g) in dry methanol (22.6 ml) at room temperature, was added sodium methoxide (4.6 ml, 25% wt. methanol). The reaction was heated to reflux for 4 hours. The reaction was cooled and concentrated in vacuo to yield an orange residue. This was taken up in ammonium chloride solution (100 ml) and extracted with ethyl acetate (100 ml). The organic layer was separated and washed with water (50 ml). The organic layer was dried over magnesium sulfate, filtered and concentrated in vacuo. This afforded the title compound as an orange foamy solid (2.06 g).

MS calcd for $(C_{17}H_{25}N_5O_4)^+=363$
MS found (electrospray): $(M+H)^+=364$ Intermediate 138

8-(Methoxy)-2-[(tetrahydro-2H-pyran-2-ylmethoxy]-9H-Purin-6-amine trifluoroacetate salt

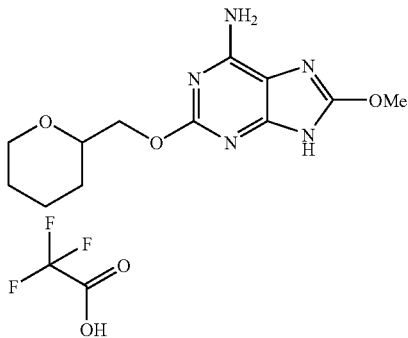

To a solution of 8-(methoxy)-9-(tetrahydro-2H-pyran-2-yl)-2-[(tetrahydro-2H-pyran-2-ylmethoxy]-9H-purin-6-amine (2.06 g) in dry methanol (20.6 ml) was added trifluoroacetic acid (2.06 ml). The reaction was stirred at room temperature for 24 hours. The reaction mixture was concentrated in vacuo and the resulting residue triturated in diethyl ether. This resulted in an off-white solid following filtration (1.59 g).

MS calcd for $(C_{12}H_{17}N_5O_3)^+=279$
MS found (electrospray): $(M+H)^+=280$ Intermediate 139

8-(Methoxy)-9-(tetrahydro-2H-pyran-4-ylmethyl)-2-[(tetrahydro-2H-Pyran-2-ylmethoxy]-9H-purin-6-amine

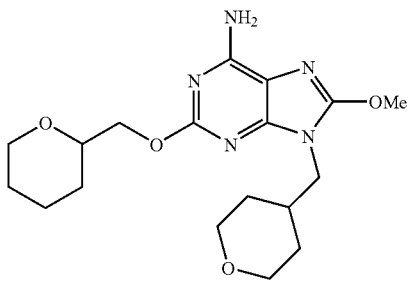

To a solution of 8-(methoxy)-2-[(tetrahydro-2H-pyran-2-ylmethoxy]-9H-purin-6-amine trifluoroacetate salt (1.59 g) in dry N,N-dimethylformamide (25 ml) was added potassium carbonate (2.24 g). The reaction was stirred at 60° C. for 1.5 hours. The reaction was cooled and tetrahydro-2H-pyran-4-ylmethyl methanesulfonate (866 mg) was added. The reaction was stirred at 90° C. for 5 hours. The reaction was cooled and taken up in ethyl acetate and washed twice with water. The organic layer was separated, dried over magnesium sulphate, filtered and concentrated in vacuo to yield a yellow solid. The product was purified by $C_{18}$ reverse phase chromatography using water (containing 0.1% formic acid)-acetonitrile (containing 0.05% formic acid) as eluant (20-50%) to afford the title compound as an off-white solid (704 mg).

MS calcd for $(C_{18}H_{27}N_5O_4)^+=377$
MS found (electrospray): $(M+H)^+=378$ Intermediate 140

2-([2-[(1-Methylethyl)oxy]ethyl]oxy)-8-(methoxy)-9-(tetrahydro-2H-pyran-4-ylmethyl)-9H-purin-6-amine

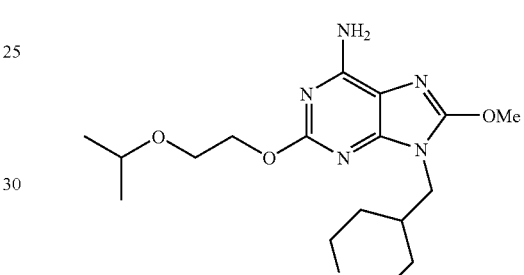

To a solution of 2-({2-[(1-methylethyl)oxy]ethyl}oxy)-8-(methoxy)-9H-purin-6-amine trifluoroacetate salt (400 mg) in dry N,N-dimethylformamide (6.4 ml) was added potassium carbonate (579 mg). The reaction was stirred at 60° C. for 1.5 hours. The reaction was cooled and tetrahydro-2H-pyran-4-ylmethyl methanesulfonate (224 mg) was added. The reaction was stirred at 90° C. for 4 hours. The reaction was cooled and taken up in ethyl acetate and washed twice with water. The organic layer was separated, dried over magnesium sulphate, filtered and concentrated in vacuo to yield a yellow oil (432 mg). The product was purified by $C_{18}$ reverse phase chromatography using water (containing 0.1% formic acid)-acetonitrile (containing 0.05% formic acid) as eluant (20-50%) to afford the title compound as a clear viscous oil (166 mg).

MS calcd for $(C_{17}H_{27}N_5O_4)^+=365$
MS found (electrospray): $(M+H)^+=366$ Intermediate 141

5-{4-[(Phenylmethyl)oxy]-1-buten-1-yl}-3,6-dihydro-2H-pyran

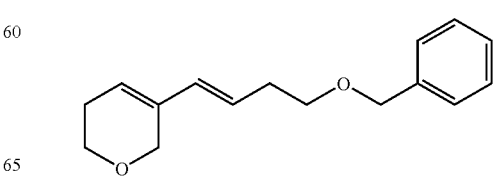

To a suspension of (3-benzyloxypropyl)triphenylphosphonium bromide (9.90 g) in dry tetrahydrofuran (30.5 ml) at −15° C. was added butyllithium (8.06 ml, 2.5M in hexanes) dropwise to give a dark orange solution. The reaction temperature was increased to 0° C. and stirring was continued for 30 minutes. A solution of 5,6-dihydro-2H-pyran-3-carbaldehyde (2.26 g) in dry tetrahydrofuran (3 ml) was added dropwise at 0° C. The reaction mixture was stirred at room temperature for 20 hours. The reaction mixture was filtered through celite and washed with diethyl ether. The filtrate was concentrated in vacuo to give an orange oil. The product was purified by silica chromatography using a gradient elution of 0-25% ethyl acetate/cyclohexane to afford the title compound as a colourless oil (2.04 g).

$^1$H-NMR (CDCl$_3$): Mixture of cis and trans δ 7.40-7.27 (5H, m), 6.02 (0.60H, d), 5.76 (1.36H, m), 5.49-5.37 (1H, m), 4.53 (2H, m), 4.29 (1.23H), 4.22 (0.74H, m), 3.77 (2H, t), 3.51 (2H, m), 2.52 (0.78H, m), 2.40 (1.29H, m), 2.24 (2H, m).

Intermediate 142

4-(Tetrahydro-2H-pyran-3-yl)-1-butanol

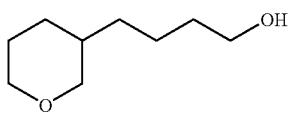

A solution of 5-{4-[(phenylmethyl)oxy]-1-buten-1-yl}-3,6-dihydro-2H-pyran (2.03 g) and 10% palladium on carbon (88 mg) in ethyl acetate (83 ml) was hydrogenated at atmospheric pressure and room temperature. Hydrogen uptake (~500 ml) was complete after 15 hours. The catalyst was filtered through celite and the filtrate concentrated in vacuo to afford a colourless oil. Analysis by $^1$H-NMR showed that the benzyl group was present in the majority of the compound. Hydrogenation was continued under the same conditions for a further 24 hours with additional hydrogen uptake of ~300 ml. The catalyst was filtered through celite and the filtrate concentrated in vacuo to afford the title compound as a colourless oil (1.21 g).

$^1$H-NMR (CDCl$_3$): δ 3.86 (2H, m), 3.63 (2H, t), 3.34 (1H, m), 3.04 (1H, t), 1.86 (1H, m), 1.75 (1H, s), 1.66-1.47 (5H, m), 1.45-1.27 (2H, m), 1.26-1.06 (3H, m).

Intermediate 143

4-(Tetrahydro-2H-pyran-3-yl)butyl methanesulfonate

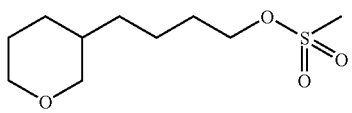

To a solution of 4-(tetrahydro-2H-pyran-3-yl)-1-butanol (1.20 g) in dry dichloromethane (30.3 ml), cooled to 0° C., was added triethylamine (2.43 ml) and methanesulphonyl chloride (0.77 ml) to give a yellow solution. The reaction mixture was stirred at room temperature overnight. The reaction mixture was washed with a saturated aqueous solution of sodium hydrogen carbonate (25 ml). The organic layer was separated, dried by passing through a hydrophobic frit and concentrated in vacuo to afford a yellow oil (1.80 g). The product was purified by silica chromatography using a gradient elution of 0-40% ethyl acetate/cyclohexane to afford the title compound as a yellow oil (1.58 g).

$^1$H-NMR (CDCl$_3$): δ 4.23 (2H, t), 3.86 (2H, m), 3.35 (1H, m), 3.05 (1H, m), 3.01 (3H, s), 1.86 (1H, m), 1.79-1.67 (2H, m), 1.64-1.52 (3H, m), 1.47-1.34 (2H, m), 1.28-1.05 (3H, m).

Intermediate 144

N$^2$-butyl-8-(methoxy)-9-[4-(tetrahydro-2H-pyran-3-yl)butyl]-9H-purine-2,6-diamine

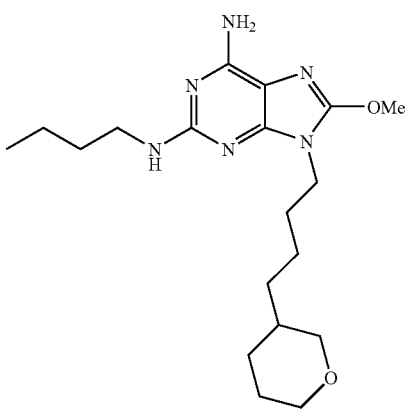

To a solution of N$^2$-butyl-8-(methoxy)-9H-purine-2,6-diamine (250 mg) in dry N,N-dimethylformamide (4.46 ml) at room temperature was added potassium carbonate (395 mg). The reaction mixture was stirred at 60° C. for 90 min. The reaction was cooled to room temperature and 4-(tetrahydro-2H-pyran-3-yl)butyl methanesulfonate (186 mg) was added and the reaction stirred at 90° C. for 2 hours. The reaction mixture was taken up in ethyl acetate (50 ml) and washed with water (2×50 ml). The organic layer was separated, dried over magnesium sulfate, filtered and concentrated in vacuo to give an orange oil (366 mg). The product was purified by C$_{18}$ reverse phase chromatography using water (containing 0.1% formic acid)-acetonitrile (containing 0.05% formic acid) as eluant (30-70%) to afford the title compound as an orange gum (172 mg).

MS calcd for $(C_{19}H_{32}N_6O_2)^+$=376
MS found (electrospray): $(M+H)^+$=377

Intermediate 145

N$^2$-(2-Cyclopropylethyl)-9-(tetrahydro-2H-pyran-2-yl)-9H-Purine-2,6-diamine

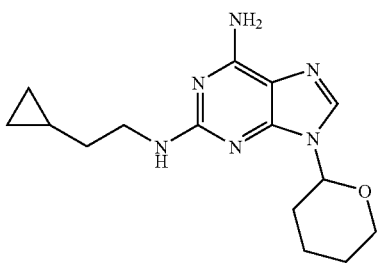

To a suspension of 2-chloro-9-(tetrahydro-2H-pyran-2-yl)-9H-purin-6-amine (3.49 g) in ethylene glycol (17 ml) at room temperature was added cyclopropylethylamine (4.69 g). The reaction mixture was heated to 120° C. with reflux condenser overnight, resulting in a yellow/brown solution. The reaction was allowed to cool, taken up in ethyl acetate (100 ml) and washed with water (2×100 ml). The organic layer was separated, dried over magnesium sulfate, filtered and concentrated in vacuo to give a dark brown gum (4.17 g)

MS calcd for $(C_{15}H_{22}N_6O)^+=302$
MS found (electrospray): $(M+H)^+=303$

Intermediate 146

8-Bromo-$N^2$-(2-cyclopropylethyl)-9-(tetrahydro-2H-pyran-2-yl)-9H-Purine-2,6-diamine

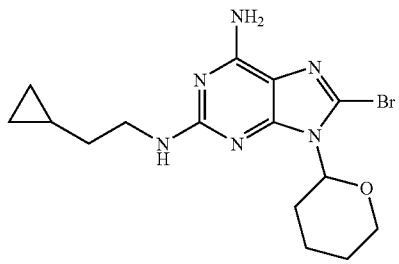

To a solution of $N^2$-(2-cyclopropylethyl)-9-(tetrahydro-2H-pyran-2-yl)-9H-purine-2,6-diamine (4.17 g) in chloroform (46.0 ml) at 0° C., was added N-bromosuccinimide (2.58 g) to give a dark green suspension. The reaction mixture was stirred at room temperature for 1 h. The reaction mixture was taken up in dichloromethane (100 ml) and washed with water (1×100 ml). The organic layer was separated, dried by passing through a hydrophobic frit and concentrated in vacuo to give a green gum (5.50 g, 80% pure).

MS calcd for $(C_{15}H_{21}BrN_6O)^+=380, 382$
MS found (electrospray): $(M+H)^+=381, 383$ Intermediate 147

$N^2$-(2-Cyploroylethyl)-8-(methoxy)-9-(tetrahydro-2H-pyran-2-yl)-9H-purine-2,6-diamine

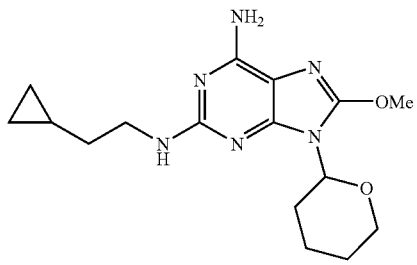

To a solution of 8-bromo-$N^2$-(2-cyclopropylethyl)-9-(tetrahydro-2H-pyran-2-yl)-9H-purine-2,6-diamine (5.50 g) in methanol (48.1 ml) at room temperature was added sodium methoxide (9.9 ml, 25% wt in methanol) to give a brown solution. The reaction mixture was stirred at reflux for 24 hours. The reaction was allowed to cool before adding ammonium chloride solution (100 ml) and extracting with ethyl acetate (150 ml). The organic layer was separated and washed with water (100 ml). The organic layer was separated, dried over magnesium sulfate, filtered and concentrated in vacuo to give a brown solid (3.79 g). The product was purified by $C_{18}$ reverse phase chromatography using water (containing 0.1% formic acid)-acetonitrile (containing 0.05% formic acid) as eluant (20-60%) to afford the title compound as an brown gum (3.3 g, 79% pure).

MS calcd for $(C_{16}H_{24}N_6O_2)^+=332$
MS found (electrospray): $(M+H)^+=333$ Intermediate 148

$N^2$-(2-Cyclopropylethyl)-8-(methoxy)-9H-Purine-2,6-diamine trifluoroacetate

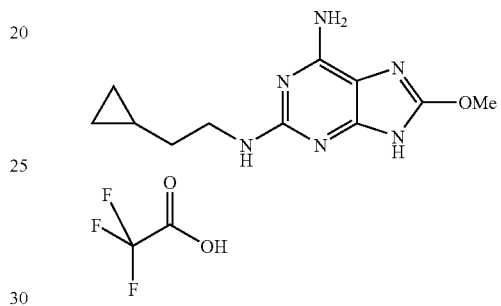

To a solution of $N^2$-(2-cyclopropylethyl)-8-(methoxy)-9-(tetrahydro-2H-pyran-2-yl)-9H-purine-2,6-diamine (3.30 g) in methanol (33.0 ml) at room temperature was added trifluoroacetic acid (3.30 ml) to give an orange solution. The reaction mixture was stirred at room temperature for 70 hours. The reaction mixture was concentrated in vacuo to give a yellow solid which was then triturated in diethyl ether (100 ml) and filtered under vacuum to give an off-white solid (2.4 g).

MS calcd for $(C_{11}H_{16}N_6O)^+=248$
MS found (electrospray): $(M+H)^+=249$

Intermediate 149

$N^2$-(2-Cyclopropylethyl)-8-(methox)-9-(tetrahydro-3-furanylmethyl)-9H-purine-2,6-diamine

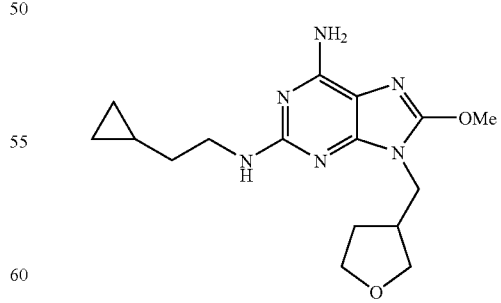

To a solution of $N^2$-(2-cyclopropylethyl)-8-(methoxy)-9H-purine-2,6-diamine trifluoroacetate (400 mg) in N,N-dimethylformamide (6.90 ml) at room temperature was added potassium carbonate (610 mg) and the reaction mixture stirred at 60° C. for 90 minutes. The reaction was cooled to room temperature and tetrahydro-3-furanylmethyl methanesulfonate (219 mg) was added, stirring was continued at 50° C. for 20 h. The reaction temperature was increased to 90° C. and stirring continued. The reaction was cooled and taken up in ethyl acetate (50 ml) and washed with water (2×50 mL). The organic layer was separated, dried over magnesium sulfate, filtered and concentrated in vacuo to give an orange oil. The product was purified by $C_{18}$ reverse phase chromatography using water (containing 0.1% formic acid)-acetonitrile (containing 0.05% formic acid) as eluant (10-45%) to afford the title compound as a yellow oil (209 mg, 84% pure).

MS calcd for $(C_{16}H_{24}N_6O_2)^+$=332
MS found (electrospray): $(M+H)^+$=333

Intermediate 150

$N^2$-(2-Cyclopropylethyl)-8-(methyoxy)-9-(tetrahydro-2H-pyran-3-ylmethyl)-9H-Purine-2,6-diamine

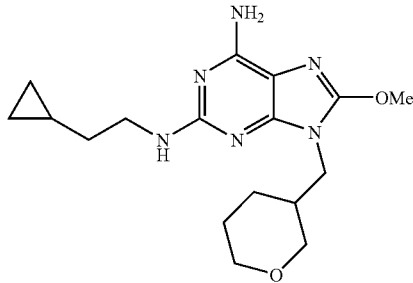

To a solution of $N^2$-(2-cyclopropylethyl)-8-(methoxy)-9H-purine-2,6-diamine trifluoroacetate (400 mg) in N,N-dimethylformamide (6.90 ml) at room temperature was added potassium carbonate (610 mg) and the reaction stirred at 60° C. for 90 minutes. The reaction mixture was cooled to room temperature and tetrahydro-2H-pyran-3-ylmethyl methanesulfonate (236 mg) was added. Stirring was continued at 50° C. for 20 hours. The reaction temperature was increased to 90° C. and stirring continued. The reaction was cooled and taken up in ethyl acetate (50 ml) and washed with water (2×50 ml). The organic layer was separated, dried over magnesium sulfate, filtered and concentrated in vacuo to give an orange oil. The product was purified by $C_{18}$ reverse phase chromatography using water (containing 0.1% formic acid)-acetonitrile (containing 0.05% formic acid) as eluant (10-50%) to afford the title compound as a colourless oil (198 mg, 88% pure).

MS calcd for $(C_{17}H_{26}N_6O_2)^+$=346
MS found (electrospray): $(M+H)^+$=347

Intermediate 151

8-Bromo-2-([2-[(1-methylethyl)oxy]ethyl]oxy)-9-(tetrahydro-2H-Pyran-2-yl)-9H-purin-6-amine

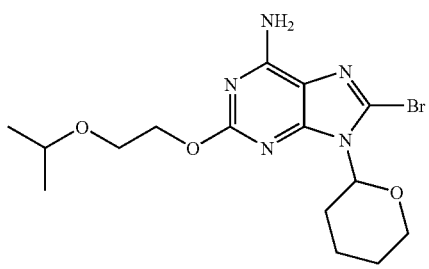

2-Chloro-9-(tetrahydro-2H-pyran-2-yl)-9H-purin-6-amine (5 g, 20 mmol) was added to a stirring solution of potassium tert.-butoxide in 2-[(1-methylethyl)oxy]ethanol (50 ml). The mixture was heated to 80-90° C. for 4 h. The alcohol was removed under reduced pressure. The residue was added to ethyl acetate and was washed with water three times, dried, filtered and concentrated to give the crude product. This product was semipurified by silica gel chromatography eluting with 1:1 ethyl acetate:petroleum ether to give material (3.3 g). This and similarly prepared material were used in the next stage. To this material (6.8 g, 21.2 mmol) in DCM was added NBS (4.15 g, 23.3 mmol). Stirred for 16 h at room temperature and washed twice with aqueous sodium bicarbonate. The crude product was purified through silica gel eluting with 1:2 ethyl acetate:petroleum ether to give the title compound (5.6 g).

$^1$H NMR (CDCl$_3$): 6.15-5.95 (2H, br. s), 5.52 (1H, m), 4.38 (2H, m), 4.15-4.0 (1H, m), 3.73 (2H, t), 3.7-3.55 (2H, m), 3.05-2.85 (1H, m), 2.1-1.95 (1H, m), 1.85-1.45 (4H, overlapping m), 1.12 (6H, d).

Intermediate 152

2-({2-[(1-Methylethyl)oxy]ethyl}oxy)-8-(methoxy)-9-(tetrahydro-2H-Pyran-2-yl)-9H-purin-6-amine

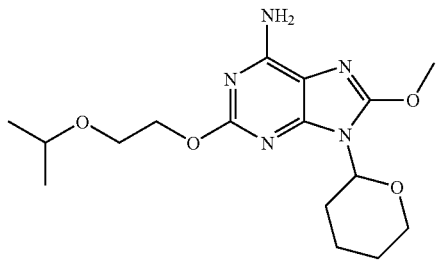

To methanol (120 ml) was added sodium (0.966 g). When the metal was dissolved, 8-bromo-2-({2-[(1-methylethyl)oxy]ethyl}oxy)-9-(tetrahydro-2H-pyran-2-yl)-9H-purin-6-amine (5.69 g, 21.2 mmol) was added, heated to reflux and the solution stirred for 16 h, cooled to room temperature. The solvent was removed. Extracted with ethyl acetate after adding water, dried and concentrated to give the crude product which was purified through silica gel eluting with 2:1 ethyl acetate:petroleum ether to give the title compound (4.8 g).

$^1$H NMR (CDCl$_3$): 5.47 (1H, m), 5.33 (2H, br. s), 4.41 (2H, m), 4.2-4.0 (4H, br. s), 3.76 (2H, m), 3.7-3.55 (2H, m), 2.85-2.65 (1H, m), 2.1-1.9 (1H, m), 1.85-1.45 (4H, overlapping m), 1.17 (6H, d).

Intermediate 153

2-({2-[(1-Methylethyl)oxy]ethyl}oxy)-8-(methoxy)-9H-purin-6-amine trifluoroacetate

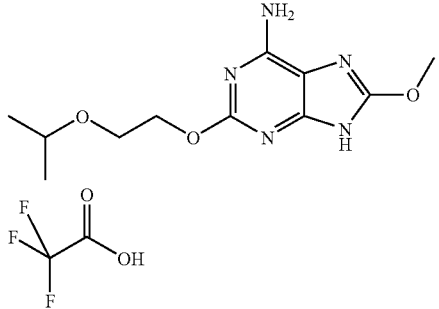

To 2-({2-[(1-methylethyl)oxy]ethyl}oxy)-8-(methoxy)-9-(tetrahydro-2H-pyran-2-yl)-9H-purin-6-amine (4.5 g, 14 mmol) in methanol (30 ml) was added trifluoroacetic acid (8 ml), stirred for 10 min and held at room temperature for 2 days. Filtered to give the crude product which was purified by preparative hplc (Gilson GX-281 instrument with YMC C18 5.0 um column (250×20 mm) eluting with water containing TFA (0.1%): acetonitrile 30-60%. This gave the title compound 2.1 g.

$^1$H NMR (CDl$_3$OD): 4.55 (2H, m), 4.13 (3H, s), 3.78 (2H, t), 3.67 (1H, m), 1.14 (6H, d). Exchangeable protons not observed.

Intermediate 154

Tetrahydro-3-furancarbonyl chloride

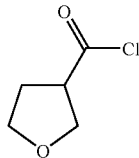

To tetrahydro-3-furancarboxylic acid (24.3 g) in anhydrous dichloromethane (299 ml) at room temperature and under nitrogen was added oxalyl chloride (27.5 ml) dropwise over 10 minutes followed by a few drops of DMF. The reaction was allowed to stir overnight. The reaction was concentrated in vacuo to yield an orange oil (28 g).

$^1$H NMR (CDCl$_3$): δ 4.11 (1H, dd), 4.01 (1H, m), 3.93 (1H, m), 3.84 (1H, m), 3.57 (1H, m), 2.34 (1H, m), 2.23 (1H, m).

Intermediate 155 (diastereoisomer 1) and Intermediate 156 (diastereoisomer 2)

(4R)-4-(Phenylmethyl)-3-[(3S)-tetrahydro-3-furanylcarbonyl]-1,3-oxazolidin-2-one and (4R)-4-(phenylmethyl)-3-[(3S)-tetrahydro-3-furanylcarbonyl]-1,3-oxazolidin-2-one

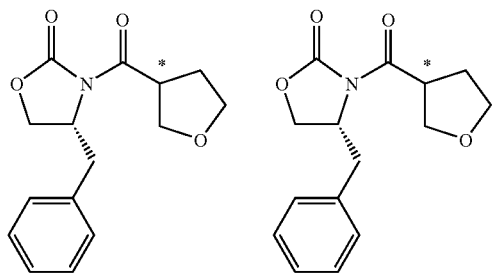

To a solution of (4R)-4-(phenylmethyl)-1,3-oxazolidin-2-one (31 g) in anhydrous tetrahydrofuran (583 ml) at −78° C. and under nitrogen, was added n-butyllithium (115 ml) dropwise over 30 minutes maintaining the internal temperature below −65° C. The reaction was stirred at −78° C. for 25 minutes and then a solution of tetrahydro-3-furancarbonyl chloride (28.2 g) in anhydrous tetrahydrofuran (20 ml) was added dropwise over 20 minutes maintaining the temperature below −65° C. Following the addition the reaction was warmed over 30 minutes to room temperature. The reaction was quenched with saturated aqueous ammonium chloride (50 ml) and then concentrated in vacuo. The residue was taken up in dichloromethane (400 ml) and washed with brine (2×50 ml). The organic layer was dried through a hydrophobic frit and concentrated in vacuo. The product was purified by silica chromatography (1.5 kg) (ISCO) using a gradient elution of 2% ethyl acetate:dichloromethane. This yielded 15 g of the faster moving product (semi-pure Diastereoisomer 1) and 15 g of the slower moving product (semi-pure Diastereoisomer 2). About 20 g of mixed fractions were also collected.

Semi-pure diastereoisomer 1 was crystallised from cyclohexane/5% ethyl acetate. The crystals were collected by suction filtration and dried on a rotary evaporator at 50° C. for 15 minutes. $^1$HNMR indicated presence of the other diastreoisomer. The product was further purified by silica chromatography (~800 g, Toluene/5% Diethyl ether) to afford diastereoisomer 1 as a white solid (6.85 g, 98.4:1.56 by chiral HPLC). Semi-pure diastereoisomer 2 was recrystallised from cyclohexane/5% ethyl acetate. The crystals were collected by suction filtration and dried on a rotary evaporator at 50° C. for 15 minutes. $^1$HNMR indicated presence of the other diastreoisomer. The product was purified by silica chromatography (~800 g, Toluene/5% Diethyl ether) to afford a white solid (96:4 by chiral HPLC). This was recrystallised from cyclohexane/15% ethyl acetate to afford diastereoisomer 2 as white crystals (6.2 g, 96.4:3.6 by chiral HPLC).

The mixed fractions (~20 g) were purified by silica chromatography ISCO (1.5 kg) (ISCO) using a gradient elution of 5% TBME/Toluene to afford semi-pure diastereoisomer 1, as a clear oil that crystallises (7.3 g, 95.2:4.80 by chiral HPLC) and semi-pure diastereoisomer 2 as a clear oil that crystallises (6.7 g, 96.1:3.80 by chiral HPLC).

The two solid batches of diastereoisomer 1 were combined and recrystallised from cyclohexane:ethyl acetate, 5:1. The crystals were filtered. This recrystallisation process was repeated 3 times to afford diastereoisomer 1 (10.7 g, 98.5:1.5 by chiral HPLC).

The two solid batches of diastereoisomer 2 were combined. The combined solids were recrystallised from Cyclohexane:ethyl acetate, 5:1. The crystals were filtered. This recrystallisation process was repeated 3 times to afford diastereoisomer 2 (9.6 g, 99.5:0.5 by chiral HPLC).

Intermediate 155 (diastereoisomer 1) $^1$H NMR (CDCl$_3$): δ 7.43-7.31 (3H, m), 7.29-7.23 (2H, m), 4.75 (1H, m), 4.33-4.25 (2H, m), 4.23-4.12 (2H, m), 4.07-4.00 (2H, m), 3.90 (1H, m), 3.33 (1H, dd), 2.86 (1H, dd), 2.39 (1H, m), 2.19 (1H, m).
Intermediate 156 (diastereoisomer 2) $^1$H NMR (CDCl$_3$): δ 7.43-7.31 (3H, m), 7.29-7.23 (2H, m), 4.74 (1H, m), 4.32-

4.19 (3H, m), 4.10-4.03 (2H, m), 4.00 (1H, m), 3.90 (1H, m), 3.36 (1H, dd), 2.84 (1H, dd), 2.31 (2H, m).

Intermediate 155 and Intermediate 156, Alternative Procedure (4R)-4-(Phenylmethyl)-3-[(3S)-tetrahydro-3-furanyl-carbonyl]-1,3-oxazolidin-2-one and (4R)-4-(phenyl-methyl)-3-[(3R)-tetrahydro-3-furanylcarbonyl]-1,3-oxazolidin-2-one

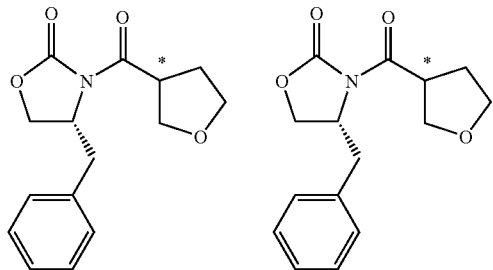

To tetrahydro-3-furoic acid (13 g) in dry toluene (90 ml) at room temperature and under nitrogen, was added (4R)-4-(phenylmethyl)-1,3-oxazolidin-2-one (10 g) in one go followed by dry triethylamine (31.5 ml) in one go. The reaction was heated to 80° C. and to the clear solution was added pivaloyl chloride (13.9 ml) dropwise over five minutes after which the reaction turns cloudy and viscous. The reaction was heated to 115° C. overnight. The reaction was cooled to room temperature and diluted with ethyl acetate (150 ml). This mixture was washed with 2M HCl (50 ml), water (50 ml) and a saturated aqueous solution of sodium hydrogen carbonate (50 ml). The organic layer was dried over magnesium sulfate, filtered and concentrated in vacuo to yield a brown viscous oil. The product was purified by silica chromatography (~750 g) using a gradient elution of toluene/10% diethyl ether to afford 4.6 g of the faster moving product (Diastereoisomer 1, 99.5:0.5 by chiral HPLC) and 4.3 g of the slower moving product (Diastereoisomer 2, 91.8:8.2 by chiral HPLC).

$^1$H NMR (CDCl$_3$): As for first procedure.

Intermediate 157

Tetrahydro-3-furanylmethanol (Isomer 1)

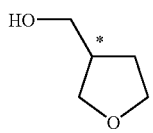

To a solution of (4R)-4-(phenylmethyl)-3-[tetrahydro-3-furanylcarbonyl]-1,3-oxazolidin-2-one, Diastereomer 1 (4.6 g) in diethyl ether (320 ml, AR grade) and water (0.33 ml), at 0° C., was added lithium borohydride (9.2 ml, 2M solution in tetrahydrofuran) dropwise over 5 minutes, maintaining the temperature between 0-5° C. The reaction was left to stir for 30 minutes at this temperature and then warmed to room temperature for 3 hours. A white precipitate forms during the reaction. 2M sodium hydroxide (8.4 ml) was then added dropwise. The reaction turns clear and is stirred for 20 minutes at room temperature. The organic layer was decanted, dried over MgSO$_4$, filtered through celite and concentrated in vacuo. The product was purified by silica chromatography (120 g) (ISCO) using a gradient elution of cyclohexane:ethyl acetate, 0-70%, to afford the title compound as a clear oil (1.3 g).

$^1$H NMR (CDCl$_3$): δ 3.90-3.81 (2H, m), 3.74 (1H, m), 3.67-3.55 (3H, m), 2.47 (1H, m), 2.03 (1H, m), 1.64 (1H, m). Exchangeable protons not observed.

Intermediate 157, Alternative Procedure

Tetrahydro-3-furanylmethanol (Isomer 1)

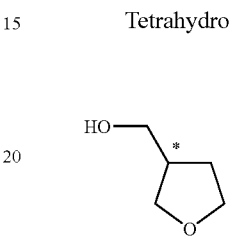

2-{[(Tetrahydro-3-furanylmethyl)oxy]carbonyl}benzoic acid (isomer 2, 3.65 gm) was dissolved in THF (25 ml) and 4N sodium hydroxide (10.94 ml) added. The mixture was refluxed with vigorous stirring for 2 h, then allowed to cool. After 16 h a few ml of brine was added and the mixture extracted 3 times with ethyl acetate, and the combined extracts washed with brine, dried by passing through a hydrophobic frit and evaporated at >10 mbar pressure, water bath 40° C. to give the title compound as a milky oil, yield 1.3 gm.

$^1$H NMR (CDCl$_3$): δ 3.91-3.81 (2H, m), 3.79-3.71 (1H, m), 3.68-3.55 (3H, m), 2.53-2.42 (1H, m), 2.09-1.99 (1H, m), 1.68-1.60 (1H, m). Exchangeable protons not observed.

Intermediate 158

Tetrahydro-3-furanylmethanol (Isomer 2)

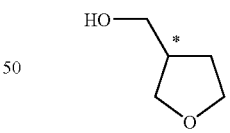

To a solution of (4R)-4-(phenylmethyl)-3-[tetrahydro-3-furanylcarbonyl]-1,3-oxazolidin-2-one, Diastereomer 2 (4.3 g) in diethyl ether (310 ml, AR grade) and water (0.31 ml), at 0° C., was added lithium borohydride (8.6 ml, 2M solution in tetrahydrofuran) dropwise over 5 minutes, maintaining the temperature between 0-5° C. The reaction was left to stir for 30 minutes at this temperature and then warmed to room temperature for 3 hours. 2M sodium hydroxide (7.6 ml) was then added over 5 minutes and the reaction was stirred for 20 minutes at room temperature. The organic layer was decanted, dried over MgSO$_4$, filtered and concentrated in vacuo. The product was purified by silica chromatography (120 g) (ISCO) using a gradient elution of cyclohexane:ethyl actetate, 0-100%, to afford the title compound as a clear oil (1.4 g).

$^1$H NMR (CDCl$_3$): δ 3.90-3.81 (2H, m), 3.74 (1H, m), 3.67-3.55 (3H, m), 2.47 (1H, m), 2.03 (1H, m), 1.64 (1H, m). Exchangeable protons not observed.

Intermediate 158, Alternative Procedure

Tetrahydro-3-furanylmethanol (Isomer 2)

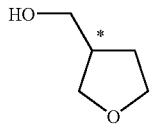

2-{[(Tetrahydro-3-furanylmethyl)oxy]carbonyl}benzoic acid (isomer 1, 4.89 gm) was dissolved in THF (30 ml) and 4N sodium hydroxide (14.7 ml) added. The mixture was refluxed with vigorous stirring for 2 h, then allowed to cool. After 16 h a few ml of brine was added and the mixture extracted 3 times with DCM. The combined extracts were dried by passing through a hydrophobic frit and evaporated at >10 mbar pressure, water bath 40° C. to give the title compound as a pinkish oil, yield 1.77 gm.

$^1$H NMR (CDCl$_3$): δ 3.89-3.82 (2H, m), 3.77-3.71 (1H, m), 3.67-3.56 (3H, m), 2.52-2.42 (1H, m), 2.07-1.99 (1H, m), 1.68-1.61 (1H, m). Exchangeable protons not observed.

Intermediate 159

Tetrahydro-3-furanylmethyl methanesulfonate (Isomer 1)

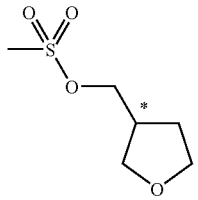

To tetrahydro-3-furanylmethanol, Isomer 1 (1.3 g) in dry dichloromethane (40 ml) at 0° C. and under nitrogen, was added triethylamine (4.09 ml) followed by methanesulfonyl chloride (1.29 ml). The reaction was stirred at room temperature overnight. The orange solution was diluted with dichloromethane (80 ml) and washed with saturated aqueous sodium bicarbonate (40 ml). The organic layer was separated, dried through a hydrophobic frit and concentrated in vacuo to yield the title compound as a yellow oil (2.2 g).

$^1$H NMR((CD$_3$)$_2$SO): δ 4.13 (2H, m), 3.77-3.68 (1H, m), 3.62 (1H, m), 3.46 (1H, m), 3.19 (3H, s), 2.58 (1H, m), 1.97 (1H, m), 1.57 (1H, m).

Intermediate 160

Tetrahydro-3-furanylmethyl methanesulfonate (Isomer 2)

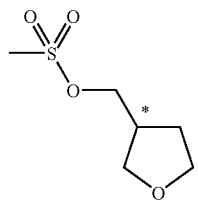

To (3S)-tetrahydro-3-furanylmethanol, Isomer 2 (1.4 g) in dry dichloromethane (40 ml) at 0° C. and under nitrogen, was added triethylamine (3.83 ml) followed by methanesulfonyl chloride (1.39 ml). The reaction was stirred at room temperature overnight. The orange solution was diluted with dichloromethane (50 ml) and washed with saturated aqueous sodium bicarbonate (20 ml). The organic layer was separated, dried through a hydrophobic frit and concentrated in vacuo to yield the title compound as an orange oil (2.6 g).

$^1$H NMR((CD$_3$)$_2$SO): δ 4.13 (2H, m), 3.77-3.68 (1H, m), 3.62 (1H, m), 3.46 (1H, m), 3.19 (3H, s), 2.58 (1H, m), 1.97 (1H, m), 1.57 (1H, m).

Intermediate 161

N$^2$-Butyl-8-(methoxy)-9-[tetrahydro-3-furanylmethyl]-9H-Purine-2,6-diamine (Isomer 1)

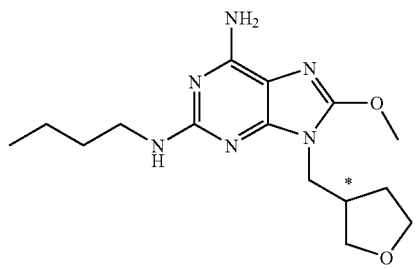

To a solution of N$^2$-butyl-8-methoxy-9H-purine-2,6-diamine trifluoroacetic acid salt (3.89 g) in dry N,N-dimethylformamide (46 ml) at room temperature and under was added potassium carbonate (6.14 g) in one go. The reaction was heated to 60° C., under nitrogen, for 1.5 hours. A solution of tetrahydro-3-furanylmethyl methanesulfonate, Isomer 1 (2.2 g) in dry N,N-dimethylformamide (2 ml) was added via a Pasteur pipette and the reaction heated at 70° C. for 16 hours. The reaction was cooled to room temperature, diluted with ethyl acetate (100 ml) and washed with brine (20 ml). The organic layer was concentrated in vacuo. The product was purified by C$_{18}$ reverse phase chromatography using water (0.1% formic acid)-acetonitrile (0.05% formic acid) as eluant (10-50%) to afford the title compound as a clear viscous oil (2.79 g).

MS calcd for $(C_{15}H_{24}N_6O_2)^+$=320
MS found (electrospray): $(M+H)^+$=321

Intermediate 162

N²-Butyl-8-(methoxy)-9-[tetrahydro-3-furanylmethyl]-9H-Purine-2,6-diamine (Isomer 2)

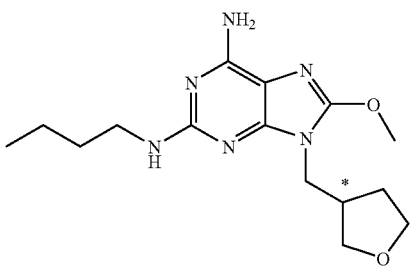

To a solution of N²-butyl-8-methoxy-9H-purine-2,6-diamine trifluoroacetic acid salt (4.60 g) in dry N,N-dimethylformamide (55 ml) at room temperature and under was added potassium carbonate (7.25 g) in one go. The reaction was heated to 60° C. for 1.5 hours. A solution of tetrahydro-3-furanylmethyl methanesulfonate, Isomer 2 (2.6 g) in dry N,N-dimethylformamide (3 ml) was added via a Pasteur pipette and the reaction heated at 70° C. for 16 hours. The reaction was cooled to room temperature, diluted with ethyl acetate (100 ml) and washed with brine (20 ml). The organic layer was concentrated in vacuo. The product was purified by $C_{18}$ reverse phase chromatography using water (0.1% formic acid)-acetonitrile (0.05% formic acid) as eluant (10-60%) to afford the title compound as a clear viscous oil (3 g).

MS calcd for $(C_{15}H_{24}N_6O_2)^+$=320
MS found (electrospray): $(M+H)^+$=321

Intermediate 163

2-{[(Tetrahydro-3-furanylmethyl)oxy]carbonyl}benzoic acid

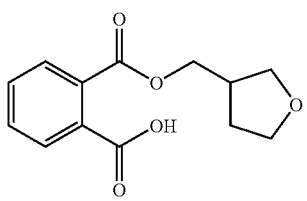

A mixture of phthalic anhydride (7.41 gm) and tetrahydro-3-furanmethanol were heated with stirring at 130° C. under nitrogen. After 1.5 h, the clear liquid was allowed to cool, treated with water and extracted with EtOAc (×3). The combined organics were dried by passing through a hydrophobic frit and evaporated to a clear oil which crystallised on trituration with light petrol. The solid was filtered, washed and dried, yield 11.93 gm.

MS calcd for $(C_{13}H_{14}O_5)^+$=250
MS found (electrospray): $(M+H)^+$=251

Intermediate 164 and Intermediate 165

2-{[(Tetrahydro-3-furanylmethyl)oxy]carbonyl}benzoic acid, (Isomers 1 and 2)

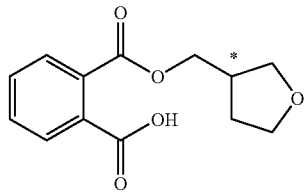

2-{[(Tetrahydro-3-furanylmethyl)oxy]carbonyl}benzoic acid (11.93 gm) was separated in 250 mg portions by chiral HPLC using a 5 cm×20 cm Chiralpak AD column, eluting with heptane:ethanol containing 0.1% trifluoroacetic acid (80:20). Mixed fractions were evaporated and separated again as described above. Fractions containing pure earlier eluting material were combined and evaporated to give a white solid, yield 4.89 gm, Isomer 1, Intermediate 164.

1H NMR (CDCl₃): 7.99 (1H, broad s), 7.93-7.86 (1H, m), 7.74-7.65 (1H, m), 7.65-7.53 (2H, overlapping m), 4.44-4.34 (1H, m), 4.29-4.18 (1H, m), 4.00-3.88 (2H, m), 3.85-3.67 (2H, overlapping m), 2.81-2.66 (1H, m), 2.17-2.05 (1H, m), 1.80-1.68 (1H, m).

Fractions containing slower running material were treated similarly to give a white solid, yield 3.65 gm, Isomer 2, Intermediate 165.

1H NMR (CDCl₃): 7.92-7.84 (1H, m), 7.74-7.66 (1H, m), 7.63-7.52 (2H, overlapping m), 7.38 (1H, broad s), 4.43-4.33 (1H, m), 4.27-4.17 (1H, m), 3.98-3.87 (2H, m), 3.83-3.65 (2H, m), 2.79-2.65 (1H, m), 2.16-2.03 (1H, m), 1.78-1.65 (1H, m).

Intermediate 166

2-[(2-Cyclopropylethyl)oxy]-9-(tetrahydro-2H-pyran-2-yl)-9H-purin-6-amine

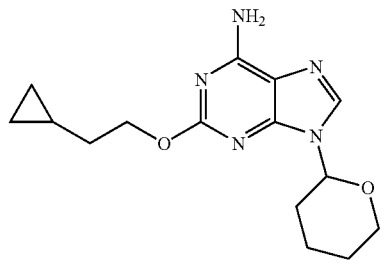

To a stirring solution of sodium tert.-butoxide (13.45 g) in DME (80 ml) was added dropwise under nitrogen a solution of 2-cyclopropylethanol (12.1 g) in DME (40 ml) over 5 min. After 30 min 2-chloro-9-(tetrahydro-2H-pyran-2-yl)-9H-purin-6-amine (11.84 g) was added and the stirring mixture refluxed for 20 h. After cooling the mixture was treated with water and extracted twice with ethyl acetate. The combined extracts were washed with water then brine, dried by passing through a hydrophobic frit and evaporated to a brown oil. This was re-evaporated twice from toluene then purified on a silica column using an ISCO Companion, eluting with methanol: ethyl acetate (0-12%) to give the title compound. Yield 6.53 gm.

MS calcd for $(C_{15}H_{21}N_5O_2)^+=303$
MS found (electrospray): $(M+H)^+=304$ Intermediate 167

8-Bromo-2-[(2-cyclopropylethyl)oxy]-9-(tetrahydro-2H-pyran-2-yl)-9H-purin-6-amine

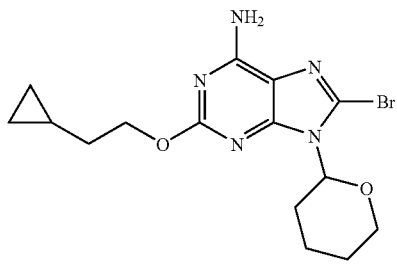

To an ice cooled stirring solution of 2-[(2-cyclopropylethyl)oxy]-9-(tetrahydro-2H-pyran-2-yl)-9H-purin-6-amine (6.53 g) in chloroform (75 ml), was added N-bromosuccinimide (4.02 g). The reaction mixture was allowed to warm to room temperature and after 16 h treated with water and extracted twice with DCM. The combined extracts were washed with dilute sodium metabisulphite then dilute brine, dried by passing through a hydrophobic frit and evaporated to give the title compound as an orange foam, yield 7.96 gm.

MS calcd for $(C_{15}H_{20}BrN_5O_2)^+=381, 383$
MS found (electrospray): $(M+H)^+=382, 384$ Intermediate 168

2-[(2-Cyclopropylethyl)oxy]-8-(methoxy)-9-(tetrahydro-2H-pyran-2-yl)-9H-purin-6-amine

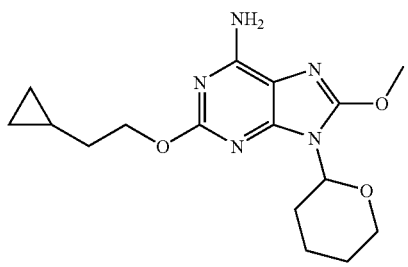

A stirring suspension of 8-bromo-2-[(2-cyclopropylethyl)oxy]-9-(tetrahydro-2H-pyran-2-yl)-9H-purin-6-amine (7.96 g) in methanol (80 ml) was treated with 25 wt % sodium methoxide in methanol (14.29 ml) and refluxed under nitrogen for 3.5 h. After allowing to cool over 16 h the solvent was evaporated and the residue treated with saturated ammonium chloride and extracted twice with ethyl acetate. The combined extracts were washed with brine, dried by passing through a hydrophobic frit and evaporated to give the title compound as a brown solid, yield 6.49 gm.

MS calcd for $(C_{16}H_{23}N_5O_3)^+=333$
MS found (electrospray): $(M+H)^+=334$ Intermediate 169

2-[(2-Cyclopropylethyl)oxy]-8-(methoxy)-1H-purin-6-amine trifluoroacetate salt

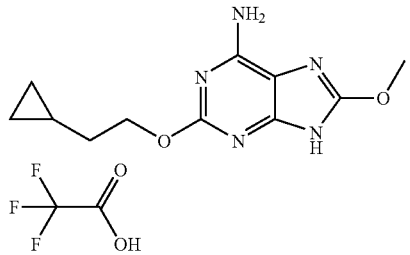

2-[(2-Cyclopropylethyl)oxy]-8-(ethoxy)-9-(tetrahydro-2H-pyran-2-yl)-9H-purin-6-amine (6.49 g) was treated with methanol (65 ml) and the resulting suspension stirred and ice cooled whilst TFA (6.5 ml) was added. The mixture was allowed to warm to room temperature and after 72 h the solvents were evaporated and the remaining orange solid triturated with cold ethyl acetate (50 ml), filtered, washed and dried under vacuum, to give the title compound yield 4.78 gm.

MS calcd for $(C_{11}H_{15}N_5O_2)^+=249$
MS found (electrospray): $(M+H)^+=250$ A second crop was obtained by evaporation of the filtrate and trituration of the residue with ether, yield 0.99 gm. Slightly less pure than first crop.

Intermediate 170

2-[(2-Cyclopropylethyl)oxy]-8-(methoxy)-9-(tetrahydro-3-furanylmethyl)-9H-purin-6-amine (Isomer 1)

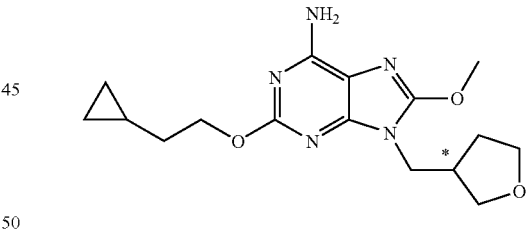

A stirring mixture of 2-[(2-cyclopropylethyl)oxy]-8-(methoxy)-1H-purin-6-amine trifluoroacetic acid salt (2.89 g), potassium carbonate (4.41 g) and dry DMF (32 ml) was heated at 60° C. under nitrogen for 90 minutes. Tetrahydro-3-furanylmethyl methanesulfonate (1.869 g, isomer 1) was then added and stirring continued at 70° C. for 1 h, then at 90° C. for 2 h. The solvent was evaporated and the residue treated with water and extracted three times with ethyl acetate. The combined extracts were washed with water then brine, dried by passing through a hydrophobic frit and evaporated to a brown oil. This was purified on a 360 gm C18 column using water (+0.1% formic acid)/acetonitrile (+0.05% formic acid). Appropriate fractions were combined and evaporated, yield 814 mg.

MS calcd for $(C_{16}H_{23}N_5O_3)^+=333$
MS found (electrospray): $(M+H)^+=334$

Intermediate 171

2-[(2-Cyclopropylethyl)oxy]-8-(methoxy)-9-[tetrahydro-3-furanylmethyl]-9H-purin-6-amine (Isomer 2)

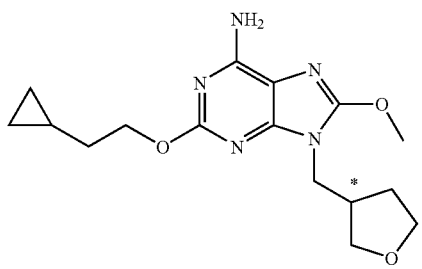

To a solution of 2-[(2-cyclopropylethyl)oxy]-8-(methoxy)-1H-purin-6-amine trifluoroacetic acid salt (2.89 g) in dry N,N-dimethylformamide (32 ml) under nitrogen and at room temperature, was added potassium carbonate (4.41 g) in one go. The reaction was heated to 60° C. and stirred for 90 minutes. A solution of tetrahydro-3-furanylmethyl methanesulfonate, Isomer 2 (1.869 g) in dry DMF (3 ml) was then added gradually via pipette. The reaction was heated to 70° C. and left to stir overnight. Still 22% starting material present by LCMS, therefore increased temperature to 90° C. and stirred for a further 3 hours at this temperature. The reaction was cooled and diluted with ethyl acetate (100 ml) and washed with water (50 ml) and brine (50 ml). The organic layer was concentrated in vacuo to yield an orange oil. The product was purified by $C_{18}$ reverse phase chromatography using water (0.1% formic acid)-acetonitrile (0.05% formic acid) as eluant (10-60%) to afford the title compound as an orange viscous oil (1.45 g).

MS calcd for $(C_{16}H_{23}N_5O_3)^+=333$
MS found (electrospray): $(M+H)^+=334$

Intermediate 172

N²-Butyl-8-(methoxy)-9-(tetrahydro-3-furanylmethyl)-9H-Purine-2,6-diamine

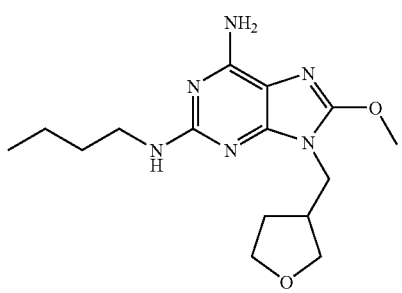

N²-Butyl-8-(methoxy)-3H-purine-2,6-diamine trifluoroacetic acid salt (0.25 g) and anhydrous potassium carbonate (0.395 g) in anhydrous DMF (3 mL) was heated for 1 hour at 60° C. (external) under nitrogen, before being allowed to cool to room temperature. To the reaction mixture was then added 3-(bromomethyl) tetrahydrofuran (0.236 g) and the reaction mixture heated under nitrogen to 50° C. (external) for 18.5 hours. The reaction mixture was then diluted with water (15 mL) and extracted with diethyl ether (15 mL, 3 times). The organic layers were combined and dried over anhydrous sodium sulphate. The sodium sulphate was filtered off and the filtrate evaporated under reduced pressure to give an oil. This oil was triturated with cyclohexane and a little diethyl ether to give a solid. The cyclohexane and diethyl ether was evaporated under reduced pressure to give a white solid. The solid (0.2606 g) was dissolved in hot ethanol (2 mL). To this solution was then added water (8 mL) and the resultant suspension was heated to reflux (93° C., external) giving a solution. The solution was then allowed to cool slowly (by not removing the flask from the reaction block and turning the power off to the heating block). This gave a solid gum on cooling which when sonicated gave a white solid. This solid was isolated by filtration under suction and then dried under vacuo at 50° C., overnight. This gave the title compound (0.1043 g) as a white solid.

MS calcd for $(C_{15}H_{24}N_6O_2)^+=320$
MS found (electrospray): $(M+H)^+=321$
¹H NMR (CDCl₃): δ 4.94 (2H, br s), 4.64-4.55 (1H, m), 4.1 (3H, s), 3.98-3.82 (3H, m), 3.81-3.72 (2H, m), 3.68-3.62 (1H, m), 3.37 (2H, q), 2.89-2.76 (1H, m), 2.02-1.91 (1H, m), 1.79-1.68 (1H, m), 1.62-1.52 (2H, m), 1.48-1.36 (2H, m), 0.95 (3H, t).

Intermediate 172, Alternative Procedure

N²-Butyl-8-(methoxy)-9-(tetrahydro-3-furanylmethyl)-9H-purine-2,6-diamine

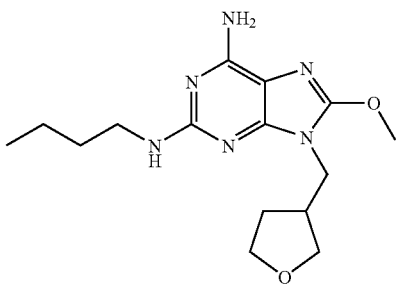

N²-Butyl-8-(methoxy)-3H-purine-2,6-diamine trifluoroacetic acid salt (0.25 g) and anhydrous potassium carbonate (0.395 g) in anhydrous DMF (3 mL) was heated under nitrogen at 60° C. (external) for 1 hour. After allowing the reaction mixture to cool to ambient room temperature, tetrahydro-2-furanylmethyl methanesulfonate (0.257 g) was added and the reaction mixture was heated for at 70° C. (external) for 18.5 hours under nitrogen. The reaction mixture [N2420-15-D3] was diluted with water (15 mL) and extracted with diethyl ether (15 mL, 3 times). The organic layers were combined and dried over anhydrous sodium sulphate. The sodium sulphate was filtered off and the filtrate evaporated under reduced pressure to give an oily gum. This material was then triturated with cyclohexane and diethyl ether with scratching until a pale yellow solid was obtained. The cyclohexane and diethyl ether was removed by evaporation under reduced pressure to give a pale yellow solid (0.2123 g). This was dissolved in hot ethanol (2 mL). To this solution was added water (8 mL) to give an oily suspension that was then heated to reflux (90° C., external) giving a solution. The resultant solution was allowed to cool slowly by not removing the flask from the heating block and turning off the power to the heating block.

On cooling to ambient temperature, the resultant gum was sonicated and scratched to give a solid. This solid was filtered off under suction and the resultant filter cake was washed with water (2 mL). The resultant white solid was then air-dried under suction before being dried further under vacuo at 50° C. to constant weight to give the title compound as a slightly off-white solid (0.109 g).

MS calcd for $(C_{15}H_{24}N_6O_2)^+$=320
MS found (electrospray): $(M+H)^+$=321
$^1$H NMR (CDCl$_3$): δ 4.93 (2H, br s), 4.64-4.53 (1H, m), 4.1 (3H, s), 3.98-3.82 (3H, m), 3.81-3.71 (2H, m), 3.69-3.61 (1H, m), 3.37 (2H, q), 2.89-2.76 (1H, m), 2.03-1.91 (1H, m), 1.79-1.68 (1H, m), 1.63-1.51 (2H, m), 1.48-1.36 (2H, m), 0.95 (3H, t).

Intermediate 173

2-[(3S)-Tetrahydro-3-furanyl]ethanol

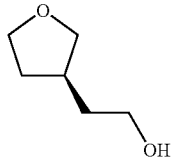

Boran-tetrahydrofuran-complex, 1M in THF (50 ml, 50.0 mmol) was added dropwise over one hour to a stirred solution of (3R)-tetrahydro-3-furanylacetic acid (2.4 g, 18.44 mmol) (*J. Med. Chem.*, 1993, 36, 2300) in dry THF (35 ml) cooled to −5° C. under a nitrogen atmosphere. The reaction mixture was warmed to room temperature and left stirring under nitrogen atmosphere for 16 hours. The reaction mixture was cooled down to −5° C. and methanol (15 ml) was added dropwise, keeping the temperature under 5° C. The solution was concentrated under vacuum and the residue was dissolved in DCM and purified by chromatography on silica (100 g) using a gradient of dichloromethane:ethyl acetate (0-100% gradient over 40 mins). The desired fractions were combined and concentrated under vacuum to give title compound as a colourless oil (1.4 g).

$^1$H NMR (400 MHz, DMSO-d$_6$) δ ppm 1.38-1.52 (m, 3 H) 1.91-2.01 (m, 1 H) 2.11-2.24 (m, 1 H) 3.17-3.23 (m, 1 H) 3.35-3.46 (m, 2 H) 3.56-3.63 (m, 1 H) 3.66-3.72 (m, 2 H excess) 3.75-3.80 (m, 2 H excess) OH not observed Intermediate 174

(3R)-3-(2-Bromoethyl)tetrahydrofuran

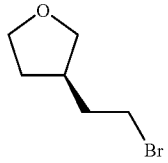

A solution of triphenylphosphine (6.32 g, 24.11 mmol) in dry dichloromethane (10 ml) was added dropwise over 30 minutes to a stirred solution of 2-[(3S)-tetrahydro-3-furanyl] ethanol (1.4 g, 12.05 mmol) and carbon tetrabromide (7.99 g, 24.11 mmol) in dry dichloromethane (20 ml) at −2° C. under a nitrogen atmosphere. The reaction mixture was warmed to room temperature and left stirring under nitrogen atmosphere for 20 hours. The reaction mixture was filtered on celite and the white solid was washed with ether and DCM. The orange filtrate was concentrated under vacuum. The residue was dissolved in DCM and purified by chromatography on silica (100 g) using a gradient of cyclohexane:ethyl acetate (0-25% gradient over 40 mins). The desired fractions were combined and concentrated under vacuum to give the title compound as a colourless oil (1.4 g).

1H NMR (400 MHz, DMSO-d$_6$) δ ppm 1.43-1.54 (m, 1 H) 1.84-1.91 (m, 2 H) 1.94-2.03 (m, 1 H) 2.23-2.31 (m, 1 H) 3.24-3.28 (m, 1 H) 3.49-3.56 (m, 2 H) 3.58-3.65 (m, 1 H) 3.68-3.74 (m, 1 H) 3.75-3.80 (m, 1 H) [α]=−9.01 (c=1 in EtOAc, 20° C.)

Intermediate 175

2-[(3R)-Tetrahydro-3-furanyl]ethanol

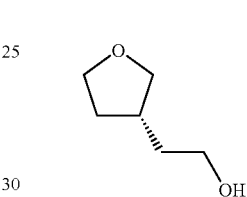

A solution of (3S)-tetrahydro-3-furanylacetic acid (1.8 g, 13.83 mmol) (*J. Med. Chem.*, 1993, 36, 2300) in dry THF (35 ml) was stirred and cooled to −5° C. under nitrogen atmosphere. Lithium Aluminium hydride, 1M in Ether (20.75 ml, 20.75 mmol) was added keeping the temperature under 0° C. The reaction mixture was then warmed to room temperature and left stirring under nitrogen atmosphere for 3 hours. The reaction mixture was cooled down to −5° C. and more lithium aluminium hydride, 1M in ether (20.75 ml, 20.75 mmol) was added, keeping the temperature under 0° C. The reaction mixture was again warmed to room temperature and left stirring under a nitrogen atmosphere for 16 hours. The reaction mixture was cooled down to −5° C. and quenched with saturated aqueous NH$_4$Cl solution (15 ml) which was added dropwise keeping the temperature under 5° C. After, ether (100 ml) was added. The mixture was filtered and the obtained white solid was washed with ether (50 ml) and saturated aqueous NH$_4$Cl solution (50 ml). The phases of the filtrate were separated and the organic layer was dried by passing through a hydrophobic frit and concentrated under vacuum. The white solid was then washed with saturated aqueous NH$_4$Cl solution (50 ml) and EtOAc (50 ml). The phases of the filtrate were separated and the organic layer was dried and concentrated under vacuum. The aqueous phases were combined and extracted with EtOAc (4×100 ml). All the organic extracts were combined, dried using a hydrophobic frit and concentrated under vacuum to give the title compound as a colourless oil (1 g).

$^1$H NMR (400 MHz, DMSO-d$_6$) δ ppm 1.38-1.52 (m, 3 H) 1.92-2.02 (m, 1 H) 2.11-2.24 (m, 1 H) 3.17-3.23 (m, 1 H) 3.34-3.47 (m, 2 H) 3.55-3.64 (m, 1 H) 3.65-3.73 (m, 1 H) 3.74-3.81 (m, 1 H) 4.35-4.41 (m, 1 H)

Intermediate 176

(3S)-3-(2-Bromoethyl)tetrahydrofuran

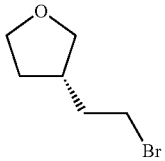

Prepared similarly to Intermediate 174 from 2-[(3R)-tetrahydro-3-furanyl]ethanol 1H NMR (400 MHz, DMSO-$d_6$) δ ppm 1.44-1.54 (m, 1 H) 1.84-1.91 (m, 2 H) 1.94-2.03 (m, 1 H) 2.21-2.33 (m, 1 H) 3.24-3.28 (m, 1 H) 3.50-3.57 (m, 2 H) 3.58-3.65 (m, 1 H) 3.68-3.75 (m, 1 H) 3.77 (dd, J=8.28, 7.28 Hz, 1 H) [α]=+9.01 (c=1 in EtOAc, 20° C.)

Intermediate 177

3-(Tetrahydro-3-furanyl)propanoic acid

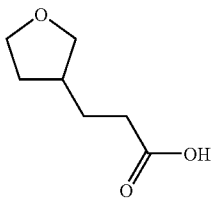

A solution of (2E)-3-(3-furanyl)-2-propenoic acid (4.75 g, 34.4 mmol) and 10% palladium on carbon (0.366 g, 3.44 mmol) in ethyl acetate (100 ml) was hydrogenated at atmospheric pressure and room temperature for 72 hours. Hydrogen uptake ~1.4 L (expected 2.4 L). The catalyst was filtered through Celite and concentrated in vacuo to give a brown oil. Analysis by $^1$H-NMR showed that the some material still contained the furan ring. Hydrogenation was continued under the same conditions with fresh catalyst for a further 24 hours with additional hydrogen uptake of 400 ml. The catalyst was filtered through Celite and the filtrate concentrated in vacuo to afford the title compound as a colourless oil (4.73 g).

1H NMR (400 MHz, DMSO-$d_6$) δ ppm 1.37-1.48 (m, 1 H) 1.50-1.63 (m, 2 H) 1.90-2.01 (m, 1 H) 2.04-2.17 (m, 1 H) 2.17-2.29 (m, 2 H) 3.18-3.25 (m, 1 H) 3.56-3.65 (m, 1 H) 3.67-3.79 (m, 2 H) 12.00 (br. s., 1 H)

Intermediate 178

3-(Tetrahydro-3-furanyl)-1-propanol

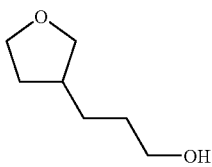

To a solution of 3-(tetrahydro-3-furanyl)propanoic acid (1 g, 6.94 mmol) in dry THF (20 ml) at 0° C. was added a 1M solution of Boron THF complex (21.16 ml, 21.16 mmol) in THF dropwise over 2 mins. The mixture was stirred at 0° C. for 1 hour then allowed to warm to room temperature and stirred for 18 h. The reaction mixture was cautiously quenched with methanol (~20 ml) and the solvent removed in vacuo. The residue was re-dissolved in methanol and concentrated in vacuo four times to give the title compound a colourless oil (3.37 g)

1H NMR (400 MHz, DMSO-$d_6$) δ ppm 1.26-1.50 (m, 5 H) 1.90-2.01 (m, 1 H) 2.09 (spt, J=7.28 Hz, 1 H) 3.13-3.22 (m, 1 H) 3.34-3.43 (m, 2 H) 3.56-3.65 (m, 1 H) 3.66-3.74 (m, 1 H) 3.74-3.81 (m, 1 H) 4.33 (br. s, 1 H)

Intermediate 179

3-(3-Bromopropyl)tetrahydrofuran

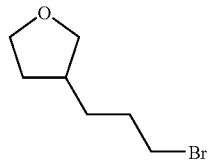

3-(Tetrahydro-3-furanyl)-1-propanol (1 g, 7.68 mmol) was dissolved in DMF (10 ml) and carbon tetrabromide (5.09 g, 15.36 mmol) added. The solution turned yellow. The solution was cooled to 0° C. and triphenylphosphine (4.03 g, 15.36 mmol) added dropwise as a solution in DMF (20 ml) (~30 mins, temperature maintained <2° C. throughout). The reaction mixture was stirred at 0° C. for 1 hour before gradually allowing to warm to room temperature and stirred for a further 2 hours. The solvent was removed in vacuo. Attempted trituration of the resultant brown oil with either DCM or cyclohexane was unsuccessful. The solvent was removed and the oil diluted with DCM and was purified by chromatography on silica (100 g) using a 0-25% ethyl acetate-cyclohexane over 40 mins using a Flashmaster II. The appropriate fractions were combined and dried down to give the title compound as a yellow oil (0.676 g).

1H NMR (400 MHz, DMSO-$d_6$) δ ppm 1.37-1.49 (m, 5 H, excess) 1.74-1.88 (m, 2 H) 1.93-2.02 (m, J=12.20, 7.58, 7.58, 4.77 Hz, 1 H) 2.13 (spt, J=7.36 Hz, 1 H) 3.18-3.24 (m, 1 H) 3.50-3.56 (m, 1 H) 3.57-3.65 (m, 1 H) 3.67-3.74 (m, 1 H) 3.75-3.81 (m, 1 H)

Intermediate 180

3-[(1 E/Z)-4-[(Phenylmethyl)oxy]-1-buten-1-yl]furan

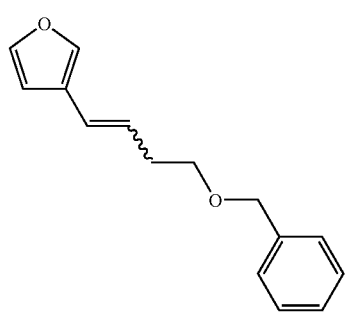

To a suspension of (3-benzyloxypropyl)triphenylphosphonium bromide (25.6 g, 52.0 mmol) in dry THF (60 ml) at −15° C. was added butyllithium (32.5 ml, 1.6M in hexanes) dropwise to give a solution. A solution of 3-furancarbaldehyde (5 g, 52.0 mmol) in THF (20 ml) was added dropwise to form a dark orange/red solution. The reaction mixture was stirred at −10° C. for 30 mins before 3-furancarbaldehyde (5 g, 52.0 mmol) was added dropwise as a solution in tetrahydrofuran (20 ml) to give a brown solution. The reaction mixture was then allowed to warm to room temperature and stirred overnight A pale brown precipitate had formed so the reaction mixture was filtered through Celite and washed with diethyl ether. The filtrate was concentrated in vacuo to give a dark orange oil which was loaded in DCM and purified in two batches by chromatography on silica (100 g) using a 0-25% gradient of ethyl acetate-cyclohexane over 40 mins using a Flashmaster II. The appropriate fractions were combined and evaporated in vacuo to give the title compound as a pale yellow oil (6.11 g).

LCMS (Method B): $t_{RET}$=1.31 min; MH$^+$ 229

Intermediate 181

4-(Tetrahydro-3-furanyl)-1-butanol

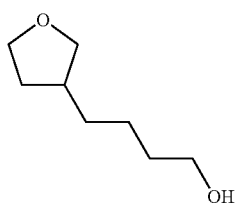

A solution of 3-{4-[(phenylmethyl)oxy]-1-buten-1-yl}furan (6.11 g, 26.8 mmol) and 10% palladium on carbon (0.285 g, 2.68 mmol) in ethyl acetate (150 ml) and acetic acid (15 ml) was hydrogentated at atmospheric pressure and room temperature for 24 hours. The catalyst was filtered through Celite and the filtrate concentrated in vacuo. $^1$H NMR showed no reduction had occurred, so the reaction mixture was hydrogenated under the same conditions for a further 72 hours. The catalyst was filtered through Celite and the filtrate concentrated in vacuo, $^1$H NMR showed the double bond had been reduced but the benzyl and furan ring were still intact. The residue was hydrogenated under the same conditions for a further 2 days. The catalyst was filtered through Celite and the filtrate concentrated in vacuo. A portion of the material (500 mg) was dissolved in ethyl acetate (5 ml) and hydrogenated using a Thales H-cube (settings: RT, 20 bar, 1 ml/min flow rate) using 10% palladium on carbon as the catalyst. The resultant solution was concentrated, $^1$H NMR showed no change.

All batches of the material were combined, loaded in dichloromethane and purified on silica (100 g) using a 0-25% gradient of ethyl acetate-cyclohexane over 40 mins using a Flashmaster II. The appropriate fractions were combined and evaporated in vacuo, a solution of the residue (3.42 g, 14.9 mmol) and 10% palladium on carbon (684 mg) in ethyl acetate (100 ml) was hydrogenated at atmospheric pressure and room temperature for 24 hours. The catalyst was filtered through Celite and the filtrate concentrated in vacuo to give the title compound as a yellow oil (2.22 g).

1H NMR (400 MHz, DMSO-d$_6$) δ ppm 1.21-1.47 (m, 7 H) 1.88-2.01 (m, 1 H) 2.01-2.15 (m, 1 H) 3.13-3.22 (m, 1 H) 3.33-3.42 (m, 2 H) 3.60 (q, J=7.78 Hz, 1 H) 3.65-3.81 (m, 2 H) 4.30-4.36 (m, 1 H)

Intermediate 182

3-(4-Bromobutyl)tetrahydrofuran

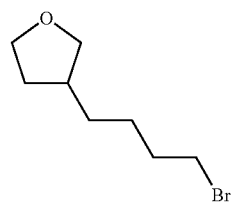

Prepared similarly to Intermediate 174 from 4-(tetrahydro-3-furanyl)-1-butanol.

1H NMR (400 MHz, DMSO-d$_6$) δ ppm 1.30-1.46 (m, 8 H) 1.76-1.85 (m, 2 H) 1.92-2.01 (m, 1 H) 2.05-2.15 (m, 1 H) 3.16-3.22 (m, 1 H) 3.50-3.55 (m, 2 H) 3.57-3.64 (m, 1 H) 3.67-3.74 (m, 1 H) 3.74-3.80 (m, 1 H)

Intermediate 183

2-(2-Bromoethyl)tetrahydro-2H-pyran

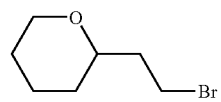

A solution of triphenylphosphine (1.93 g, 7.37 mmol) in DCM (10 ml) was added dropwise to a solution of intermediate 72 (0.80 g, 6.15 mmol) and carbon tetrabromide (2853 mg, 8.60 mmol) in DCM (40 ml) at 0° C. under nitrogen. The solution was stirred at 0° C. for 15 min, cyclohexane (30 ml) was added and the mixture was evaporated gently to remove DCM. The resulting cyclohexane solution was decanted from the gummy precipitate directly onto a silica cartridge (50 g) (pre-wetted with cyclohexane) and eluted with cyclohexane—DCM 1:1 to give the title compound as a colourless oil (0.68 g).

1H NMR (400 MHz, CDCl$_3$) ppm 1.23-1.35 (m, 1 H) 1.48-1.62 (m, 4 H) 1.80-1.96 (m, 2 H) 1.98-2.08 (m, 1 H) 3.39-3.58 (m, 4 H) 3.93-4.00 (m, 1 H)

Intermediate 184

2-(3-Bromopropyl)tetrahydro-2H-pyran

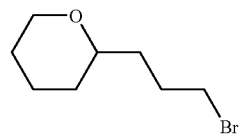

Prepared similarly to Intermediate 174 from 3-(tetrahydro-2H-pyran-2-yl)-1-propanol (WO 2007/70201).

1H NMR (400 MHz, DMSO-d$_6$) δ ppm 1.08-1.21 (m, 1 H) 1.36-1.57 (m, 8 H excess) 1.70-1.95 (m, 3 H) 3.17-3.32 (m, 2 H) 3.43-3.57 (m, 2 H) 3.49-3.56 (m, 2 H) 3.80-3.87 (m, 1 H)

Intermediate 185

2-(4-Bromobutyl)tetrahydro-2H-pyran

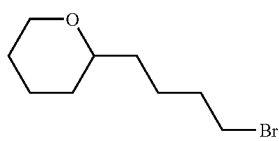

Prepared similarly to Intermediate 174 from 4-(tetrahydro-2H-pyran-2-yl)-1-butanol (J. Am. Chem. Soc, 2005, 127, 12180).

1H NMR (400 MHz, CDCl$_3$) δ ppm 1.20-1.32 (m, 1 H) 1.37-1.64 (m, 11 H excess) 1.78-1.93 (m, 2 H) 3.20-3.28 (m, 1 H) 3.38-3.46 (m, 3 H) 3.94-4.00 (m, 1 H)

Intermediate 186

2-(Tetrahydro-2H-pyran-3-yl)ethanol

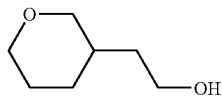

A solution of lithium aluminium hydride in Et$_2$O (4.16 ml, 4.16 mmol) was added dropwise to a solution of tetrahydro-2H-pyran-3-ylacetic acid (Tet. Lett. 2003, 44, 6355) (0.6 g, 4.16 mmol) in THF (5 ml) at room temperature under nitrogen. The mixture was stirred for 1 hour and was treated very slowly dropwise with water (1 ml). After the reaction was quenched, aqueous sodium hydroxide (2N, 1 ml) was added and the mixture was stirred for 5 min. The suspension was filtered through Hyflo and evaporated to the title compound as a colourless oil (0.3 g).

1H NMR (400 MHz, CDCl$_3$) δ ppm 1.12-1.94 (m, 9 H excess) 3.06-3.15 (m, 1 H) 3.33-3.42 (m, 1 H) 3.63-3.72 (m, 2 H) 3.83-3.91 (m, 2 H)

Intermediate 187

3-(2-Bromoethyl)tetrahydro-2H-pyran

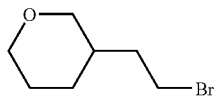

A solution of triphenylphosphine (725 mg, 2.77 mmol) in DCM (4 ml) was added dropwise with water-bath cooling to a solution of 2-(tetrahydro-2H-pyran-3-yl)ethanol (300 mg, 2.304 mmol) and carbon tetrabromide (917 mg, 2.77 mmol) in DCM (6 ml).

The solution was stirred at room temperature for 2 hour and was evaporated onto florisil and applied to a silica cartridge (20 g) pre-wetted with cyclohexane. Elution with cyclohexane-DCM (3:1) gave the title compound as a colourless oil (0.42 g).

1H NMR (400 MHz, CDCl$_3$) δ ppm 1.13-1.26 (m, 1 H) 1.59-1.94 (m, 6 H) 3.08-3.16 (m, 1 H) 3.35-3.48 (m, 3 H) 3.82-3.91 (m, 2 H)

Intermediate 188

3-(3-Bromopropyl)tetrahydro-2H-pyran

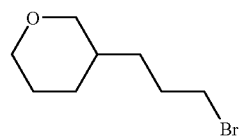

Prepared similarly to Intermediate 174 from 3-(tetrahydro-2H-pyran-3-yl)-1-propanol.

1H NMR (400 MHz, CDCl$_3$) δ ppm 1.09-1.40 (m, 5 H excess) 1.56-1.67 (m, 3 H excess) 1.81-1.92 (m, 4 H) 3.02-3.11 (m, 1 H) 3.32-3.45 (m, 3 H) 3.82-3.92 (m, 2 H)

Intermediate 189

3-(4-Bromobutyl)tetrahydro-2H-pyran

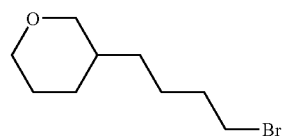

Prepared similarly to Intermediate 174 from 4-(tetrahydro-2H-pyran-3-yl)-1-butanol.

1H NMR (400 MHz, CDCl$_3$) δ ppm 1.05-1.30 (m, 3 H) 1.36-1.65 (m, 8 H excess) 1.79-1.92 (m, 3 H) 2.99-3.10 (m, 1 H) 3.30-3.46 (m, 3 H) 3.81-3.92 (m, 2 H)

Intermediate 190

4-(3-Bromopropyl)tetrahydro-2H-pyran

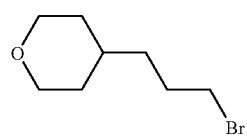

Prepared similarly to Intermediate 174 from 3-(tetrahydro-2H-pyran-4-yl)-1-propanol.

1H NMR (400 MHz, DMSO-d$_6$) δ ppm 1.04-1.19 (m, 2 H) 1.25-1.36 (m, 2 H) 1.41-1.60 (m, 3 H) 1.75-1.86 (m, 2 H) 3.20-3.34 (m, 2 H) 3.47-3.56 (m, 2 H) 3.76-3.85 (m, 2 H)

Intermediate 191

4-[(1 E/Z)-4-[(Phenylmethyl)oxy]-1-buten-1-yl]tetrahydro-2H-Pyran

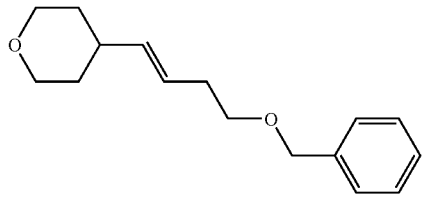

To a suspension of (3-benzyloxy-propyl)triphenyl-phosphonium bromide (21.57 g, 43.8 mmol) in dry THF (67 ml) at −15° C. was added 1.6M BuLi in Hexanes (27.4 ml, 43.8 mmol) dropwise for an hour to give a dark orange solution. The reaction was increased to 0° C. and stirring was continued for 30 minutes. A solution of tetrahydro-2H-pyran-4-carbaldehyde (5 g, 43.8 mmol) in dry THF (7 ml) was added dropwise at 0° C. for 15 minutes. The reaction mixture was stirred at room temperature for 20 hours. This was filtered through pre packed celite (10 g) and washed with diethyl ether. The filtrate was concentrated in vacuo to give orange oil.

The crude material split into two batches and each preabsorbed on silica and purified by chromatography on silica (50 g) using a gradient of 0-25% ethyl acetate-cyclohexane over 60 mins using the Flashmaster II. The appropriate fractions were combined and evaporated in vacuo to give the title compound as a colourless oil (4.5059 g).

1H NMR (400 MHz, DMSO-d$_6$) δ ppm 1.22-1.35 (m, 2 H) 1.40 (s, 5 H excess) 2.29-2.36 (m, 1 H) 3.27-3.37 (m, 2 H) 3.39-3.46 (m, 2 H) 3.74-3.84 (m, 2 H) 4.46 (s, 2 H) 5.21-5.46 (m, 2 H) 7.22-7.42 (m, 5 H)

Intermediate 192

4-(Tetrahydro-2H-pyran-4-yl)-1-butanol

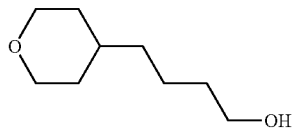

A solution of 4-{(1E)-4-[(phenylmethyl)oxy]-1-buten-1-yl}tetrahydro-2H-pyran (4.5059 g, 18.29 mmol) and palladium on carbon (0.195 g, 0.183 mmol) in ethyl acetate (140 ml) was hydrogenated at atmospheric pressure and room temperature. This was left to stir overnight in hydrogen. The mixture was then filtered through pre-packed celite (10 g) to remove the palladium and washed with ether (~30 ml). The organic layer was concentrated in vacuo, 1H NMR was carried out on the resulting oil to show that benzyl group and double bonds were still present.

A solution of the material and palladium on carbon (0.3 g) in ethyl acetate (140 ml) was hydrogenated at atmospheric pressure and room temperature. This was left to stir overnight in atmosphere of hydrogen.

The mixture was then put through pre-packed celite (10 g) to remove the palladium and washed with ether (~30 ml). The organic filtrate was concentrated in vacuo to give the title compound as a colourless oil (2.27 g)

1H NMR (400 MHz, DMSO-d$_6$) δ ppm 0.80-0.92 (m, 1 H) 1.01-1.60 (m, 10 H) 3.17-3.42 (m, 4 H) 3.74-3.87 (m, 2 H) 4.32 (s, 0.6 H)

Intermediate 193

4-(4-Bromobutyl)tetrahydro-2H-pyran

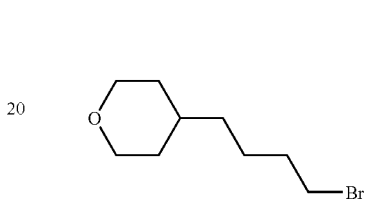

Prepared similarly to Intermediate 174 from 4-(tetrahydro-2H-pyran-4-yl)-1-butanol.

1H NMR (400 MHz, DMSO-d$_6$) δ ppm 1.04-1.27 (m, 4 H) 1.33-1.60 (m, 5 H) 1.72-1.84 (m, 2 H) 3.20-3.33 (m, 2 H) 3.49-3.57 (m, 2 H) 3.77-3.86 (m, 2 H)

Intermediate 194

2,2-Dimethyl-4-[(E)-2-(methyloxy)ethenyl]tetrahydro-2H-pyran

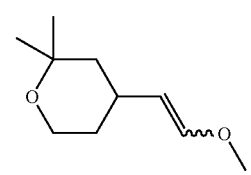

To a stirred suspension of [(methyloxy)methyl](triphenyl)phosphonium chloride (24.1 g, 70.3 mmol) in dry THF (70 ml) at −40° C. under nitrogen was added potassium t-butoxide, 1M soln in THF, (70 ml, 70.0 mmol) dropwise over 30 mins. After stirring for 40 mins, the mixture was cooled to −70° C. and added a solution of 2,2-dimethyltetrahydro-2H-pyran-4-carbaldehyde (2.5 g, 17.58 mmol) in dry THF (10 ml) dropwise over 10 mins. The mixture was stirred at this temp for 10 mins and the cooling bath was removed. The mixture was stirred for a further 30 mins at ambient then quenched by pouring onto ice. The aqueous phase was extracted with Et$_2$O (3×100 ml), combined the organic extracts and washed with saturated NaCl solution (100 ml), dried (Na$_2$SO$_4$) filtered and evaporated to dryness to give an amber oil (19 g). 2 g of the crude product was loaded diethyl ether and purified on silica 50 g using a 0-25% ethyl acetate-cyclohexane over 40 mins using Flashmaster II. The fractions were monitored by staining in an Iodine tank and the appropriate fractions were combined and evaporated in vacuo to give the required product as a colourless oil.

The bulk of the crude mixture was then purified in the same way: cyclohexane followed by ether was added to the residue the mixture was filtered and the filtrate purified on silica 2×100 g using a gradient of 0-25% ethyl acetate-cyclohexane over 40 mins on a Flashmaster II. The appropriate fractions were identified by iodine staining and combined and evaporated in vacuo. This was combined with the product obtained from the first small scale purification to give the title compound as a colourless liquid (2.96 g).

1H NMR (400 MHz, CDCl$_3$) δ ppm 1.17-1.25 (m, 8 H excess) 1.25-1.39 (m, 2 H) 1.48-1.59 (m, 2 H) 2.22-2.34 (m, 0.6 H) 2.76-2.88 (m, 0.3 H) 3.50 (s, 2 H) 3.58 (s, 1 H) 3.62-3.77 (m, 2 H) 4.14 (dd, J=8.53, 6.27 Hz, 0.3 H) 4.61 (dd, J=12.67, 7.65 Hz, 0.6 H) 5.82 (dd, J=6.27, 1.00 Hz, 0.3 H) 6.32 (d, J=12.80 Hz, 0.6 H)

Intermediate 195

(2,2-Dimethyltetrahydro-2H-pyran-4-yl)acetaldehyde

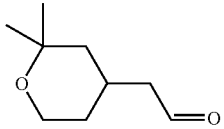

To a stirred solution of 2,2-dimethyl-4-[(E)-2-(methyloxy) ethenyl]tetrahydro-2H-pyran (2.93 g, 17.21 mmol) in THF (15 ml) was added 2N HCl (15 ml, 30.0 mmol) and the mixture was stirred at 20° C. After 1 hour the mixture was extracted with diethyl ether (3×25 ml); the combined ether extracts dried (Na$_2$SO$_4$), filtered and evaporated in vacuo (at 50 mbar and water bath at 15° C.) to give the title compound as a pale yellow oil (2.56 g).

1H NMR (400 MHz, CDCl$_3$) δ ppm 1.19-1.29 (m, 9 H excess) 1.53-1.65 (m, 4 H) 1.83-1.88 (m, 1 H) 2.25-2.38 (m, 2 H) 3.65-3.77 (m, 2 H) 9.77-9.79 (m, 1 H)

Intermediate 196

2-(2,2-Dimethyltetrahydro-2H-pyran-4-yl)ethanol

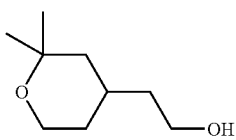

A stirred suspension of sodium borohydride (0.620 g, 16.39 mmol) in dry ethanol (20 ml) was cooled to 0° C. (ice bath) under nitrogen and a solution of (2,2-dimethyltetrahydro-2H-pyran-4-yl)acetaldehyde (2.56 g, 16.39 mmol) in ethanol (20 ml) was added dropwise over a period of 20 mins. The mixture was then stirred in the cold for a further 1 hour then allowed to warm to ambient and stirred for 72 hours. The solvent was removed by evaporation and the residual oil was poured into ice and extracted with DCM (3×30 ml). Combined the organic extracts and dried by passing through a hydrophobic frit and evaporated in vacuo to give a colourless oil which contained the title compound.

1H NMR (400 MHz, CDCl$_3$) δ ppm 1.04-1.27 (m, 11 H excess) 1.43-1.64 (m, 5 H excess) 1.77-1.93 (m, 1 H) 3.44-3.55 (m, 1 H) 3.59-3.77 (m, 4 H)

Intermediate 197

4-(2-Bromoethyl)-2,2-dimethyltetrahydro-2H-pyran

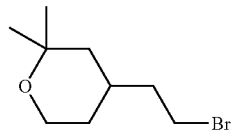

Prepared similarly to Intermediate 174 from 2-(2,2-dimethyltetrahydro-2H-pyran-4-yl)ethanol.

1H NMR (400 MHz, CDCl$_3$) δ ppm 1.04-1.12 (m, 1 H) 1.14-1.20 (m, 1 H) 1.20-1.25 (m, 6 H) 1.54-1.64 (m, 6 H excess) 1.71-1.83 (m, 2 H) 1.87-2.01 (m, 1 H) 3.42-3.49 (m, 2 H) 3.62-3.80 (m, 1 H)

Intermediate 198

(4E/Z)-2,2-dimethyl-4-{3-[(phenylmethyl)oxyl] proylidene}tetrahydro-2H-pyran

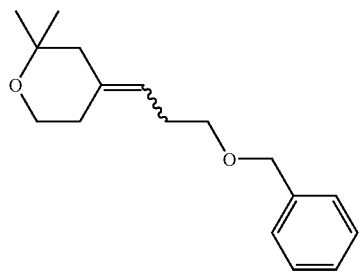

To a stirred suspension of triphenyl{3-[(phenylmethyl) oxy]propyl}phosphonium bromide (23.00 g, 46.8 mmol) in THF (60 ml) at −15° C. under nitrogen atmosphere was added n-butyllithium, 1.6M in hexane (29.3 ml, 46.8 mmol) dropwise over 30 mins. The orange/red solution was stirred at −10° C. for 30 mins. A solution of 2,2-dimethyltetrahydro-4H-pyran-4-one (6 g, 46.8 mmol) in THF (10 ml) was added dropwise at −10° C. over 25 mins. The reaction mixture was then stirred at −10° C. for 15 mins and then gradually allowed to warm up to room temperature while stirring under nitrogen atmosphere for 20 hours. 10 ml of ether were added and the suspension was filtered on Celite. The Celite was washed with ether (2×40 mL). The filtrate was concentrated under vacuum. The residue was purified by chromatography on silica (2×100 g) using a Cyclohexane:Ethyl Acetate 0->25% gradient over 40 mins on a Flashmaster II. The fractions were analysed by TLC (revealed with a permanganate dip). The desired fractions were combined and concentrated under vacuum to yield the title compound as a colourless oil (5.98 g).

1H NMR (400 MHz, DMSO-d$_6$) δ ppm 1.97-2.01 (m, 1 H) 2.01-2.14 (m, 3 H) 2.19-2.33 (m, 2 H) 3.36-3.44 (m, 2 H) 3.48-3.58 (m, 2 H) 4.45 (s, 2H) 5.09-5.19 (m, 0.6 H) 5.26-5.33 (m, 0.4 H) 7.22-7.38 (m, 5 H)

Intermediate 199

3-(2,2-Dimethyltetrahydro-2H-pyran-4-yl)-1-propanol

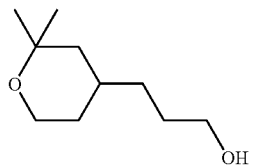

A solution of 2,2-dimethyl-4-{3-[(phenylmethyl)oxy]propylidene}tetrahydro-2H-pyran (5.98 g, 22.97 mmol) in ethyl acetate (70 ml) was hydrogenated over 10% palladium on activated carbon (0.733 g, 0.689 mmol) at atmospheric pressure and room temperature. After 16 hours, the mixture was filtered under vacuum through Celite, washed through with EtOAc (2×50 mL) and the filtrate was evaporated to dryness to give a yellowish mobile oil. 1H NMR showed that most of the benzyl group had been hydrogenated but the double bond was still present. The residue was dissolved in ethyl acetate (70 ml) and was hydrogenated over 10% palladium on activated carbon (1.1 g) at atmospheric pressure and room temperature. After 16 hours, the mixture was filtered under vacuum through Celite, washed through with EtOAc (2×50 mL) and the filtrate was evaporated to dryness to give a yellowish mobile oil. The residue was purified by chromatography on silica (100 g) using a cyclohexane:ethyl acetate 0->50% gradient over 40 mins on a Flashmaster II. The desired fractions (analysed with a permanganate dip) were combined and concentrated under vacuum to give the title compound as a pale yellow oil (2.17 g).

1H NMR (400 MHz, CDCl$_3$) δ ppm 1.01-1.31 (m, 12 H excess) 1.50-1.74 (m, 6 H excess) 3.59-3.69 (m, 3 H) 3.70-3.78 (m, 1 H)

Intermediate 200

4-(3-Bromopropyl)-2,2-dimethyltetrahydro-2H-pyran

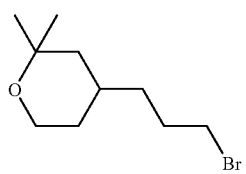

Prepared similarly to Intermediate 174 from 4-(3-bromopropyl)-2,2-dimethyltetrahydro-2H-pyran.

1H NMR (400 MHz, CDCl$_3$) δ ppm 0.98-1.27 (m, 9 H excess) 1.27-1.37 (m, 2 H) 1.45-1.71 (m, 3 H) 1.79-1.91 (m, 2 H) 3.31-3.43 (m, 4 H) 3.56-3.66 (m, 2 H) 3.67-3.75 (m, 2 H)

Intermediate 201

2,2-Dimethyl-4-[(1E)-4-[(phenylmethyl)oxy]-1-buten-1-yl]tetrahydro-2H-pyran

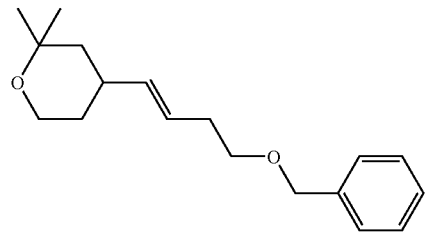

To a stirred suspension of triphenyl{3-[(phenylmethyl)oxy]propyl}phosphonium bromide (20.74 g, 42.2 mmol) in THF (60 ml) at −15° C. under a nitrogen atmosphere was added n-butyl lithium, 1.6M in hexane (26.4 ml, 42.2 mmol) dropwise over 30 mins. The orange/red solution was stirred at −10° C. for 30 mins. A solution of 2,2-dimethyltetrahydro-2H-pyran-4-carbaldehyde (6 g, 42.2 mmol) in THF (10 ml) was added dropwise at −10° C. over 25 mins. The reaction mixture was then stirred at −10° C. for 15 mins and then gradually allowed to warm up to room temperature while stirring under nitrogen atmosphere for 16 hours. Ether (10 ml) was added and the suspension was filtered on Celite. The Celite was washed with ether (2×40 mL). The filtrate was concentrated under vacuum. The residue was purified by chromatography on silica (2×100 g) using a cyclohexane:ethyl acetate 0->25% gradient over 40 mins on a Flashmaster II. The fractions were analysed by TLC (revealed with a permanganate dip). The desired fractions were combined and concentrated under vacuum to yield the title compound as a colourless oil (7.46 g).

1H NMR (400 MHz, DMSO-d$_6$) δ ppm 1.01-1.20 (m, 8 H) 1.31-1.40 (m, 2 H) 2.27-2.36 (m, 2 H) 2.59-2.72 (m, 1 H) 3.39-3.47 (m, 2 H) 3.51-3.58 (m, 2 H) 4.42-4.48 (m, 2 H) 5.13-5.42 (m, 2 H) 7.23-7.38 (m, 5 H)

Intermediate 202

4-(2,2-Dimethyltetrahydro-2H-pyran-4-yl)-1-butanol

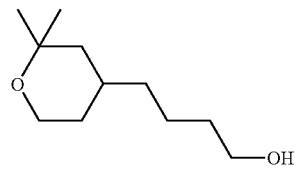

A solution of 2,2-dimethyl-4-{4-[(phenylmethyl)oxy]-1-buten-1-yl}tetrahydro-2H-pyran (7.46 g, 27.2 mmol) I ethyl acetate (70 ml) was hydrogenated over 10% palladium on activated carbon (1.447 g, 1.359 mmol) at atmospheric pressure and room temperature. After 16 hours, the mixture was filtered under vacuum through Celite, washed through with EtOAc (2×50 ml) and the filtrate was evaporated to dryness to give a yellowish mobile oil (4.8 g). The residue was purified by chromatography on silica (70 g) using a cyclohexane:ethyl acetate 0->50% gradient over 40 mins using a Flashmaster II. The desired fractions (analysed with a permanganate dip) were combined and concentrated under vacuum to give the title compound as a yellow oil (1.675 g).

1H NMR (400 MHz, CDCl$_3$) δ ppm 1.00-1.29 (m, 10 H) 1.33-1.44 (m, 2 H) 1.50-1.71 (m, 5 H) 3.62-3.68 (m, 3 H) 3.70-3.76 (m, 1 H)

Intermediate 203

4-(4-Bromobutyl)-2,2-dimethyltetrahydro-2H-pyran

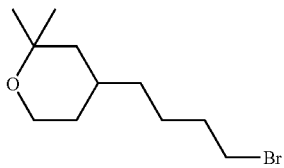

Prepared similarly to Intermediate 174 from 4-(2,2-dimethyltetrahydro-2H-pyran-4-yl)-1-butanol.

1H NMR (400 MHz, CDCl$_3$) δ ppm 1.00-1.29 (m, 10 H) 1.39-1.71 (m, 5 H) 1.79-1.90 (m, 2 H) 3.37-3.47 (m, 2 H) 3.59-3.78 (m, 2 H)

Intermediate 204

2-{[(1R)-1-Methylbutyl]oxy}-9-(tetrahydro-2H-pyran-2-yl)-9H-purin-6-amine

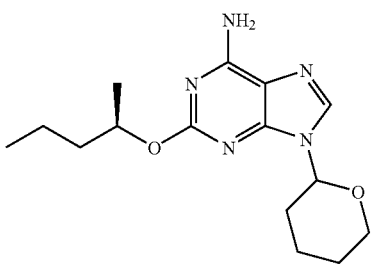

Sodium t-butoxide (27.3 g, 284 mmol) was added portionwise to (R)-2-pentanol (140 ml) at room temperature, the mixture was stirred until homogeneous. 2-Chloro-9-(tetrahydro-2H-pyran-2-yl)-9H-purin-6-amine (18.0 g, 71.0 mmol) was added and the reaction mixture heated at 50° C. for 160 hours. The reaction was cooled to room temperature and partitioned between ethyl acetate (500 ml) and water (500 ml). The organic phase was washed with saturated sodium chloride solution (100 ml), dried (MgSO$_4$), filtered and evaporated. The residue was triturated with ether and the solid material filtered. The precipitate was re-washed with ether and the filtrates combined and evaporated. The crude material (ca. 10 g) was dissolved in DMSO:methanol (1:1) and purified on a reverse phase (C18) column (330 g) using a gradient of 25-65% acetonitrile (+0.1% TFA)-water (+0.1% TFA) over 8 column volumes, the fractions were immediately neutralised with saturated aqueous sodium carbonate solution. Appropriate fractions were combined and partitioned between dichloromethane and saturated aqueous sodium hydrogen carbonate. The organic phase was dried (MgSO$_4$), filtered and evaporated to give the title compound as a pale cream foam (5.05 g).

LCMS (Method A): $t_{RET}$=2.95 min; MH$^+$ 306

Intermediate 205

8-Bromo-2-{[(1R)-1-methylbutyl]oxy}-9-(tetrahydro-2H-pyran-2-yl)-9H-purin-6-amine

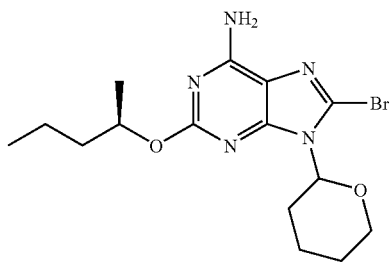

2-{[(1R)-1-methylbutyl]oxy}-9-(tetrahydro-2H-pyran-2-yl)-9H-purin-6-amine (5.05 g, 16.54 mmol) was dissolved in chloroform (30 ml) and cooled to 0° C. To this solution N-bromosuccinimide (3.24 g, 18.19 mmol) was added portionwise keeping the temperature below 2° C. This gave a dark green solution which was stirred at 0° C. for 30 minutes before allowing to warm to room temperature and stirring for 6 hours. The reaction mixture was washed with water (2×50 ml) and the layers separated using hydrophobic frit. The organic layer was concentrated to give a dark brown gum which was dissolved in dichloromethane and purified by chromatography silica (100 g) using a 0-50% gradient of ethyl acetate-cyclohexane over 60 mins on a Flashmaster II. The appropriate fractions were combined and evaporated in vacuo to give the title compound as a yellow foam (5.23 g).

LCMS (Method B): $t_{RET}$=1.21 min; MH$^+$ 384/386

Intermediate 206

2-{[(1R)-1-Methylbutyl]oxy}-8-(methyloxy)-9-(tetrahydro-2H-pyran-2-yl)-9H-purin-6-amine

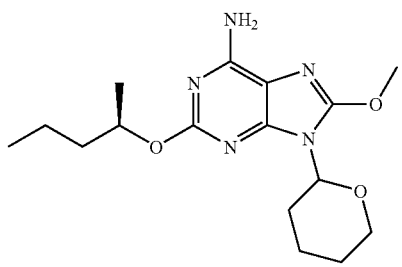

8-bromo-2-{[(1R)-1-methylbutyl]oxy}-9-(tetrahydro-2H-pyran-2-yl)-9H-purin-6-amine (5.23 g, 13.61 mmol) was heated to reflux with 25% sodium methoxide in methanol (8.8 ml, 13.61 mmol) and methanol (40 ml) for 4 hours. The reaction mixture was concentrated under reduced pressure and partitioned between saturated ammonium chloride (100 ml) and dichloromethane (100 ml). The aqueous was washed with further dichloromethane (100 ml) and the combined

Intermediate 207

2-{[(1R)-1-Methylbutyl]oxy}-8-(methyloxy)-1H-purin-6-amine trifluoroacetate

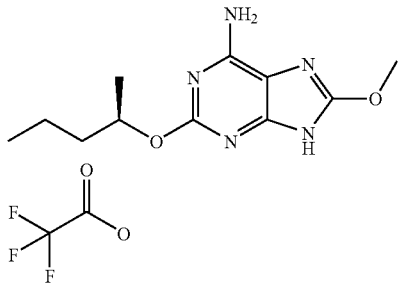

To a solution of 2-{[(1R)-1-methylbutyl]oxy}-8-(methyloxy)-9-(tetrahydro-2H-pyran-2-yl)-9H-purin-6-amine (4.8 g, 14.31 mmol) in methanol (100 ml) was added trifluoroacetic acid (8 ml, 104 mmol). The reaction mixture was stirred at room temperature for 72 hours. The solvent was removed in vacuo to give a pale yellow solid which was suspended in ethyl acetate (30 ml). The precipitate was filtered off and washed with further ethyl acetate until the filtrate was colourless. The remaining solid was dried by air and then in vacuo to give the title compound as a cream solid (3.85 g).
LCMS (Method B): $t_{RET}$=0.82 min; MH⁺ 252

Intermediate 208

2-{[(1S)-1-Methylbutyl]oxy}-9-(tetrahydro-2H-pyran-2-yl)-9H-purin-6-amine

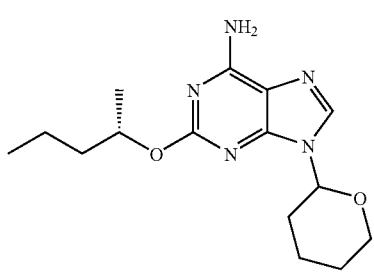

Prepared similarly to Intermediate 204 using (2S)-pentanol.
LCMS (Method A): $t_{RET}$=2.95 min; MH⁺ 306

Intermediate 209

8-Bromo-2-{[(1S)-1-methylbutyl]oxy}-9-(tetrahydro-2H-pyran-2-yl)-9H-purin-6-amine

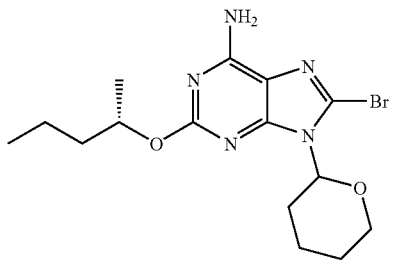

Prepared similarly to Intermediate 205 from 2-{[(1S)-1-Methylbutyl]oxy}-9-(tetrahydro-2H-pyran-2-yl)-9H-purin-6-amine.
LCMS (Method A): $t_{RET}$=3.30 min; MH⁺ 384/386

Intermediate 210

2-{[(1S)-1-Methylbutyl]oxy}-8-(methyloxy)-9-(tetrahydro-2H-pyran-2-yl)-9H-purin-6-amine

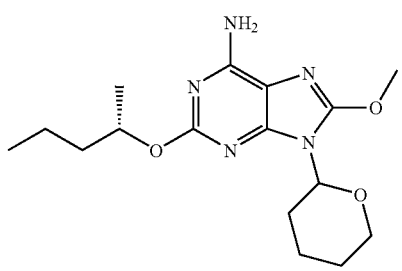

Prepared similarly to Intermediate 206 from 8-Bromo-2-{[(1S)-1-methylbutyl]oxy}-9-(tetrahydro-2H-pyran-2-yl)-9H-purin-6-amine.
LCMS (Method A): $t_{RET}$=3.08 min; MH⁺ 336

Intermediate 211

2-{[(1S)-1-Methylbutyl]oxy}-8-(methyloxy)-1H-purin-6-amine trifluoroacetate

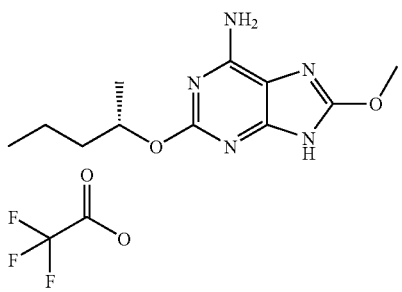

Prepared similarly to Intermediate 207 from 2-{[(1S)-1-Methylbutyl]oxy}-8-(methyloxy)-9-(tetrahydro-2H-pyran-2-yl)-9H-purin-6-amine.
LCMS (Method A): $t_{RET}$=2.31 min; MH⁺ 252

Intermediate 212

$N^2$-Butyl-8-(methyloxy)-9-[3-(tetrahydro-2-furanyl)propyl]-9H-Purine-2,6-diamine

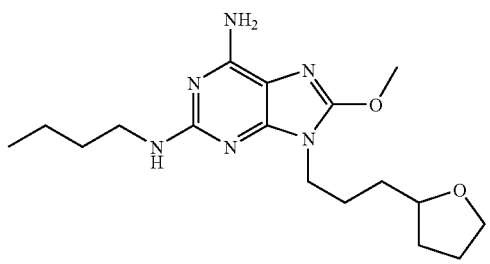

(methyloxy)-3H-purine-2,6-diamine trifluoroacetate and 2-(3-bromopropyl)tetrahydrofuran.

LCMS (Method A): $t_{RET}$=2.53 min; MH$^+$=349

Intermediate 213

N$^2$-Butyl-8-(methyloxy)-9-[4-(tetrahydro-2-furanyl)butyl]-9H-purine-2,6-diamine

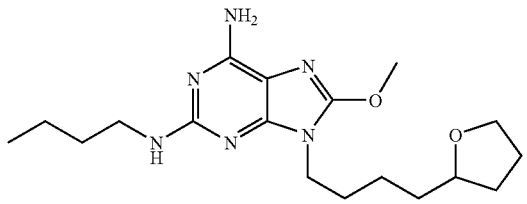

2-(Butyloxy)-8-(methyloxy)-1H-purin-6-amine trifluoroacetate (120 mg, 0.342 mmol) was heated with potassium carbonate (189 mg, 1.366 mmol) in dry DMF (5 ml) at 60° C. for 1 hour and then cooled to room temperature. 2-(4-Bromobutyl)tetrahydrofuran (82 mg, 0.394 mmol) was added and the reaction mixture heated at 50° C. under nitrogen for 16 hours and then partitioned between water (2 ml) and DCM (5 ml). The aqueous layer was further extracted with DCM (2×5 ml) and the combined organic layers were dried by passage through a hydrophobic frit and evaporated to dryness using a nitrogen blowdown unit. The residue was dissolved in methanol (0.6 ml) and purified by mass directed autopreparation. Product containing fractions were combined and evaporated to dryness in a nitrogen blowdown apparatus to give the title compound (76 mg).

LCMS (Method B): $t_{RET}$=1.20 min; MH$^+$=363

Intermediate 214

N$^2$-Butyl-8-(methyloxy)-9-{2-[(3S)-tetrahydro-3-furanyl]ethyl}-9H-Purine-2,6-diamine

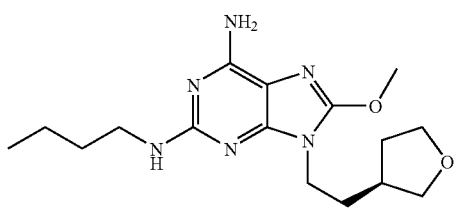

Prepared similarly to Intermediate 215 from N$^2$-butyl-8-(methyloxy)-3H-purine-2,6-diamine trifluoroacetate and (3R)-3-(2-Bromoethyl)tetrahydrofuran.

LCMS (Method B): $t_{RET}$=1.07 min; MH$^+$=335

Intermediate 215

N$^2$-Butyl-8-(methyloxy)-9-{2-[(3R)-tetrahydro-3-furanyl]ethyl}-9H-Purine-2,6-diamine

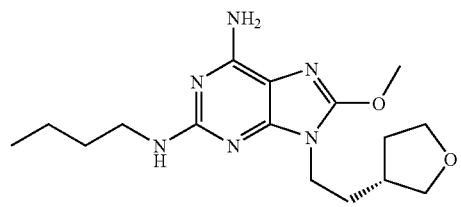

N$^2$-Butyl-8-(methyloxy)-3H-purine-2,6-diamine (157 mg, 0.447 mmol) was heated in dry DMF (3 ml) with potassium carbonate (232 mg, 1.675 mmol) at 60° C. for one hour. (3S)-3-(2-Bromoethyl)tetrahydrofuran (100 mg, 0.558 mmol) in dry DMF (2 ml) was added and the mixture stirred and heated to 60° C. under nitrogen for 4 hours. The mixture was cooled to room temperature, quenched into water (40 ml) and extracted with ethyl acetate (3×25 ml). The organic extracts were combined, dried by passage through a hydrophobic frit and concentrated under vacuum. The residue was dissolved in 1:1 MeOH:DMSO and purified by mass directed autopreparation. The desired fractions were combined and concentrated using a nitrogen blowdown unit to give the title compound as a white solid (119 mg).

LCMS (Method B): $t_{RET}$=1.00 min; MH$^+$=335

Intermediate 216

N$^2$-Butyl-8-(methyloxy)-9-[3-(tetrahydro-3-furanyl)propyl]-9H-Purine-2,6-diamine

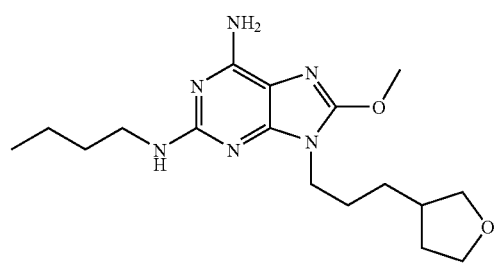

N$^2$-Butyl-8-(methyloxy)-3H-purine-2,6-diamine trifluoroacetate (150 mg, 0.428 mmol) was heated in dry DMF (2.5 ml) at 60° C. for 1 hour with potassium carbonate (237 mg, 1.713 mmol). The reaction mixture was cooled to room temperature and 3-(3-bromopropyl)tetrahydrofuran (99 mg, 0.514 mmol) was added. The mixture was then heated at 50° C. overnight. The reaction mixture was quenched with water (50 ml) and extracted with ethyl acetate (3×25 ml). The combined organic layers were separated and then dried by passage through a hydrophobic frit and evaporated to dryness. The residue was dissolved in 1:1 MeOH:DMSO (2.8 ml) and purified by mass directed autopreparation. Product containing fractions were evaporated under a stream of nitrogen in a blowdown apparatus to give the title compound as a clear gum (84 mg).

LCMS (Method B): $t_{RET}$=1.14 min; MH$^+$=349

Intermediate 217

N²-Butyl-8-(methyloxy)-9-[4-(tetrahydro-3-furanyl)butyl]-9H-purine-2,6-diamine

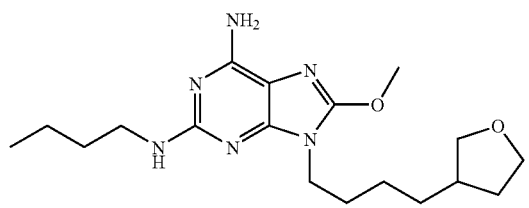

Prepared similarly to Intermediate 216 from N²-butyl-8-(methyloxy)-3H-purine-2,6-diamine trifluoroacetate and 3-(4-bromobutyl)tetrahydrofuran.

LCMS (Method B): $t_{RET}$=1.05 min; MH⁺=363

Intermediate 218

N²-Butyl-8-(methyloxy)-9-[3-(tetrahydro-2H-pyran-2-yl)propyl]-9H-Purine-2,6-diamine

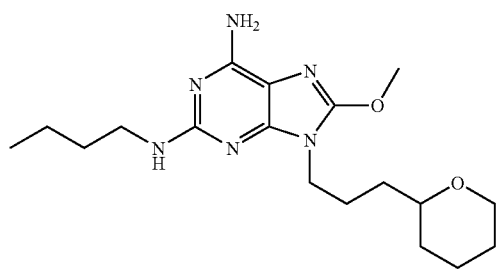

Prepared similarly to Intermediate 216 from N²-butyl-8-(methyloxy)-3H-purine-2,6-diamine trifluoroacetate and 2-(3-bromopropyl)tetrahydro-2H-pyran.

LCMS (Method B): $t_{RET}$=1.16 min; MH⁺=363

Intermediate 219

N²-Butyl-8-(methyloxy)-9-[4-(tetrahydro-2H-pyran-2-yl)butyl]-9H-purine-2,6-diamine

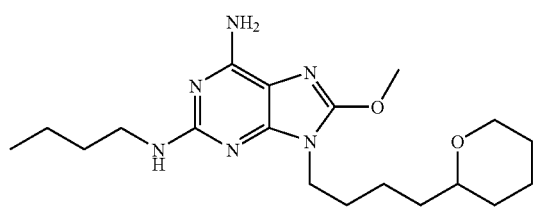

Prepared similarly to Intermediate 220 from N²-butyl-8-(methyloxy)-3H-purine-2,6-diamine trifluoroacetate and 2-(4-bromobutyl)tetrahydro-2H-pyran.

LCMS (Method B): $t_{RET}$=1.50 min; MH⁺=377

Intermediate 220

N²-Butyl-8-(methyloxy)-9-[3-(tetrahydro-2H-pyran-4-yl)propyl]-9H-purine-2,6-diamine

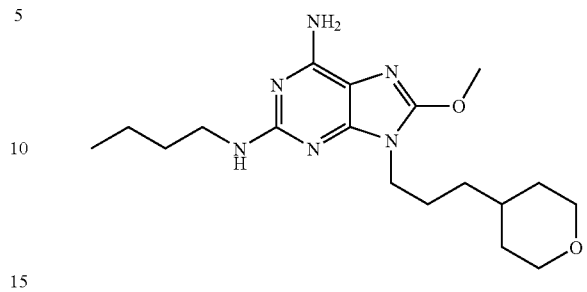

A mixture of N²-butyl-8-(methyloxy)-3H-purine-2,6-diamine (150 mg, 0.429 mmol) and potassium carbonate (237 mg, 1.718 mmol) in dry DMF (5 ml) was stirred at 60° C. for 1 hour under an atmosphere of nitrogen and then cooled to room temperature. 4-(3-Bromopropyl)tetrahydro-2H-pyran (0.087 ml, 0.515 mmol) was added and the mixture stirred at 50° C. overnight. The mixture was cooled and partitioned between 1:1 ethyl acetate:DCM (10 ml) and water (10 ml). The organic phase was separated using a hydrophobic frit and evaporated under a stream of nitrogen using a blowdown apparatus. The residue was dissolved in 1:1 methanol:DCM (2.8 ml) and purified by mass directed autopreparation. Product containing fractions were evaporated under a stream of nitrogen to give the title compound as a white solid (93.13 mg).

LCMS (Method B): $t_{RET}$=1.27 min; MH⁺=363

Intermediate 221

N²-Butyl-8-(methyloxy)-9-[4-(tetrahydro-2H-pyran-4-yl)butyl]-9H-purine-2,6-diamine

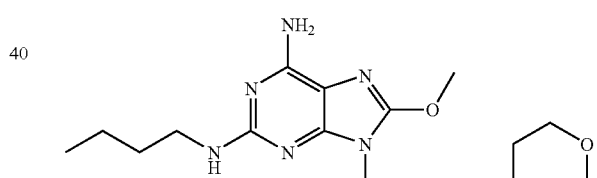

Prepared similarly to Intermediate 220 from N²-butyl-8-(methyloxy)-3H-purine-2,6-diamine trifluoroacetate and 4-(4-bromobutyl)tetrahydro-2H-pyran.

LCMS (Method B): $t_{RET}$=1.38 min; MH⁺=377

Intermediate 222

N²-Butyl-9-[2-(2,2-dimethyltetrahydro-2H-pyran-4-yl)ethyl]-8-(methyloxy)-9H-purine-2,6-diamine

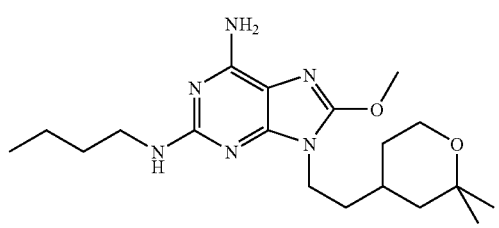

A mixture of N²-butyl-8-(methyloxy)-3H-purine-2,6-diamine trifluoroacetate, (0.2 g, 0.571 mmol) and anhydrous potassium carbonate (0.316 g, 2.284 mmol) in DMF (2.5 ml) was heated at 50° C. for 1 hour. The mixture was cooled to room temperature and 4-(2-bromoethyl)-2,2-dimethyltetrahydro-2H-pyran (0.152 g, 0.685 mmol) was added and the mixture heated at 50° C. for 18 hours. The mixture was quenched with water (2 ml) and then extracted with DCM (2×5 ml). The DCM was separated through a hydrophobic frit and evaporated by blowing down under a stream of nitrogen. DMSO:MeOH (1:1) was added to the residue and the resulting precipitate was collected by filtration, washed with methanol and dried in vacuo to give the title compound as a white solid (136 mg).

LCMS (Method A): $t_{RET}$=2.65 min; MH⁺=377

Intermediate 223

N²-Butyl-9-[3-(2,2-dimethyltetrahydro-2H-pyran-4-yl)propyl]-8-(methyloxy)-9H-purine-2,6-diamine

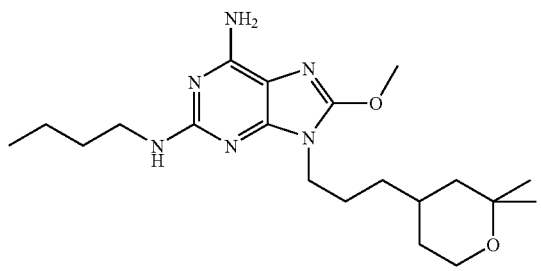

A mixture of N²-butyl-8-(methyloxy)-3H-purine-2,6-diamine trifluoroacetate (149 mg, 0.425 mmol) and potassium carbonate (294 mg, 2.126 mmol) in DMF (2 ml) was stirred and heated at 60° C. under nitrogen for one hour. 4-(3-Bromopropyl)-2,2-dimethyltetrahydro-2H-pyran (125 mg, 0.532 mmol) in dry DMF (1 ml) was added and the mixture heated at 60° C. under nitrogen for a further 2.5 hours. The reaction mixture was cooled to room temperature, quenched into water (10 ml) and extracted with DCM:EtOAc (1:1, 2×20 ml). The organic extracts were combined, dried by passage through a hydrophobic frit and concentrated under vacuum. The residue was purified by mass directed autopreparation. Product containing fractions were combined and evaporated to give the title compound (40 mg).

LCMS (Method A): $t_{RET}$=2.81 min; MH⁺=391

Intermediate 224

N²-Butyl-9-[4-(2,2-dimethyltetrahydro-2H-pyran-4-yl)butyl]-8-(methyloxy)-9H-purine-2,6-diamine

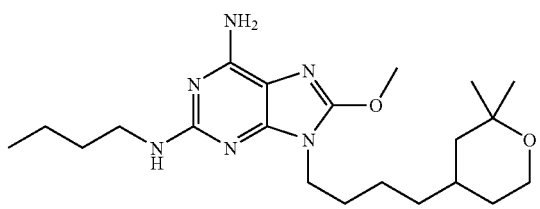

Prepared similarly to Intermediate 223 from N²-butyl-8-(methyloxy)-3H-purine-2,6-diamine trifluoroacetate and 4-(4-bromobutyl)-2,2-dimethyltetrahydro-2H-pyran but conducting the alkylation over 1.5 hours at 60° C.

LCMS (Method A): $t_{RET}$=2.95 min; MH⁺=405

Intermediate 225

2-(Butyloxy)-8-(methyloxy)-9-[3-(tetrahydro-2-furanyl)proyl]-9H-Purin-6-amine

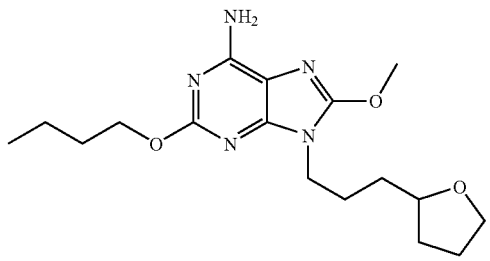

Prepared similarly to Intermediate 216 from 2-(butyloxy)-8-(methyloxy)-1H-purin-6-amine trifluoroacetate and 2-(3-bromopropyl)tetrahydrofuran.

LCMS (Method A): $t_{RET}$=2.96 min; MH⁺=350

Intermediate 226

2-(Butyloxy)-8-(methyloxy)-9-[4-(tetrahydro-2-furanyl)butyl]-9H-Purin-6-amine

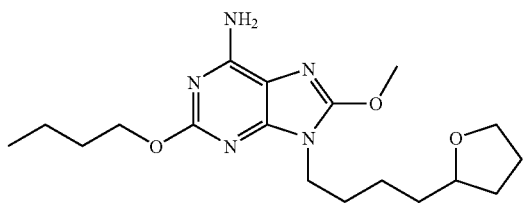

Prepared similarly to Intermediate 213 from 2-(butyloxy)-8-(methyloxy)-1H-purin-6-amine trifluoroacetate and 2-(4-bromobutyl)tetrahydrofuran.

LCMS (Method B): $t_{RET}$=1.14 min; MH⁺=364

Intermediate 227

2-(Butyloxy)-8-(methyloxy)-9-[2-[(3S)-tetrahydro-3-furanyl]ethyl]-9H-purin-6-amine

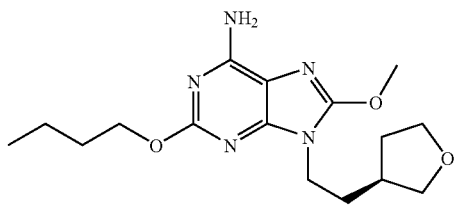

Prepared similarly to Intermediate 215 from 2-(butyloxy)-8-(methyloxy)-1H-purin-6-amine trifluoroacetate and (3R)-3-(2-bromoethyl)tetrahydrofuran.
LCMS (Method B): $t_{RET}$=0.99 min; MH$^+$=336

Intermediate 228

2-(Butyloxy)-8-(methyloxy)-9-[2-[(3R)-tetrahydro-3-furanyl]ethyl]-9H-purin-6-amine

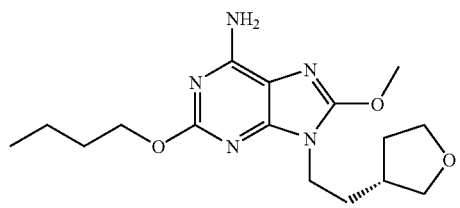

Prepared similarly to Intermediate 215 from 2-(butyloxy)-8-(methyloxy)-1H-purin-6-amine trifluoroacetate and (3S)-3-(2-bromoethyl)tetrahydrofuran.
LCMS (Method B): $t_{RET}$=0.99 min; MH$^+$=336

Intermediate 229

2-(Butyloxy)-8-(methyloxy)-9-[3-(tetrahydro-3-furanyl)propyl]-9H-purin-6-amine

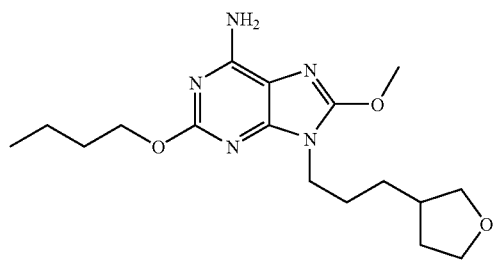

Prepared similarly to Intermediate 216 from 2-(butyloxy)-8-(methyloxy)-1H-purin-6-amine trifluoroacetate and 3-(3-bromopropyl)tetrahydrofuran.
LCMS (Method B): $t_{RET}$=1.04 min; MH$^+$=350

Intermediate 230

2-(Butyloxy)-8-(methyloxy)-9-[4-(tetrahydro-3-furanyl)butyl]-9H-Purin-6-amine

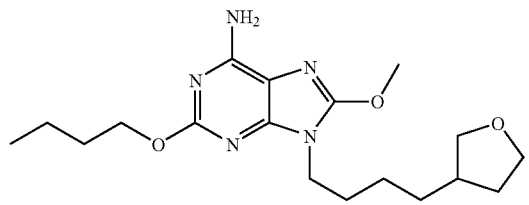

Prepared similarly to Intermediate 216 from 2-(butyloxy)-8-(methyloxy)-1H-purin-6-amine trifluoroacetate and 3-(4-bromobutyl)tetrahydrofuran.
LCMS (Method B): $t_{RET}$=1.11 min; MH$^+$=364

Intermediate 231

2-(Butyloxy)-8-(methyloxy)-9-[3-(tetrahydro-2H-Pyran-2-yl)propyl]-9H-purin-6-amine

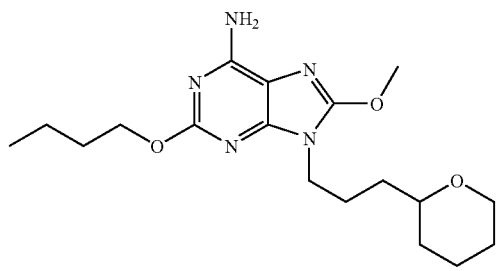

Prepared similarly to Intermediate 216 from 2-(butyloxy)-8-(methyloxy)-1H-purin-6-amine trifluoroacetate and 2-(3-bromopropyl)tetrahydro-2H-pyran.
LCMS (Method B): $t_{RET}$=1.19 min; MH$^+$=364

Intermediate 232

2-(Butyloxy)-8-(methyloxy)-9-[4-(tetrahydro-2H-pyran-2-yl)butyl]-9H-purin-6-amine

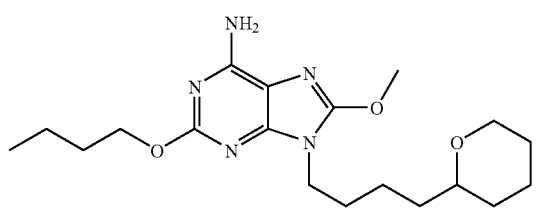

Prepared similarly to Intermediate 216 from 2-(butyloxy)-8-(methyloxy)-1H-purin-6-amine trifluoroacetate and 2-(4-bromobutyl)tetrahydro-2H-pyran.
LCMS (Method B): $t_{RET}$=1.25 min; MH$^+$=378

Intermediate 233

2-(Butyloxy)-8-(methyloxy)-9-[3-(tetrahydro-2H-pyran-3-yl)propyl]-9H-purin-6-amine

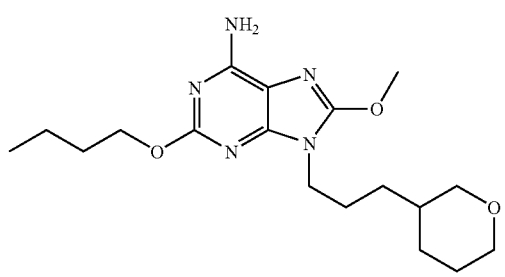

Prepared similarly to Intermediate 213 from 2-(butyloxy)-8-(methyloxy)-1H-purin-6-amine trifluoroacetate and 3-(3-bromopropyl)tetrahydro-2H-pyran. LCMS (Method B): $t_{RET}$=1.13 min; MH$^+$=364

Intermediate 234

2-(Butyloxy)-8-(methyloxy)-9-[4-(tetrahydro-2H-pyran-3-yl)butyl]-9H-purin-6-amine

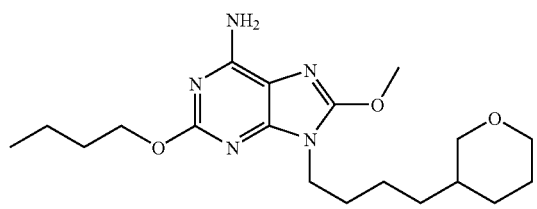

Prepared similarly to Intermediate 243 from 2-(butyloxy)-8-(methyloxy)-1H-purin-6-amine trifluoroacetate and 3-(4-bromobutyl)tetrahydro-2H-pyran.
LCMS (Method A): $t_{RET}$=3.27 min; MH$^+$=378

Intermediate 235

2-(Butyloxy)-8-(methyloxy)-9-[3-(tetrahydro-2H-Pyran-4-yl)propyl]-9H-purin-6-amine

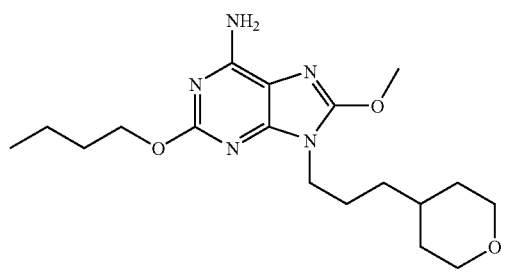

Prepared similarly to Intermediate 216 from 2-(butyloxy)-8-(methyloxy)-1H-purin-6-amine trifluoroacetate and 4-(3-bromobutyl)tetrahydro-2H-pyran.
LCMS (Method B): $t_{RET}$=1.11 min; MH$^+$=364

Intermediate 236

2-(Butyloxy)-8-(methyloxy)-9-[4-(tetrahydro-2H-pyran-4-yl)butyl]-9H-purin-6-amine

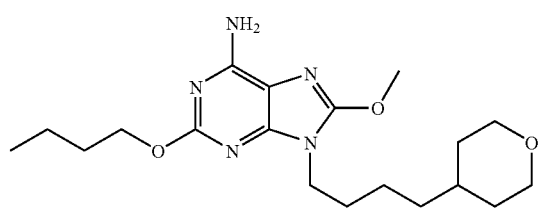

Prepared similarly to Intermediate 216 from 2-(butyloxy)-8-(methyloxy)-1H-purin-6-amine trifluoroacetate and 4-(4-bromobutyl)tetrahydro-2H-pyran.
LCMS (Method B): $t_{RET}$=1.18 min; MH$^+$=378

Intermediate 237

2-(Butyloxy)-9-[2-(2,2-dimethyltetrahydro-2H-pyran-4-yl)ethyl]-8-(methyloxy)-9H-purin-6-amine

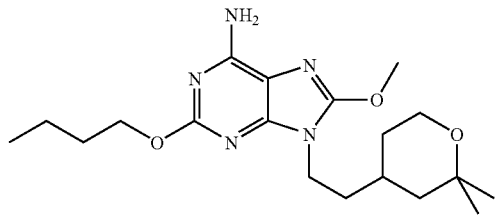

A mixture of 2-(butyloxy)-8-(methyloxy)-1H-purin-6-amine trifluoroacetate (0.2 g, 0.569 mmol) and anhydrous potassium carbonate (0.315 g, 2.277 mmol) in DMF was heated at 60° C. for 1 hour. The mixture was cooled to room temperature and 4-(2-bromoethyl)-2,2-dimethyltetrahydro-2H-pyran (0.151 g, 0.683 mmol) was added and the mixture heated at 50° C. for 18 hours. The mixture was quenched with water (2 ml) and extracted with DCM (2×5 ml). The DCM was separated through a hydrophobic frit and evaporated by blowing down under a stream of nitrogen. Addition of DMSO:MeOH (1:1) gave a precipitate which was collected by filtration, washed with methanol and dried in vacuo to give the title compound (29 mg).

LCMS (Method A): $t_{RET}$=3.10 min; MH$^+$=378

Evaporation of the filtrate to dryness and trituration of the residue with DMSO:MeOH (1:1, 0.5 ml) gave a second batch of material (101 mg).

LCMS (Method A): $t_{RET}$=3.10 min; MH$^+$=378

Intermediate 238

2-(Butyloxy)-9-[3-(2,2-dimethyltetrahydro-2H-pyran-4-yl)Propyl]-8-(methyloxy)-9H-purin-6-amine

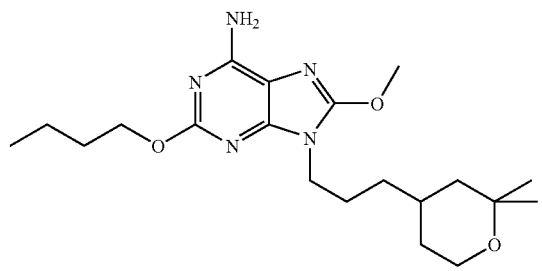

Prepared similarly to Intermediate 224 from 2-(butyloxy)-8-(methyloxy)-1H-purin-6-amine trifluoroacetate and 4-(3-bromopropyl)-2,2-dimethyltetrahydro-2H-pyran.
LCMS (Method A): $t_{RET}$=3.25 min; MH$^+$=392

Intermediate 239

2-(Butyloxy)-9-[4-(2,2-dimethyltetrahydro-2H-pyran-4-yl)butyl]-8-(methyloxy)-9H-purin-6-amine

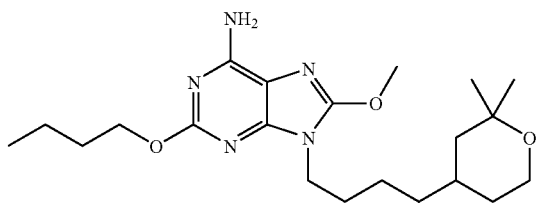

Prepared similarly to Intermediate 224 from 2-(butyloxy)-8-(methyloxy)-1H-purin-6-amine trifluoroacetate and 4-(4-bromobutyl)-2,2-dimethyltetrahydro-2H-pyran but conducting the alkylation over 1.5 hours at 60° C.
LCMS (Method A): $t_{RET}$=3.43 min; MH$^+$=406

Intermediate 240

2-[(2-Cyclopropylethyl)oxy]-8-(methyloxy)-9-[2-(tetrahydro-2-furanyl)ethyl]-9H-purin-6-amine

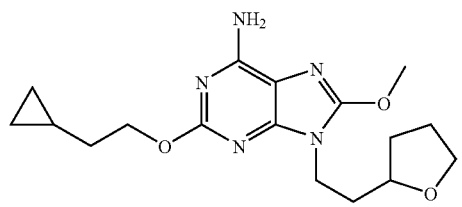

Prepared similarly to Intermediate 213 from 2-[(2-cyclopropylethyl)oxy]-8-(methyloxy)-1H-purin-6-amine trifluoroacetate and 2-(2-bromoethyl)tetrahydrofuran.
LCMS (Method B): $t_{RET}$=1.05 min; MH$^+$=348

Intermediate 241

2-[(2-Cyclopropylethyl)oxy]-8-(methyloxy)-9-[3-(tetrahydro-2-furanyl)propyl]-9H-purin-6-amine

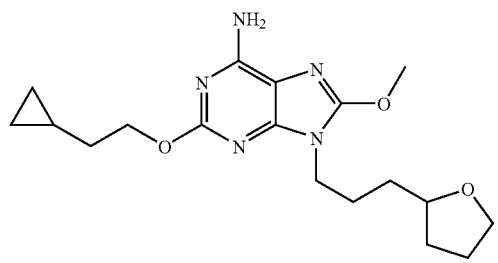

Prepared similarly to Intermediate 216 from 2-[(2-cyclopropylethyl)oxy]-8-(methyloxy)-1H-purin-6-amine trifluoroacetate and 2-(3-bromopropyl)tetrahydrofuran.
LCMS (Method A): $t_{RET}$=2.98 min; MH$^+$=362

Intermediate 242

2-[(2-Cyclopropylethyl)oxy]-8-(methyloxy)-9-[4-(tetrahydro-2-furanyl)butyl]-9H-purin-6-amine

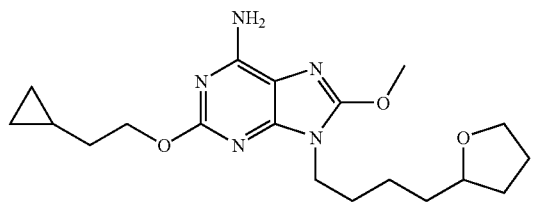

Prepared similarly to Intermediate 213 from 2-[(2-cyclopropylethyl)oxy]-8-(methyloxy)-1H-purin-6-amine trifluoroacetate and 2-(4-bromobutyl)tetrahydrofuran.
LCMS (Method B): $t_{RET}$=1.15 min; MH$^+$=376

Intermediate 243

2-[(2-cyclopropylethyl)oxy]-8-(methyloxy)-9-[2-(tetrahydro-3-furanyl)ethyl]-9H-purin-6-amine

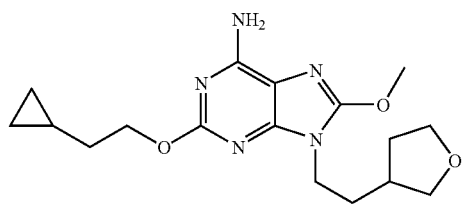

A mixture of 2-[(2-cyclopropylethyl)oxy]-8-(methyloxy)-1H-purin-6-amine trifluoroacetate (0.16 g, 0.450 mmol) and anhydrous potassium carbonate (0.243 g, 1.762 mmol) in DMF (2.5 ml) was heated at 50° C. for 1 hour. The mixture was cooled to room temperature and 3-(2-bromoethyl)tetrahydrofuran (0.095 g, 0.528 mmol) was added and the mixture heated at 50° C. for 18 hours. The mixture was quenched with water (2 ml) and extracted with DCM (2×5 ml). The DCM was separated through a hydrophobic frit and evaporated by blowing down under a stream of nitrogen. The sample was dissolved in 1:1 MeOH:DMSO (3×0.5 ml) and purified by mass directed autopreparation. Product containing fractions were evaporated under a stream of nitrogen in a blowdown apparatus to give the title compound as a white solid (98 mg).
LCMS (Method A): $t_{RET}$=2.80 min; MH$^+$=348

Intermediate 244

2-[(2-Cyclopropylethyl)oxy]-8-(methyloxy)-9-{2-[(3S)-tetrahydro-3-furanyl]ethyl}-9H-purin-6-amine

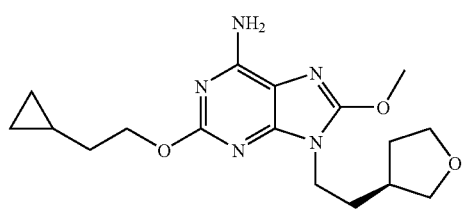

Prepared similarly to Intermediate 215 from 2-[(2-cyclopropylethyl)oxy]-8-(methyloxy)-1H-purin-6-amine trifluoroacetate and (3R)-3-(2-bromoethyl)tetrahydrofuran.
LCMS (Method B): $t_{RET}$=1.00 min; MH$^+$=348

Intermediate 245

2-[(2-Cyclopropylethyl)oxy]-8-(methyloxy)-9-{2-[(3R)-tetrahydro-3-furanyl]ethyl}-9H-purin-6-amine

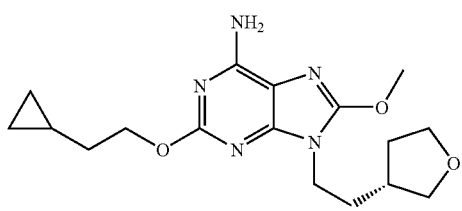

Prepared similarly to Intermediate 215 from 2-[(2-cyclopropylethyl)oxy]-8-(methyloxy)-1H-purin-6-amine trifluoroacetate and (3S)-3-(2-bromoethyl)tetrahydrofuran.
LCMS (Method A): $t_{RET}$=2.80 min; MH$^+$=348

Intermediate 246

2-[(2-Cyclopropylethyl)oxy]-8-(methyloxy)-9-[3-(tetrahydro-3-furanyl)propyl]-9H-purin-6-amine

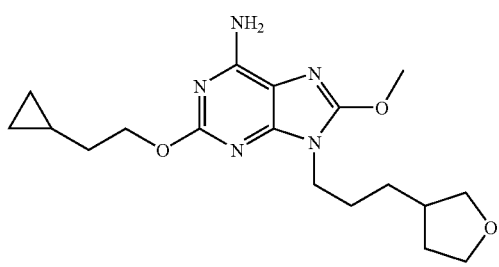

Prepared similarly to Intermediate 216 from 2-[(2-cyclopropylethyl)oxy]-8-(methyloxy)-1H-purin-6-amine trifluoroacetate and 3-(3-bromopropyl)tetrahydrofuran.
LCMS (Method B): $t_{RET}$=1.04 min; MH$^+$=362

Intermediate 247

2-[(2-Cyclopropylethyl)oxy]-8-(methyloxy)-9-[4-(tetrahydro-3-furanyl)butyl]-9H-purin-6-amine

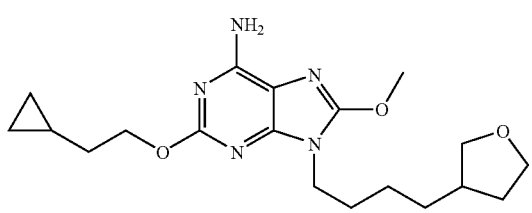

Prepared similarly to Intermediate 216 from 2-[(2-cyclopropylethyl)oxy]-8-(methyloxy)-1H-purin-6-amine trifluoroacetate and 3-(4-bromobutyl)tetrahydrofuran.
LCMS (Method B): $t_{RET}$=1.11 min; MH$^+$=376

Intermediate 248

2-[(2-Cyclopropylethyl)oxy]-8-(methyloxy)-9-[2-(tetrahydro-2H-pyran-2-yl)ethyl]-9H-purin-6-amine

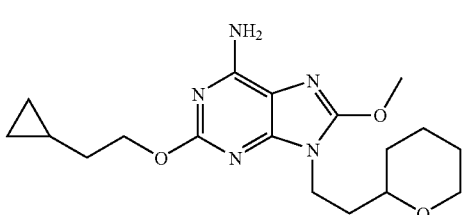

Prepared similarly to Intermediate 216 from 2-[(2-cyclopropylethyl)oxy]-8-(methyloxy)-1H-purin-6-amine trifluoroacetate and 2-(2-bromoethyl)tetrahydro-2H-pyran.
LCMS (Method A): $t_{RET}$=3.12 min; MH$^+$=362

Intermediate 249

2-[(2-Cyclopropylethyl)oxy]-8-(methyloxy)-9-[3-(tetrahydro-2H-Pyran-2-yl)propyl]-9H-purin-6-amine

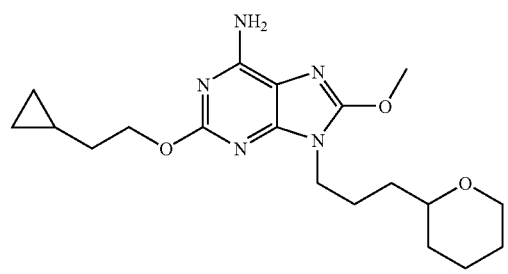

Prepared similarly to Intermediate 216 from 2-[(2-cyclopropylethyl)oxy]-8-(methyloxy)-1H-purin-6-amine trifluoroacetate and 2-(3-bromopropyl)tetrahydro-2H-pyran.
LCMS (Method B): $t_{RET}$=1.18 min; MH$^+$=376

Intermediate 250

2-[(2-Cyclopropylethyl)oxy]-8-(methyloxy)-9-[4-(tetrahydro-2H-Pyran-2-yl)butyl]-9H-purin-6-amine

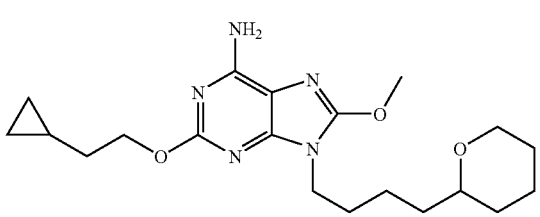

Prepared similarly to Intermediate 213 from 2-[(2-cyclopropylethyl)oxy]-8-(methyloxy)-1H-purin-6-amine trifluoroacetate and 2-(4-bromobutyl)tetrahydro-2H-pyran.
LCMS (Method A): $t_{RET}$=3.27 min; MH$^+$=390

Intermediate 251

2-[(2-Cyclopropylethyl)oxy]-8-(methyloxy)-9-[2-(tetrahydro-2H-Pyran-3-yl)ethyl]-9H-purin-6-amine

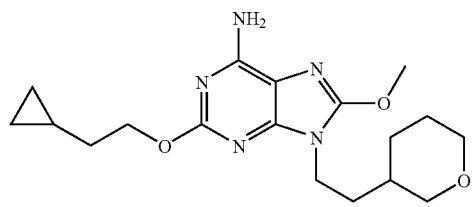

Prepared similarly to Intermediate 216 from 2-[(2-cyclopropylethyl)oxy]-8-(methyloxy)-1H-purin-6-amine trifluoroacetate and 3-(2-bromoethyl)tetrahydro-2H-pyran.

LCMS (Method A): $t_{RET}$=2.99 min; MH$^+$=362

Intermediate 252

2-[(2-Cyclopropylethyl)oxy]-8-(methyloxy)-9-[4-(tetrahydro-2H-Pyran-3-yl)butyl]-9H-purin-6-amine

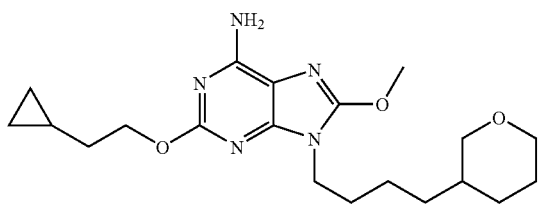

Prepared similarly to Intermediate 243 from 2-[(2-cyclopropylethyl)oxy]-8-(methyloxy)-1H-purin-6-amine trifluoroacetate and 3-(4-bromobutyl)tetrahydro-2H-pyran.

LCMS (Method A): $t_{RET}$=3.28 min; MH$^+$=390

Intermediate 253

2-[(2-Cyclopropylethyl)oxy]-8-(methyloxy)-9-[2-(tetrahydro-2H-Pyran-4-yl)ethyl]-9H-purin-6-amine

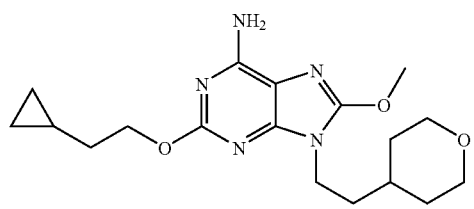

Prepared similarly to Intermediate 215 from 2-[(2-cyclopropylethyl)oxy]-8-(methyloxy)-1H-purin-6-amine trifluoroacetate and 4-(2-bromoethyl)tetrahydro-2H-pyran.

LCMS (Method B): $t_{RET}$=1.04 min; MH$^+$=362

Intermediate 254

2-[(2-Cyclopropylethyl)oxy]-8-(methyloxy)-9-[3-(tetrahydro-2H-pyran-4-yl)propyl]-9H-purin-6-amine

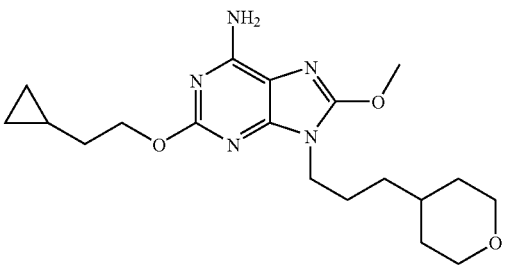

Prepared similarly to Intermediate 220 from 2-[(2-cyclopropylethyl)oxy]-8-(methyloxy)-1H-purin-6-amine trifluoroacetate and 4-(3-bromopropyl)tetrahydro-2H-pyran.

LCMS (Method B): $t_{RET}$=1.12 min; MH$^+$=376

Intermediate 255

2-[(2-Cyclopropylethyl)oxy]-8-(methyloxy)-9-[4-(tetrahydro-2H-Pyran-4-yl)butyl]-9H-purin-6-amine

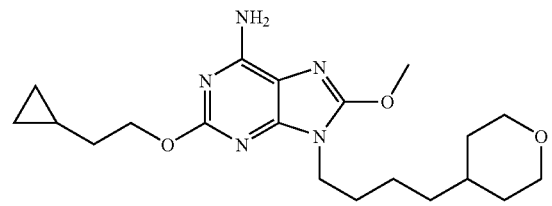

Prepared similarly to Intermediate 220 from 2-[(2-cyclopropylethyl)oxy]-8-(methyloxy)-1H-purin-6-amine trifluoroacetate and 4-(4-bromobutyl)tetrahydro-2H-pyran.

LCMS (Method B): $t_{RET}$=1.19 min; MH$^+$=390

Intermediate 256

2-[(2-Cyclopropylethyl)oxy]-9-[2-(2,2-dimethyltetrahydro-2H-pyran-4-yl)ethyl]-8-(methyloxy)-9H-purin-6-amine

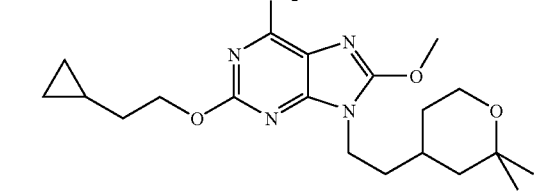

Prepared similarly to Intermediate 216 from 2-[(2-cyclopropylethyl)oxy]-8-(methyloxy)-1H-purin-6-amine trifluoroacetate and 4-(2-bromoethyl)-2,2-dimethyltetrahydro-2H-pyran.

LCMS (Method A): $t_{RET}$=3.12 min; MH$^+$=390

Intermediate 257

2-[(2-Cyclopropylethyl)oxy]-9-[3-(2,2-dimethyltetrahydro-2H-pyran-4-yl)propyl]-8-(methyloxy)-9H-purin-6-amine

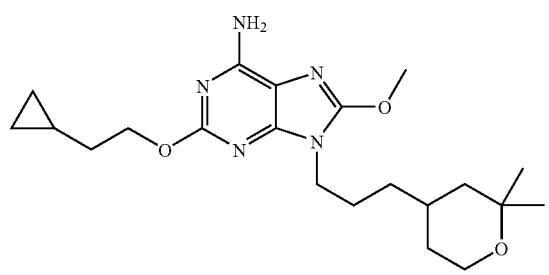

Prepared similarly to Intermediate 223 from 2-[(2-cyclopropylethyl)oxy]-8-(methyloxy)-1H-purin-6-amine trifluoroacetate and 4-(3-bromopropyl)-2,2-dimethyltetrahydro-2H-pyran.
LCMS (Method A): $t_{RET}$=3.26 min; MH$^+$=404

Intermediate 258

2-[(2-Cyclopropylethyl)oxy]-9-[4-(2,2-dimethyltetrahydro-2H-pyran-4-yl)butyl]-8-(methyloxy)-9H-Purin-6-amine

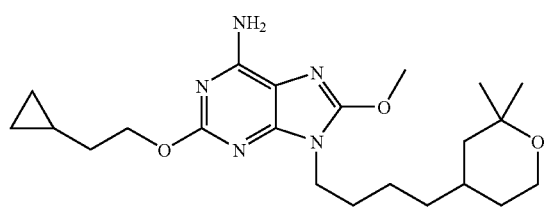

Prepared similarly to Intermediate 223 from 2-[(2-cyclopropylethyl)oxy]-8-(methyloxy)-1H-purin-6-amine trifluoroacetate and 4-(4-bromobutyl)-2,2-dimethyltetrahydro-2H-pyran but conducting the alkylation over 1.5 hours at 60° C.
LCMS (Method A): $t_{RET}$=3.43 min; MH$^+$=418

Intermediate 259

2-{[(1S)-1-Methylbutyl]oxy}-8-(methyloxy)-9-[2-(tetrahydro-2-furanyl)ethyl]-9H-purin-6-amine

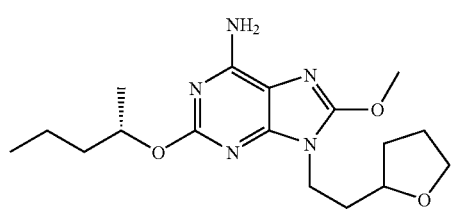

Prepared similarly to Intermediate 243 from 2-{[(1S)-1-methylbutyl]oxy}-8-(methyloxy)-1H-purin-6-amine trifluoroacetate and 2-(2-bromoethyl)tetrahydrofuran.
LCMS (Method A): $t_{RET}$=3.07 min; MH$^+$=350

Intermediate 260

2-{[(1S)-1-Methylbutyl]oxy}-8-(methyloxy)-9-[3-(tetrahydro-2-furanyl)propyl]-9H-purin-6-amine

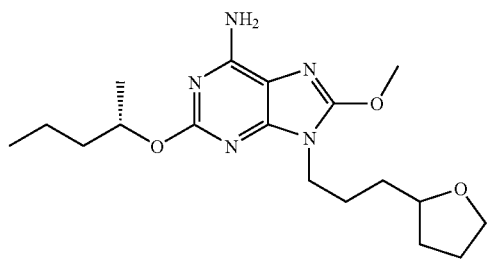

Prepared similarly to Intermediate 215 from 2-{[(11S)-1-methylbutyl]oxy}-8-(methyloxy)-1H-purin-6-amine trifluoroacetate and 2-(3-bromopropyl)tetrahydrofuran but conducting the alkylation over 1 hour at 60° C.
LCMS (Method A): $t_{RET}$=3.00 min; MH$^+$=364

Intermediate 261

2-{[(1S)-1-Methylbutyl]oxy}-8-(methyloxy)-9-{2-[(3S)-tetrahydro-3-furanyl]ethyl}-9H-purin-6-amine

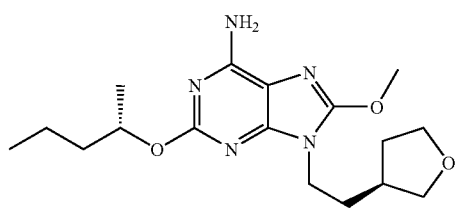

Prepared similarly to Intermediate 216 from 2-{[(11S)-1-methylbutyl]oxy}-8-(methyloxy)-1H-purin-6-amine trifluoroacetate and (3R)-3-(2-bromoethyl)tetrahydrofuran.
LCMS (Method A): $t_{RET}$=2.81 min; MH$^+$=350

Intermediate 262

2-{[(1S)-1-Methylbutyl]oxy}-8-(methyloxy)-9-{2-[(3R)-tetrahydro-3-furanyl]ethyl}-9H-purin-6-amine

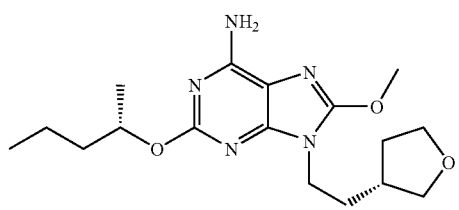

Prepared similarly to Intermediate 215 from 2-{[(11S)-1-methylbutyl]oxy}-8-(methyloxy)-1H-purin-6-amine trifluoroacetate and (3S)-3-(2-bromoethyl)tetrahydrofuran but conducting the alkylation over 1 hour at 60° C.
LCMS (Method A): $t_{RET}$=2.96 min; MH$^+$=350

Intermediate 263

2-{[(1S)-1-Methylbutyl]oxy}-8-(methyloxy)-9-[3-(tetrahydro-3-furanyl)propyl]-9H-purin-6-amine

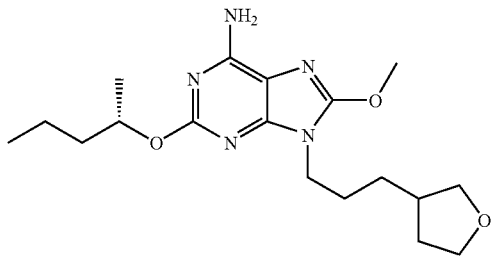

Prepared similarly to Intermediate 220 from 2-{[(1S)-1-methylbutyl]oxy}-8-(methyloxy)-1H-purin-6-amine trifluoroacetate and 3-(3-bromopropyl)tetrahydrofuran.

LCMS (Method B): $t_{RET}$=1.13 min; MH$^+$=364

Intermediate 264

2-{[(1S)-1-Methylbutyl]oxy}-8-(methyloxy)-9-[4-(tetrahydro-3-furanyl)butyl]-9H-purin-6-amine

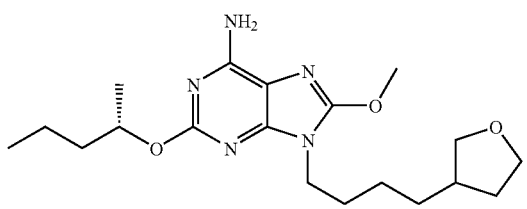

Prepared similarly to Intermediate 220 from 2-{[(1S)-1-methylbutyl]oxy}-8-(methyloxy)-1H-purin-6-amine trifluoroacetate and 3-(4-bromobutyl)tetrahydrofuran.

LCMS (Method B): $t_{RET}$=1.19 min; MH$^+$=378

Intermediate 265

2-{[(1S)-1-Methylbutyl]oxy}-8-(methyloxy)-9-[2-(tetrahydro-2H-Pyran-2-yl)ethyl]-9H-purin-6-amine

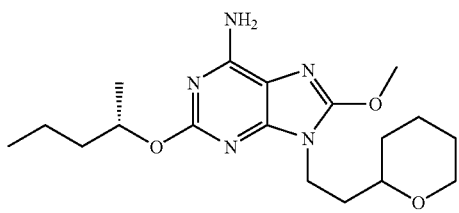

Prepared similarly to Intermediate 243 from 2-{[(1S)-1-methylbutyl]oxy}-8-(methyloxy)-1H-purin-6-amine trifluoroacetate and 2-(2-bromoethyl)tetrahydro-2H-pyran.

LCMS (Method A): $t_{RET}$=3.27 min; MH$^+$=364

Intermediate 266

2-{[(1S)-1-Methylbutyl]oxy}-8-(methyloxy)-9-[3-(tetrahydro-2H-pyran-2-yl)propyl]-9H-purin-6-amine

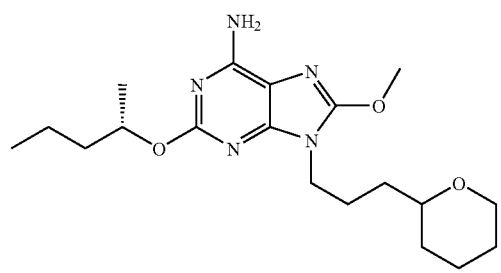

Prepared similarly to Intermediate 220 from 2-{[(1S)-1-methylbutyl]oxy}-8-(methyloxy)-1H-purin-6-amine trifluoroacetate and 2-(3-bromopropyl)tetrahydro-2H-pyran.

LCMS (Method B): $t_{RET}$=1.26 min; MH$^+$=378

Intermediate 267

2-{[(1S)-1-Methylbutyl]oxy}-8-(methyloxy)-9-[4-(tetrahydro-2H-pyran-2-yl)butyl]-9H-purin-6-amine

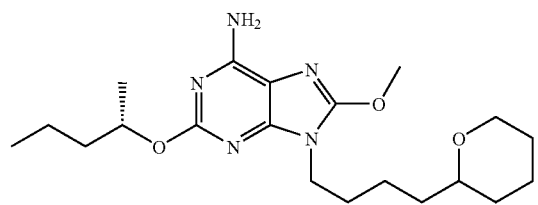

Prepared similarly to Intermediate 213 from 2-{[(11S)-1-methylbutyl]oxy}-8-(methyloxy)-1H-purin-6-amine trifluoroacetate and 2-(4-bromobutyl)tetrahydro-2H-pyran.

LCMS (Method A): $t_{RET}$=3.33 min; MH$^+$=392

Intermediate 268

2-{[(1S)-1-Methylbutyl]oxy}-8-(methyloxy)-9-[2-(tetrahydro-2H-Pyran-3-yl)ethyl]-9H-purin-6-amine

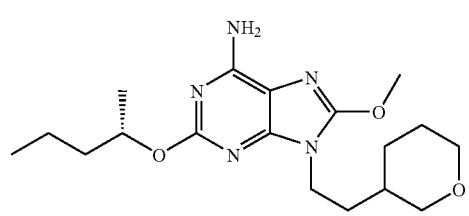

Prepared similarly to Intermediate 243 from 2-{[(1S)-1-methylbutyl]oxy}-8-(methyloxy)-1H-purin-6-amine trifluoroacetate and 3-(2-bromoethyl)tetrahydro-2H-pyran.

LCMS (Method A): $t_{RET}$=3.13 min; MH$^+$=364

Intermediate 269

2-{[(1S)-1-Methylbutyl]oxy}-8-(methyloxy)-9-[4-(tetrahydro-2H-Pyran-3-yl)butyl]-9H-purin-6-amine

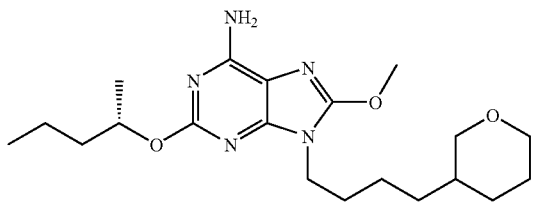

Prepared similarly to Intermediate 243 from 2-{[(1S)-1-methylbutyl]oxy}-8-(methyloxy)-1H-purin-6-amine trifluoroacetate and 3-(4-bromobutyl)tetrahydro-2H-pyran.

LCMS (Method A): $t_{RET}$=3.42 min; MH$^+$=392

Intermediate 270

2-{[(1S)-1-Methylbutyl]oxy}-8-(methyloxy)-9-[2-(tetrahydro-2H-Pyran-4-yl)ethyl]-9H-purin-6-amine

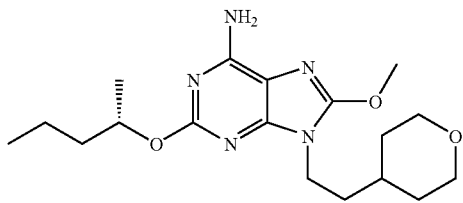

Prepared similarly to Intermediate 215 from 2-{[(11S)-1-methylbutyl]oxy}-8-(methyloxy)-1H-purin-6-amine trifluoroacetate and 4-(2-bromoethyl)tetrahydro-2H-pyran but conducting the alkylation over 1 hour at 60° C.

LCMS (Method A): $t_{RET}$=2.97 min; MH$^+$=364

Intermediate 271

2-{[(1S)-1-Methylbutyl]oxy}-8-(methyloxy)-9-[3-(tetrahydro-2H-pyran-4-yl)propyl]-9H-purin-6-amine

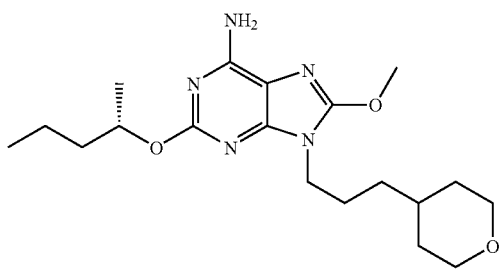

Prepared similarly to Intermediate 216 from 2-{[(11S)-1-methylbutyl]oxy}-8-(methyloxy)-1H-purin-6-amine trifluoroacetate and 4-(3-bromopropyl)tetrahydro-2H-pyran.

LCMS (Method B): $t_{RET}$=1.19 min; MH$^+$=378

Intermediate 272

2-{[(1S)-1-Methylbutyl]oxy}-8-(methyloxy)-9-[4-(tetrahydro-2H-Pyran-4-yl)butyl]-9H-purin-6-amine

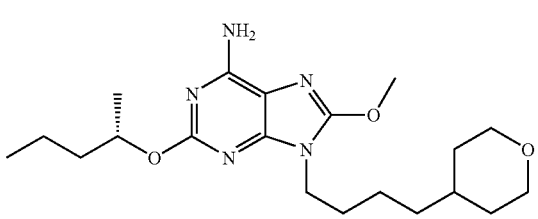

Prepared similarly to Intermediate 216 from 2-{[(11S)-1-methylbutyl]oxy}-8-(methyloxy)-1H-purin-6-amine trifluoroacetate and 4-(4-bromobutyl)tetrahydro-2H-pyran.

LCMS (Method B): $t_{RET}$=1.26 min; MH$^+$=392

Intermediate 273

9-[2-(2,2-Dimethyltetrahydro-2H-pyran-4-yl)ethyl]-2-{[(1S)-1-methylbutyl]oxy}-8-(methyloxy)-9H-purin-6-amine

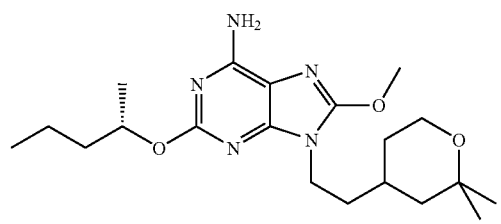

Prepared similarly to Intermediate 243 from 2-{[(1S)-1-methylbutyl]oxy}-8-(methyloxy)-1H-purin-6-amine trifluoroacetate and 4-(2-bromoethyl)-2,2-dimethyltetrahydro-2H-pyran.

LCMS (Method A): $t_{RET}$=3.26 min; MH$^+$=392

Intermediate 274

9-[3-(2,2-Dimethyltetrahydro-2H-pyran-4-yl)prolyl]-2-{[(1S)-1-methylbutyl]oxy}-8-(methyloxy)-9H-purin-6-amine

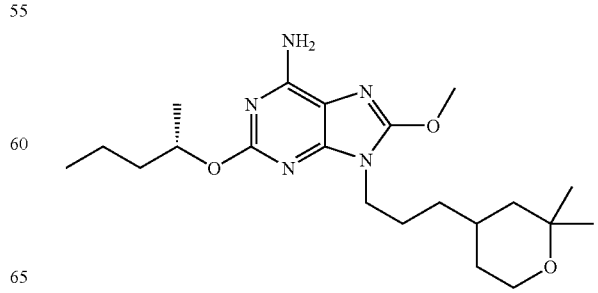

Prepared similarly to Intermediate 215 from 2-{[(1S)-1-methylbutyl]oxy}-8-(methyloxy)-1H-purin-6-amine trifluoroacetate and 4-(3-bromopropyl)-2,2-dimethyltetrahydro-2H-pyran but conducting the alkylation over 1 hour at 60° C.
LCMS (Method A): $t_{RET}$=3.37 min; MH$^+$=406

Intermediate 275

9-[4-(2,2-Dimethyltetrahydro-2H-pyran-4-yl)butyl]-2-{[(1S)-1-methylbutyl]oxy}-8-(methyloxy)-9H-purin-6-amine

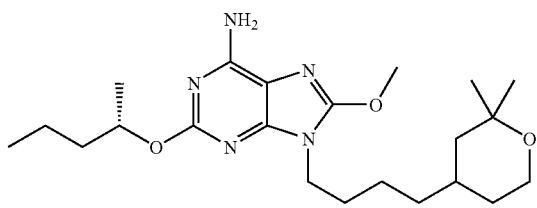

Prepared similarly to Intermediate 215 from 2-{[(1S)-1-methylbutyl]oxy}-8-(methyloxy)-1H-purin-6-amine trifluoroacetate and 4-(4-bromobutyl)-2,2-dimethyltetrahydro-2H-pyran but conducting the alkylation over 1 hour at 60° C.
LCMS (Method A): $t_{RET}$=3.44 min; MH$^+$=420

Intermediate 276

2-{[(1R)-1-methylbutyl]oxy}-8-(methyloxy)-9-[2-(tetrahydro-2-furanyl)ethyl]-9H-purin-6-amine

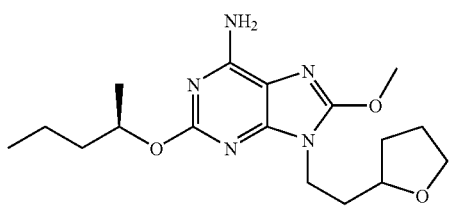

Prepared similarly to Intermediate 290 from 2-{[(1R)-1-methylbutyl]oxy}-8-(methyloxy)-1H-purin-6-amine trifluoroacetate and 2-(2-bromoethyl)tetrahydrofuran.
LCMS (Method B): $t_{RET}$=1.11 min; MH$^+$=350

Intermediate 277

2-{[(1R)-1-Methylbutyl]oxy}-8-(methyloxy)-9-[3-(tetrahydro-2-furanyl)propyl]-9H-purin-6-amine

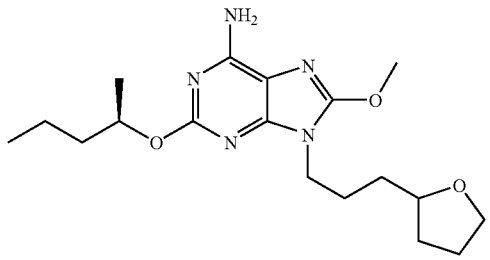

Prepared similarly to Intermediate 223 from 2-{[(1R)-1-methylbutyl]oxy}-8-(methyloxy)-1H-purin-6-amine trifluoroacetate and 2-(3-bromopropyl)tetrahydrofuran but conducting the alkylation over 1 hour at 60° C.
LCMS (Method A): $t_{RET}$=3.00 min; MH$^+$=364

Intermediate 278

2-{[(1R)-1-Methylbutyl]oxy}-8-(methyloxy)-9-{2-[(3S)-tetrahydro-3-furanyl]ethyl}-9H-purin-6-amine

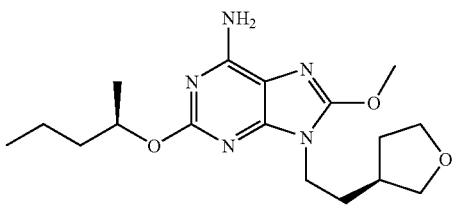

Prepared similarly to Intermediate 216 from 2-{[(1R)-1-methylbutyl]oxy}-8-(methyloxy)-1H-purin-6-amine trifluoroacetate and (3R)-3-(2-bromoethyl)tetrahydrofuran.
LCMS (Method A): $t_{RET}$=2.81 min; MH$^+$=350

Intermediate 279

2-{[(1R)-1-Methylbutyl]oxy}-8-(methyloxy)-9-{2-[(3R)-tetrahydro-3-furanyl]ethyl}-9H-purin-6-amine

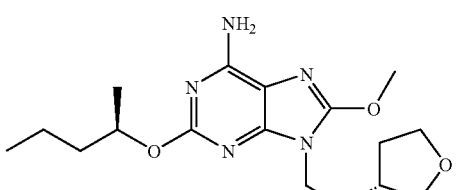

Prepared similarly to Intermediate 223 from 2-{[(1R)-1-methylbutyl]oxy}-8-(methyloxy)-1H-purin-6-amine trifluoroacetate and (3S)-3-(2-bromoethyl)tetrahydrofuran but conducting the alkylation over 1 hour at 60° C.
LCMS (Method A): $t_{RET}$=2.81 min; MH$^+$=350

Intermediate 280

2-{[(1R)-1-Methylbutyl]oxy}-8-(methyloxy)-9-[3-(tetrahydro-3-furanyl)propyl]-9H-purin-6-amine

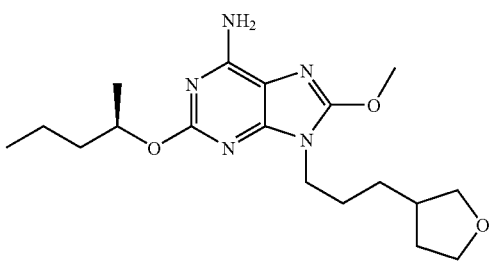

Prepared similarly to Intermediate 216 from 2-{[(1R)-1-methylbutyl]oxy}-8-(methyloxy)-1H-purin-6-amine trifluoroacetate and 3-(3-bromopropyl)tetrahydrofuran.
LCMS (Method B): $t_{RET}$=1.09 min; MH$^+$=364

Intermediate 281

2-{[(1R)-1-Methylbutyl]oxy}-8-(methyloxy)-9-[4-(tetrahydro-3-furanyl)butyl]-9H-purin-6-amine

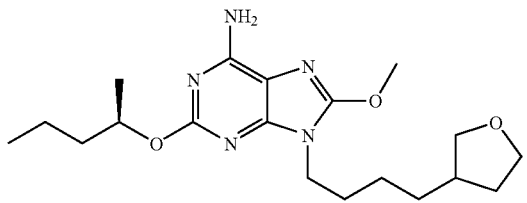

Prepared similarly to Intermediate 216 from 2-{[(1R)-1-methylbutyl]oxy}-8-(methyloxy)-1H-purin-6-amine trifluoroacetate and 3-(4-bromobutyl)tetrahydrofuran.

LCMS (Method B): $t_{RET}$=1.16 min; MH$^+$=378

Intermediate 282

2-{[(1R)-1-Methylbutyl]oxy}-8-(methyloxy)-9-[2-(tetrahydro-2H-Pyran-2-yl)ethyl]-9H-purin-6-amine

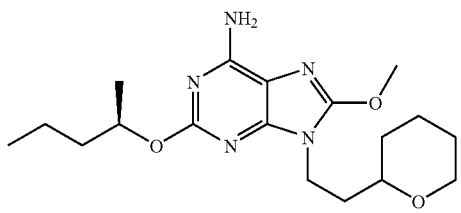

Prepared similarly to Intermediate 213 from 2-{[(1R)-1-methylbutyl]oxy}-8-(methyloxy)-1H-purin-6-amine trifluoroacetate and 2-(2-bromoethyl)tetrahydro-2H-pyran.

LCMS (Method B): $t_{RET}$=1.21 min; MH$^+$=364

Intermediate 283

2-{[(1R)-1-Methylbutyl]oxy}-8-(methyloxy)-9-[3-(tetrahydro-2H-Pyran-2-yl)propyl]-9H-purin-6-amine

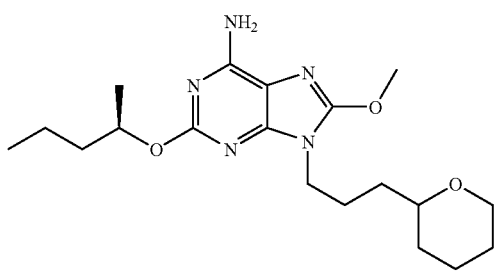

Prepared similarly to Intermediate 216 from 2-{[(1R)-1-methylbutyl]oxy}-8-(methyloxy)-1H-purin-6-amine trifluoroacetate and 2-(3-bromopropyl)tetrahydro-2H-pyran.

LCMS (Method B): $t_{RET}$=1.25 min; MH$^+$=378

Intermediate 284

2-{[(1R)-1-Methylbutyl]oxy}-8-(methyloxy)-9-[4-(tetrahydro-2H-pyran-2-yl)butyl]-9H-purin-6-amine

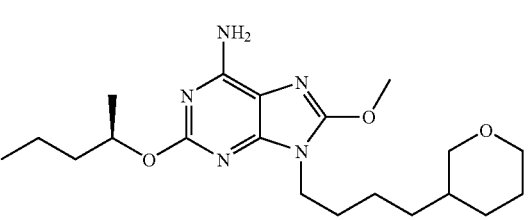

Prepared similarly to Intermediate 213 from 2-{[(1R)-1-methylbutyl]oxy}-8-(methyloxy)-1H-purin-6-amine trifluoroacetate and 2-(4-bromobutyl)tetrahydro-2H-pyran.

LCMS (Method A): $t_{RET}$=3.33 min; MH$^+$=392?

Intermediate 285

2-{[(1R)-1-Methylbutyl]oxy}-8-(methyloxy)-9-[2-(tetrahydro-2H-Pyran-3-yl)ethyl]-9H-purin-6-amine

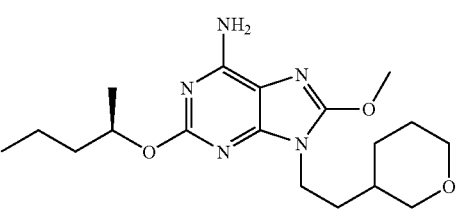

Prepared similarly to Intermediate 213 from 2-{[(1R)-1-methylbutyl]oxy}-8-(methyloxy)-1H-purin-6-amine trifluoroacetate and 3-(2-bromoethyl)tetrahydro-2H-pyran.

LCMS (Method B): $t_{RET}$=1.13 min; MH$^+$=364

Intermediate 286

2-{[(1R)-1-Methylbutyl]oxy}-8-(methyloxy)-9-[4-(tetrahydro-2H-Pyran-3-yl)butyl]-9H-purin-6-amine

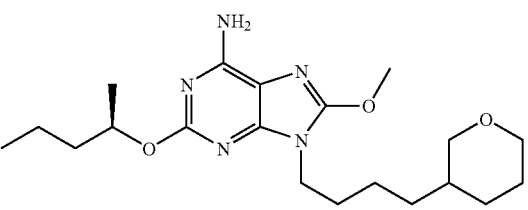

Prepared similarly to Intermediate 213 from 2-{[(1R)-1-methylbutyl]oxy}-8-(methyloxy)-1H-purin-6-amine trifluoroacetate and 3-(4-bromobutyl)tetrahydro-2H-pyran.

LCMS (Method B): $t_{RET}$=1.26 min; MH$^+$=392

Intermediate 287

2-{[(1R)-1-Methylbutyl]oxy}-8-(methyloxy)-9-[2-(tetrahydro-2H-Pyran-4-yl)ethyl]-9H-purin-6-amine

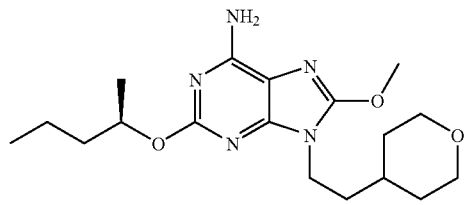

Prepared similarly to Intermediate 223 from 2-{[(1R)-1-methylbutyl]oxy}-8-(methyloxy)-1H-purin-6-amine trifluoroacetate and 4-(2-bromoethyl)tetrahydro-2H-pyran but conducting the alkylation over 1 hour at 60° C.

LCMS (Method A): $t_{RET}$=2.94 min; MH$^+$=364

Intermediate 288

2-{[(1R)-1-Methylbutyl]oxy}-8-(methyloxy)-9-[3-(tetrahydro-2H-Pyran-4-yl)propyl]-9H-purin-6-amine

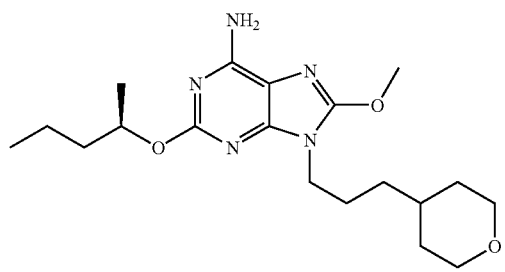

Prepared similarly to Intermediate 216 from 2-{[(1R)-1-methylbutyl]oxy}-8-(methyloxy)-1H-purin-6-amine trifluoroacetate and 4-(3-bromopropyl)tetrahydro-2H-pyran.

LCMS (Method B): $t_{RET}$=1.16 min; MH$^+$=378

Intermediate 289

2-{[(1R)-1-Methylbutyl]oxy}-8-(methyloxy)-9-[4-(tetrahydro-2H-Pyran-4-yl)butyl]-9H-purin-6-amine

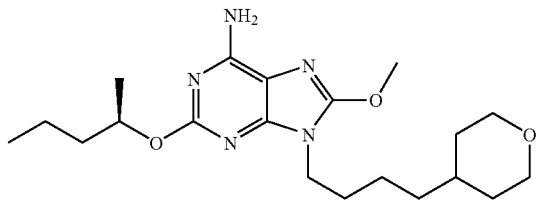

Prepared similarly to Intermediate 216 from 2-{[(1R)-1-methylbutyl]oxy}-8-(methyloxy)-1H-purin-6-amine trifluoroacetate and 4-(4-bromobutyl)tetrahydro-2H-pyran.

LCMS (Method B): $t_{RET}$=1.24 min; MH$^+$=392

Intermediate 290

9-[2-(2,2-Dimethyltetrahydro-2H-pyran-4-yl)ethyl]-2-{[(1R)-1-methylbutyl]oxy}-8-(methyloxy)-9H-purin-6-amine

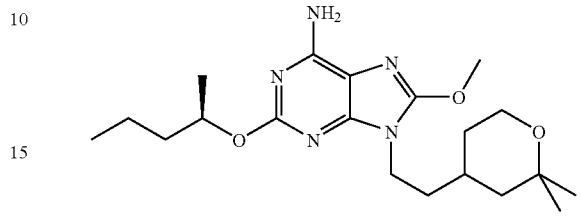

2-{[(1R)-1-Methylbutyl]oxy}-8-(methyloxy)-1H-purin-6-amine trifluoroacetate (100 mg, 0.274 mmol) was heated with potassium carbonate (37.8 mg, 0.274 mmol) in dry DMF (2 ml) at 60° C. under nitrogen for 1 hour and then cooled to room temperature. 4-(2-Bromoethyl)-2,2-dimethyltetrahydro-2H-pyran (72.6 mg, 0.328 mmol) was added and the reaction mixture heated at 50° C., for 16 hours. LCMS indicated the reaction to be incomplete and more 4-(2-bromoethyl)-2,2-dimethyltetrahydro-2H-pyran (35 mg) was added, and the reaction stirred at 50° C. for a further 5 hours and then partitioned between water (2 ml) and DCM (5 ml). The aqueous layer was further extracted with DCM (2×5 ml). The combined organic layers were combined and dried by passing through a hydrophobic frit and then evaporated to dryness using a nitrogen blowdown unit. The residue was dissolved in methanol (0.6 ml) and purified by mass directed autopreparation. Evaporation of the product containing fractions under a stream of nitrogen in a blowdown apparatus gave the title compound as a white solid (92 mg).

LCMS (Method B): $t_{RET}$=1.19 min; MH$^+$=392

Intermediate 291

9-[3-(2,2-Dimethyltetrahyro-2H-pyran-4-yl)propyl]-2-{[(1R)-1-methylbutyl]oxy}-8-(methyloxy)-9H-purin-6-amine

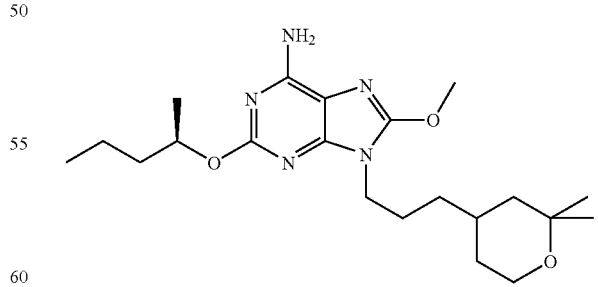

Prepared similarly to Intermediate 223 from 2-{[(1R)-1-methylbutyl]oxy}-8-(methyloxy)-1H-purin-6-amine trifluoroacetate and 4-(3-bromopropyl)-2,2-dimethyltetrahydro-2H-pyran but conducting the alkylation over 1 hour at 60° C.

LCMS (Method A): $t_{RET}$=3.27 min; MH$^+$=406

Intermediate 292

9-[4-(2,2-Dimethyltetrahydro-2H-pyran-4-yl)butyl]-2-{[(1R)-1-methylbutyl]oxy}-8-(methyloxy)-9H-purin-6-amine

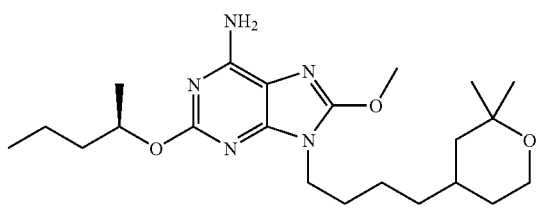

Prepared similarly to Intermediate 223 from 2-{[(R)-methylbutyl]oxy}-8-(methyloxy)-1H-purin-6-amine trifluoroacetate and 4-(4-bromobutyl)-2,2-dimethyltetrahydro-2H-pyran but conducting the alkylation over 1 hour at 60° C.

LCMS (Method A): $t_{RET}$=3.44 min; MH$^+$=420

Example 1

6-Amino-2-butoxy-9-(tetrahydro-2H-Pyran-4-ylmethyl)-7,9-dihydro-8H-Purin-8-one

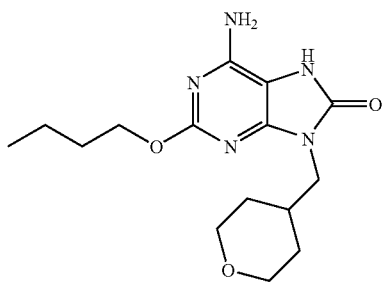

2-Butoxy-8-methoxy-9-(tetrahydro-2H-pyran-4-ylmethyl)-9H-purin-6-amine (0.22 g) was dissolved in methanol (10 mL) and treated with 4N hydrogen chloride in 1,4-dioxane (1 mL). The reaction was stirred at room temperature 16 hours and stripped to give a solid that was suspended in water (2 mL) before sufficient methanol was added until a solution was obtained. 2N Sodium hydroxide solution was added to bring to pH 7, and the solution concentrated until a suspension formed. The white solid was filtered and washed with water (2 mL, twice to complete transfer and wash). This was dried under suction and then under vacuum at 50° C. to give the title compound as a white solid (0.189 g).

MS calcd for $(C_{15}H_{23}N_5O_3)^+$=321

MS found (electrospray): (M+H)$^+$=322

1H NMR((CD$_3$)$_2$SO): 9.86 (1H, s), 6.41 (2H, s), 4.14 (2H, t), 3.81 (2H, m), 3.55 (2H, d), 3.22 (2H, m), 2.03 (1H, m), 1.64 (2H, m), 1.49-1.33 (4H, overlapping m), 1.22 (2H, m), 0.92 (3H, t).

Example 2

6-Amino-2-butoxy-9-(tetrahydro-2H-Pyran-2-ylmethyl)-7,9-dihydro-8H-purin-8-one

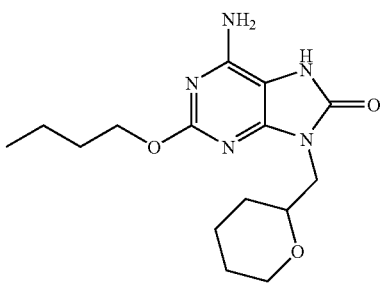

2-Butoxy-8-methoxy-9-(tetrahydro-2H-pyran-2-ylmethyl)-9H-purin-6-amine (6 mg, 85% pure) was dissolved in methanol (1 mL), treated with 4N hydrogen chloride in 1,4-dioxane (0.5 mL) and stirred for 5 hours at room temperature. The mixture was stripped to dryness to give the title compound (77.8:10.8 by LCMS) as a colourless gum (8 mg).

MS calcd for $(C_{15}H_{23}N_5O_3)^+$=321

MS found (electrospray): (M+H)$^+$=322

1H NMR (CD$_3$OD): 4.54 (2H, t), 4.06-3.65 (5H, overlapping m), 1.87-1.83 (3H, overlapping m), 1.69 (1H, d), 1.52 (4H, overlapping m), 1.35 (2H, m), 1.01 (3H, t) (NH$_2$ & NH protons exchanged).

Example 3

6-Amino-2-butoxy-9-(tetrahydrofuran-2-ylmethyl)-7,9-dihydro-8H-Purin-8 one

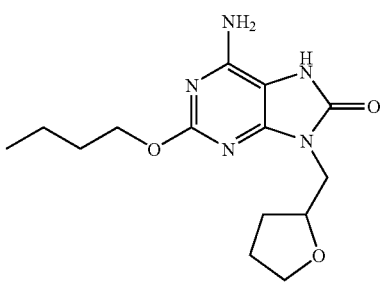

To 2-butoxy-8-methoxy-9H-purin-6-amine trifluoroacetate salt (0.20 g) in dry DMF (5 mL) was added anhydrous potassium carbonate (0.315 g). This was heated to 60° C. for 1 hour and then cooled to room temperature. Tetrahydrofurfuryl bromide (65 uL) was added and the reaction mixture was then heated to 50° C. overnight. The reaction was quenched with water and extracted with ethyl acetate (twice). The organic phase was separated, combined and dried by passing through a hydrophobic frit. Evaporation of the organic phase and purification of the oil so formed by silica chromatography (40 g) (ISCO) eluting with 0-100% ethyl acetate:cyclohexane and then 0-10% methanol:ethyl acetate then methanol gave a gum. This gum was dissolved in methanol (5 mL) and treated with 4N hydrogen chloride in 1,4-dioxane (1 mL) and stirred overnight at room temperature. The reaction mixture was stripped to dryness to give a gum (~44 mg) that was purified by MDAP to give the title compound (slower-running isomer by LCMS) as a white solid (15.2 mg).

MS calcd for $(C_{14}H_{21}N_5O_3)^+$=307
MS found (electrospray): $(M+H)^+$=308
1H NMR (CD$_3$OD): 4.36 (1H, m), 4.27 (2H, t), 3.90 (2H, m), 3.75 (2H, d), 2.00 (2H, m), 1.90 (1H, m), 1.73 (3H, overlapping m), 1.48 (2H, m), 0.98 (3H, t) (NH$_2$ and NH exchanged).

Example 4

6-Amino-2-butylamino-9-(tetrahydro-2H-Pyran-4-ylmethyl)-7,9-dihydro-8H-Purin-8-one

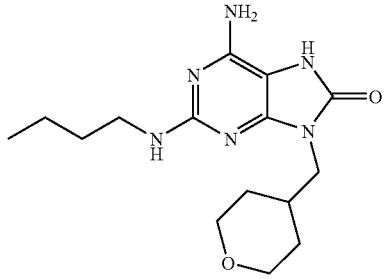

To a solution of N$^2$-butyl-8-methoxy-9-(tetrahydro-2H-pyran-4-ylmethyl)-9H-purine-2,6-diamine (310 mg) in dry methanol (30 ml) at room temperature and under nitrogen was added 4.0M hydrogen chloride in 1,4-dioxane (5.5 ml) in one go. The reaction was left to stir at room temperature for 16 hours. The reaction was neutralised by the addition of 2.0M sodium hydroxide solution and concentrated in vacuo. The residue was taken up in water (10 ml) and the solid filtered and dried on the rotary evaporator (60° C.) for 30 minutes. This afforded the title compound as a solid (170 mg).

MS calcd for $(C_{15}H_{24}N_6O_2)^+$=320
MS found (electrospray): $(M+H)^+$=321
$^1$H NMR((CD$_3$)$_2$SO): δ 9.82 (1H, s), 6.16 (1H, t), 6.09 (2H, s), 3.81 (2H, m), 3.50 (2H, d), 3.21 (2H, m), 3.16 (2H, m), 2.03 (1H, m), 1.44 (4H, m), 1.29 (2H, m), 1.22 (2H, m), 0.88 (3H, t).

Example 4, Alternative Procedure

6-Amino-2-(butylamino)-9-(tetrahydro-2H-Pyran-4-ylmethyl)-7,9-dihydro-8H-Purin-8-one

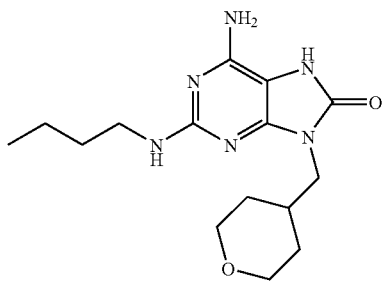

N$^2$-Butyl-8-(methoxy)-9-(tetrahydro-2H-pyran-4-ylmethyl)-9H-purine-2,6-diamine (5.16 g) was dissolved in methanol (50 mL) to give an orange solution. To this solution was then added 4N hydrogen chloride in 1,4-dioxane (5 mL). The resultant orange solution was stirred at ambient temperature (~22° C.) for ~17 hours. The reaction mixture was examined by LCMS and this showed the reaction had not proceeded to completion. To the reaction mixture was then added a further aliquot of 4N hydrogen chloride in 1,4-dioxane (5 mL) and the reaction mixture was stirred for a further 5.25 hours. Examination of the reaction mixture by LCMS showed reaction nearly complete with a small quantity of N$^2$-butyl-8-(methoxy)-9-(tetrahydro-2H-pyran-4-ylmethyl)-9H-purine-2,6-diamine remaining. The reaction was evaporated under reduced pressure to give a light tan solid to avoid undesired reaction/decomposition through the reaction being left unattended over weekend. On resuming the experiment, the material was re-dissolved in methanol (50 mL) to give an orange solution to which was then added 4N hydrogen chloride in 1,4-dioxane (5 mL). The reaction mixture was then stirred at ambient temperature (~20° C.) for 1.6 hours after which the reaction was found to be complete by LCMS.

The reaction mixture was then evaporated under reduced pressure to give a light tan-solid. The material was suspended in a mixture of water (10 mL) and methanol (60 mL) and then sonicated to give a finely-divided suspension before 2M sodium hydroxide solution was added gradually to neutralise (a further volume of water (10 mL) was added when the suspension began to thicken).

The resultant suspension was filtered under suction and the filter-cake washed with water (30 mL) before being air-dried under suction to give an off-white solid. The filtrate was evaporated under suction to give a light-tan solid which was suspended in water (10 mL) and isolated by filtration under suction. This solid then washed with water:methanol (10 mL, 1:1 v/v) to give a light-tan solid which was air-dried under suction to give (~0.3 g). Combined solids were then dried under vacuo (50° C.) overnight until a free-flowing off-white solid (4.69 g) was obtained.

This material (4.69 g) was added to a round bottom flask (250 mL) equipped with a magnetic stirrer bar. To the round bottom flask was then added absolute ethanol (94 mL). The resultant suspension was heated gently with stirring until the solid dissolved. Water (94 mL) was then added and a precipitate formed. The resultant suspension was then heated (round bottom flask now equipped with a reflux condenser) (external, 95° C.) until the solid re-dissolved. Heating was continued for 5 minutes, before the heat source was removed and allowed to cool with stirring. The resultant solid was then isolated by filtration and washed using absolute ethanol:water (50 mL, 1:1 v/v). The resultant filter-cake was then air-dried under suction before being dried to constant weight under vacuo (50° C.) over ~24 hours, this gave the title compound as an off-white solid (3.57 g).

MS calcd for $(C_{15}H_{24}N_6O_2)^+$=320
MS found (electrospray): $(M+H)^+$=321
1H NMR((CD$_3$)$_2$SO): 10.56 (1H, s), 7.77 (3H, broad s), 3.87-3.78 (2H, m), 3.61-3.53 (2H, m), 3.34-3.26 (2H, m), 3.26-3.18 (2H, m), 2.09-1.94 (1H, m), 1.59-1.44 (4H, overlapping m), 1.40-1.29 (2H, m), 1.29-1.14 (2H, m), 0.95-0.87 (3H, m).

Example 5

6-Amino-2-butylamino-9-(tetrahydro-2H-Pyran-2-ylmethyl)-7,9-dihydro-8H-Purin-8-one

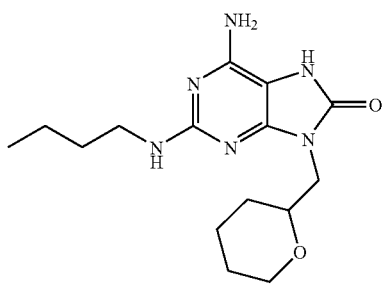

To a solution of $N^2$-butyl-8-methoxy-9-(tetrahydro-2H-pyran-2-ylmethyl)-9H-purine-2,6-diamine in dry methanol (5 ml) at room temperature and under nitrogen was added 4.0M hydrogen chloride in 1,4-dioxane (1.5 ml) in one go. The reaction was left to stir at room temperature overnight. The reaction was concentrated in vacuo and the product purified by MDAP. This afforded the title compound 6 mg (slower-running on MDAP).

MS calcd for $(C_{15}H_{24}N_6O_2)^+=320$
MS found (electrospray): $(M+H)^+=321$
$^1$H NMR$((CD_3)_2SO)$: δ 10.71 (1H, s), 7.91 (3H, br. s), 3.79-3.85 (1H, m), 3.71-3.78 (1H, m), 3.62-3.71 (1H, m), 3.54-3.60 (1H, m), 3.26-3.38 (2H, m), 3.19-3.27 (1H, m), 1.70-1.80 (1H, m), 1.53-1.59 (1H, m), 1.49-1.54 (2H, m), 1.43 (3H, s), 1.29-1.39 (2H, m), 1.12-1.25 (1H, m), 0.90 (3H, t).

Example 6

6-Amino-2-butylamino-9-(tetrahydrofuran-2-ylmethyl)-7,9-dihydro-8H-Purin-8-one

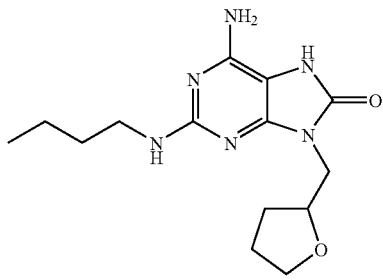

To a solution of $N^2$-butyl-8-methoxy-9H-purine-2,6-diamine trifluoroacetic acid salt (400 mg) in dry N,N-dimethylformamide (6 ml) at room temperature and under nitrogen was added potassium carbonate (630 mg) in one go. The reaction was stirred at 60° C. for 1.5 hours and then cooled to 40° C. 2-(bromomethyl)tetrahydrofuran (156 μl) was added in one go and the reaction heated at 50° C. overnight and then at 90° C. for 2 hours. The reaction was diluted with ethyl acetate (20 ml) and washed with water (10 ml). The organic layer was separated and concentrated in vacuo. The product was semi-purified by MDAP to afford a mixture. To this mixture, in dry methanol (5 ml) at room temperature and under nitrogen was added 4.0M hydrogen chloride in 1,4-dioxane (1.5 ml) in one go. The reaction was left to stir at room temperature overnight. The reaction was concentrated in vacuo and the product purified by MDAP (slower-running isomer). This afforded the title compound as a white solid (15 mg).

MS calcd for $(C_{14}H_{22}N_6O_2)^+=306$
MS found (electrospray): $(M+H)^+=307$
$^1$H NMR$((CD_3)_2SO)$: δ 10.69 (1H, s), 7.82 (3H, br. s), 4.18 (1H, m), 3.67-3.79 (2H, m), 3.56-3.64 (2H, m), 3.28 (2H, s), 1.76-1.92 (3H, m), 1.65 (1H, m), 1.52 (2H, m), 1.32 (2H, m), 0.88 (3H, t).

Example 7

6-Amino-2-butylamino-9-[2-(tetrahydro-2H-Pyran-4-yl)ethyl]-7,9-dihydro-8H-Purin-8-one

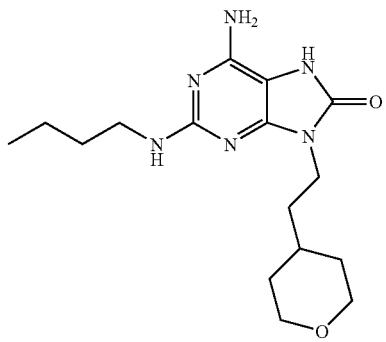

To a solution of $N^2$-butyl-8-methoxy-9H-purine-2,6-diamine trifluoroacetic acid salt (100 mg) in dry N,N-dimethylformamide (1 ml) at room temperature and under nitrogen was added potassium carbonate (158 mg) in one go. The reaction was stirred at 60° C. for 1.5 hours and then cooled to 50° C. A solution of 4-(2-bromoethyl)tetrahydro-2H-pyran (60 mg) in dry N,N-dimethylformamide (0.5 ml) was added in one go and the reaction heated at 50° C. overnight. The reaction was diluted with ethyl acetate (15 ml) and washed with water (5 ml). The organic layer was separated and concentrated in vacuo. The product was purified by $C_{18}$ reverse phase chromatography using water (0.1% formic acid)-acetonitrile (0.05% formic acid) as eluant (20-60%) to afford a yellow viscous oil (47 mg) that was dissolved in dry methanol (4 ml) at room temperature and under nitrogen was added 4.0M hydrogen chloride in 1,4-dioxane (0.8 ml) in one go. The reaction was left to stir at room temperature overnight. The reaction was neutralised by the addition of 2.0M sodium hydroxide solution and concentrated in vacuo. The residue was taken up in water (5 ml) and the solid filtered and dried in vacuo (60° C.) for 30 minutes. This afforded the title compound as a beige solid (23 mg).

MS calcd for $(C_{16}H_{26}N_6O_2)=334$
MS found (electrospray): $(M+H)^+=335$
$^1$H NMR$((CD_3)_2SO)$: δ 9.78 (1H, s), 6.08-6.21 (3H, br. s), 3.80 (2H, m), 3.65 (2H, t), 3.21 (2H, m), 3.16 (2H, m), 1.66 (2H, m), 1.57 (2H, m), 1.36-1.49 (3H, m), 1.29 (2H, m), 1.13 (2H, m), 0.88 (3H, t).

Example 8

6-Amino-2-butylamino-9-(tetrahydrofuran-3-ylmethyl)-7,9-dihydro-8H-Purin-8-one

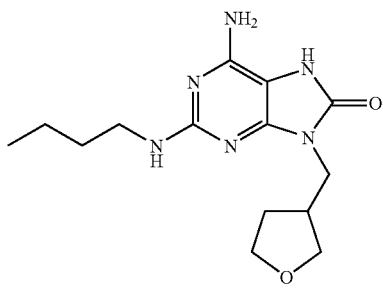

To a solution of $N^2$-butyl-8-methoxy-9H-purine-2,6-diamine trifluoroacetic acid salt (100 mg) in dry N,N-dimethylformamide (1 ml) at room temperature and under nitrogen was added potassium carbonate (158 mg) in one go. The reaction was stirred at 60° C. for 1.5 hours and then cooled to 50° C. A solution of 3-(bromomethyl)tetrahydrofuran (52 mg) in dry N,N-dimethylformamide (0.5 ml) was added in one go and the reaction heated at 50° C. overnight. The reaction was diluted with ethyl acetate (15 ml) and washed with water (5 ml). The organic layer was separated and concentrated in vacuo. The product was semi-purified by $C_{18}$ reverse phase chromatography using water (containing 0.1% formic acid)-acetonitrile (containing 0.05% formic acid) as eluant (10-45%) to give a yellow oil (32 mg) that was dissolved in dry methanol (3 ml) at room temperature and under nitrogen was added 4.0M hydrogen chloride in 1,4-dioxane (0.6 ml) in one go. The reaction was left to stir at room temperature overnight. The reaction was neutralised by the addition of 2.0M sodium hydroxide solution and concentrated in vacuo. The residue was taken up in water (5 ml) and the solid filtered and dried in vacuo (60° C.) for 15 minutes. This afforded the title compound as a white solid (20 mg).

MS calcd for $(C_{14}H_{22}N_6O_2)^+=306$
MS found (electrospray): $(M+H)^+=307$
$^1$H NMR((CD$_3$)$_2$SO): δ 9.73 (1H, s), 6.17 (1H, m), 6.04 (1H, m), 3.74 (2H, m), 3.56-3.64 (4H, m), 3.53 (1H, m), 3.16 (2H, m), 2.69 (1H, m), 1.85 (1H, m), 1.64 (1H, m), 1.46 (2H, m), 1.29 (2H, m), 0.87 (3H, t).

Example 8, Alternative Method

6-Amino-2-(butylamino)-9-(tetrahydro-3-furanylmethyl)-7,9-dihydro-8H-purin-8-one

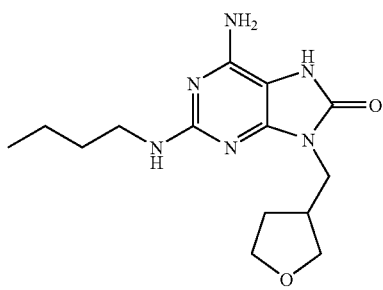

$N^2$-Butyl-8-(methoxy)-9-(tetrahydro-3-furanylmethyl)-9H-purine-2,6-diamine (98 mg) was dissolved in methanol (2 mL). To the resultant solution was added 4N hydrogen chloride in 1,4-dioxane (0.5 mL). The reaction mixture was then stirred at ambient temperature until completion (monitored by LCMS) over 2.5 hours. The reaction mixture was then evaporated under reduced pressure to give an oil. To this oil was added water (2 mL) and methanol (2 mL). The resultant solution was then neutralised using 2M sodium hydroxide solution. Further water (5 mL) was added when the product precipitated (pH 4-5). The white solid was isolated by filtration under suction and then washed with water (5 mL). The filter cake was then air-dried under suction to give (68 mg) that was dissolved in ethanol (2 mL). To this solution was added water (2 mL) to give a precipitate. The resultant suspension was heated (90° C., external) to reflux to give a solution. The resultant solution was refluxed for a few minutes before being allowed to cool to ambient room temperature to give a flocculent white solid. This solid was isolated by filtration under suction and the residues transferred using water (8 mL). The filter cake was air-dried under suction and was then dried under vacuo at 50° C. for 4 hours to give a white solid which was then transferred to a vial and dried further at 50° C. (16 hours) to give 55 mg of the title compound as a white solid.

MS calcd for $(C_{14}H_{22}N_6O_2)^+=306$
MS found (electrospray): $(M+H)^+=307$
$^1$H NMR((CD$_3$)$_2$SO): δ 9.55 (1H, brs), 6.11-6.19 (1H, m), 5.95 (2H, brs), 3.80-3.70 (1H, m), 3.66-3.56 (4H, m), 3.56-3.49 (1H, m), 3.16 (2H, q), 2.76-2.63 (1H, m), 1.91-1.80 (1H, m), 1.69-1.59 (1H, m), 1.52-1.41 (2H, m), 1.36-1.22 (2H, m), 0.88 (3H, t).

Example 9

6-Amino-2-butylamino-9-(tetrahydro-2H-pyran-3-ylmethyl)-7,9-dihydro-8H-Purin-8-one

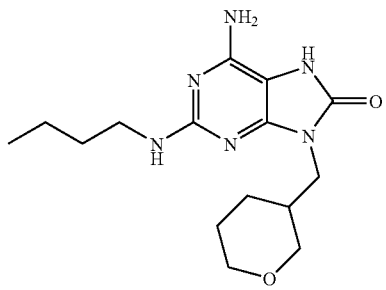

To a solution of $N^2$-butyl-8-methoxy-9-(tetrahydro-2H-pyran-3-ylmethyl)-9H-purine-2,6-diamine (45 mg) in dry methanol (3 ml) at room temperature and under nitrogen was added 4.0M hydrogen chloride in 1,4-dioxane (0.7 ml) in one go. The reaction was left to stir at room temperature for 3 hours. The reaction was neutralised by the addition of 2.0M sodium hydroxide solution and concentrated in vacuo. The residue was taken up in water (5 ml) and the solid filtered and dried in vacuo (60° C.) for 30 minutes. This afforded the title compound as a solid (25 mg).

MS calcd for $(C_{15}H_{24}N_6O_2)^+=320$
MS found (electrospray): $(M+H)^+=321$
$^1$H NMR((CD$_3$)$_2$SO): δ 9.59 (1H, s), 6.17 (1H, t), 5.90 (2H, t), 3.65 (2H, m), 3.42-3.67 (2H, m), 3.31 (1H, m), 3.10-3.20 (3H, m), 2.14 (1H, m), 1.64 (2H, m), 1.36-1.50 (3H, m), 1.30 (2H, m), 1.22 (1H, m), 0.88 (3H, t).

Example 10

6-Amino-2-butoxy-9-(tetrahydrofuran-3-ylmethyl)-7,9-dihydro-8H-purin-8-one

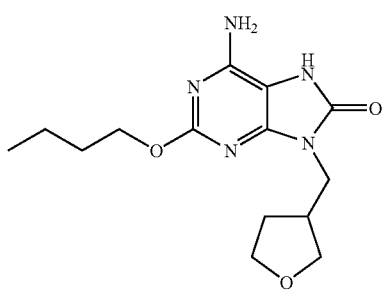

2-Butoxy-8-methoxy-9-(tetrahydrofuran-3-ylmethyl)-9H-purin-6-amine (97 mg) was dissolved in methanol (2 mL) and treated with 4N hydrogen chloride in 1,4-dioxane (1 mL). The reaction mixture was stirred for 4 hours. The reaction was stripped to dryness. Water (2 mL) and methanol (15 mL) was added to the residue and then neutralised by the addition of 2N sodium hydroxide solution. The above was stripped to near dryness (small quantity of water remaining) and the solid thus obtained was filtered (transferred and washed the solid with water (2 mL, 3 times)). The solid was dried under suction before being dried further in vacuo (50° C.) for 2 hours. This afforded the title compound as a white solid (62 mg).

MS calcd for $(C_{14}H_{21}N_5O_3)^+$=307
MS found (electrospray): $(M+H)^+$=308
1H NMR((CD$_3$)$_2$SO): 9.88 (1H, s), 6.42 (2H, s), 4.13 (2H, t), 3.75 (1H, m), 3.65-3.56 (4H, overlapping m), 3.51 (1H, m), 2.68 (1H, m), 1.87 (1H, m), 1.66-1.57 (3H, overlapping m), 1.38 (2H, m), 0.90 (3H, t).

Example 11

6-Amino-2-butoxy-9-[2-(tetrahydro-2H-pyran-4-yl)ethyl]-7,9-dihydro-8H-Purin-8-one

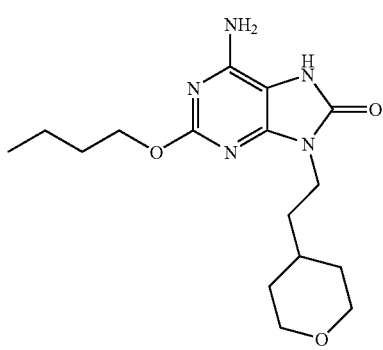

2-Butoxy-8-methoxy-9-[2-(tetrahydro-2H-pyran-4-yl)ethyl]-9H-purin-6-amine (0.11 g) was dissolved in methanol (2 mL) and treated with 4N hydrogen chloride in 1,4-dioxane (1 mL). The reaction mixture was stirred for 4 hours and was stripped to dryness. Water (2 mL) and methanol (15 mL) were added to the residue and then neutralised by the addition of 2N sodium hydroxide solution. The above was stripped to near dryness (small quantity of water remaining) and the solid thus obtained was filtered (transferred and washed the solid with water (3 mL)). The solid was dried under suction before being dried further in vacuo to afford the title compound as a white solid (82 mg).

MS calcd for $(C_{16}H_{25}N_5O_3)^+$=335
MS found (electrospray): $(M+H)^+$=336
1H NMR((CD$_3$)$_2$SO): 9.84 (1H, s), 6.40 (2H, s), 4.13 (2H, t), 3.79 (2H, dd), 3.70 (2H, d), 3.21 (2H, t), 1.70-1.53 (6H, overlapping m), 1.46-1.32 (3H, overlapping m), 1.14 (2H, m), 0.91 (3H, t).

Example 12

6-Amino-2-butoxy-9-(tetrahydro-2H-pyran-3-ylmethyl)-7,9-dihydro-8H-Purin-8-one

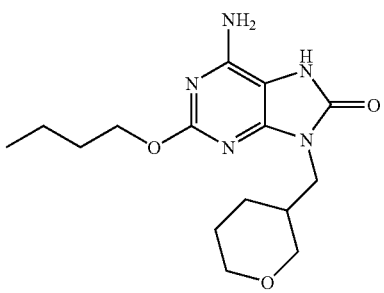

2-Butoxy-8-methoxy-9-(tetrahydro-2H-pyran-3-ylmethyl)-9H-purin-6-amine (105 mg) was dissolved in methanol (2 mL) and treated with 4N hydrogen chloride in 1,4-dioxane (1 mL). The reaction mixture was stirred for 4 hours and stripped to dryness. Water (2 mL) and methanol (15 mL) were added to the residue and then neutralised by the addition of 2N sodium hydroxide solution. The above was stripped to near dryness (small volume of water remaining) and the solid thus obtained was filtered off under suction (transferred and washed with water (2 mL, 3 times)). The solid was dried under suction before being dried further in vacuo to afford the title compound as a white solid (71.5 mg).

MS calcd for $(C_{15}H_{23}N_5O_3)^+$=321
MS found (electrospray): $(M+H)^+$=322
1H NMR((CD$_3$)$_2$SO): 9.85 (1H, s), 6.40 (2H, s), 4.13 (2H, t), 3.65 (2H, m), 3.54 (2H, m), 3.32 (1H, m), 3.15 (1H, dd), 2.02 (1H, m), 1.69-1.56 (4H, overlapping m), 1.45-1.32 (3H, overlapping m), 1.21 (1H, m), 0.91 (3H, t).

Example 13

6-Amino-2-butoxy-9-[2-(tetrahydrofuran-2-yl)ethyl]-7,9-dihydro-8H-Purin-8-one

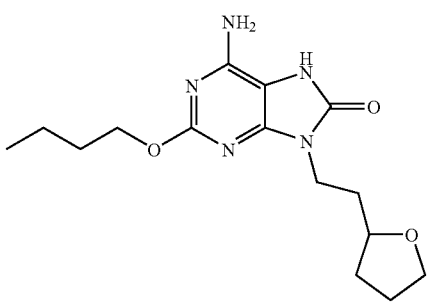

2-Butoxy-8-methoxy-9-[2-(tetrahydrofuran-2-yl)ethyl]-9H-purin-6-amine (122 mg) was dissolved in methanol (2 ml) and 4N hydrogen chloride in dioxan (1 ml) added. After 4 h the reaction mixture was made basic with 2N sodium hydroxide (2.2 ml) then the organic solvents stripped. A few drops of 2N hydrochloric acid were added and the pH adjusted back to 7-8 with saturated sodium hydrogen carbonate. The resulting solid was filtered, washed and dried to give the title compound as a solid, yield 65 mg.

MS calcd for $(C_{15}H_{23}N_5O_3)^+=321$

MS found (electrospray): $(M+H)^+=322$ $^1$H NMR$((CD_3)_2SO)$: δ 9.83 (1H, s), 6.39 (2H, s), 4.14 (2H, t), 3.72 (4H, m), 3.56 (1H, m), 1.96 (1H, m), 1.80 (4H, m), 1.64 (2H, m), 1.38 (3H, m), 1.91 (3H, t). 25 mg of this mixture of enantiomers was resolved by chiral HPLC on a 2×25 cm Chiralpak AS column eluted with heptane:ethanol 7:3 with a flow rate of 15 mL/min over 30 min to provide Example 13 Isomer 1 (9.9 mg) and Example 13 Isomer 2 (10.8 mg).

Example 13 Isomer 1

Analytical chiral HPLC (25×0.46 cm Chiralpak AS column, heptane:ethanol 7:3 eluting at 1 mL/min, 30 min run): $t_{RET}$=10.8 min.

LCMS (Method A): $t_{RET}$=2.78 min; $MH^+$=322

Example 13 Isomer 2

Analytical chiral HPLC (25×0.46 cm Chiralpak AS column, heptane:ethanol 7:3 eluting at 1 mL/min, 30 min run): $t_{RET}$=15.8 min.

LCMS (Method A): $t_{RET}$=2.78 min; $MH^+$=322

Example 14

6-Amino-2-butylamino-9-[2-(tetrahydrofuran-2-yl)ethyl]-7,9-dihydro-8H-purin-8-one

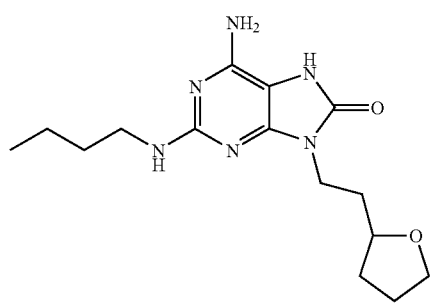

$N^2$-Butyl-8-methoxy-9-[2-(tetrahydrofuran-2-yl)ethyl]-9H-purine-2,6-diamine (107 mg) was dissolved in methanol (2 ml) and 4N hydrogen chloride in dioxan (1 ml) added. After 4 h the solvents were stripped and the residue taken up in water and basified with 2N sodium hydroxide. A few drops of 2N hydrochloric acid were added and the pH adjusted to 7-8 by addition of saturated sodium hydrogen carbonate. The resulting solid was filtered, washed and dried to give the title compound as a solid, yield 101 mg.

MS calcd for $(C_{15}H_{24}N_6O_2)^+=320$

MS found (electrospray): $(M+H)^+=321$ $^1$H NMR$((CD_3)_2SO)$: δ 9.51 (1H, s), 6.17 (1H, m), 5.94 (2H, s), 3.77-3.53 (5H, m), 3.16 (2H, m), 1.96 (1H, m), 1.80 (4H, m), 1.51-1.24 (5H, m), 0.88 (3H, t).

Example 15

6-Amino-2-butoxy-9-[2-(tetrahydro-2H-pyran-3-yl)ethyl]-7,9-dihydro-8H-Purin-8-one

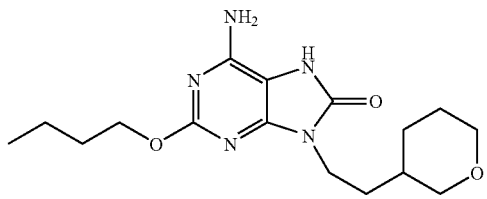

2-Butoxy-8-methoxy-9-[2-(tetrahydro-2H-pyran-3-yl)ethyl]-9H-purin-6-amine (108 mg) was dissolved in methanol (2 ml) and 4N hydrogen chloride in dioxan (1 ml) added. After 16 h the reaction mixture was stripped, quenched with water then saturated sodium hydrogen carbonate added, when a solid precipitated. This was filtered, washed with water and dried. The solid was treated with hot methanol and was filtered after allowing to cool to yield 66 mg of the title compound.

MS calcd for $(C_{16}H_{25}N_5O_3)^+=335$

MS found (electrospray): $(M+H)^+=336$ $^1$H NMR$((CD_3)_2SO)$: δ 9.85 (1H, s), 6.40 (2H, br. s), 4.15 (2H, t), 3.79 (1H, m), 3.68 (3H, m), 3.25 (1H, m), 2.99 (1H, m), 1.87 (1H, m), 1.64 (2H, m), 1.58-1.34 (7H, m), 1.14 (1H, m), 0.91 (3H, t).

Example 16

6-Amino-2-butylamino-9-[2-(tetrahydro-2H-Pyran-3-yl)ethyl]-7,9-dihydro-8H-Purin-8-one

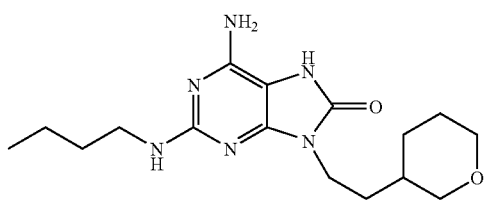

$N^2$-Butyl-8-methoxy-9-[2-(tetrahydro-2H-pyran-3-yl)ethyl]-9H-purine-2,6-diamine (138 mg) was dissolved in methanol (2 ml) and 4N hydrogen chloride in dioxan (1 ml) added. After 4 h the reaction mixture was stripped, quenched with water then made basic with saturated sodium hydrogen carbonate. The resulting solid was filtered, washed and dried to give the title compound, yield 105 mg.

MS calcd for $(C_{16}H_{26}N_6O_2)^+=334$

MS found (electrospray): $(M+H)^+=335$ $^1$H NMR((CD$_3$)$_2$SO): δ 9.52 (1H, s), 6.14 (1H, t), 5.94 (2H, br. s), 3.78 (1H, m), 3.71 (1H, m), 3.62 (2H, m), 3.24 (1H, m), 3.16 (2H, m), 2.98 (1H, m), 1.87 (1H, m), 1.57-1.36 (7H, m), 1.29 (2H, m), 1.12 (1H, m), 0.88 (3H, t). A sample of this mixture of enantiomers was resolved by chiral HPLC on a 2×25 cm Chiralpak AS column eluted with heptane:ethanol 85:15 with a flow rate of 15 mL/min over 60 min to provide Example 16 Isomer 1 (7.6 mg) and Example 16 Isomer 2 (7.5 mg).

Example 16 Isomer 1

Analytical chiral HPLC (25×0.46 cm Chiralpak AS column, heptane:ethanol 85:15 eluting at 1 mL/min, 40 min run): $t_{RET}$=24.2 min LCMS (Method A): $t_{RET}$=2.51 min; MH$^+$=335

Example 16 Isomer 2

Analytical chiral HPLC (25×0.46 cm Chiralpak AS column, heptane:ethanol 85:15 eluting at 1 mL/min, 40 min run): $t_{RET}$=29.0 min.

LCMS (Method A): $t_{RET}$=2.51 min; MH$^+$=335

Example 17

6-Amino-2-[(2,2-dimethylpentyl)oxy]-9-(tetrahydro-2H-pyran-4-ylmethyl)-7,9-dihydro-8H-purin-8-one

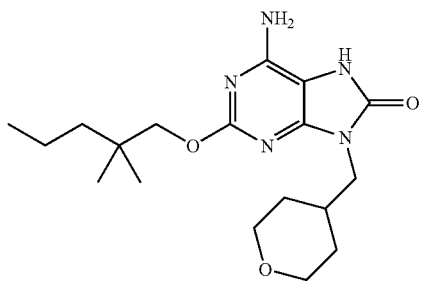

To a solution of 2-[(2,2-dimethylpentyl)oxy]-8-methoxy-9-(tetrahydro-2H-pyran-4-ylmethyl)-9H-purin-6-amine (116 mg) in dry MeOH (14.5 mL) was added 4N HCl in 1,4-dioxane (2.48 mL). The mixture was stirred at room temperature for 3 h. The reaction was neutralised to pH 7 with 2M sodium hydroxide solution and was concentrated in vacuo to give and off-white solid. The solid was triturated with water (30 mL) and was filtered under reduced pressure to give the title compound as an off-white solid (76 mg).

MS calcd for (C$_{18}$H$_{29}$N$_5$O$_3$)$^+$=363

MS found (electrospray): (M+H)$^+$=364

$^1$H NMR((CD$_3$)$_2$SO): δ 9.86 (1H, s), 6.42 (2H, s), 3.87 (2H, s), 3.81 (2H, br. d), 3.60-3.52 (2H, m), 3.29-3.15 (2H, m), 2.10-1.96 (1H, m), 1.50-1.40 (2H, m), 1.31-1.16 (6H, m), 0.96-0.81 (9H, m).

Example 18

6-Amino-2-(Pentylamino)-9-(tetrahydro-2H-pyran-4-ylmethyl)-7,9-dihydro-8H-Purin-8-one

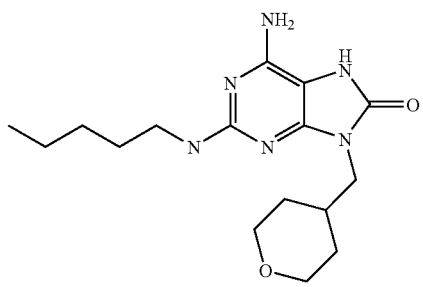

To a solution of 8-methoxy-N$^2$-pentyl-9-(tetrahydro-2H-pyran-4-ylmethyl)-9H-purine-2,6-diamine (140 mg) in dry MeOH (15.7 mL) was added 4N HCl in 1,4-dioxane (2.65 mL). The reaction mixture was stirred at room temperature for 3 h and was then neutralised with 2M sodium hydroxide solution. The mixture was concentrated in vacuo and the residue was taken up into water (20 mL). The mixture was filtered under reduced pressure to give the title compound (95 mg) as an off-white solid.

MS calcd for (C$_{16}$H$_{26}$N$_6$O$_2$)$^+$=334

MS found (electrospray): (M+H)$^+$=335

$^1$H NMR((CD$_3$)$_2$SO): δ 9.55 (1H, s), 6.19 (1H, s), 5.96 (2H, s), 3.81 (2H, d), 3.50 (2H, d), 3.27-3.07 (4H, m), 2.10-1.96 (1H, m), 1.55-1.37 (4H, m), 1.35-1.13 (6H, m), 0.92-0.79 (3H, m).

Example 19

6-Amino-2-[(3-methylbutyl)oxy]-9-(tetrahydro-2H-Pyran-4-ylmethyl)-7,9-dihydro-8H-purin-8-one

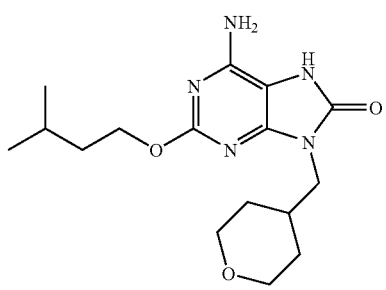

To a solution of 2-[(3-methylbutyl)oxy]-8-methoxy-9-(tetrahydro-2H-pyran-4-ylmethyl)-9H-purin-6-amine (52 mg) in dry MeOH (5.7 mL) was added 4N HCl in 1,4-dioxane (0.971 mL) and the reaction mixture was stirred at room temperature for 3 h. The reaction was neutralised to pH7 with 2M sodium hydroxide solution and concentrated in vacuo to give a white solid. The solid was washed with water (20 mL)

and was filtered under reduced pressure to give the title compound as an off-white solid (31 mg).

MS calcd for $(C_{16}H_{25}N_5O_3)^+$=335
MS found (electrospray): $(M+H)^+$=336
$^1$H NMR$((CD_3)_2SO)$: δ 9.86 (1H, s), 6.40 (2H, s), 4.18 (2H, t), 3.81 (2H, dd), 3.55 (2H, t), 3.22 (2H, t), 2.09-1.95 (1H, m), 1.78-1.64 (1H, m), 1.61-1.51 (2H, m), 1.49-1.40 (2H, m), 1.29-1.15 (2H, m), 0.91 (6H, d).

Example 20

6-Amino-2-[(2-methylbutyl)oxy]-9-(tetrahydro-2H-Pyran-4-ylmethyl)-7,9-dihydro-8H-purin-8-one

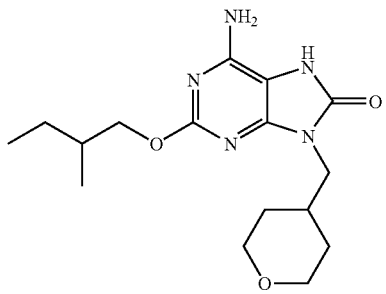

To a solution of 2-[(2-methylbutyl)oxy]-8-methoxy-9-(tetrahydro-2H-pyran-4-ylmethyl)-9H-purin-6-amine (41 mg) in dry MeOH (4.5 mL) was added 4N HCl in 1,4-dioxane (0.766 mL) and the reaction mixture was stirred at room temperature for 3 h. The reaction was neutralised with 2M sodium hydroxide solution and concentrated in vacuo. The resulting white residue was taken up in water (20 mL) and was filtered under reduced pressure to give the title compound as an off-white solid (20 mg).

MS calcd for $(C_{16}H_{25}N_5O_3)^+$=335
MS found (electrospray): $(M+H)^+$=336
$^1$H NMR$((CD_3)_2SO)$: δ 9.88 (1H, br), 6.41 (2H, s), 4.08-4.00 (1H, m), 3.97-3.90 (1H, m), 3.85-3.76 (2H, m), 3.56 (2H, d), 3.22 (2H, t), 2.10-1.95 (1H, m), 1.82-1.68 (1H, m), 1.50-1.39 (3H, m), 1.29-1.12 (3H, m), 0.97-0.84 (6H, m).

Example 21

6-Amino-2-[(1-methylbutyl)oxy]-9-(tetrahydro-2H-Pyran-4-ylmethyl)-7,9-dihydro-8H-purin-8-one

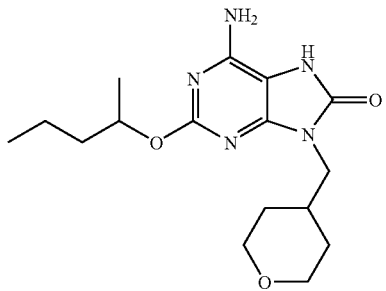

To a solution of 2-[(1-methylbutyl)oxy]-8-methoxy-9-(tetrahydro-2H-pyran-4-ylmethyl)-9H-purin-6-amine (92 mg) in dry MeOH (9.9 mL) was added 4N HCl in 1,4-dioxane (1.7 mL) and the reaction mixture was stirred at room temperature for 3 h. The reaction was neutralised to pH7 with 2M sodium hydroxide solution and concentrated in vacuo to give an off-white solid. The solid was triturated with water (30 mL) and filtered under reduced pressure to give the title compound as an off-white solid (55 mg).

MS calcd for $(C_{16}H_{25}N_5O_3)^+$=335
MS found (electrospray): $(M+H)^+$=336
$^1$H NMR$((CD_3)_2SO)$: δ 9.84 (1H, s), 6.36 (2H, s), 5.04-4.94 (1H, m), 3.86-3.76 (2H, m), 3.53 (2H, d), 3.21 (2H, t), 2.08-1.96 (1H, m), 1.68-1.55 (1H, m), 1.53-1.14 (10H, m), 0.92-0.83 (3H, m).

Example 22

6-Amino-2-[(2-methylbutyl)amino]-9-(tetrahydro-2H-Pyran-4-ylmethyl)-7,9-dihydro-8H-Purin-8-one

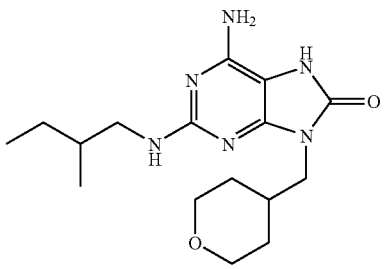

A mixture of 2-chloro-8-methoxy-9-(tetrahydro-2H-pyran-4-ylmethyl)-9H-purin-6-amine (40 mg) in 2-methyl-1-butylamine (117 mg) was heated in a microwave at 170° C. for 15 mins. The mixture was concentrated in vacuo to give a green oily residue which was purified by $C_{18}$ reverse phase chromatography (ISCO) using water (0.1% formic acid)-acetonitrile (0.05% formic acid) as eluent (20-60%) to give the title compound as an off-white solid (9 mg).

MS calcd for $(C_{16}H_{26}N_6O_2)^+$=334
MS found (electrospray): $(M+H)^+$=335
$^1$H NMR$((CD_3)_2SO)$: δ 9.60 (1H, br), 6.18 (1H, t), 5.95 (2H, br), 3.86-3.77 (2H, m), 3.50 (2H, d), 3.27-3.09 (3H, m), 3.00-2.89 (1H, m), 2.11-1.98 (1H, m), 1.67-1.55 (1H, m), 1.49-1.33 (3H, m), 1.28-1.02 (3H, m), 0.91-0.80 (6H, m).

Example 23

6-amino-2-[(3-methylbutyl)amino]-9-(tetrahydro-2H-pyran-4-ylmethyl)-7,9-dihydro-8H-purin-8-one

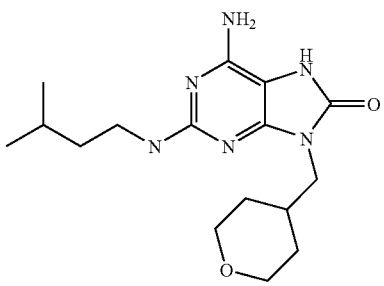

A mixture of 2-chloro-8-methoxy-9-(tetrahydro-2H-pyran-4-ylmethyl)-9H-purin-6-amine (45 mg) in 3-methyl-1- butylamine (0.234 mL) was heated in a microwave at 170° C. for 10 mins. The mixture was concentrated in vacuo to give a green oily residue. This was purified by $C_{18}$ reverse phase chromatography (ISCO) using water (0.1% formic acid)-acetonitrile (0.05% formic acid) as eluent (20-60%) to give the title compound as a white solid (10 mg).

MS calcd for $(C_{16}H_{26}N_6O_2)^+$=334
MS found (electrospray): $(M+H)^+$=335
$^1H$ NMR$((CD_3)_2SO)$: δ 9.61 (1H, s), 6.12 (1H, t), 5.97 (2H, s), 3.86-3.77 (2H, m), 3.50 (2H, d), 3.27-3.14 (4H, m), 2.13-1.95 (1H, m), 1.68-1.12 (7H, m), 0.96-0.79 (6H, m).

Example 24

6-Amino-2-[(1-methylbutyl)amino]-9-(tetrahydro-2H-pyran-4-ylmethyl)-7,9-dihydro-8H-Purin-8-one

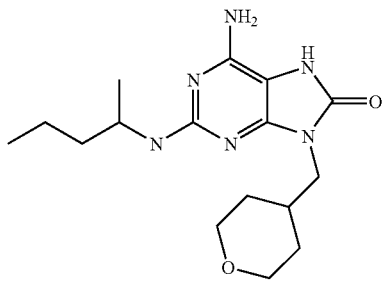

To a solution of 2-chloro-8-methoxy-9-(tetrahydro-2H-pyran-4-ylmethyl)-9H-purin-6-amine (40 mg) in ethylene glycol (1.5 mL) was added 2-aminopentane (0.16 mL) and the mixture was heated in a microwave at 170° C. for 2×30 mins. A further portion of 2-aminopentane (0.08 mL) was added and the reaction was heated in a microwave at 180° C. for 30 mins. The mixture was taken up in EtOAc (15 mL) and was washed with water (3×15 mL). The organics were separated, dried over MgSO$_4$, filtered and concentrated in vacuo to give a brown residue. This was taken up in DCM and concentrated in a vacuum oven to give the title compound as a brown solid (18 mg).

MS calcd for $(C_{16}H_{26}N_6O_2)^+$=334
MS found (electrospray): $(M+H)^+$=335
$^1H$ NMR$((CD_3)_2SO)$: δ 9.56 (1H, br), 5.93 (2H, s), 5.88 (1H, d), 3.85-3.76 (2H, m), 3.50 (2H, d), 3.26-3.14 (2H, m), 2.09-1.97 (1H, m), 1.54-1.12 (9H, m), 1.05 (3H, d), 0.91-0.82 (3H, m).

Example 25

6-Amino-2-[(2-cyclopropylethyl)oxy]-9-(tetrahydro-3-furanylmethyl)-7,9-dihydro-8H-purin-8-one

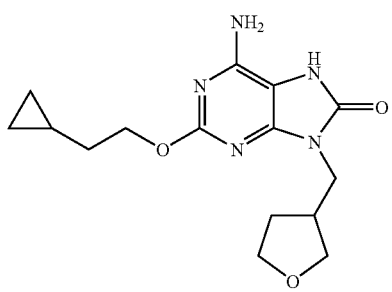

To a solution of 2-[(2-cyclopropylethyl)oxy]-8-methoxy-9-(tetrahydro-3-furanylmethyl)-9H-purin-6-amine (103.8 mg) in methanol (5 mL) was added 4N HCl in 1,4-dioxane (2 mL) and the reaction mixture was stirred at room temperature for 4 h. The reaction was evaporated under reduced pressure to give a gum. Water (3 mL) was added to give a white solid. The mixture was adjusted to pH 7 by adding 2N sodium hydroxide solution and the white solid was filtered off under suction, then washed with a few drops of MeOH. The material was air dried under suction, then in a vacuum oven (50° C.) to give the title compound as white solid (77 mg).

MS calcd for $(C_{15}H_{21}N_5O_3)^+$=319
MS found (electrospray): $(M+H)^+$=320
$^1H$ NMR$((CD_3)_2SO)$: δ 9.89 (1H, s), 6.44 (2H, s), 4.19 (2H t), 3.80-3.72 (1H, m), 3.69-3.56 (4H, m), 3.55-3.49 (1H, m), 2.75-2.63 (1H, m), 1.94-1.82 (1H, m), 1.68-1.53 (3H, m), 0.83-0.72 (1H, m), 0.47-0.37 (2H, m), 0.13-0.06 (2H, m).

Example 26

6-Amino-2-butyloxy-9-[2-(tetrahydro-2H-Pyran-2-yl)ethyl]-7,9-dihydro-8H-Purin-8-one

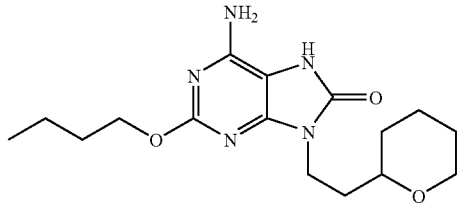

A solution of 2-butyloxy-8-methoxy-9-[2-(tetrahydro-2H-pyran-2-yl)ethyl]-9H-purin-6-amine (88 mg) in methanol (2 mL) was treated with 4N HCl in 1,4-dioxane (1 mL) for 1 h. The reaction was evaporated and the residue treated with water then basified with saturated sodium bicarbonate solution. The resulting white solid was filtered, washed with water and dried to give the title compound (78.1 mg).

MS calcd for $(C_{16}H_{25}N_5O_3)^+$=335
MS found (electrospray): $(M+H)^+$=336
$^1H$ NMR$((CD_3)_2SO)$: δ 9.80 (1H, s), 6.37 (2H, s), 4.14 (2H, t), 3.87-3.62 (3H, m), 3.30-3.16 (2H, m), 1.80-1.50 (6H, m), 1.48-1.31 (5H, m), 1.23-1.10 (1H, m), 0.91 (3H, t).

24 mg of this mixture of enantiomers was resolved by chiral HPLC on a 2×25 cm Chiralpak AD column eluted with heptane:ethanol 90:10 with a flow rate of 15 mL/min over 40 min to provide Example 26 Isomer 1 (12.2 mg) and Example 26 Isomer 2 (9.4 mg).

Example 26 Isomer 1

Analytical chiral HPLC (25×0.46 cm Chiralpak AD column, heptane:ethanol 90:10 eluting at 1 mL/min, 30 min run): $t_{RET}$=12.3 min.

LCMS (Method A): $t_{RET}$=2.97 min; $MH^+$=336

Example 26 Isomer 2

Analytical chiral HPLC (25×0.46 cm Chiralpak AD column, heptane:ethanol 90:10 eluting at 1 mL/min, 30 min run): $t_{RET}$=15.4 min.

LCMS (Method A): $t_{RET}$=2.97 min; $MH^+$=336

Example 27

6-Amino-2-butyloxy-9-[(2,2-dimethyltetrahydro-2H-Pyran-4-yl)methyl]-7,9-dihydro-8H-Purin-8-one

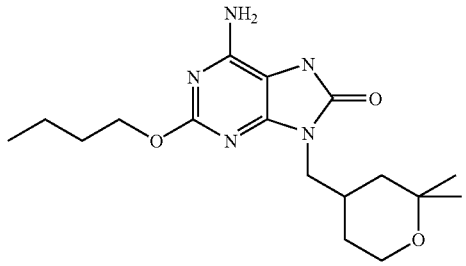

A solution of 2-butyloxy-9-[(2,2-dimethyltetrahydro-2H-pyran-4-yl)methyl]-8-methoxy-9H-purin-6-amine (161 mg) in methanol (1 mL) was treated with 4N HCl in 1,4-dioxane (0.5 mL) for 1 h. The reaction was evaporated and the residue treated with water then basified with saturated sodium bicarbonate solution. The resulting solid was filtered, washed with water and dried to give the title compound (122 mg).

MS calcd for $(C_{17}H_{27}N_5O_3)^+=349$
MS found (electrospray): $(M+H)^+=350$
$^1H$ NMR($(CD_3)_2SO$): δ 9.85 (1H, s), 6.40 (2H, s), 4.21-4.10 (2H, m), 3.62-3.42 (4H, m), 2.27-2.14 (1H, m), 1.69-1.59 (2H, m), 1.46-1.33 (4H, m), 1.14-0.98 (8H, m), 0.95-0.88 (3H, m).

A sample of this mixture of enantiomers was resolved by chiral HPLC on a 2×25 cm
Chiralpak AS column eluted with heptane:ethanol 95:5 with a flow rate of 15 mL/min over 60 min to provide Example 27 Isomer 1 (9.07 mg) and Example 27 Isomer 2 (7.7 mg).

Example 27 Isomer 1

Analytical chiral HPLC (25×0.46 cm Chiralpak AS column, heptane:ethanol 95:5 eluting at 1 mL/min, 40 min run): $t_{RET}$=18.6 min.

LCMS (Method A): $t_{RET}$=2.81 min; MH$^+$=350

Example 27 Isomer 2

Analytical chiral HPLC (25×0.46 cm Chiralpak AS column, heptane:ethanol 95:5 eluting at 1 mL/min, 40 min run): $t_{RET}$=23.5 min.

LCMS (Method A): $t_{RET}$=2.81 min; MH$^+$=350

Example 28

6-Amino-2-(butylamino)-9-[(2,2-dimethyltetrahydro-2H-pyran-4-yl)methyl]-7,9-dihydro-8H-purin-8-one

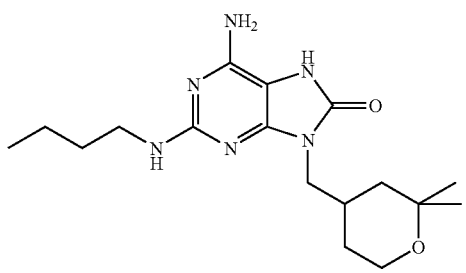

A solution of $N^2$-butyl-9-[(2,2-dimethyltetrahydro-2H-pyran-4-yl)methyl]-8-methoxy-9H-purine-2,6-diamine (73 mg) in MeOH (2 mL) was treated with 4N HCl in 1,4-dioxane (1 mL) and was stirred for 4 h. The reaction was evaporated and the residue treated with water then basified with saturated sodium bicarbonate solution. The resulting solid was filtered, washed with water and dried. The solid was re-precipitated from ether/light petrol to give the title compound (37 mg).

MS calcd for $(C_{17}H_{28}N_6O_2)^+=348$
MS found (electrospray): $(M+H)^+=349$
$^1H$ NMR($(CD_3)_2SO$): δ 9.54 (1H, s), 6.17 (1H, br.t), 5.95 (2H, br), 3.62-3.54 (1H, m), 3.52-3.39 (3H, m), 3.23-3.12 (2H, m), 2.29-2.14 (1H, m), 1.52-1.37 (4H, m), 1.36-1.23 (2H, m), 1.14-0.95 (8H, m), 0.92-0.83 (3H, m).

Example 29

6-Amino-2-butyloxy-9-[2-(tetrahydro-3-furanyl)ethyl]-7,9-dihydro-8H-Purin-8-one

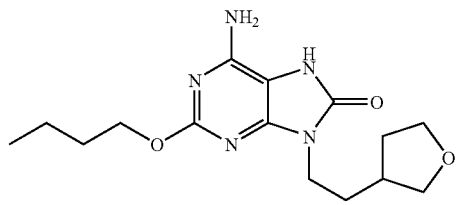

A solution of 2-butyloxy-8-methoxy-9-[2-(tetrahydro-3-furanyl)ethyl]-9H-purin-6-amine (102 mg) in methanol (1 mL) was treated with 4N HCl in 1,4-dioxane (0.5 mL) for 1.5 h. The reaction was evaporated and the residue treated with water then basified with saturated sodium bicarbonate solution. The resulting solid was filtered, washed with water and dried to give the title compound (65 mg).

MS calcd for $(C_{15}H_{23}N_5O_3)^+=321$
MS found (electrospray): $(M+H)^+=322$
$^1H$ NMR($(CD_3)_2SO$): δ 9.86 (1H, s), 6.41 (2H, s), 4.19-4.09 (2H, m), 3.83-3.53 (5H, m), 3.25-3.17 (1H, m), 2.12-1.94 (2H, m), 1.77-1.58 (4H, m), 1.51-1.31 (3H, m), 0.91 (3H, t).

Example 30

6-Amino-2-(butylamino)-9-[2-(tetrahydro-2H-Pyran-2-yl)ethyl]-7,9-dihydro-8H-Purin-8-one

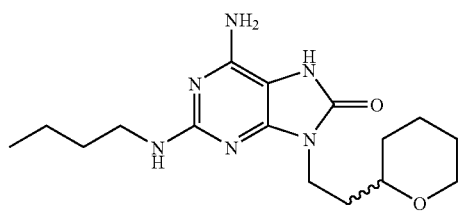

A solution of N2-butyl-8-(methoxy)-9-[2-(tetrahydro-2H-pyran-2-yl)ethyl]-9H-purine-2,6-diamine (54 mg) in methanol (1 ml) was treated with 4N HCl in dioxin (0.5 ml) and stood for 1.5 h. The solvents were stripped and the residue treated with water and made basic with saturated aqueous sodium bicarbonate. The precipitated material was filtered, washed with water and dried to give the title compound as a solid, yield 22.5 mg.

MS calcd for $(C_{16}H_{26}N_6O_2)$=334
MS found (electrospray): $(M+H)^+$=335
$^1$H NMR$((CD_3)_2SO)$: δ 9.49 (1H, s), 6.14 (1H, m), 5.93 (2H, m), 3.83 (1H, m), 3.78-3.58 (2H, m), 3.34-3.12 (4H, m), 1.79-1.10 (12H, m), 0.87 (3H, t).

Example 31

6-Amino-2-(butylamino)-9-[2-(tetrahydro-3-furanyl)ethyl]-7,9-dihydro-8H-Purin-8-one

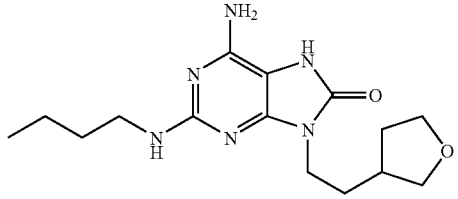

A solution of N²-butyl-8-(methoxy)-9-[2-(tetrahydro-3-furanyl)ethyl]-9H-purine-2,6-diamine (181 mg) in methanol (1 mL) was treated with 4N HCl in 1,4-dioxane (0.5 mL) for 1.5 h. The reaction was evaporated and the residue treated with water then basified with saturated sodium bicarbonate solution. The resulting solid was filtered, washed with water and dried to give the title compound (111 mg).

MS calcd for $(C_{15}H_{24}N_6O_2)^+$=320
MS found (electrospray): $(M+H)^+$=321
$^1$H NMR$((CD_3)_2SO)$: δ 9.54 (1H, s), 6.17 (1H, br.t), 5.97 (2H, s), 3.79 (1H, m), 3.74-3.54 (4H, m), 3.18 (3H, m), 2.02 (2H, m), 1.70 (2H, m), 1.45 (3H, m), 1.28 (2H, m), 0.87 (3H, t).

Example 32

6-Amino-2-(butyloxy)-9-(tetrahydro-3-furanylmethyl)-7,9-dihydro-8H-Purin-8-one, Isomer 1

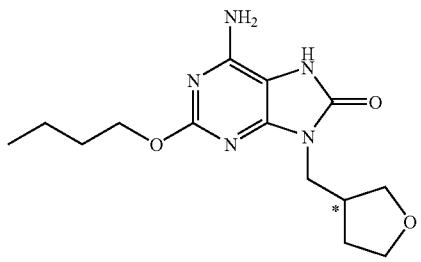

Example 32 (Isomer 1)

2-Butoxy-8-methoxy-9-(tetrahydrofuran-3-ylmethyl)-9H-purin-6-amine (isomer 1, 176 mg) was suspended in methanol (2 ml) and 4N HCl in dioxan (1 ml) added. The resulting clear solution was stripped and the residue treated with water and basified with saturated aqueous sodium bicarbonate. The solid obtained was filtered, washed with water and dried to give the title compound yield 145 mg.

MS calcd for $(C_{14}H_{21}N_5O_3)^+$=307
MS found (electrospray): $(M+H)^+$=308 1H NMR$((CD_3)_2SO)$: 9.88 (1H, s), 6.43 (2H, s), 4.14 (2H, t), 3.76 (1H, m), 3.68-3.57 (4H, m), 3.52 (1H, m), 2.69 (1H, m), 1.88 (1H, m), 1.64 (3H, m), 1.38 (2H, m), 0.92 (3H, t).

Example 32, Alternative Procedure

6-Amino-2-(butyloxy)-9-(tetrahydro-3-furanylmethyl)-7,9-dihydro-8H-purin-8-one (Isomer 1)

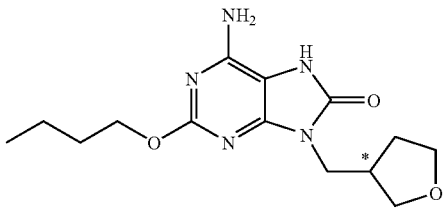

2-(Butyloxy)-8-(methoxy)-9-(tetrahydro-3-furanylmethyl)-9H-purin-6-amine (Isomer 1, 1.54 gm) was suspended in methanol (20 ml) and 4N HCl in dioxan (4 ml) added with stirring to give a clear solution. After 6.5 h, the solvents were evaporated to low volume and water added with stirring, followed by neutralisation with saturated sodium bicarbonate. The resulting off-white solid was filtered, washed with water and dried, yield 1.26 gm. This material was added portionwise to boiling methanol (130 ml), adding a further 20 ml of methanol. The suspension was filtered, and the solid treated with boiling methanol (20 ml) and added to the filtrate. This was reboiled, then allowed to cool with stirring when a white solid crystallised out. This was filtered, washed with methanol and dried, to give the title compound yield 932 mg.

MS calcd for $(C_{14}H_{21}N_5O_3)^+$=307
MS found (electrospray): $(M+H)^+$=308
$^1$H NMR$((CD_3)_2SO)$: δ 9.89 (1H, s), 6.43 (2H, s), 4.14 (2H, m), 3.81-3.72 (1H, m), 3.70-3.55 (4H, m), 3.55-3.48 (1H, m), 2.75-2.64 (1H, m), 1.94-1.83 (1H, m), 1.70-1.58 (3H, m), 1.45-1.33 (2H, m), 0.96-0.88 (3H, q).

Example 33

6-Amino-2-(butyloxy)-9-(tetrahydro-3-furanylmethyl)-7,9-dihydro-8H-Purin-8-one, Isomer 2

2-Butoxy-8-methoxy-9-(tetrahydrofuran-3-ylmethyl)-9H-purin-6-amine (Isomer 2, 178 mg) was suspended in methanol (2 ml) and 4N HCl in dioxan (1 ml) added. The resulting clear solution was stripped and the residue treated with water and basified with saturated aqueous sodium bicarbonate. The solid obtained was filtered, washed with water and dried to give the title compound (isomer 2), yield 72 mg (low due to mechanical losses).

MS calcd for $(C_{14}H_{21}N_5O_3)^+=307$

MS found (electrospray): $(M+H)^+=308$ 1H NMR((CD$_3$)$_2$SO): 9.88 (1H, s), 6.42 (2H, s), 4.15 (2H, t), 3.76 (1H, m), 3.68-3.57 (4H, m), 3.52 (1H, m), 2.69 (1H, m), 1.88 (1H, m), 1.64 (3H, m), 1.38 (2H, m), 0.92 (3H, t).

Example 33, Alternative Procedure

6-Amino-2-(butyloxy)-9-(tetrahydro-3-furanylmethyl)-7,9-dihydro-8H-purin-8-one (Isomer 2)

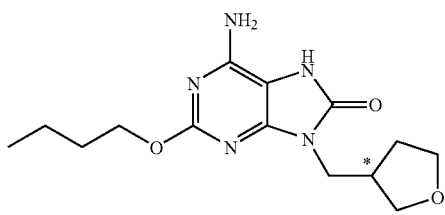

2-(Butyloxy)-8-(methoxy)-9-(tetrahydro-3-furanylmethyl)-9H-purin-6-amine (Isomer 2, 1.96 gm) was suspended in methanol (20 ml) and 4N HCl in dioxan (10 ml) added with stirring to give a clear solution. After 1.5 h, the solvents were evaporated to low volume and water added with stirring, followed by neutralisation with saturated sodium bicarbonate. The resulting off-white solid was filtered, washed with water and dried, yield 1.73 gm. Initial attempts to recrystallise from methanol or ethanol were unsuccessful. The recovered material was dissolved in glacial acetic acid (10 ml) with heating but precipitated immediately on addition of water (10 ml). Further addition of acetic acid (4 ml) and heating gave a clear solution, from which the product crystallised on allowing to cool. The solid was filtered, washed and dried, yield 1.06 gm (Crop 1). A second crop was obtained from the filtrate on standing, yield 460 mg, which was dissolved in sodium hydroxide and precipitated by the addition of acetic acid and then the recovered solid was heated in methanol (20 ml) with further additions of methanol (15 ml) to the boiling mixture to give a cloudy solution, which was allowed to cool. The resulting solid was filtered off, yield 257 mg. This was combined with the first batch of solid (Crop 1) and added portionwise to boiling methanol (130 ml) to give a slightly cloudy solution. On allowing to cool with stirring, a white solid crystallised out which was filtered off, washed with methanol and dried, to give the title compound yield 1.02 gm.

MS calcd for $(C_{14}H_{21}N_5O_3)^+=307$

MS found (electrospray): $(M+H)^+=308$ $^1$H NMR((CD$_3$)$_2$SO): δ 9.89 (1H, s), 6.43 (2H, s), 4.15 (2H, m), 3.81-3.72 (1H, m), 3.70-3.55 (4H, m), 3.55-3.48 (1H, m), 2.75-2.64 (1H, m), 1.94-1.83 (1H, m), 1.70-1.58 (3H, m), 1.45-1.33 (2H, m), 0.96-0.88 (3H, q).

Example 34

6-Amino-2-{[2-(ethyloxy)ethyl]oxy}-9-(tetrahydro-2H-pyran-4-ylmethyl)-7,9-dihydro-8H-Purin-8-one

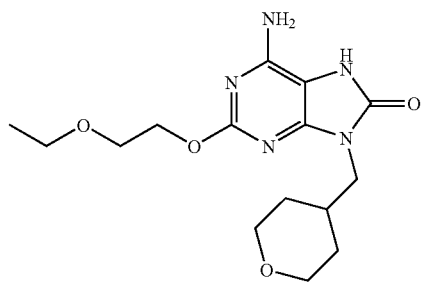

To a solution of 2-(2-ethoxyethoxy)-8-methoxy-9-(tetrahydro-2H-pyran-4-ylmethyl)-9H-purin-6-amine (240 mg) in dry methanol (10 ml) at room temperature and under nitrogen was added 4.0M hydrogen chloride in 1,4-dioxane (4.0 ml). The reaction was left to stir at room temperature for 3 hours. The reaction was neutralised by the addition of 2.0M sodium hydroxide solution and concentrated in vacuo. The residue was taken up in water (15 ml) and the solid filtered and washed with water (2×5 ml). The solid was dried en vacuo (60° C.) for 30 minutes. This afforded the title compound as an off-white solid (129 mg).

MS calcd for $(C_{15}H_{23}N_5O_4)^+=337$

MS found (electrospray): $(M+H)^+=338$ $^1$H NMR((CD$_3$)$_2$SO): δ 9.92 (1H, s), 6.44 (2H, s), 4.25 (2H, s), 3.81 (2H, m), 3.63 (2H, m), 3.55 (2H, d), 3.47 (2H, q), 3.22 (2H, m), 2.03 (1H, m), 1.45 (2H, m), 1.22 (2H, m), 1.12 (3H, t).

Example 35

6-Amino-2-{[1-methyl-2-(methoxy)ethyl]oxy}-9-(tetrahydro-2H-pyran-4-ylmethyl)-7,9-dihydro-8H-Purin-8-one

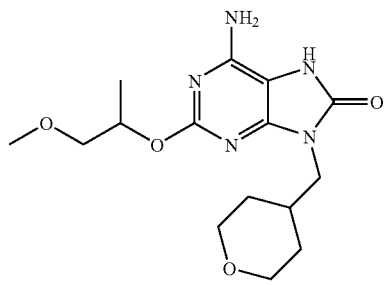

To a solution of 2-{[1-methyl-2-(methoxy)ethyl]oxy}-8-(methoxy)-9-(tetrahydro-2H-pyran-4-ylmethyl)-9H-purin-6-amine (260 mg) in dry methanol (10 ml) at room temperature and under nitrogen was added 4.0M hydrogen chloride in 1,4-dioxane (4.0 ml). The reaction was left to stir at room temperature for 3 hours. The reaction was neutralised by the addition of 2.0M sodium hydroxide solution and concentrated in vacuo. The residue was taken up in water (15 ml) and the solid filtered and washed with water (2×5 ml). The solid was dried en vacuo (60° C.) for 30 minutes. This afforded the title compound as an off-white solid (70 mg).

MS calcd for $(C_{15}H_{23}N_5O_4)^+$=337
MS found (electrospray): $(M+H)^+$=338
$^1$H NMR((CD$_3$)$_2$SO): δ 9.89 (1H, s), 6.41 (2H, br. s), 5.13 (1H, m), 3.81 (2H, m), 3.55 (2H, d), 3.43 (2H, m), 3.27 (3H, s), 3.22 (2H, m), 2.02 (1H, m), 1.46 (2H, m), 1.24 (2H, m), 1.21 (3H, d).

Example 36

6-Amino-2-{[2-(ethyloxy)ethyl]oxy}-9-(tetrahydro-2H-pyran-3-ylmethyl)-7,9-dihydro-8H-Purin-8-one

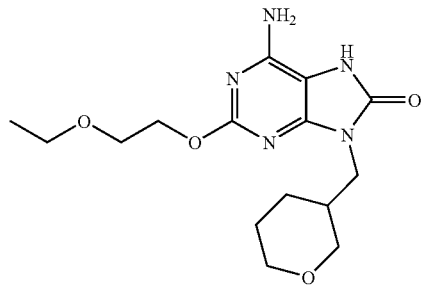

To a solution of 2-(2-ethoxyethoxy)-8-methoxy-9-(tetrahydro-2H-pyran-3-ylmethyl)-9H-purin-6-amine (245 mg) in dry methanol (10 ml) at room temperature and under nitrogen was added 4.0M hydrogen chloride in 1,4-dioxane (4.0 ml). The reaction was left to stir at room temperature for 1 hour. The reaction was concentrated in vacuo and the resulting residue purified by C$_{18}$ reverse phase chromatography using water (containing 0.1% formic acid)-acetonitrile (containing 0.05% formic acid) as eluant (10-45%) to afford a white solid. This was taken up in water (15 ml) and neutralised by the addition of 2.0M sodium hydroxide solution. The solid was filtered and dried on the rotary evaporator (60° C.) for 30 minutes (90 mg).

MS calcd for $(C_{15}H_{23}N_5O_4)^+$=337
MS found (electrospray): $(M+H)^+$=338
$^1$H NMR((CD$_3$)$_2$SO): δ 9.90 (1H, s), 6.45 (2H, s), 4.25 (2H, m), 3.70-3.61 (5H, m), 3.55 (1H, m), 3.47 (2H, q), 3.30 (1H, m), 3.16 (1H, m), 2.03 (1H, m), 1.64 (2H, m), 1.40 (1H, m), 1.22 (1H, m), 1.11 (3H, t).

Example 37

6-Amino-2-{[1-methyl-2-(methoxy)ethyl]oxy}-9-(tetrahydro-2H-pyran-3-ylmethyl)-7,9-dihydro-8H-Purin-8-one

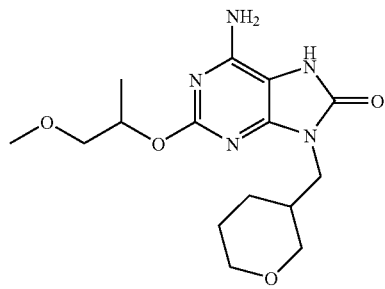

To a solution of 2-{[1-methyl-2-(methoxy)ethyl]oxy}-8-(methyloxy)-9-(tetrahydro-2H-pyran-3-ylmethyl)-9H-purin-6-amine (290 mg) in dry methanol (12 ml) at room temperature and under nitrogen was added 4.0M hydrogen chloride in 1,4-dioxane (5.0 ml). The reaction was left to stir at room temperature for 1 hour. The reaction was concentrated in vacuo and the resulting residue purified by C$_{18}$ reverse phase chromatography using water (containing 0.1% formic acid)-acetonitrile (containing 0.05% formic acid) as eluant (10-45%) to afford a white solid. This was taken up in water (15 ml) and neutralised by the addition of 2.0M sodium hydroxide solution. The solid was filtered and dried on the rotary evaporator (60° C.) for 30 minutes (50 mg).

MS calcd for $(C_{15}H_{23}N_5O_4)^+$=337
MS found (electrospray): $(M+H)^+$=338
$^1$H NMR((CD$_3$)$_2$SO): δ 9.90 (1H, s), 6.43 (2H, s), 5.12 (1H, m), 3.66 (2H, m), 3.55 (2H, m), 3.47 (1H, m), 3.38 (1H, m), 3.30 (1H, m), 3.27 (3H, s), 3.16 (1H, m), 2.02 (1H, m), 1.63 (2H, m), 1.40 (1H, m), 1.23 (1H, m), 1.20 (3H, t).

Example 38

6-Amino-2-[(cyclohexylmethyl)amino]-9-(tetrahydro-2H-Pyran-4-ylmethyl)-7,9-dihydro-8H-Purin-8-one

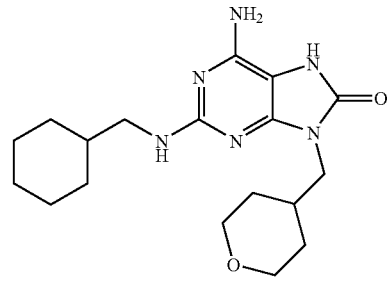

To a solution of 8-bromo-N$^2$-(cyclohexylmethyl)-9-(tetrahydro-2H-pyran-4-ylmethyl)-9H-purine-2,6-diamine (110 mg) in dry n-butanol (1.5 ml) was added 37% grade hydrochloric acid (1.5 ml) at RT. The reaction was heated to 100° C. for six hours. The reaction was concentrated in vacuo, taken up in water (5 ml) and neutralised by the addition of 2.0M sodium hydroxide solution. The resulting white precipitate was filtered. This was purified by C$_{18}$ reverse phase chromatography using water (containing 0.1% formic acid)-acetonitrile (containing 0.05% formic acid) as eluant (20-60%) to afford a white solid (20 mg).

MS calcd for $(C_{18}H_{28}N_6O_2)^+$=360
MS found (electrospray): $(M+H)^+$=361
$^1$H NMR((CD$_3$)$_2$SO): δ 9.59 (1H, s), 6.21 (1H, s), 5.97 (2H, s), 3.81 (2H, m), 3.51 (2H, d), 3.21 (2H, m), 3.01 (2H, m), 2.04 (1H, m), 1.74-1.54 (5H, m), 1.52 (1H, m), 1.44 (2H, m), 1.28-1.04 (5H, m), 0.84 (2H, m).

Example 39

6-Amino-2-[(cycloientylmethyl)amino]-9-(tetrahydro-2H-pyran-4-ylmethyl)-7,9-dihydro-8H-Purin-8-one

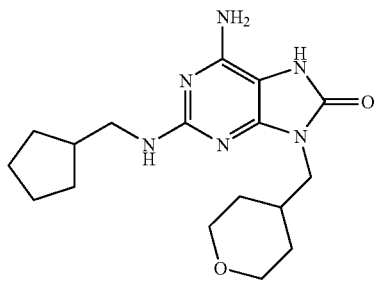

To a solution of 8-bromo-$N^2$-(cyclopentylmethyl)-9-(tetrahydro-2H-pyran-4-ylmethyl)-9H-purine-2,6-diamine (40 mg) in dry n-butanol (0.5 ml) was added 37% grade hydrochloric acid (1.5 ml) in one go and at RT. The reaction was heated to 10° C. for thirty minutes. The reaction was concentrated in vacuo and the product was purified by $C_{18}$ reverse phase chromatography using water (containing 0.1% formic acid)-acetonitrile (containing 0.05% formic acid) as eluant (20-60%) to afford the title compound as a white solid (10 mg).

MS calcd for $(C_{17}H_{26}N_6O_2)^+$=346
MS found (electrospray): $(M+H)^+$=347
$^1$H NMR($(CD_3)_2SO$): δ 9.55 (1H, s), 6.19 (1H, s), 5.95 (2H, s), 3.81 (2H, m), 3.50 (2H, d), 3.21 (2H, m), 3.10 (2H, t), 2.13 (1H, m), 2.04 (1H, m), 1.69-1.59 (2H, m), 1.59-1.50 (2H, m), 1.50-1.40 (4H, m), 1.21 (4H, m).

Example 40

6-Amino-2-[(2-cyclopropylethyl)amino]-9-(tetrahydro-2H-pyran-4-ylmethyl)-7,9-dihydro-8H-purin-8-one

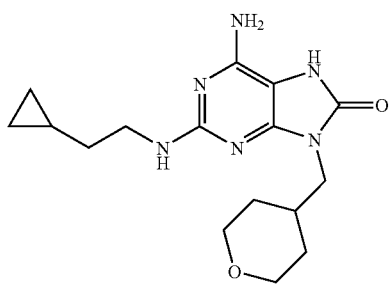

To a solution of 2-chloro-9-(tetrahydro-2H-pyran-2-yl)-9H-purin-6-amine (550 mg) in dry ethylene glycol (27 ml) at room temperature was added 2-cyclopropylethylamine (740 mg). The reaction was heated at 120° C. overnight. The reaction was cooled to RT, diluted with ethyl acetate (70 ml) and washed with water (3×20 ml). The organic layer was dried over MgSO$_4$, filtered and concentrated in vacuo. This afford a brown viscous oil (580 mg) that was used in the next step without further purification. To a solution of this oil (580 mg) in dry chloroform (6.5 ml) at RT was added NBS (320 mg) and the reaction was stirred for 15 minutes. The reaction was diluted with DCM (20 ml) and washed with water (10 ml). The organics were passed through a hydrophobic frit and concentrated in vacuo. This afforded a light brown oil which was dissolved in dry methanol (5 ml) and at room temperature was added sodium methoxide solution (25 wt. % in methanol, 1.3 ml). The reaction was heated at 60° C., with a condenser attached, overnight. The reaction was cooled and concentrated in vacuo. The resultant orange residue was taken up in ethyl acetate (30 ml) and washed with saturated aqueous ammonium chloride (20 ml). The organic layer was separated and washed further with water (2×15 ml). The organic layer was dried over MgSO$_4$, filtered and concentrated in vacuo. To this material in dry methanol (3.5 ml) at RT was added trifluoroacetic acid (0.35 ml) in one go. The reaction was stirred at RT for 16 hours and concentrated in vacuo. This was taken up in diethyl ether and triturated to afford a brown solid (227 mg). To a solution of this solid (160 mg) in dry N,N-dimethylformamide (1.5 ml) at room temperature and under nitrogen was added potassium carbonate (240 mg). The reaction was stirred at 60° C. for 1.5 hours and then cooled to 50° C. 4-(bromomethyl)tetrahydro-2H-pyran (59 ul) was added and the reaction heated at 50° C. overnight. An additional amount of 4-(bromomethyl)tetrahydro-2H-pyran (29 ul) was added and the reaction heated at 70° C. for 8 hours. The reaction was cooled to RT and diluted with ethyl acetate (20 ml) and washed with water (5 ml). The organic layer was dried over MgSO$_4$, filtered and concentrated in vacuo to afford a brown oil. This was purified by $C_{18}$ reverse phase chromatography using water (containing 0.1% formic acid)-acetonitrile (containing 0.05% formic acid) as eluant (20-60%). The resulting clear viscous oil (50 mg) was dissolved in dry methanol (1.8 ml) at RT and under nitrogen. To this was added 4.0M hydrogen chloride in 1,4-dioxane (0.8 ml). The reaction was left to stir at RT for 3 hours. The reaction was neutralised by the addition of saturated NaHCO$_3$ solution and concentrated in vacuo. The white residue was taken up in water (15 ml) and the solid filtered. The solid was dried en vacuo (60° C.) for 30 minutes. This afforded the title compound as a beige solid (33 mg).

MS calcd for $(C_{16}H_{24}N_6O_2)^+$=332
MS found (electrospray): $(M+H)^+$=333
$^1$H NMR($(CD_3)_2SO$): δ 9.55 (1H, s), 6.16 (1H, s), 5.97 (2H, s), 3.81 (2H, m), 3.50 (2H, d), 3.21 (4H, m), 2.03 (1H, m), 1.40 (4H, m), 1.21 (2H, m), 0.69 (1H, m), 0.38 (2H, m), 0.03 (2H, m).

Example 41 and Example 42

Isomers of 6-Amino-2-(butylamino)-9-(tetrahydro-3-furanylmethyl)-7,9-dihydro-8H-purin-8-one

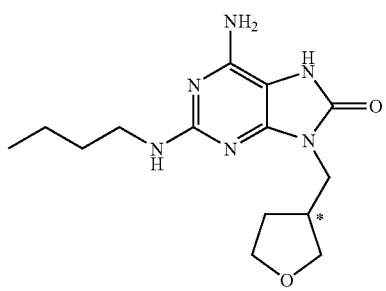

The enantiomers of 6-amino-2-(butylamino)-9-(tetrahydro-3-furanylmethyl)-7,9-dihydro-8H-purin-8-one were separated by chiral chromatography (Chiralpak AS) using heptane-IPA (containing 0.15% triethylamine) as eluant (20%). Thus racemic 6-amino-2-(butylamino)-9-(tetrahydro-3-furanylmethyl)-7,9-dihydro-8H-purin-8-one (700 mg) afforded both enantiomers as yellow/orange liquids. These were triturated with water (15 ml) to yield off white solids, which were filtered and dried on a rotary evaporator (60° C.) for 15 minutes. This afforded Enantiomer 1 (163 mg) and Enantiomer 2 (145 mg) both containing some triethylamine. These were further purified by $C_{18}$ reverse phase chromatography using water (containing 0.1% formic acid)-acetonitrile (containing 0.05% formic acid) as eluant (10-45%) to afford isomer 1 (40 mg) as a white solid and isomer 2 (55 mg) as a white solid.

Example 41 (Isomer 1)

MS calcd for $(C_{14}H_{22}N_6O_2)^+$=306

MS found (electrospray): $(M+H)^+$=307

$^1$H NMR((CD$_3$)$_2$SO): δ 9.67 (1H, s), 6.43 (1H, m), 6.21 (1H, m), 3.75 (2H, m), 3.61 (4H, m), 3.53 (1H, m), 3.18 (2H, m), 2.68 (1H, m), 1.86 (1H, m), 1.64 (1H, m), 1.47 (2H, m), 1.30 (2H, m), 0.88 (3H, t).

Example 42 (Isomer 2)

MS calcd for $(C_{14}H_{22}N_6O_2)^+$=306

MS found (electrospray): $(M+H)^+$=307

$^1$H NMR((CD$_3$)$_2$SO): δ 9.69 (1H, s), 6.44 (1H, m), 6.22 (1H, m), 3.75 (2H, m), 3.61 (4H, m), 3.52 (1H, m), 3.18 (2H, m), 2.68 (1H, m), 1.86 (1H, m), 1.64 (1H, m), 1.47 (2H, m), 1.30 (2H, m), 0.88 (3H, t).

Example 41 alternative method

6-Amino-2-(butylamino)-9-[tetrahydro-3-furanylmethyl]-7,9-dihydro-8H-purin-8-one, Isomer 1

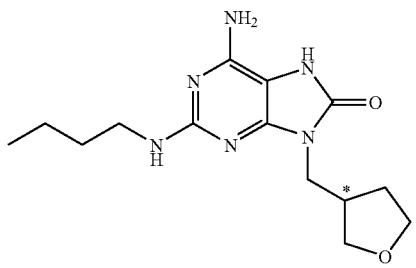

To a solution of N$^2$-butyl-8-(methoxy)-9-[tetrahydro-3-furanylmethyl]-9H-purine-2,6-diamine, Isomer 1 (2.79 g) in dry methanol (100 ml) at room temperature and under nitrogen was added 4.0M hydrochloric acid in 1,4-dioxane (28 ml). The reaction was left to stir at room temperature for 2 hours. The reaction was neutralised by the addition of 2.0M sodium hydroxide solution and concentrated in vacuo to yield an off white residue. The residue was taken up in water (30 ml) and the solid filtered and washed with water (15 ml). The beige solid was dried on a rotary evaporator (60° C.) for 30 minutes. This was crystallised from water/ethanol (1:1, 35 ml) to yield a white solid (1.3 g). This was only partially crystalline. Recrystallisation of this compound with water/ethanol (1:1, 80 ml) afforded an off-white solid which was dried on the rotary evaporator (60° C.) for 1 hour (1.2 g, 100% e.e.).

MS calcd for $(C_{14}H_{22}N_6O_2)^+$=306

MS found (electrospray): $(M+H)^+$=307

$^1$H NMR((CD$_3$)$_2$SO): δ 9.57 (1H, s), 6.18 (1H, m), 5.97 (2H, m), 3.75 (1H, m), 3.64-3.56 (4H, m), 3.52 (1H, m), 3.16 (2H, m), 2.69 (1H, m), 1.86 (1H, m), 1.64 (1H, m), 1.46 (2H, m), 1.29 (2H, m), 0.88 (3H, t).

Example 42 Alternative Method

6-Amino-2-(butylamino)-9-[tetrahydro-3-furanylmethyl]-7,9-dihydro-8H-purin-8-one, Isomer 2

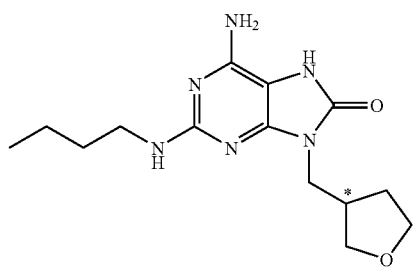

To a solution of N$^2$-butyl-8-(methoxy)-9-[tetrahydro-3-furanylmethyl]-9H-purine-2,6-diamine, Isomer 2 (3 g) in dry methanol (100 ml) at room temperature and under nitrogen was added 4.0M hydrochloric acid in 1,4-dioxane (30 ml). The reaction was left to stir at room temperature for 2 hours. The reaction was neutralised by the addition of 2.0M sodium hydroxide solution and concentrated in vacuo to yield an off white residue. The residue was taken up in water (30 ml) and the solid filtered and washed with water (15 ml). The beige solid was dried on a rotary evaporator (60° C.) for 30 minutes. This was recrystallised from water/ethanol (1:1, 40 ml) to yield a white solid (1.5 g). This was only partially crystalline. Recrystallisation of this compound with water/ethanol (1:1, 80 ml) afforded an off-white solid which was dried on the rotary evaporator (60° C.) for 1 hour (1.3 g). This was only partially crystalline. Repeated recrystallisation of this compound with water/ethanol (1:1, 80 ml) afforded an off-white solid which was dried on the rotary evaporator (60° C.) for 1 hour (1.3 g, 91% e.e.).

MS calcd for $(C_{14}H_{22}N_6O_2)^+$=306

MS found (electrospray): $(M+H)^+$=307

$^1$H NMR((CD$_3$)$_2$SO): δ 9.57 (1H, s), 6.19 (1H, m), 5.97 (2H, m), 3.75 (1H, m), 3.67-3.48 (5H, m), 3.16 (2H, m), 2.68 (1H, m), 1.85 (1H, m), 1.64 (1H, m), 1.46 (2H, m), 1.29 (2H, m), 0.87 (3H, t).

Example 43

6-Amino-2-[(2-methylproyl)oxy]-9-(tetrahydro-2H-pyran-4-ylmethyl)-7,9-dihydro-8H-Purin-8-one

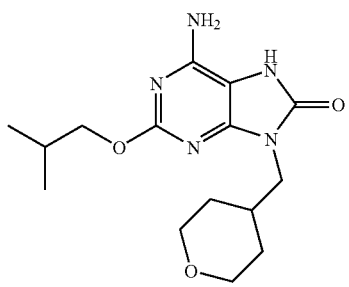

8-Bromo-2-[(2-methylpropyl)oxy]-9-(tetrahydro-2H-pyran-4-ylmethyl)-9H-purin-6-amine (100 mg) in n-butanol (2 mL) was refluxed with concentrated hydrochloric acid (2 mL) at 100° C. (external temperature) for 3 hours. The reaction mixture was evaporated under reduced pressure to dryness. To the reaction mixture was then added a small volume of water and an equivalent volume of methanol to give a suspension, which was then neutralised to by the addition of 2M sodium hydroxide (from pH ~3 to 7). This was then evaporated under reduced pressure to give a beige solid which was purified by $C_{18}$ reverse phase chromatography using water (containing 0.1% formic acid)-acetonitrile (containing 0.05% formic acid) as eluent (20-60%). This gave the title compound (13 mg) as white solid.

$^1$H NMR((CD$_3$)$_2$SO): 9.95 (1H, s), 6.50 (2H, broad s), 3.96-3.92 (2H, m), 3.85-3.78 (2H, m), 3.57-3.55 (2H, m, [overlapped by water]), 3.27-3.18 (2H, m), 2.09-1.92 (2H, m), 1.50-1.42 (2H, m), 1.29-1.15 (2H, m), 0.98-0.92 (6H, m).

MS calcd for $(C_{15}H_{23}N_5O_3)^+$=321
MS found (electrospray): (M+H)$^+$=322

Example 44

6-Amino-2-[(2-cyclopropylethyl)oxy]-9-(tetrahydro-2H-pyran-4-ylmethyl)-7,9-dihydro-8H-Purin-8-one

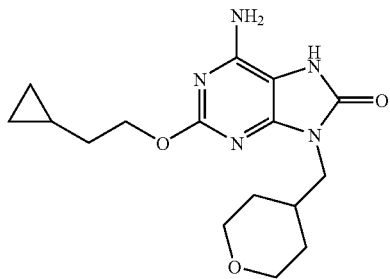

2-[(2-Cyclopropylethyl)oxy]-8-(methoxy)-9-(tetrahydro-2H-pyran-4-ylmethyl)-9H-purin-6-amine (0.1259 g) was dissolved in methanol (5 mL) and added 4N hydrogen chloride in 1,4-dioxane (2 mL). The reaction was stirred at room temperature for 4 hours. The reaction mixture was evaporated under reduced pressure to give a solid which was then suspended in water (1 mL) and small quantity of methanol (2-3 mL). This was then neutralised (to pH 7) by the addition of 2N sodium hydroxide. The suspension was evaporated to near dryness under reduced pressure and then suspended the solid in water (3 mL). The solid was filtered off under suction and washed with a few drops of methanol before being air-dried under suction. This material was then dried to constant weight under vacuo at 50° C. to give the title compound (94 mg).

$^1$H NMR((CD$_3$)$_2$SO): 9.87 (1H, s), 6.42 (2H, s), 4.25-4.16 (2H, m), 3.86-3.78 (2H, m), 3.59-3.53 (2H, m), 3.27-3.18 (2H, m) 2.09-1.96 (1H, m), 1.61-1.53 (2H, m) 1.50-1.41 (2H, m), 1.29-1.14 (2H, m), 0.82-0.72 (1H, m), 0.45-0.39 (2H, m) 0.13-0.07 (2H, m).

LCMS HE101125-2
MS calcd for $(C_{16}H_{23}N_5O_3)^+$=333
MS found (electrospray): (M+H)$^+$=334

Example 45

6-Amino-2-[(cyclohexylmethyl)oxy]-9-(tetrahydro-2H-pyran-4-ylmethyl)-7,9-dihydro-8H-Purin-8-one

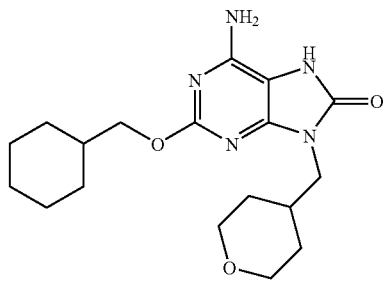

2-[(Cyclohexylmethyl)oxy]-8-(methoxy)-9-(tetrahydro-2H-pyran-4-ylmethyl)-9H-purin-6-amine (RS105369-181A2) (0.1657 g) was dissolved in methanol (5 mL) and then added 4N hydrogen chloride in 1,4-dioxane (2 mL). The reaction mixture was stirred at room temperature for 4 hours. The reaction mixture was then evaporated under reduced pressure to give a solid that was then suspended in water (1 mL) and methanol (~2-3 mL) before being neutralised (to pH 7) by the addition of 2N sodium hydroxide. The resultant mixture was evaporated to near dryness before being suspended in water (3 mL) and the solid is filtered off under suction. This solid was then washed with a few drops of methanol and then air-dried under suction before finally being dried to constant weight under vacuo at 50° C. This gave the title compound as a white solid (134 mg).

$^1$H NMR((CD$_3$)$_2$SO): 9.86 (1H, s), 6.41 (2H, s), 3.99-3.93 (2H, m), 3.85-3.78 (2H, m), 3.59-3.52 (2H, m), 3.27-3.18 (2H, m), 2.09-1.96 (1H, m), 1.79-1.60 (6H, overlapping m), 1.50-1.41 (2H, m), 1.29-1.09 (5H, overlapping m), 1.06-0.93 (2H, m).

MS calcd for $(C_{18}H_{27}N_5O_3)^+$=361
MS found (electrospray): (M+H)$^+$=362

Example 46

6-Amino-2-{[2-(methoxy)ethyl]oxy}-9-(tetrahydro-2H-pyran-4-ylmethyl)-7,9-dihydro-8H-Purin-8-one

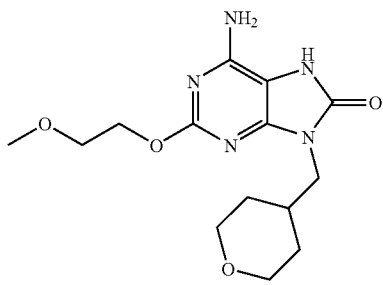

8-(Methoxy)-2-{[2-(methoxy)ethyl]oxy}-9-(tetrahydro-2H-pyran-4-ylmethyl)-9H-purin-6-amine (0.1434 g) was dissolved in methanol (5 mL) and treated with 4N hydrogen chloride in 1,4-dioxane (2 mL). The reaction mixture was stirred at room temperature for 4 hours. The reaction mixture was evaporated under reduced pressure to give a solid, which was suspended in water (1 mL) and methanol (2-3 mL) before 2N sodium hydroxide was added to neutralise (to pH 7). After evaporating the suspension to near dryness under reduced pressure, the solid was suspended in water (3 mL) and filtered under suction and then washed with a few drops of methanol. This solid was dried to constant weight under vacuo at 50° C. after being initially air-dried under suction. This gave the title compound as a white solid (94 mg).

$^1$H NMR((CD$_3$)$_2$SO): 9.89 (1H, s), 6.44 (2H, broad s), 4.30-4.22 (2H, m) 3.86-3.77 (2H, m), 3.65-3.87 (4H, overlapping m), 3.29 (3H, s), 3.27-3.17 (2H, m), 2.10-1.96 (1H, m), 1.50-1.40 (2H, m), 1.29-1.15 (2H, m).

MS calcd for (C$_{14}$H$_{21}$N$_5$O$_4$)$^+$=323

MS found (electrospray): (M+H)$^+$=324

Example 47

6-Amino-2-{[2-(methoxy)ethyl]oxy}-9-(tetrahydro-3-furanylmethyl)-7,9-dihydro-8H-Purin-8-one

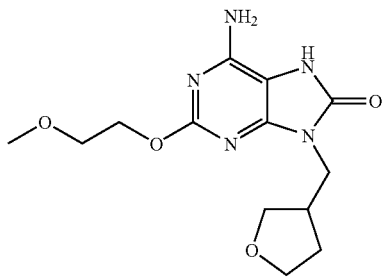

8-(Methoxy)-2-{[2-(methoxy)ethyl]oxy}-9-(tetrahydro-3-furanylmethyl)-9H-purin-6-amine (0.1233 g) was dissolved in methanol (5 mL). To this solution was added 4N hydrogen dioxane (2 mL), stirred at room temperature for 4 hours. The reaction mixture was evaporated under reduced pressure to give a gum. To this material was added water (3 mL) to give a solution, which was then neutralised (to pH 7) using 2N sodium hydroxide. This gave a white solid which was filtered under suction and then washed with a few drops of methanol. The solid was then air-dried under suction before being dried in under vacuo at 50° C. for 2 hours. This gave the title compound as a white solid (86 mg).

$^1$H NMR((CD$_3$)$_2$SO): 9.92 (1H, s), 6.46 (2H, s), 4.29-4.23 (2H, m), 3.80-3.72 (1H, m), 3.69-3.56 (6H, overlapping m), 3.55-3.48 (1H, m), 3.28 (3H, s), 2.75-2.63 (1H, m), 1.94-1.83 (1H, m), 1.68-1.58 (1H, m).

MS calcd for (C$_{13}$H$_{19}$N$_5$O$_4$)$^+$=309

MS found (electrospray): (M+H)$^+$=310

Example 48

6-Amino-2-[(tetrahydro-2-furanylmethyl)oxy]-9-(tetrahydro-2H-pyran-4-ylmethyl)-7,9-dihydro-8H-Purin-8-one

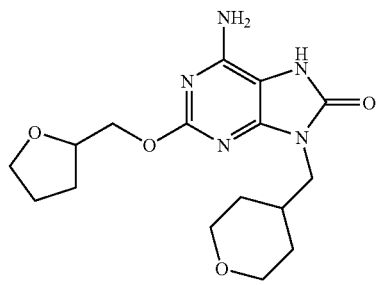

8-(Methoxy)-2-[(tetrahydro-2-furanyl methyl)oxy]-9-(tetrahydro-2H-pyran-4-ylmethyl)-9H-purin-6-amine (0.1500 g) was dissolved in methanol (10 mL). To this solution was added 4N hydrogen chloride in 1,4-dioxane (2 mL). The reaction mixture was stirred for 5 hours at room temperature. The reaction mixture was evaporated under reduced pressure and then water (3 mL) and methanol (3 mL) was added to the residue to give a finely divided suspension. This was neutralised (to pH 7) by the addition of 2N sodium hydroxide and then evaporated under reduced pressure to dryness. Water (3 mL) was then added to the residue and the resultant white suspension of solid was isolated by filtration under suction. The solid was washed with methanol (1 mL) and then air-dried under suction. The solid was then dried further to constant weight under vacuo at 50° C. (~1 hour). This gave the title compound as a white solid (0.1130 g)

$^1$H NMR((CD$_3$)$_2$SO): 9.88 (1H, s), 6.44 (2H, s), 4.15-4.06 (3H, overlapping m+s), 3.86-3.73 (3H, overlapping m), 3.69-3.62 (1H, m), 3.59-3.53 (2H, m), 3.28-3.15 (2H, m), 2.10-1.76 (4H, m), 1.67-1.56 (1H, m), 1.50-1.41 (2H, m), 1.29-1.16 (2H, m).

MS calcd for (C$_{16}$H$_{23}$N$_5$O$_4$)$^+$=349

MS found (electrospray): (M+H)$^+$=350

Example 49

6-Amino-2-(butyloxy)-9-(tetrahydro-3-furanylmethyl)-7,9-dihydro-8H-Purin-8-one hydrochloride salt

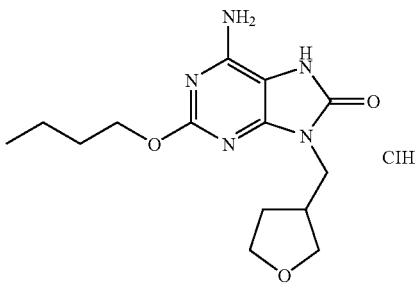

To 6-Amino-2-(propyloxy)-9-(tetrahydro-3-furanylmethyl)-7,9-dihydro-8H-purin-8-one (52.6 mg) was added an excess of 4N hydrogen chloride in 1,4-dioxane (1 mL). The resultant solution was evaporated under reduced pressure (after 5 minutes) to give a colourless gum containing some crystals. To this material was added diethyl ether to triturate out the 1,4-dioxane, giving a free flowing solid on scratching. After evaporation to dryness under reduced pressure for 2 hours (water bath at 50° C., minimum vacuo ~38 mbar) gave the title compound (61 mg) an off-white free flowing solid.

$^1$H NMR((CD$_3$)$_2$SO): 10.37 (1H, s), 6.88 (1H, very broad s), 5.46 (representing 1H, very broad s [appears that shifted water peak from DMSO interfering]), 4.26-4.19 (2H, m), 3.80-3.72 (1H, m), 3.71-3.56 (4H, overlapping m), 3.54-3.48 (1H, m), 2.74-2.63 (1H, m), 1.94-1.84 (1H, m), 1.71-1.59 (3H, overlapping m), 1.46-1.34 (2H, m), 0.96-0.88 (3H, m).

MS calcd for $(C_{14}H_{21}N_5O_3)^+=307$
MS found (electrospray): $(M+H)^+=308$
Elemental Analysis

| Calculated (%) | | Found (%) | | | Found Average (%) | |
|---|---|---|---|---|---|---|
| C | 48.91 | C | 48.60 | 48.46 | C | 48.53 |
| H | 6.45 | H | 6.29 | 6.30 | H | 6.30 |
| N | 20.37 | N | 19.90 | 19.77 | N | 19.84 |
| Cl | 10.31 | Cl | 10.48 | 10.0* | Cl | 10.24 |

Sample weight <3 mg

Example 50

6-Amino-2-(butylamino)-9-[3-(tetrahydro-2H-pyran-3-yl)propyl]-7,9-dihydro-8H-Purin-8-one

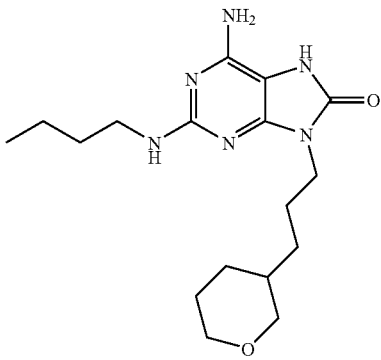

To a solution of N$^2$-butyl-8-(methoxy)-9-[3-(tetrahydro-2H-pyran-3-yl)propyl]-9H-purine-2,6-diamine (198 mg) in dry methanol (20.8 ml) was added 4.0M hydrochloric acid in 1,4-dioxane (3.6 ml) in one go. The reaction was left to stir at room temperature for 4 hours. The reaction was neutralised by the addition of 2.0M sodium hydroxide solution and concentrated in vacuo. to give an off-white solid. To this solid was added water, triturated, and the solid filtered under vacuum until dry. This afforded the title compound as an off-white solid (151 mg).

MS calcd for $(C_{17}H_{28}N_6O_2)^+=348$
MS found (electrospray): $(M+H)^+=349$ $^1$H NMR (DMSO): δ 9.52 (1H, s), 6.15 (1H, s), 5.94 (2H, s), 3.71 (2H, m), 3.58 (2H, m), 3.27-3.12 (3H, m), 2.91 (1H, m), 1.77 (1H, m), 1.69-1.55 (2H, m), 1.54-1.39 (5H, m), 1.35-1.22 (2H, m), 1.16-0.99 (3H, m), 0.88 (3H, m).

Example 51

6-Amino-9-(tetrahydro-2H-Pyran-4-ylmethyl)-2-[(tetrahydro-2H-pyran-2-ylmethoxy]-7,9-dihydro-8H-purin-8-one

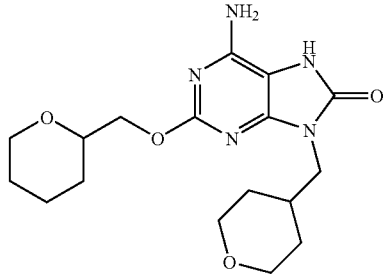

To a solution of 8-(methoxy)-9-(tetrahydro-2H-pyran-4-ylmethyl)-2-[(tetrahydro-2H-pyran-2-ylmethoxy]-9H-purin-6-amine (704 mg) in dry methanol (71 ml) was added 4.0M hydrogen chloride in 1,4-dioxane (12.2 ml). The reaction was left to stir at room temperature for 6 hours. The reaction was neutralised by the addition of 2.0M sodium hydroxide solution and concentrated in vacuo to give an off-white residue. The residue was triturated in water, and the solid filtered to give a brown solid (588 mg). The product was purified by C$_{18}$ reverse phase chromatography using water (containing 0.1% formic acid)-acetonitrile (containing 0.05% formic acid) as eluant (10-45%) to afford the title compound as a white solid (145 mg).

MS calcd for $(C_{17}H_{25}N_5O_4)^+=363$
MS found (electrospray): $(M+H)^+=364$ $^1$H NMR((CD3)$_2$SO): δ 9.88 (1H, s), 6.43 (2H, s), 4.07 (2H, d), 3.87 (1H, m), 3.81 (2H, m), 3.57 (1H, m), 3.55 (2H, d), 3.36 (1H, m), 3.22 (2H, m), 2.02 (1H, m), 1.79 (1H, m), 1.60 (1H, m), 1.51-1.41 (5H, m), 1.31-1.15 (3H, m).

Example 52

6-Amino-2-({2-[(1-methylethyl)oxy]ethyl}oxy)-9-(tetrahydro-2H-pyran-4-ylmethyl)-7,9-dihydro-8H-purin-8-one

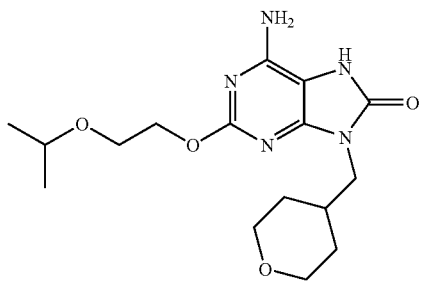

To a solution of 2-({2-[(1-methylethyl)oxy]ethyl}oxy)-8-(methoxy)-9-(tetrahydro-2H-pyran-4-ylmethyl)-9H-purin-6-amine (165 mg) in dry methanol (17 ml) was added 4.0M hydrogen chloride in 1,4-dioxane (2.95 ml) in one go. The reaction was left to stir at room temperature for 5 hours. The reaction was neutralised by the addition of 2.0M sodium hydroxide solution and concentrated in vacuo to give an off-white solid. The solid was triturated in water, and filtered under vacuum, washing with more water, to give an off-white solid (120 mg).

MS calcd for $(C_{16}H_{25}N_5O_4)^+=351$
MS found (electrospray): $(M+H)^+=352$
$^1$H NMR((CD3)$_2$SO): δ 9.88 (1H, s), 6.43 (2H, s), 4.22 (2H, m), 3.81 (2H, m), 3.68-3.50 (5H, m), 3.22 (2H, m), 2.03 (1H, m), 1.45 (2H, m), 1.22 (2H, m), 1.09 (6H, d).

Example 53

6-Amino-2-(butylamino)-9-[4-(tetrahydro-2H-Pyran-3-yl)butyl]-7,9-dihydro-8H-Purin-8-one

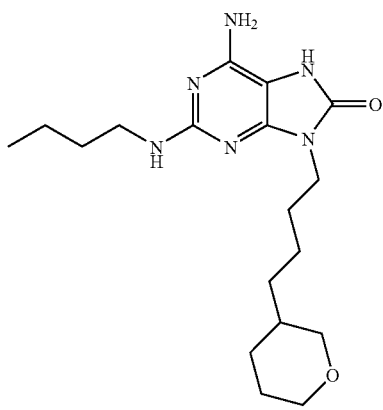

To a solution of $N^2$-butyl-8-(methoxy)-9-[4-(tetrahydro-2H-pyran-3-yl)butyl]-9H-purine-2,6-diamine (172 mg) in methanol (15.2 ml) at room temperature was added 4.0M hydrogen chloride in 1,4-dioxane (2.86 ml, 11.42 mmol) to give a colourless solution. The reaction mixture was stirred at room temperature for 5 hours. The reaction mixture was neutralised with 2M NaOH and concentrated in vacuo to give a white solid. This solid was triturated in water and filtered under vacuum to give an off-white solid (85 mg).

MS calcd for $(C_{18}H_{30}N_6O_2)^+=362$
MS found (electrospray): $(M+H)^+=363$
$^1$H NMR((CD3)$_2$SO): δ 9.51 (1H, s), 6.14 (1H, m), 5.94 (2H, s), 3.70 (2H, m), 3.59 (2H, m), 3.26-3.11 (3H, m), 2.90 (1H, m), 1.74 (1H, m), 1.60 (2H, m), 1.54-1.35 (5H, m), 1.35-0.96 (7H, m), 0.88 (3H, t).

Example 54

6-Amino-2-[(2-cyclopropylethyl)amino]-9-(tetrahydro-3-furanylmethyl)-7,9-dihydro-8H-Purin-8-one

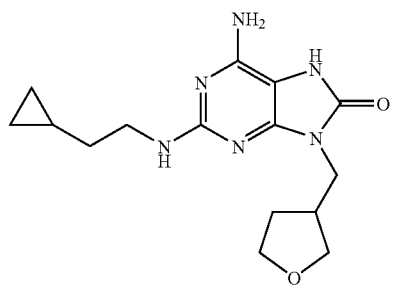

To a solution of $N^2$-(2-cyclopropylethyl)-8-(methoxy)-9-(tetrahydro-3-furanylmethyl)-9H-purine-2,6-diamine (209 mg) in methanol (21 ml) at room temperature was added 4.0M hydrogen chloride in 1,4-dioxane (3.93 ml) to give a colorless solution. The reaction mixture was stirred at room temperature for 4 hours. The reaction mixture was neutralised with 2M NaOH and concentrated in vacuo. The resultant solid was taken up in water (50 ml) and filtered off to give a white solid. This solid was recrystallised from ethanol:water (1:1) and filtered to afford an off-white crystalline solid (105 mg).

MS calcd for $(C_{15}H_{22}N_6O_2)^+=318$
MS found (electrospray): $(M+H)^+=319$
$^1$H NMR((CD3)$_2$SO): δ 9.57 (1H, s), 6.17 (1H, m), 5.98 (2H, s), 3.75 (1H, m), 3.65-3.55 (4H, m), 3.53 (1H, m), 3.22 (2H, m), 2.69 (1H, m), 1.85 (1H, m), 1.64 (1H, m), 1.38 (2H, m), 0.68 (1H, m), 0.38 (2H, m), 0.02 (2H, m).

Example 55

6-Amino-2-[(2-cyclopropylethyl)amino]-9-(tetrahydro-2H-pyran-3-ylmethyl)-7,9-dihydro-8H-purin-8-one

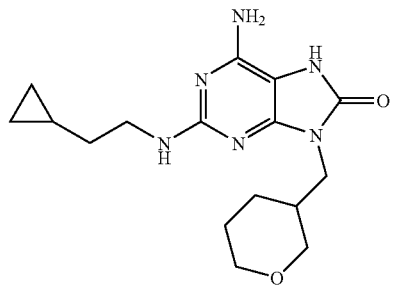

To a solution of $N^2$-(2-cyclopropylethyl)-8-(methoxy)-9-(tetrahydro-2H-pyran-3-ylmethyl)-9H-purine-2,6-diamine (198 mg) in methanol (19.1 ml) at room temperature was added 4.0M hydrogen chloride in 1,4-dioxane (3.57 ml) to give a colorless solution. The reaction mixture was stirred at room temperature for 4 hours. The reaction mixture was neutralised with 2M NaOH and concentrated in vacuo. The resulting solid was taken up in water (50 ml) and filtered off to give a white solid. This solid was recrystallised from ethanol:water (1:1) and filtered to afford an off-white crystalline solid (113 mg).

MS calcd for $(C_{16}H_{24}N_6O_2)^+=332$
MS found (electrospray): $(M+H)^+=333$
$^1$H NMR((CD3)$_2$SO): δ 9.55 (1H, s), 6.15 (1H, m), 5.97 (2H, s), 3.72-3.61 (2H, m), 3.58-3.43 (2H, m), 3.29 (1H, m), 3.22 (2H, m), 3.15 (1H, m), 2.03 (1H, m), 1.71-1.57 (2H, m), 1.39 (3H, m), 1.21 (1H, m), 0.69 (1H, m), 0.38 (2H, m), 0.03 (2H, m).

Example 56

6-Amino-2-[(2-cyclopropylethyl)oxy]-9-(tetrahydro-3-furanylmethyl)-7,9-dihydro-8H-purin-8-one (Isomer 1)

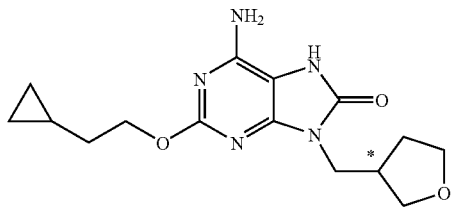

To a stirring suspension of 2-[(2-cyclopropylethyl)oxy]-8-(methyloxy)-9-(tetrahydro-3-furanylmethyl)-9H-purin-6-amine (814 mg) in methanol (3 ml) was added 4N HCl in dioxan (3 ml). After 3 h, the solvents were evaporated and the residue treated with water and neutralised by addition of saturated sodium bicarbonate with stirring. The resulting cream coloured solid was filtered off, washed with water and dried. The material was suspended in 1:1 ethanol:water (42 ml) but did not dissolve on boiling/stirring. Complete solution was obtained on adding a further 10 ml ethanol. More water (3 ml) was added and the clear solution allowed to cool to room temperature with stirring. The resulting cream coloured solid was filtered, washed with 1:1 ethanol:water (10 ml) and dried, yield 537 mg.

MS calcd for $(C_{15}H_{21}N_5O_3)^+=319$ MS found (electrospray): $(M+H)^+=320$
$^1$H NMR((CD$_3$)$_2$SO): δ 9.89 (1H, s), 6.43 (2H, s), 4.23-4.15 (2H, m), 3.79-3.71 (1H, m), 3.69-3.55 (4H, m), 3.54-3.48 (1H, m), 2.76-2.63 (1H, m), 1.94-1.82 (1H, m), 1.68-1.51 (3H, m), 0.83-0.71 (1H, m), 0.0.47-0.36 (2H, m), 0.14-0.04 (2H, m).

Example 57

6-Amino-2-[(2-cyclopropylethyl)oxy]-9-[tetrahydro-3-furanylmethyl]-7,9-dihydro-8H-purin-8-one (Isomer 2)

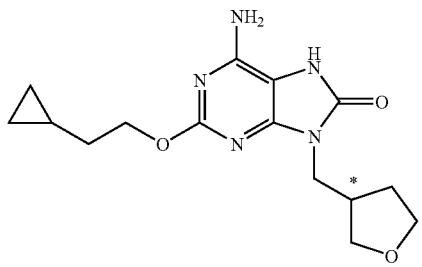

To 2-[(2-cyclopropylethyl)oxy]-8-(methoxy)-9-[tetrahydro-3-furanylmethyl]-9H-purin-6-amine, Isomer 2 (1.45 g) in dry methanol (50 ml) at room temperature and under nitrogen, was added 4.0M hydrochloric acid in 1,4-dioxane (14 ml) in one go. The reaction was stirred at room temperature for 4 hours. The reaction was neutralised by the addition of 2M aqueous sodium hydroxide solution and concentrated in vacuo to yield an off white residue. This was taken up in water (40 ml) and filtered to afford a sand coloured solid. This was recrystallised from water:ethanol, 1:1 (75 ml) to afford a beige solid (765 mg).

MS calcd for $(C_{15}H_{21}N_5O_3)^+=319$
MS found (electrospray): $(M+H)^+=320$
$^1$H NMR((CD$_3$)$_2$SO): δ 9.79 (1H, s), 6.33 (2H, s), 4.09 (2H, t), 3.66 (1H, m), 3.58-3.47 (4H, m), 3.42 (1H, m), 2.60 (1H, m), 1.78 (1H, m), 1.53 (1H, m), 1.47 (2H, q), 0.67 (1H, m), 0.32 (2H, m), 0 (2H, m).

Example 58

6-Amino-2-(butylamino)-9-(tetrahydro-2H-pyran-4-ylmethyl)-7,9-dihydro-8H-Purin-8-one hydrochloride hydrate

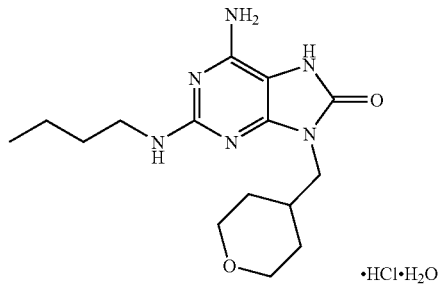

6-Amino-2-(butylamino)-9-(tetrahydro-2H-pyran-4-ylmethyl)-7,9-dihydro-8H-purin-8-one (1.00 g) in a round bottom flask (100 mL) was dissolved (with sonication to break up the solid) in an excess of 4N hydrogen chloride in 1,4-dioxane (15 mL). The solution soon formed a suspension that was stirred at ambient room temperature (21° C.) for 30 minutes before being evaporated to dryness under reduced pressure. To the resultant solid was then added diethyl ether (~40 mL) to give a suspension, which was then evaporated under reduced pressure to 18 mbar (water bath, 50° C.) to give an off-white solid (1.11 g). This solid was transferred to a round bottom flask (250 mL) equipped with magnetic stirrer and reflux condenser. To the flask was added 2-butanone (111 mL) and the resultant suspension heated to reflux (external heating, 95° C.). 2-Butanol (racemic) was then added portion wise (1 mL per addition) allowing the suspension to return to reflux. After the addition of 14 mL of 2-butanol a light tan solution was obtained which was refluxed for a few minutes, before the heat source was removed and the solution was allowed to cool with stirring over a period of 21 hours. The resultant suspension was then filtered under suction and the resultant filter-cake then washed with a minimum volume of acetone. The filter-cake was initially dried under suction, before then being dried further under vacuo at 50° C. until free from solvent. This gave the title compound (Batch A) as a white solid (470 mg).

MS calcd for $(C_{15}H_{24}N_6O_2)^+$=320
MS found (electrospray): $(M+H)^+$=321 1H NMR$((CD_3)_2$SO): 12.20 (1H, very broad s), 10.55 (1H, s), 7.77 (2H, broad s) 3.87-3.77 (2H, m), 3.61-3.53 (2H, m), 3.34-3.15 (4H, partially overlapping m), 2.07-1.94 (1H, m), 1.59-1.43 (4H, overlapping m), 1.40-1.28 (2H, m), 1.28-1.15 (2H, m), 0.97-0.85 (3H, m). Some exchangeable protons not observed. A second crop (Batch B) was isolated from the filtrate by filtration under suction and the resultant filter-cake was dried under suction before being dried further under vacuo at 50° C. The resultant slightly impure product (349 mg) was washed with acetone (4 mL) and then dried under vacuo at 50° C. (18 hours). This gave little or no change in purity. This material (338 mg) was suspended in 2-butanone (35 mL) in a round bottom flask (100 mL) equipped with magnetic stirrer and reflux condenser. The resultant suspension was heated to reflux with stirring (external heating, 95° C.) before 2-butanol (racemic) was added (4 times, 1 mL) and allowed the resultant suspension to return to reflux. After the addition of additional 2-butanol (racemic, 0.26 mL) the resultant solution was refluxed for 5 minutes before the heat source was removed and the solution was allowed to cool to ambient temperature over 21 hours. This gave a thick suspension which was cooled in a fridge to 3° C. for 2.5 hours. The suspension was filtered under suction and the filter-cake washed with acetone (8 mL). The filter-cake was air-dried under suction and then dried further under vacuo at 50° C. until free of solvent. This gave the title compound (Batch B) (167 mg).
MS calcd for $(C_{15}H_{24}N_6O_2)^+$=320
MS found (electrospray): $(M+H)^+$=321
NMR$((CD_3)_2$SO): consistent with Batch A.
Additional Supporting Data:

| Batch A Found % | Batch B Found % |
| --- | --- |
| C: 48.36, 48.43 (48.40) | C: 48.54, 48.58 (48.56) |
| H: 7.02, 6.99 (7.01) | H: 6.95, 6.97 (6.96) |
| N: 22.35, 22.33 (22.34) | N: 22.39, 22.35 (22.37) |
| Cl: 9.07, 9.19 (9.13) | Cl: 9.13, 9.03 (9.08) |

Best fits: $C_{15}H_{24}N_6O_2 \cdot HCl \cdot H_2O$
Calculated % C, 48.06; H, 7.26; N, 22.42; Cl: 9.46

Example 59

6-Amino-2-(butylamino)-9-(tetrahydro-3-furanylmethyl)-7,9-dihydro-8H-Purin-8-one hydrochloride salt Isomer 1

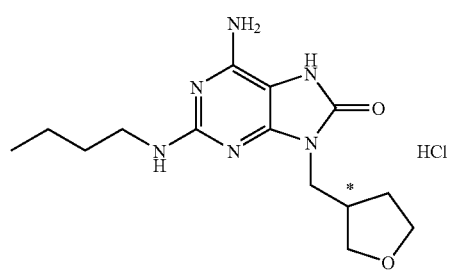

To 6-amino-2-(butylamino)-9-(tetrahydro-3-furanylmethyl)-7,9-dihydro-8H-purin-8-one (isomer 1) (1.0 g) at room temperature and under nitrogen, was added 4.0M hydrochloric acid in 1,4-dioxane (10.61 ml) and the reaction stirred for 30 minutes. The reaction was then concentrated in vacuo and left on the rotary evaporator for 2 hours at 50° C. The beige solid was recrystallised overnight from 2-butanone (18 ml). The crystals were collected by suction filtration and dried in vacuo at 50° C. for 30 minutes (850 mg).
MS calcd for $(C_{14}H_{22}N_6O_2)^+$=306
MS found (electrospray): $(M+H)^+$=307
$^1$H NMR$((CD_3)_2$SO): δ 12.37 (1H, brs), 10.64 (1H, brs), 7.85 (2H, br m), 3.75 (1H, m), 3.69-3.56 (4H, m), 3.51 (1H, m), 3.30 (2H, m), 2.66 (1H, m), 1.90 (1H, m), 1.63 (1H, m), 1.53 (2H, m), 1.34 (2H, m), 0.90 (3H, t). One exchangeable not observed.

Example 60

6-Amino-2-(butylamino)-9-(tetrahydro-3-furanylmethyl)-7,9-dihydro-8H-Purin-8-one hydrochloride salt Isomer 2

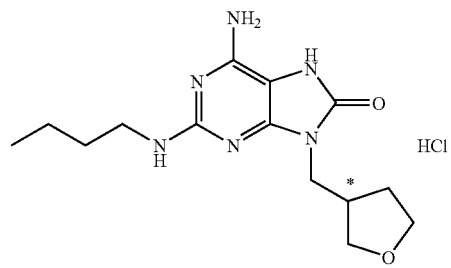

To 6-amino-2-(butylamino)-9-(tetrahydro-3-furanylmethyl)-7,9-dihydro-8H-purin-8-one (isomer 2) (1.2 g) at room temperature and under nitrogen was added 4.0M hydrochloric acid in 1,4-dioxane (12.73 ml) and the reaction stirred at for 30 minutes. The reaction was then concentrated in vacuo and left on the rotary evaporator for 2 hours at 50° C. The beige solid was recrystallised overnight from 2-butanone (18 ml). The crystals were collected by suction filtration and dried in vacuo at 50° C. for 30 minutes (960 mg).
MS calcd for $(C_{14}H_{22}N_6O_2)^+$=306
MS found (electrospray): $(M+H)^+$=307
$^1$H NMR$((CD_3)_2$SO): δ 12.36 (1H, brs), 10.62 (1H, brs), 7.82 (2H, br m), 3.75 (1H, m), 3.69-3.58 (4H, m), 3.51 (1H, m), 3.30 (2H, m), 2.66 (1H, m), 1.90 (1H, m), 1.63 (1H, m), 1.53 (2H, m), 1.34 (2H, m), 0.90 (3H, t). One exchangeable not observed.

Example 61

6-Amino-2-(butylamino)-9-[3-(tetrahydro-2-furanyl)prolyl]-7,9-dihydro 8H-Purin-8-one

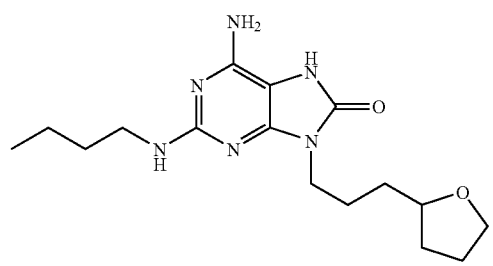

Prepared similarly to Example 97 from $N^2$-butyl-8-(methyloxy)-9-[3-(tetrahydro-2-furanyl)propyl]-9H-purine-2,6-diamine.

LCMS (Method A): $t_{RET}$=2.50 min; MH$^+$=335

Example 62

6-Amino-2-(butylamino)-9-[4-(tetrahydro-2-furanyl)butyl]-7,9-dihydro-8H-Purin-8-one

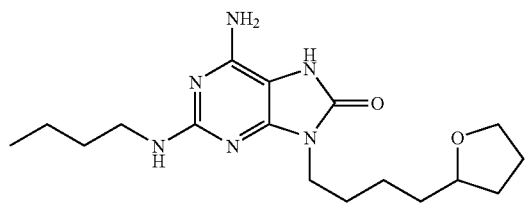

To a solution of $N^2$-butyl-8-(methyloxy)-9-[4-(tetrahydro-2-furanyl)butyl]-9H-purine-2,6-diamine (75 mg, 0.207 mmol) in methanol (10 ml) at room temperature was added 4M HCl in 1,4-dioxane (1.324 ml, 5.30 mmol) to give a pale straw coloured solution. The reaction mixture was stirred at ambient temperature overnight (16 hours) when LCMS showed the reaction had not proceeded to completion. The solvent was removed overnight (16 hours) using a nitrogen blowdown unit when LCMS confirmed the presence of the desired product. This crude product was loaded in methanol onto a 5 g aminopropyl SPE cartridge and eluted with methanol over 20 mins. The appropriate fractions were combined and evaporated under a stream of nitrogen to give the title compound as a white powder (49 mg).

LCMS (Method B): $t_{RET}$=1.06 min; MH$^+$=349

Example 63

6-Amino-2-(butylamino)-9-{2-[(3S)-tetrahydro-3-furanyl]ethyl}-7,9-dihydro-8H-Purin-8-one

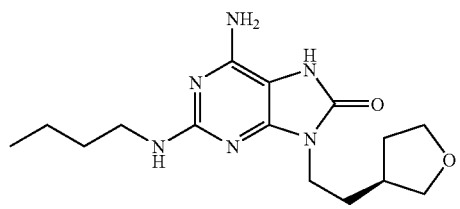

Prepared similarly to Example 73 from $N^2$-butyl-8-(methyloxy)-9-{2-[(3S)-tetrahydro-3-furanyl]ethyl}-9H-purine-2,6-diamine.

LCMS (Method B): $t_{RET}$=0.94 min; MH$^+$=321

Example 64

6-Amino-2-(butylamino)-9-[2-[(3R)-tetrahydro-3-furanyl]ethyl]-7,9-dihydro-8H-Purin-8-one

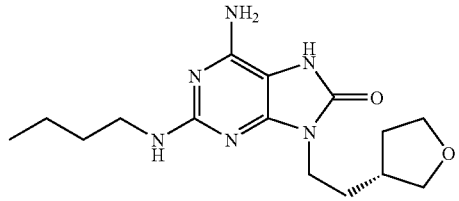

Prepared similarly to Example 73 from $N^2$-butyl-8-(methyloxy)-9-{2-[(3R)-tetrahydro-3-furanyl]ethyl}-9H-purine-2,6-diamine.

LCMS (Method B): $t_{RET}$=0.93 min; MH$^+$=321

Example 65

6-Amino-2-(butylamino)-9-[3-(tetrahydro-3-furanyl)propyl]-7,9-dihydro 8H-Purin-8-one

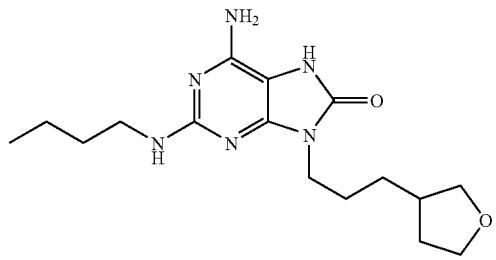

Prepared similarly to Example 129 from $N^2$-butyl-8-(methyloxy)-9-[3-(tetrahydro-3-furanyl)propyl]-9H-purine-2,6-diamine.

LCMS (Method B): $t_{RET}$=0.97 min; MH$^+$=335

Example 66

6-Amino-2-(butylamino)-9-[4-(tetrahydro-3-furanyl)butyl]-7,9-dihydro-8H-Purin-8-one

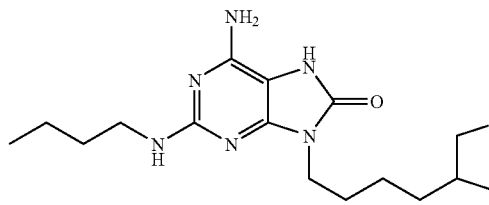

Prepared similarly to Example 129 from $N^2$-butyl-8-(methyloxy)-9-[4-(tetrahydro-3-furanyl)butyl]-9H-purine-2,6-diamine.

LCMS (Method B): $t_{RET}$=1.02 min; MH$^+$=349

Example 67

6-Amino-2-(butylamino)-9-[3-(tetrahydro-2H-pyran-2-yl)propyl]-7,9-dihydro-8H-purin-8-one

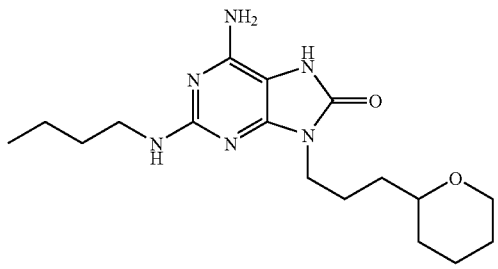

Prepared similarly to Example 129 from $N^2$-butyl-8-(methyloxy)-9-[3-(tetrahydro-2H-pyran-2-yl)propyl]-9H-purine-2,6-diamine.

LCMS (Method B): $t_{RET}$=1.02 min; MH$^+$=349

Example 68

6-Amino-2-(butylamino)-9-[4-(tetrahydro-2H-Pyran-2-yl)butyl]-7,9-dihydro-8H-Purin-8-one

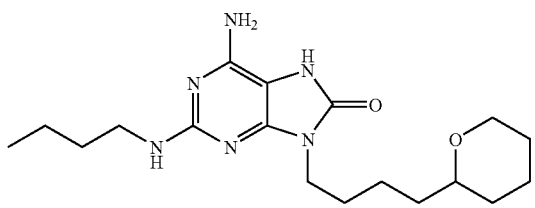

Prepared similarly to Example 69 from $N^2$-butyl-8-(methyloxy)-9-[4-(tetrahydro-2H-pyran-2-yl)butyl]-9H-purine-2,6-diamine.

LCMS (Method B): $t_{RET}$=1.26 min; MH$^+$=363

Example 69

6-Amino-2-(butylamino)-9-[3-(tetrahydro-2H-Pyran-4-yl)propyl]-7,9-dihydro-8H-Purin-8-one

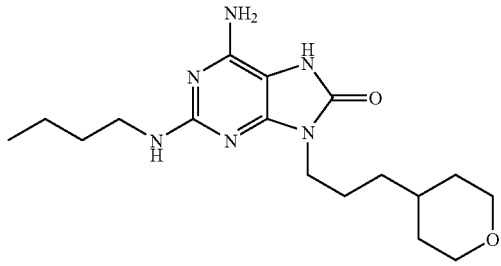

To a solution of $N^2$-butyl-8-(methyloxy)-9-[3-(tetrahydro-2H-pyran-4-yl)propyl]-9H-purine-2,6-diamine (93.13 mg, 0.257 mmol) in methanol (10 ml) was added 4M HCl in dioxane (1.5 ml, 6 mmol) and the mixture stirred at room temperature overnight. The solvent was evaporated under a steam of nitrogen and the residue was redissolved in methanol (5 ml) and loaded onto a 5 g aminopropyl SPE cartridge and eluted with methanol. The eluant was evaporated under a stream of nitrogen to give the title compound (64 mg).

LCMS (Method B): $t_{RET}$=1.10 min; MH$^+$=349

Example 70

6-Amino-2-(butylamino)-9-[4-(tetrahydro-2H-Pyran-4-yl)butyl]-7,9-dihydro-8H-purin-8-one

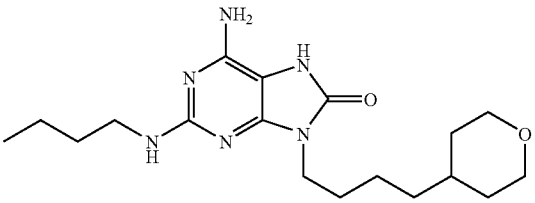

Prepared similarly to Example 69 from $N^2$-butyl-8-(methyloxy)-9-[4-(tetrahydro-2H-pyran-4-yl)butyl]-9H-purine-2,6-diamine.

LCMS (Method B): $t_{RET}$=1.19 min; MH$^+$=363

Example 71

6-Amino-2-(butylamino)-9-[2-(2,2-dimethyltetrahydro-2H-pyran-4-yl)ethyl]-7,9-dihydro-8H-purin-8-one

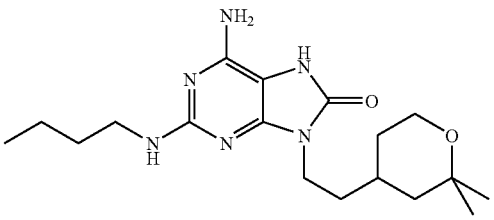

To a solution of $N^2$-butyl-9-[2-(2,2-dimethyltetrahydro-2H-pyran-4-yl)ethyl]-8-(methyloxy)-9H-purine-2,6-diamine (135 mg, 0.359 mmol) in methanol (10 ml) was added 4M HCl solution in dioxane (2.241 ml, 8.96 mmol) and the mixture was left standing at 20° C. After 6 hours the solvent was evaporated under a stream of nitrogen. The residue was loaded in methanol onto a 10 g aminopropyl SPE cartridge and eluted with methanol. The solvent was removed by evaporation to give the title compound (129 mg).

LCMS (Method A): $t_{RET}$=2.63 min; MH$^+$=363

Example 72

6-Amino-2-(butylamino)-9-[3-(2,2-dimethyltetrahydro-2H-Pyran-4-yl)propyl]-7,9-dihydro-8H-purin-8-one

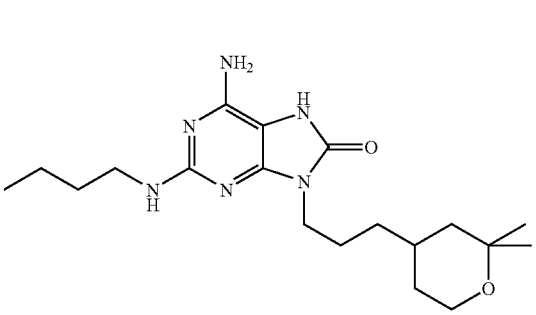

4M HCl in 1,4-dioxane (3 ml, 12.00 mmol) was added in one portion to a stirred solution of N²-butyl-9-[3-(2,2-dimethyltetrahydro-2H-pyran-4-yl)propyl]-8-(methyloxy)-9H-purine-2,6-diamine (40 mg, 0.102 mmol) in methanol (3 ml) at room temperature and the mixture stirred under nitrogen overnight. The mixture was then concentrated and the residue dissolved in MeOH:DCM (1:15 ml) and loaded onto a 2 g aminopropyl SPE cartridge. The cartridge was washed with MeOH:DCM (1:1, 3 column volumes) and the desired fractions were concentrated in vacuo to give material of ca. 80% purity. This material was dissolved in DCM:MeOH (1:1), applied to a 2 g SCX column and eluted firstly with MeOH:DCM (3 column volumes) and the product then released by 2M ammonia in methanol: DCM (1:1, 3 column volumes). The solvent was removed to yield the title compound as a yellow solid (14 mg).

LCMS (Method A): $t_{RET}$=2.77 min; $MH^+$=377

Example 73

6-Amino-2-(butylamino)-9-[4-(2,2-dimethyltetrahydro-2H-Pyran-4-yl)butyl]-7,9-dihydro-8H-purin-8-one

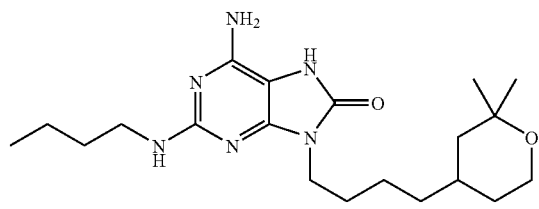

4M HCl in 1,4-dioxane (3 ml, 12.00 mmol) was added in one portion to a stirred solution of N²-butyl-9-[4-(2,2-dimethyltetrahydro-2H-pyran-4-yl)butyl]-8-(methyloxy)-9H-purine-2,6-diamine (130 mg, 0.321 mmol) in methanol (3 ml) at room temperature and the mixture stirred under nitrogen overnight. The mixture was then concentrated and the residue dissolved in MeOH:DCM (1:15 ml) and loaded onto a 2 g aminopropyl SPE cartridge. The cartridge was washed with MeOH:DCM (1:1, 3 column volumes) and the desired fractions were concentrated in vacuo to give the title compound as a yellow solid (102 mg).

LCMS (Method A): $t_{RET}$=2.93 min; $MH^+$=391

Example 74

6-Amino-2-(butyloxy)-9-[3-(tetrahydro-2-furanyl)propyl]-7,9-dihydro-8H-purin-8-one

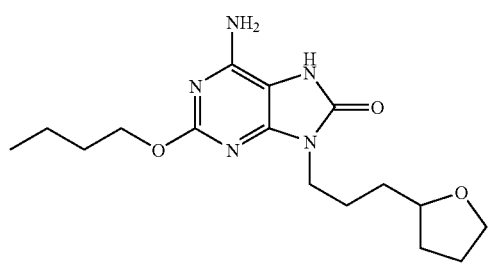

Prepared similarly to Example 97 from 2-(butyloxy)-8-(methyloxy)-9-[3-(tetrahydro-2-furanyl)propyl]-9H-purin-6-amine.

LCMS (Method A): $t_{RET}$=2.85 min; $MH^+$=336

Example 75

6-Amino-2-(butyloxy)-9-[4-(tetrahydro-2-furanyl)butyl]-7,9-dihydro-8H-Purin-8-one

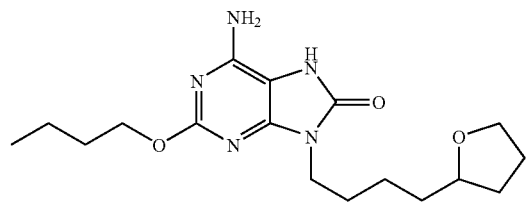

Prepared similarly to Example 62 from 2-(butyloxy)-8-(methyloxy)-9-[4-(tetrahydro-2-furanyl)butyl]-9H-purin-6-amine.

LCMS (Method B): $t_{RET}$=1.02 min; $MH^+$=350

Example 76

6-Amino-2-(butyloxy)-9-{2-[(3S)-tetrahydro-3-furanyl]ethyl}-7,9-dihydro-8H-Purin-8-one

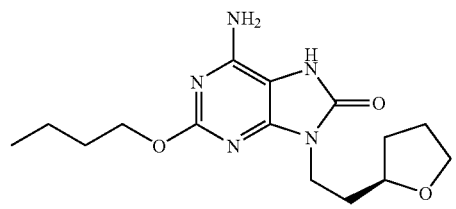

Prepared similarly to Example 73 from 2-(butyloxy)-8-(methyloxy)-9-{2-[(3S)-tetrahydro-3-furanyl]ethyl}-9H-purin-6-amine.

LCMS (Method B): $t_{RET}$=0.90 min; $MH^+$=322

Example 77

6-Amino-2-(butyloxy)-9-{2-[(3R)-tetrahydro-3-furanyl]ethyl}-7,9-dihydro-8H-Purin-8-one

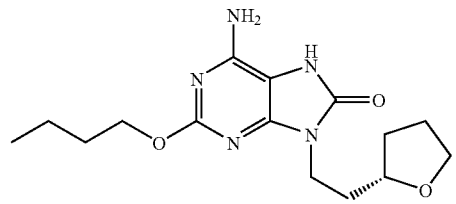

Prepared similarly to Example 73 from 2-(butyloxy)-8-(methyloxy)-9-{2-[(3R)-tetrahydro-3-furanyl]ethyl}-9H-purin-6-amine.

LCMS (Method B): $t_{RET}$=0.90 min; $MH^+$=322

Example 78

6-Amino-2-(butyloxy)-9-[3-(tetrahydro-3-furanyl)propyl]-7,9-dihydro-8H-purin-8-one

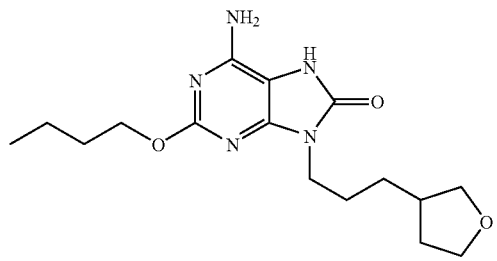

To a solution of 2-(butyloxy)-8-(methyloxy)-9-[3-(tetrahydro-3-furanyl)propyl]-9H-purin-6-amine (110 mg, 0.315 mmol) in methanol (9 ml) at room temperature was added 4M HCl in dioxane (1.89 ml). The pale yellow solution was stirred at room temperature for 18 hrs and then neutralised with 2M sodium hydroxide solution and evaporated to give a white solid. Trituration with water and filtration afforded the title compound as a cream solid (74 mg).

LCMS (Method B): $t_{RET}$=0.94 min; MH$^+$=336

Example 79

6-Amino-2-(butyloxy)-9-[4-(tetrahydro-3-furanyl)butyl]-7,9-dihydro-8H-purin-8-one

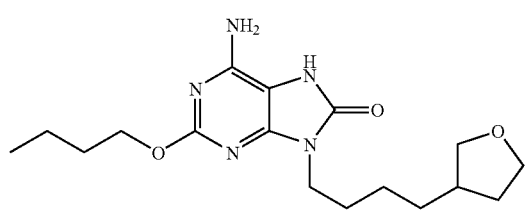

Prepared similarly to Example 129 from 2-(butyloxy)-8-(methyloxy)-9-[4-(tetrahydro-3-furanyl)butyl]-9H-purin-6-amine.

LCMS (Method B): $t_{RET}$=1.00 min; MH$^+$=350

Example 80

6-Amino-2-(butyloxy)-9-[3-(tetrahydro-2H-pyran-2-yl)propyl]-7,9-dihydro-8H-Purin-8-one

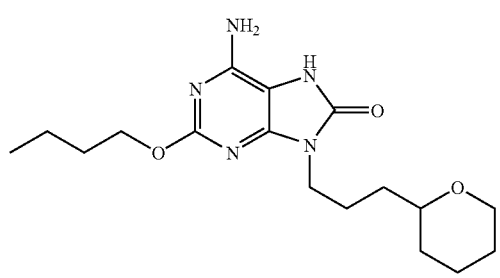

Prepared similarly to Example 129 from 2-(butyloxy)-8-(methyloxy)-9-[3-(tetrahydro-2H-pyran-2-yl)propyl]-9H-purin-6-amine.

LCMS (Method B): $t_{RET}$=1.06 min; MH$^+$=350

Example 81

6-Amino-2-(butyloxy)-9-[4-(tetrahydro-2H-Pyran-2-yl)butyl]-7,9-dihydro-8H-Purin-8-one

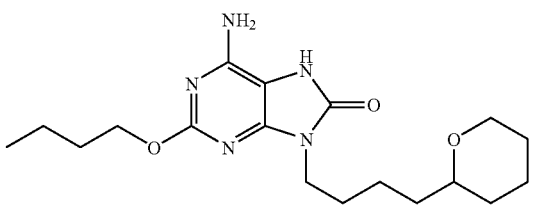

Prepared similarly to Example 69 from 2-(butyloxy)-8-(methyloxy)-9-[4-(tetrahydro-2H-pyran-2-yl)butyl]-9H-purin-6-amine.

LCMS (Method B): $t_{RET}$=1.10 min; MH$^+$=364

Example 82

6-Amino-2-(butyloxy)-9-[3-(tetrahydro-2H-Pyran-3-yl)propyl]-7,9-dihydro-8H-Purin-8-one

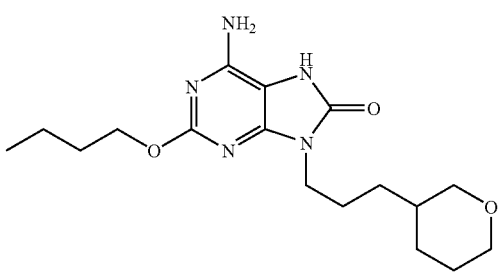

Prepared similarly to Example 62 from 2-(butyloxy)-8-(methyloxy)-9-[3-(tetrahydro-2H-pyran-3-yl)propyl]-9H-purin-6-amine.

LCMS (Method B): $t_{RET}$=1.01 min; MH$^+$=350

Example 83

6-Amino-2-(butyloxy)-9-[4-(tetrahydro-2H-Pyran-3-yl)butyl]-7,9-dihydro-8H-Purin-8-one

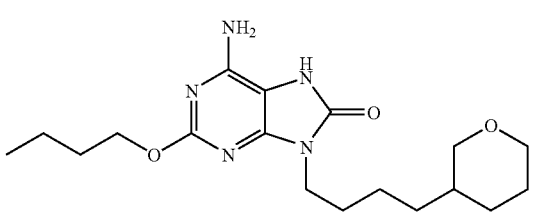

To a solution of 2-(butyloxy)-8-(methyloxy)-9-[4-(tetrahydro-2H-pyran-3-yl)butyl]-9H-purin-6-amine (135 mg, 0.358 mmol) in methanol (10 ml) was added 4M HCl in dioxane (2.235 ml, 8.94 mmol) and the mixture was left standing at 20° C. for 18 hours. The solvent was evaporated in vacuo to give a white solid which was loaded in methanol onto a 10 g aminopropyl SPE cartridge and eluted with methanol. The appropriate fractions were combined and evaporated in vacuo to give the title compound as a white solid (50 mg).

LCMS (Method A): $t_{RET}$=3.14 min; MH$^+$=364

Example 84

6-Amino-2-(butyloxy)-9-[3-(tetrahydro-2H-Pyran-4-yl)propyl]-7,9-dihydro-8H-Purin-8-one

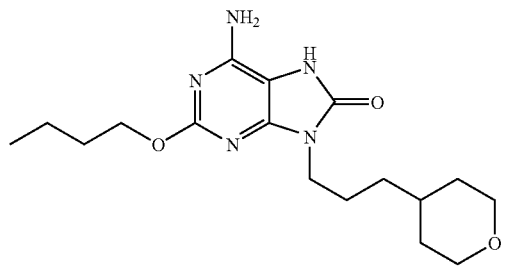

Prepared similarly to Example 69 from 2-(butyloxy)-8-(methyloxy)-9-[3-(tetrahydro-2H-pyran-4-yl)propyl]-9H-purin-6-amine.

LCMS (Method B): $t_{RET}$=0.99 min; MH$^+$=350

Example 85

6-Amino-2-(butyloxy)-9-[4-(tetrahydro-2H-Pyran-4-yl)butyl]-7,9-dihydro-8H-purin-8-one

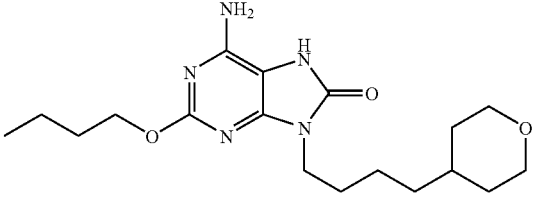

Prepared similarly to Example 69 from 2-(butyloxy)-8-(methyloxy)-9-[4-(tetrahydro-2H-pyran-4-yl)butyl]-9H-purin-6-amine.

LCMS (Method B): $t_{RET}$=1.05 min; MH$^+$=364

Example 86

6-Amino-2-(butyloxy)-9-[2-(2,2-dimethyltetrahydro-2H-pyran-4-yl)ethl]-7,9-dihydro-8H-Purin-8-one

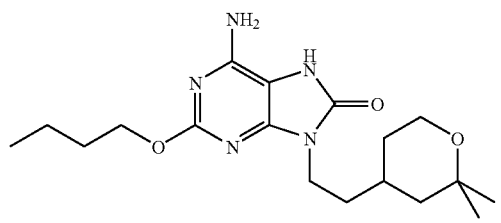

Prepared similarly to Example 71 from 2-(butyloxy)-9-[2-(2,2-dimethyltetrahydro-2H-pyran-4-yl)ethyl]-8-(methyloxy)-9H-purin-6-amine.

LCMS (Method A): $t_{RET}$=2.99 min; MH$^+$=364

Example 87

6-Amino-2-(butyloxy)-9-[3-(2,2-dimethyltetrahydro-2H-Pyran-4-yl)propyl]-7,9-dihydro-8H-purin-8-one

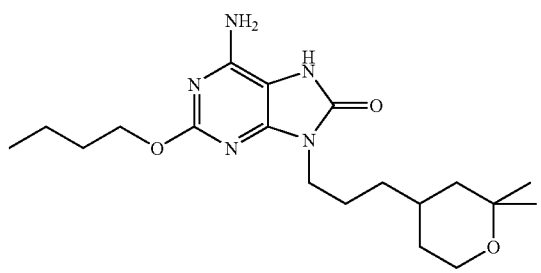

Prepared similarly to Example 72 from 2-(butyloxy)-9-[3-(2,2-dimethyltetrahydro-2H-pyran-4-yl)propyl]-8-(methyloxy)-9H-purin-6-amine.

LCMS (Method A): $t_{RET}$=3.12 min; MH$^+$=378

Example 88

6-Amino-2-(butyloxy)-9-[4-(2,2-dimethyltetrahydro-2H-pyran-4-yl)butyl]-7,9-dihydro-8H-Purin-8-one

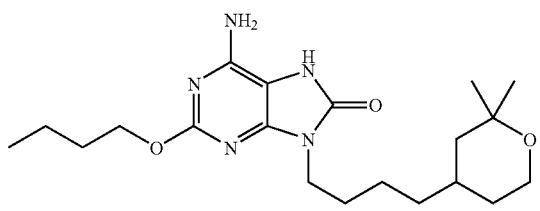

Prepared similarly to Example 73 from 2-(butyloxy)-9-[4-(2,2-dimethyltetrahydro-2H-pyran-4-yl)butyl]-8-(methyloxy)-9H-purin-6-amine.

LCMS (Method A): $t_{RET}$=3.30 min; MH$^+$=392

Example 89

6-Amino-2-[(2-cyclopropylethyl)oxy]-9-[2-(tetrahydro-2-furanyl)ethyl]-7,9-dihydro-8H-Purin-8-one

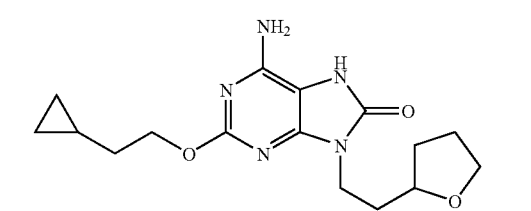

To a solution of 2-[(2-cyclopropylethyl)oxy]-8-(methyloxy)-9-[2-(tetrahydro-2-furanyl)ethyl]-9H-purin-6-amine (88 mg, 0.253 mmol) in methanol (10 ml) at room temperature was added 4M HCl in 1,4 dioxane (2.106 ml, 8.42 mmol) to give a pale straw coloured solution. The reaction mixture was stirred at ambient temperature overnight (16 hours) and then loaded in methanol onto a 5 g aminopropyl SPE cartridge and eluted with methanol. The filtrate was evaporated on a nitrogen blowdown unit to give the title compound as a white solid (41 mg).

LCMS (Method B): $t_{RET}$=0.95 min; MH$^+$=334

Example 90

6-Amino-2-[(2-cyclopropylethyl)oxy]-9-[3-(tetrahydro-2-furanyl)propyl]-7,9-dihydro-8H-Purin-8-one

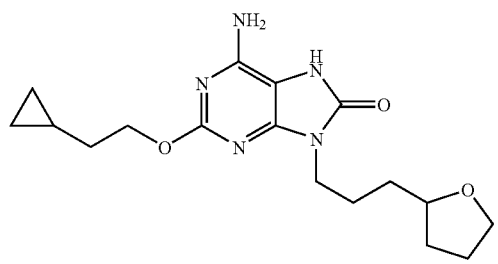

Prepared similarly to Example 97 from 2-[(2-cyclopropylethyl)oxy]-8-(methyloxy)-9-[3-(tetrahydro-2-furanyl)propyl]-9H-purin-6-amine.
LCMS (Method A): $t_{RET}$=2.86 min; MH$^+$=348

Example 91

6-Amino-2-[(2-cyclopropylethyl)oxy]-9-[4-(tetrahydro-2-furanyl)butyl]-7,9-dihydro-8H-Purin-8-one

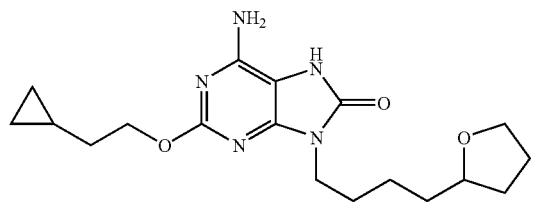

Prepared similarly to Example 62 from 2-[(2-cyclopropylethyl)oxy]-8-(methyloxy)-9-[4-(tetrahydro-2-furanyl)butyl]-9H-purin-6-amine.

LCMS (Method B): $t_{RET}$=1.03 min; MH$^+$=362

Example 92

6-Amino-2-[(2-cyclopropylethyl)oxy]-9-[2-(tetrahydro-3-furanyl)ethyl]-7,9-dihydro-8H-Purin-8-one

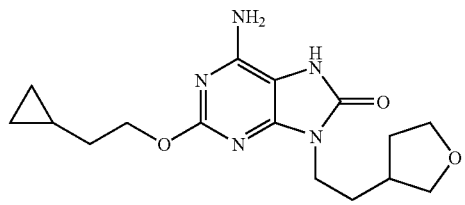

Prepared similarly to Example 71 from 2-[(2-cyclopropylethyl)oxy]-8-(methyloxy)-9-[2-(tetrahydro-3-furanyl)ethyl]-9H-purin-6-amine.
LCMS (Method A): $t_{RET}$=2.72 min; MH$^+$=334

Example 93

6-Amino-2-[(2-cyclopropylethyl)oxy]-9-{2-[(3S)-tetrahydro-3-furanyl]ethyl}-7,9-dihydro-8H-purin-8-one

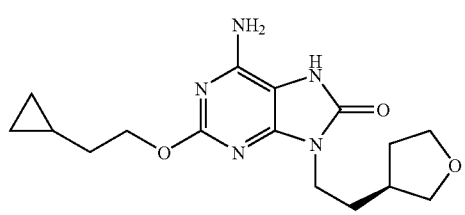

Prepared similarly to Example 73 from 2-[(2-cyclopropylethyl)oxy]-8-(methyloxy)-9-{2-[(3S)-tetrahydro-3-furanyl]ethyl}-9H-purin-6-amine.
LCMS (Method B): $t_{RET}$=0.90 min; MH$^+$=334

Example 94

6-Amino-2-[(2-cyclopropylethyl)oxy]-9-{2-[(3R)-tetrahydro-3-furanyl]ethyl}-7,9-dihydro-8H-purin-8-one

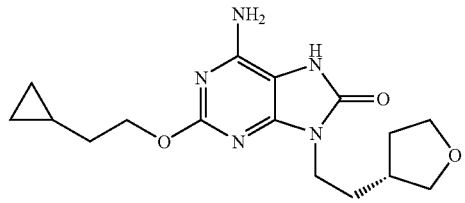

Prepared similarly to Example 73 from 2-[(2-cyclopropylethyl)oxy]-8-(methyloxy)-9-{2-[(3R)-tetrahydro-3-furanyl]ethyl}-9H-purin-6-amine.
LCMS (Method B): $t_{RET}$=0.90 min; MH$^+$=334

Example 95

6-Amino-2-[(2-cyclopropylethyl)oxy]-9-[3-(tetrahydro-3-furanyl)propyl]-7,9-dihydro-8H-Purin-8-one

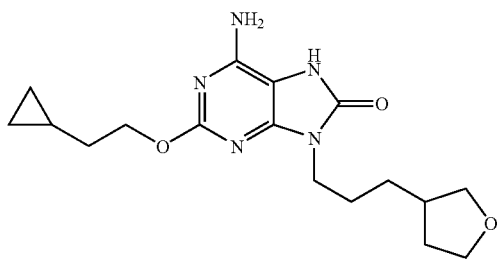

Prepared similarly to Example 78 from 2-[(2-cyclopropylethyl)oxy]-8-(methyloxy)-9-[3-(tetrahydro-3-furanyl)propyl]-9H-purin-6-amine.
LCMS (Method B): $t_{RET}$=0.94 min; MH$^+$=348

Example 96

6-Amino-2-[(2-cyclopropylethyl)oxy]-9-[4-(tetrahydro-3-furanyl)butyl]-7,9-dihydro-8H-purin-8-one

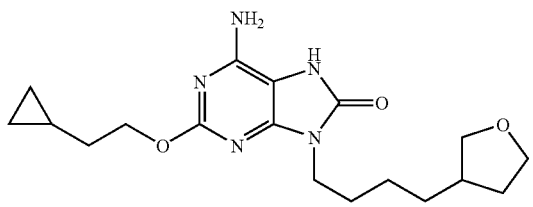

Prepared similarly to Example 129 from 2-[(2-cyclopropylethyl)oxy]-8-(methyloxy)-9-[4-(tetrahydro-3-furanyl)butyl]-9H-purin-6-amine.
LCMS (Method B): $t_{RET}$=1.00 min; MH$^+$=362

Example 97

6-Amino-2-[(2-cyclopropylethyl)oxy]-9-[2-(tetrahydro-2H-pyran-2-yl)ethyl]-7,9-dihydro-8H-purin-8-one

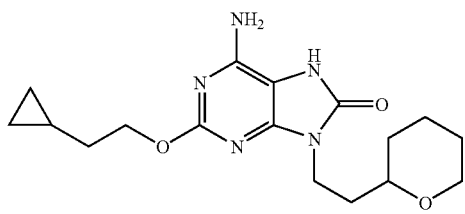

To a solution of 2-[(2-cyclopropylethyl)oxy]-8-(methyloxy)-9-[2-(tetrahydro-2H-pyran-2-yl)ethyl]-9H-purin-6-amine (84.7 mg, 0.234 mmol) in methanol (7.9 ml) at room temperature was added 4.0 M HCl in 1,4-dioxane (1.46 ml) to give a pale straw coloured solution. The reaction mixture was stirred at ambient temperature overnight (20 hours) and then evaporated in vacuo to give a colourless oil/gum. This material was re-dissolved in methanol and passed down a 5 g aminopropyl SPE cartridge (pre-conditioned in methanol), washed through with methanol and evaporated to give the title compound as a white solid (58.5 mg).
LCMS (Method A): $t_{RET}$=3.00 min; MH$^+$=348

Example 98

6-Amino-2-[(2-cyclopropylethyl)oxy]-9-[3-(tetrahydro-2H-pyran-2-yl)propyl]-7,9-dihydro-8H-purin-8-one

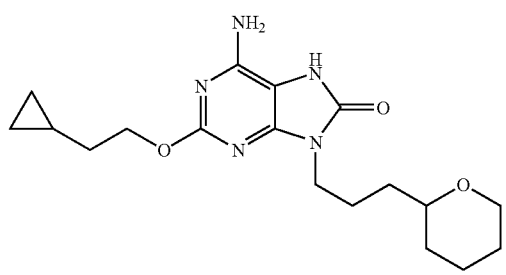

Prepared similarly to Example 129 from 2-[(2-cyclopropylethyl)oxy]-8-(methyloxy)-9-[3-(tetrahydro-2H-pyran-2-yl)propyl]-9H-purin-6-amine.
LCMS (Method B): $t_{RET}$=1.06 min; MH$^+$=362

Example 99

6-Amino-2-[(2-cyclopropylethyl)oxy]-9-[4-(tetrahydro-2H-pyran-2-yl)butyl]-7,9-dihydro-8H-purin-8-one

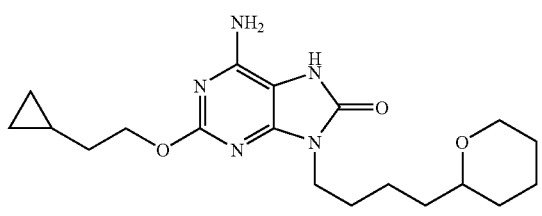

Prepared similarly to Example 84 from 2-[(2-cyclopropylethyl)oxy]-8-(methyloxy)-9-[4-(tetrahydro-2H-pyran-2-yl)butyl]-9H-purin-6-amine.
LCMS (Method A): $t_{RET}$=3.25 min; MH$^+$=376

Example 100

6-Amino-2-[(2-cyclopropylethyl)oxy]-9-[2-(tetrahydro-2H-pyran-3-yl)ethyl]-7,9-dihydro-8H-purin-8-one

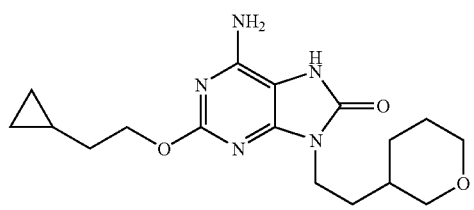

Prepared similarly to Example 97 from 2-[(2-cyclopropylethyl)oxy]-8-(methyloxy)-9-[2-(tetrahydro-2H-pyran-3-yl)ethyl]-9H-purin-6-amine.
LCMS (Method A): $t_{RET}$=2.89 min; MH$^+$=348.

Example 101

6-Amino-2-[(2-cyclopropylethyl)oxy]-9-[4-(tetrahydro-2H-pyran-3-yl)butyl]-7,9-dihydro-8H-Purin-8-one

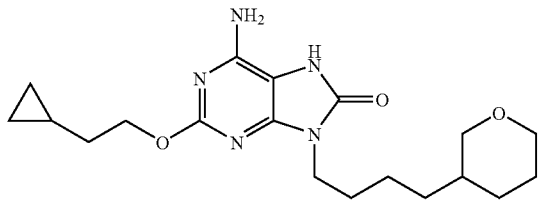

Prepared similarly to Example 84 from 2-[(2-cyclopropylethyl)oxy]-8-(methyloxy)-9-[4-(tetrahydro-2H-pyran-3-yl)butyl]-9H-purin-6-amine.
LCMS (Method A): $t_{RET}$=3.15 min; MH$^+$=3376

Example 102

6-Amino-2-[(2-cyclopropylethyl)oxy]-9-[2-(tetrahydro-2H-pyran-4-yl)ethyl]-7,9-dihydro-8H-Purin-8-one

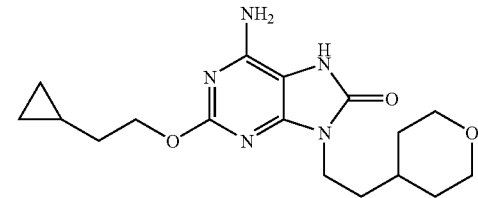

Prepared similarly to Example 73 from 2-[(2-cyclopropylethyl)oxy]-8-(methyloxy)-9-[2-(tetrahydro-2H-pyran-4-yl)ethyl]-9H-purin-6-amine.
LCMS (Method B): $t_{RET}$=0.94 min; MH$^+$=348

Example 103

6-Amino-2-[(2-cyclopropylethyl)oxy]-9-[3-(tetrahydro-2H-pyran-4-yl)propyl]-7,9-dihydro-8H-purin-8-one

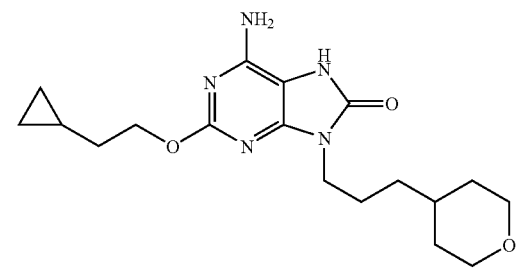

Prepared similarly to Example 69 from 2-[(2-cyclopropylethyl)oxy]-8-(methyloxy)-9-[3-(tetrahydro-2H-pyran-4-yl)propyl]-9H-purin-6-amine.
LCMS (Method B): $t_{RET}$=0.99 min; MH$^+$=362

Example 104

6-Amino-2-[(2-cyclopropylethyl)oxy]-9-[4-(tetrahydro-2H-pyran-4-yl)butyl]-7,9-dihydro-8H-Purin-8-one

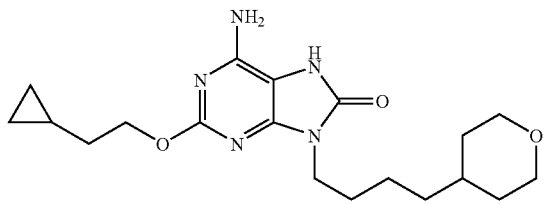

Prepared similarly to Example 69 from 2-[(2-cyclopropylethyl)oxy]-8-(methyloxy)-9-[4-(tetrahydro-2H-pyran-4-yl)butyl]-9H-purin-6-amine.
LCMS (Method B): $t_{RET}$=1.05 min; MH$^+$=376

Example 105

6-Amino-2-[(2-cyclopropylethyl)oxy]-9-[2-(2,2-dimethyltetrahydro-2H-pyran-4-yl)ethyl]-7,9-dihydro-8H-purin-8-one

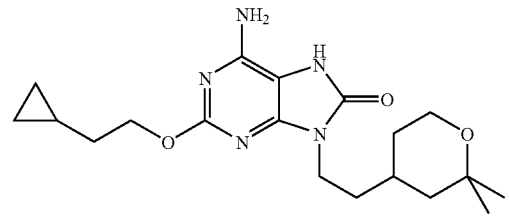

Prepared similarly to Example 71 from 2-[(2-cyclopropylethyl)oxy]-9-[2-(2,2-dimethyltetrahydro-2H-pyran-4-yl)ethyl]-8-(methyloxy)-9H-purin-6-amine.
LCMS (Method A): $t_{RET}$=3.00 min; MH$^+$=376

Example 106

6-Amino-2-[(2-cyclopropylethyl)oxy]-9-[3-(2,2-dimethyltetrahydro-2H-Pyran-4-yl)propyl]-7,9-dihydro-8H-purin-8-one

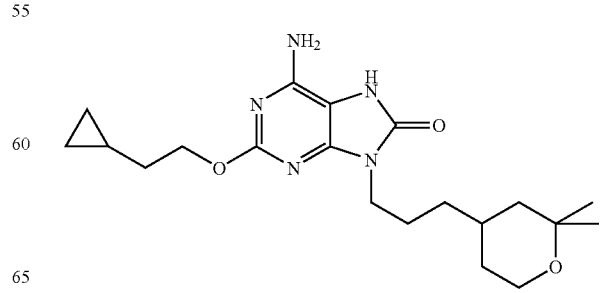

Prepared similarly to Example 72 from 2-[(2-cyclopropylethyl)oxy]-9-[3-(2,2-dimethyltetrahydro-2H-pyran-4-yl)propyl]-8-(methyloxy)-9H-purin-6-amine.
LCMS (Method A): $t_{RET}$=3.13 min; MH$^+$=390

Example 107

6-Amino-2-[(2-cyclopropylethyl)oxy]-9-[4-(2,2-dimethyltetrahydro-2H-pyran-4-yl)butyl]-7,9-dihydro-8H-purin-8-one

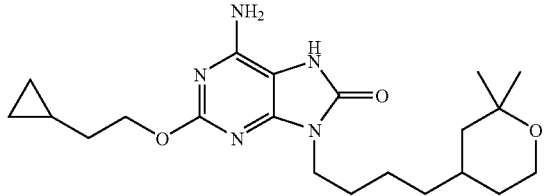

Prepared similarly to Example 73 from 2-[(2-cyclopropylethyl)oxy]-9-[4-(2,2-dimethyltetrahydro-2H-pyran-4-yl)butyl]-8-(methyloxy)-9H-purin-6-amine.
LCMS (Method A): $t_{RET}$=3.30 min; MH$^+$=404

Example 108

6-Amino-2-{[(1S)-1-methylbutyl]oxy}-9-[2-(tetrahydro-2-furanyl)ethyl]-7,9-dihydro-8H-purin-8-one

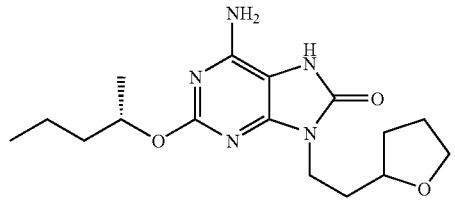

Prepared similarly to Example 84 from 2-{[(1S)-1-methylbutyl]oxy}-8-(methyloxy)-9-[2-(tetrahydro-2-furanyl)ethyl]-9H-purin-6-amine.
LCMS (Method A): $t_{RET}$=2.91 min; MH$^+$=336

Example 109

6-Amino-2-{[(1S)-1-methylbutyl]oxy}-9-[3-(tetrahydro-2-furanyl)propyl]-7,9-dihydro-8H-purin-8-one

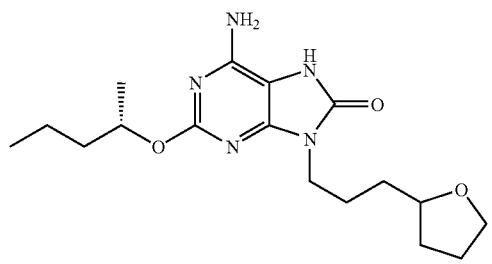

Prepared similarly to Example 73 from 2-{[(1S)-1-methylbutyl]oxy}-8-(methyloxy)-9-[3-(tetrahydro-2-furanyl)propyl]-9H-purin-6-amine. LCMS (Method A): $t_{RET}$=3.01 min; MH$^+$=350

Example 110

6-Amino-2-{[(1S)-1-methylbutyl]oxy}-9-{2-[(3S)-tetrahydro-3-furanyl]ethyl}-7,9-dihydro-8H-purin-8-one

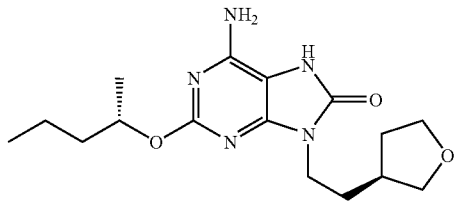

Prepared similarly to Example 97 from 2-{[(1S)-1-methylbutyl]oxy}-8-(methyloxy)-9-{2-[(3S)-tetrahydro-3-furanyl]ethyl}-9H-purin-6-amine.
LCMS (Method A): $t_{RET}$=2.73 min; MH$^+$=336

Example 111

6-Amino-2-{[(1S)-1-methylbutyl]oxy}-9-{2-[(3R)-tetrahydro-3-furanyl]ethyl}-7,9-dihydro-8H-purin-8-one

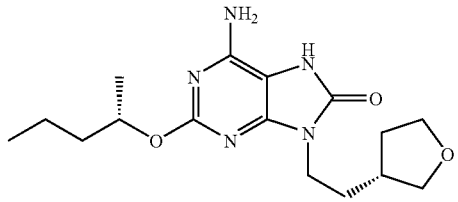

Prepared similarly to Example 73 from 2-{[(1S)-1-methylbutyl]oxy}-8-(methyloxy)-9-{2-[(3R)-tetrahydro-3-furanyl]ethyl}-9H-purin-6-amine.
LCMS (Method A): $t_{RET}$=2.75 min; MH$^+$=336

Example 112

6-Amino-2-{[(1S)-1-methylbutyl]oxy}-9-[3-(tetrahydro-3-furanyl)propyl]-7,9-dihydro-8H-Purin-8-one

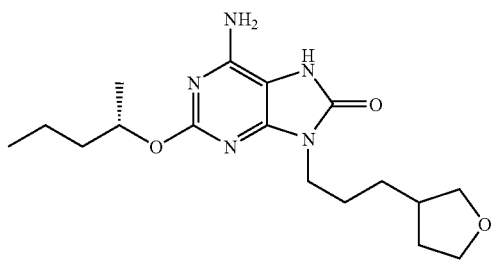

Prepared similarly to Example 69 from 2-{[(1S)-1-methylbutyl]oxy}-8-(methyloxy)-9-[3-(tetrahydro-3-furanyl)propyl]-9H-purin-6-amine.
LCMS (Method B): $t_{RET}$=0.99 min; MH$^+$=350

Example 113

6-Amino-2-{[(11S)-1-methylbutyl]oxy}-9-[4-(tetrahydro-3-furanyl)butyl]-7,9-dihydro-8H-purin-8-one

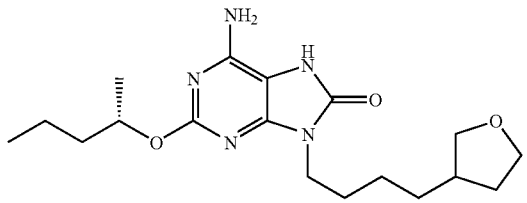

Prepared similarly to Example 69 from 2-{[(1S)-1-methylbutyl]oxy}-8-(methyloxy)-9-[4-(tetrahydro-3-furanyl)butyl]-9H-purin-6-amine.
LCMS (Method B): $t_{RET}$=1.05 min; MH$^+$=364

Example 114

6-Amino-2-{[(1S)-1-methylbutyl]oxy}-9-[2-(tetrahydro-2H-pyran-2-yl)ethyl]-7,9-dihydro-8H-purin-8-one

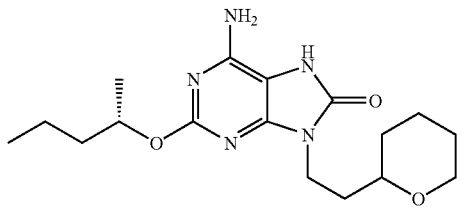

Prepared similarly to Example 84 from 2-{[(1S)-1-methylbutyl]oxy}-8-(methyloxy)-9-[2-(tetrahydro-2H-pyran-2-yl)ethyl]-9H-purin-6-amine.
LCMS (Method A): $t_{RET}$=3.03 min; MH$^+$=350

Example 115

6-Amino-2-{[(1S)-1-methylbutyl]oxy}-9-[3-(tetrahydro-2H-pyran-2-yl)propyl]-7,9-dihydro-8H-purin-8-one

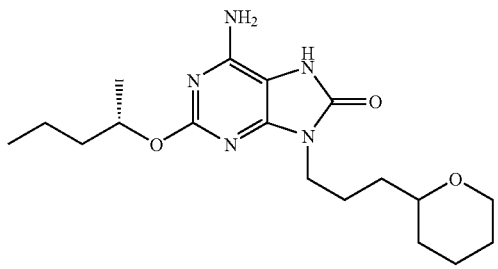

Prepared similarly to Example 69 from 2-{[(1S)-1-methylbutyl]oxy}-8-(methyloxy)-9-[3-(tetrahydro-2H-pyran-2-yl)propyl]-9H-purin-6-amine.
LCMS (Method B): $t_{RET}$=1.11 min; MH$^+$=364

Example 116

6-Amino-2-{[(1S)-1-methylbutyl]oxy}-9-[4-(tetrahydro-2H-pyran-2-yl)butyl]-7,9-dihydro-8H-purin-8-one

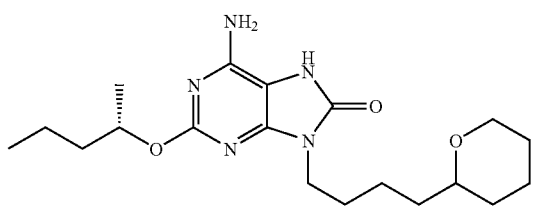

Prepared similarly to Example 84 from 2-{[(1S)-1-methylbutyl]oxy}-8-(methyloxy)-9-[4-(tetrahydro-2H-pyran-2-yl)butyl]-9H-purin-6-amine.
LCMS (Method A): $t_{RET}$=3.29 min; MH$^+$=378

Example 117

6-Amino-2-{[(1S)-1-methylbutyl]oxy}-9-[2-(tetrahydro-2H-pyran-3-yl)ethyl]-7,9-dihydro-8H-purin-8-one

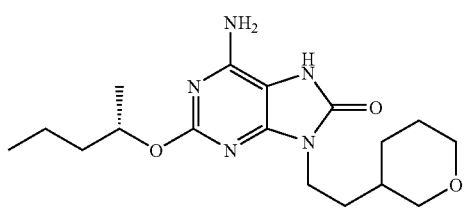

Prepared similarly to Example 84 from 2-{[(1S)-1-methylbutyl]oxy}-8-(methyloxy)-9-[2-(tetrahydro-2H-pyran-3-yl)ethyl]-9H-purin-6-amine.
LCMS (Method A): $t_{RET}$=2.91 min; MH$^+$=350

Example 118

6-Amino-2-{[(1S)-1-methylbutyl]oxy}-9-[4-(tetrahydro-2H-pyran-3-yl)butyl]-7,9-dihydro-8H-purin-8-one

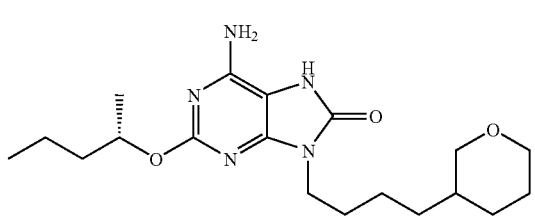

Prepared similarly to Example 84 from 2-{[(1S)-1-methylbutyl]oxy}-8-(methyloxy)-9-[4-(tetrahydro-2H-pyran-3-yl)butyl]-9H-purin-6-amine.
LCMS (Method A): $t_{RET}$=3.17 min; MH$^+$=378

Example 119

6-Amino-2-{[(11S)-1-methylbutyl]oxy}-9-[2-(tetrahydro-2H-pyran-4-yl)ethyl]-7,9-dihydro-8H-purin-8-one

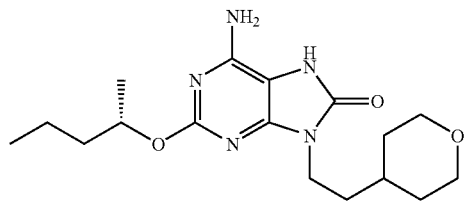

Prepared similarly to Example 73 from 2-{[(1S)-1-methylbutyl]oxy}-8-(methyloxy)-9-[2-(tetrahydro-2H-pyran-4-yl)ethyl]-9H-purin-6-amine.
LCMS (Method A): $t_{RET}$=2.85 min; MH$^+$=350

Example 120

6-Amino-2-{[(1S)-1-methylbutyl]oxy}-9-[3-(tetrahydro-2H-pyran-4-yl)propyl]-7,9-dihydro-8H-purin-8-one

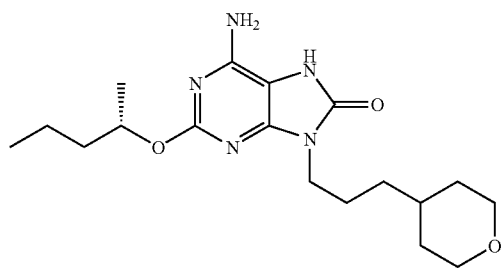

Prepared similarly to Example 69 from 2-{[(1S)-1-methylbutyl]oxy}-8-(methyloxy)-9-[3-(tetrahydro-2H-pyran-4-yl)propyl]-9H-purin-6-amine.
LCMS (Method B): $t_{RET}$=1.04 min; MH$^+$=364

Example 121

6-Amino-2-{[(1S)-1-methylbutyl]oxy}-9-[4-(tetrahydro-2H-pyran-4-yl)butyl]-7,9-dihydro-8H-purin-8-one

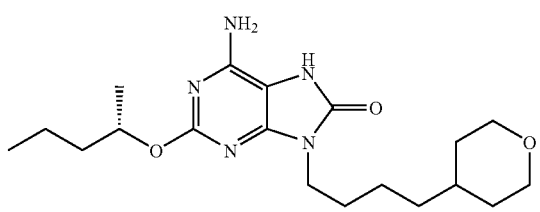

Prepared similarly to Example 69 from 2-{[(1S)-1-methylbutyl]oxy}-8-(methyloxy)-9-[4-(tetrahydro-2H-pyran-4-yl)butyl]-9H-purin-6-amine.
LCMS (Method B): $t_{RET}$=1.10 min; MH$^+$=378

Example 122

6-Amino-9-[2-(2,2-dimethyltetrahydro-2H-Pyran-4-yl)ethyl]-2-{[(1S)-1-methylbutyl]oxy}-7,9-dihydro-8H-purin-8-one

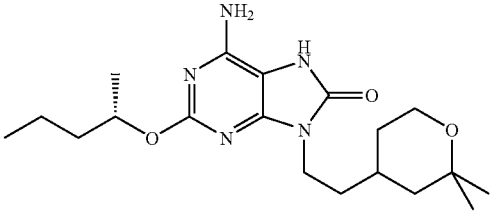

Prepared similarly to Example 84 from 9-[2-(2,2-dimethyltetrahydro-2H-pyran-4-yl)ethyl]-2-{[(1S)-1-methylbutyl]oxy}-8-(methyloxy)-9H-purin-6-amine.
LCMS (Method A): $t_{RET}$=3.24 min; MH$^+$=378

Example 123

6-Amino-9-[3-(2,2-dimethyltetrahydro-2H-pyran-4-yl)propyl]-2-{[(1S)-1-methylbutyl]oxy}-7,9-dihydro-8H-purin-8-one

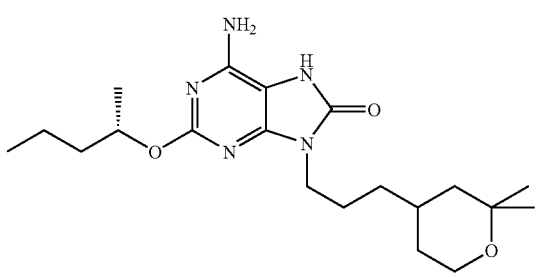

Prepared similarly to Example 73 from 9-[3-(2,2-dimethyltetrahydro-2H-pyran-4-yl)propyl]-2-{[(1S)-1-methylbutyl]oxy}-8-(methyloxy)-9H-purin-6-amine.
LCMS (Method A): $t_{RET}$=3.15 min; MH$^+$=392

Example 124

6-Amino-9-[4-(2,2-dimethyltetrahydro-2H-Pyran-4-yl)butyl]-2-{[(1S)-1-methylbutyl]oxy}-7,9-dihydro-8H-purin-8-one

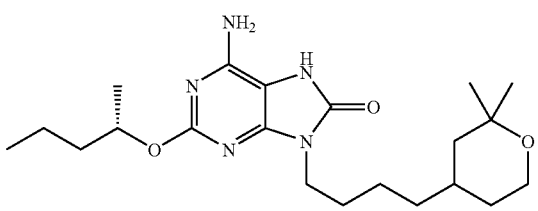

Prepared similarly to Example 73 from 9-[4-(2,2-dimethyltetrahydro-2H-pyran-4-yl)butyl]-2-{[(1S)-1-methylbutyl]oxy}-8-(methyloxy)-9H-purin-6-amine.
LCMS (Method A): $t_{RET}$=3.32 min; MH$^+$=406

Example 125

6-Amino-2-{[(1R)-1-methylbutyl]oxy}-9-[2-(tetrahydro-2-furanyl)ethyl]-7,9-dihydro-8H-Purin-8-one

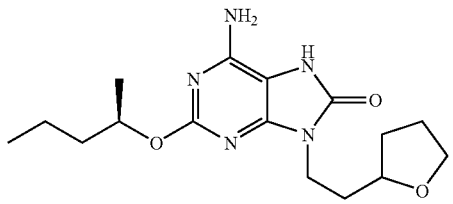

To a solution of 2-{[(1R)-1-methylbutyl]oxy}-8-(methyloxy)-9-[2-(tetrahydro-2-furanyl)ethyl]-9H-purin-6-amine (50 mg, 0.143 mmol) in methanol (10 ml) at room temperature was added 4M HCL in 1,4 dioxane (0.894 ml, 3.58 mmol) to give a pale straw coloured solution. The reaction mixture was stirred at 37° C. for 3 hours, and the solvent removed on a nitrogen blowdown unit overnight. The residue was dissolved in methanol and loaded onto a 2 g aminopropyl SPE cartridge and eluted with methanol. The appropriate fractions were combined and dried under a stream of nitrogen in a blowdown apparatus to give the title compound as a white solid (26 mg).

LCMS (Method B): $t_{RET}$=0.99 min; MH$^+$=336

Example 126

6-Amino-2-{[(1R)-1-methylbutyl]oxy}-9-[3-(tetrahydro-2-furanyl)propyl]-7,9-dihydro-8H-Purin-8-one

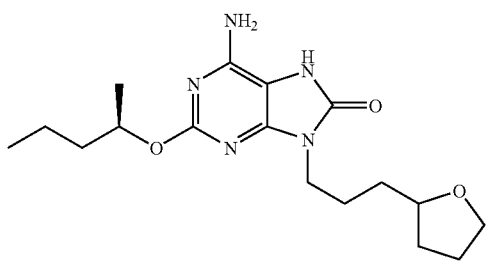

Prepared similarly to Example 73 from 2-{[(1R)-1-methylbutyl]oxy}-8-(methyloxy)-9-[3-(tetrahydro-2-furanyl)propyl]-9H-purin-6-amine.

LCMS (Method A): $t_{RET}$=2.90 min; MH$^+$=350

Example 127

6-Amino-2-{[(1R)-1-methylbutyl]oxy}-9-{2-[(3S)-tetrahydro-3-furanyl]ethyl}-7,9-dihydro-8H-purin-8-one

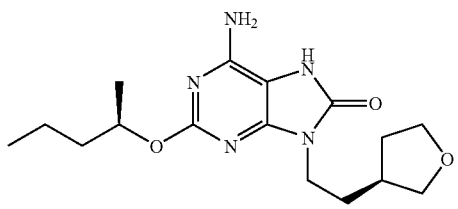

Prepared similarly to Example 97 from 2-{[(1R)-1-methylbutyl]oxy}-8-(methyloxy)-9-{2-[(3S)-tetrahydro-3-furanyl]ethyl}-9H-purin-6-amine.

LCMS (Method A): $t_{RET}$=2.72 min; MH$^+$=336

Example 128

6-Amino-2-{[(1R)-1-methylbutyl]oxy}-9-{2-[(3R)-tetrahydro-3-furanyl]ethyl}-7,9-dihydro-8H-purin-8-one

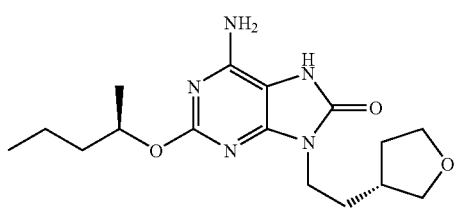

Prepared similarly to Example 73 from 2-{[(1R)-1-methylbutyl]oxy}-8-(methyloxy)-9-{2-[(3R)-tetrahydro-3-furanyl]ethyl}-9H-purin-6-amine.

LCMS (Method A): $t_{RET}$=2.73 min; MH$^+$=336

Example 129

6-Amino-2-{[(1R)-1-methylbutyl]oxy}-9-[3-(tetrahydro-3-furanyl)propyl]-7,9-dihydro-8H-Purin-8-one

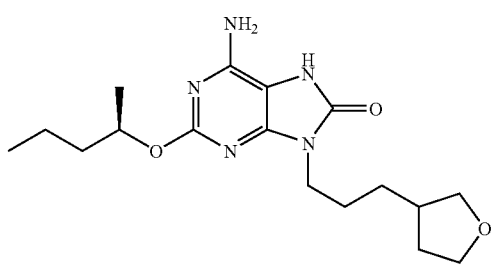

To a solution of 2-{[(1R)-1-methylbutyl]oxy}-8-(methyloxy)-9-[3-(tetrahydro-3-furanyl)propyl]-9H-purin-6-amine (52 mg, 0.143 mmol) in methanol (5 ml) at room temperature was added 4M HCl in dioxane (0.894 ml, 3.58 mmol). The reaction mixture was stirred at room temperature for 18 hrs and concentrated in vacuo to give a white solid. This material was dissolved in methanol and loaded onto a 2 g aminopropyl SPE cartridge, eluting with methanol. The solvent was removed to give the title compound as a white solid (36 mg).

LCMS (Method B): $t_{RET}$=0.99 min; MH$^+$=350

Example 130

6-Amino-2-{[(1R)-1-methylbutyl]oxy}-9-[4-(tetrahydro-3-furanyl)butyl]-7,9-dihydro-8H-Purin-8-one

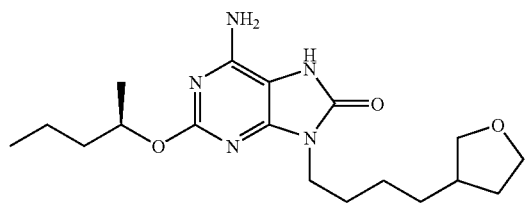

Prepared similarly to Example 129 from 2-{[(1R)-1-methylbutyl]oxy}-8-(methyloxy)-9-[4-(tetrahydro-3-furanyl)butyl]-9H-purin-6-amine.
LCMS (Method B): $t_{RET}$=1.05 min; MH$^+$=364

Example 131

6-Amino-2-{[(1R)-1-methylbutyl]oxy}-9-[2-(tetrahydro-2H-pyran-2-yl)ethyl]-7,9-dihydro-8H-purin-8-one

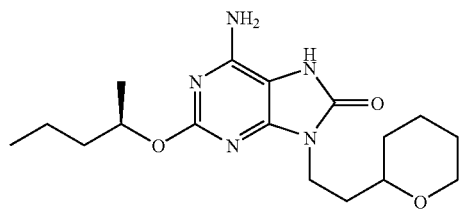

Prepared similarly to Example 125 from 2-{[(1R)-1-methylbutyl]oxy}-8-(methyloxy)-9-[2-(tetrahydro-2H-pyran-2-yl)ethyl]-9H-purin-6-amine.
LCMS (Method B): $t_{RET}$=1.08 min; MH$^+$=350

Example 132

6-Amino-2-{[(1R)-1-methylbutyl]oxy}-9-[3-(tetrahydro-2H-pyran-2-yl)propyl]-7,9-dihydro-8H-purin-8-one

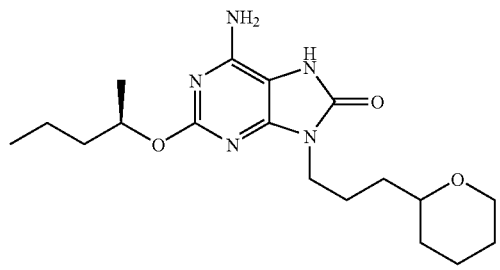

Prepared similarly to Example 129 from 2-{[(1R)-1-methylbutyl]oxy}-8-(methyloxy)-9-[3-(tetrahydro-2H-pyran-2-yl)propyl]-9H-purin-6-amine.
LCMS (Method B): $t_{RET}$=1.11 min; MH$^+$=364

Example 133

6-Amino-2-{[(1R)-1-methylbutyl]oxy}-9-[4-(tetrahydro-2H-pyran-2-yl)butyl]-7,9-dihydro-8H-purin-8-one

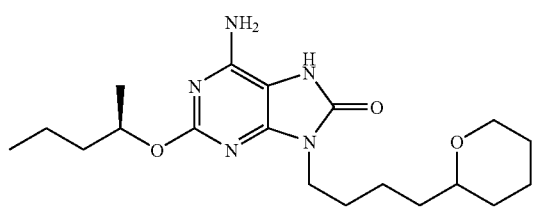

Prepared similarly to Example 84 from 2-{[(1R)-1-methylbutyl]oxy}-8-(methyloxy)-9-[4-(tetrahydro-2H-pyran-2-yl)butyl]-9H-purin-6-amine.
LCMS (Method A): $t_{RET}$=3.26 min; MH$^+$=378

Example 134

6-Amino-2-{[(1R)-1-methylbutyl]oxy}-9-[2-(tetrahydro-2H-pyran-3-yl)ethyl]-7,9-dihydro-8H-purin-8-one

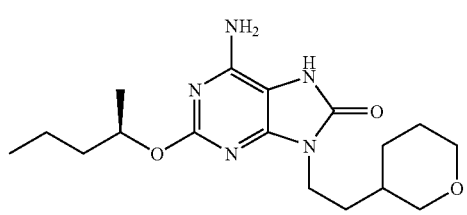

Prepared similarly to Example 125 from 2-{[(1R)-1-methylbutyl]oxy}-8-(methyloxy)-9-[2-(tetrahydro-2H-pyran-3-yl)ethyl]-9H-purin-6-amine.
LCMS (Method B): $t_{RET}$=1.02 min; MH$^+$=350

Example 135

6-Amino-2-{[(1R)-1-methylbutyl]oxy}-9-[4-(tetrahydro-2H-pyran-3-yl)butyl]-7,9-dihydro-8H-purin-8-one

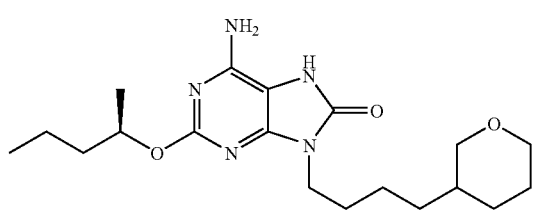

Prepared similarly to Example 125 from 2-{[(1R)-1-methylbutyl]oxy}-8-(methyloxy)-9-[4-(tetrahydro-2H-pyran-3-yl)butyl]-9H-purin-6-amine.
LCMS (Method B): $t_{RET}$=1.13 min; MH$^+$=378

Example 136

6-Amino-2-{[(1R)-1-methylbutyl]oxy}-9-[2-(tetrahydro-2H-pyran-4-yl)ethyl]-7,9-dihydro-8H-purin-8-one

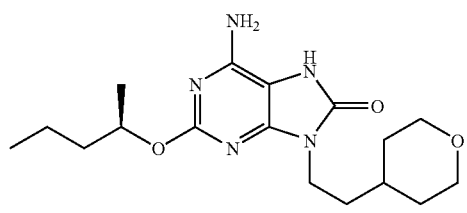

Prepared similarly to Example 73 from 2-{[(1R)-1-methylbutyl]oxy}-8-(methyloxy)-9-[2-(tetrahydro-2H-pyran-4-yl)ethyl]-9H-purin-6-amine.
LCMS (Method A): $t_{RET}$=2.84 min; MH$^+$=350

Example 137

6-Amino-2-{[(1R)-1-methylbutyl]oxy}-9-[3-(tetrahydro-2H-pyran-4-yl)propyl]-7,9-dihydro-8H-purin-8-one

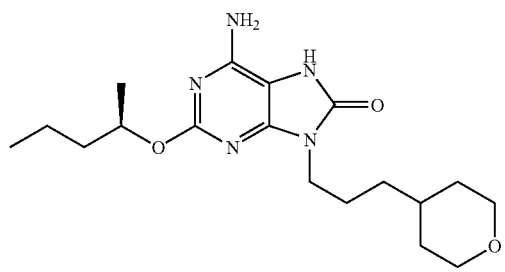

Prepared similarly to Example 129 from 2-{[(1R)-1-methylbutyl]oxy}-8-(methyloxy)-9-[3-(tetrahydro-2H-pyran-4-yl)propyl]-9H-purin-6-amine. LCMS (Method B): $t_{RET}$=1.04 min; MH$^+$=364

Example 138

6-Amino-2-{[(1R)-1-methylbutyl]oxy}-9-[4-(tetrahydro-2H-pyran-4-yl)butyl]-7,9-dihydro-8H-purin-8-one

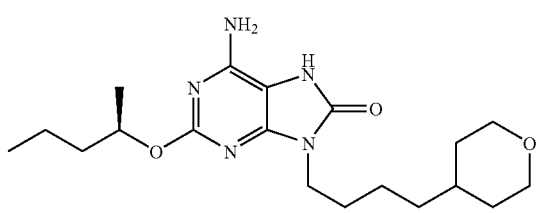

Prepared similarly to Example 129 from 2-{[(1R)-1-methylbutyl]oxy}-8-(methyloxy)-9-[4-(tetrahydro-2H-pyran-4-yl)butyl]-9H-purin-6-amine.
LCMS (Method B): $t_{RET}$=1.10 min; MH$^+$=378

Example 139

6-Amino-9-[2-(2,2-dimethyltetrahydro-2H-pyran-4-yl)ethyl]-2-{[(1R)-1-methylbutyl]oxy}-7,9-dihydro-8H-purin-8-one

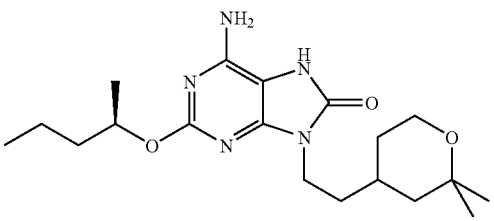

Prepared similarly to Example 125 from 9-[2-(2,2-dimethyltetrahydro-2H-pyran-4-yl)ethyl]-2-{[(1R)-1-methylbutyl]oxy}-8-(methyloxy)-9H-purin-6-amine.
LCMS (Method B): $t_{RET}$=1.07 min; MH$^+$=378

Example 140

6-Amino-9-[3-(2,2-dimethyltetrahydro-2H-Pyran-4-yl)propyl]-2-{[(1R)-1-methylbutyl]oxy}-7,9-dihydro-8H-purin-8-one

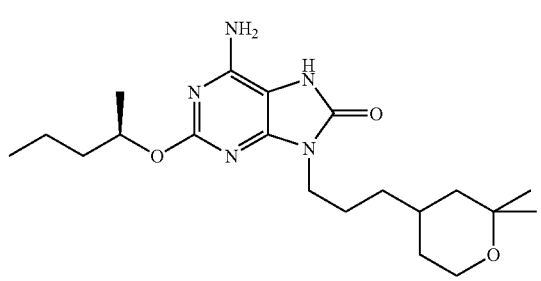

Prepared similarly to Example 73 from 9-[3-(2,2-dimethyltetrahydro-2H-pyran-4-yl)propyl]-2-{[(1R)-1-methylbutyl]oxy}-8-(methyloxy)-9H-purin-6-amine.
LCMS (Method A): $t_{RET}$=3.16 min; MH$^+$=392

Example 141

6-Amino-9-[4-(2,2-dimethyltetrahydro-2H-pyran-4-yl)butyl]-2-{[(1R)-1-methylbutyl]oxy}-7,9-dihydro-8H-purin-8-one

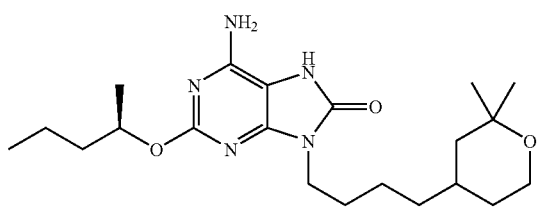

Prepared similarly to Example 73 from 9-[4-(2,2-dimethyltetrahydro-2H-pyran-4-yl)butyl]-2-{[(1R)-1-methylbutyl]oxy}-8-(methyloxy)-9H-purin-6-amine.

LCMS (Method A): $t_{RET}$=3.33 min; MH$^+$=406

Polymorphism

X-ray powder diffraction (XRPD) and differential scanning calorimetry (DSC) were performed on samples of certain compounds of the invention according to the following methods.

XRPD

The X-ray powder diffraction data were acquired on a PANalytical X'Pert Pro powder diffractometer, model PW3040/60, serial number DY1850 using an XCelerator detector. The acquisition conditions were: radiation: Cu Kα, generator tension: 40 kV, generator current: 45 mA, start angle 20° 2θ, end angle: 40° 2θ, step size: 0.0167° 2θ, time per step: 31.75 seconds. The sample was prepared by mounting a few milligrams of sample on a Si wafer (zero background) plates, resulting in a thin layer of powder.

DSC

The DSC thermograms were obtained using a TA Q1000 calorimeter, serial number 1000-0126. The sample was weighed into an aluminium pan, a pan lid placed on top and lightly crimped without sealing the pan. The experiment was conducted using a heating rate of 10° C. min$^{-1}$.

Figure 2:
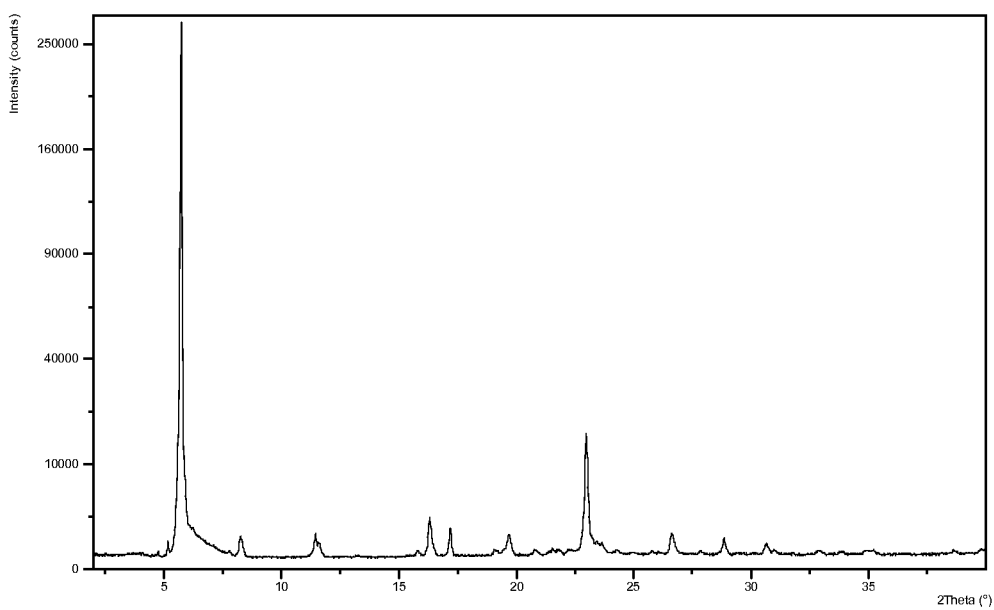
FIG. 2 shows an XRPD diffractogram of 6-amino-2-(butyloxy)-9-(tetrahydro-3-furanylmethyl)-7,9-dihydro-8H-purin-8-one, Isomer 1.
Figure 3:
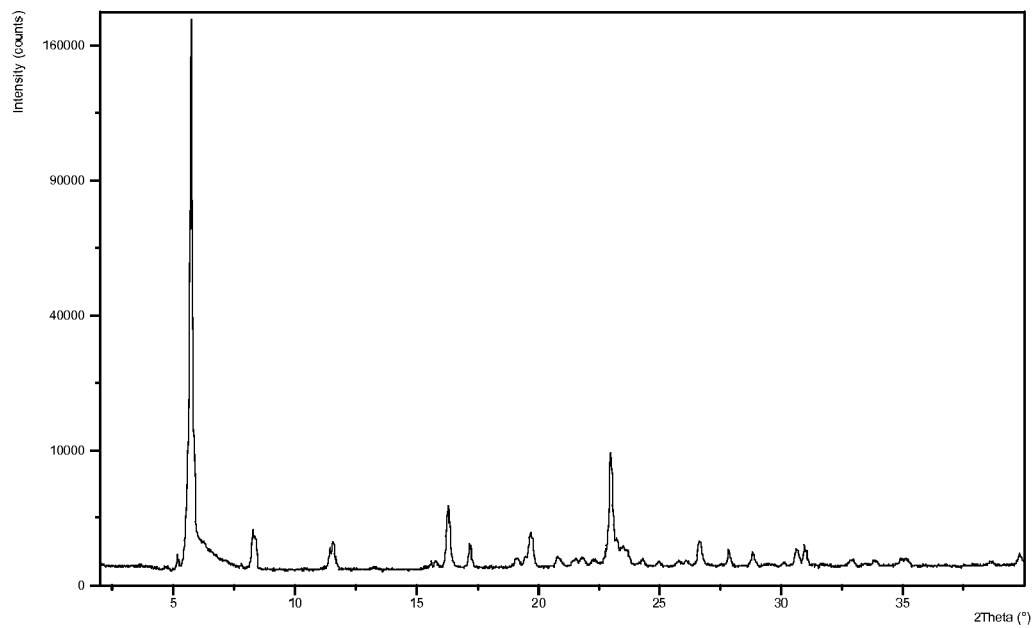
FIG. 3 shows an XRPD diffractogram of 6-amino-2-(butyloxy)-9-(tetrahydro-3-furanylmethyl)-7,9-dihydro-8H-purin-8-one, Isomer 2.
Figure 4:
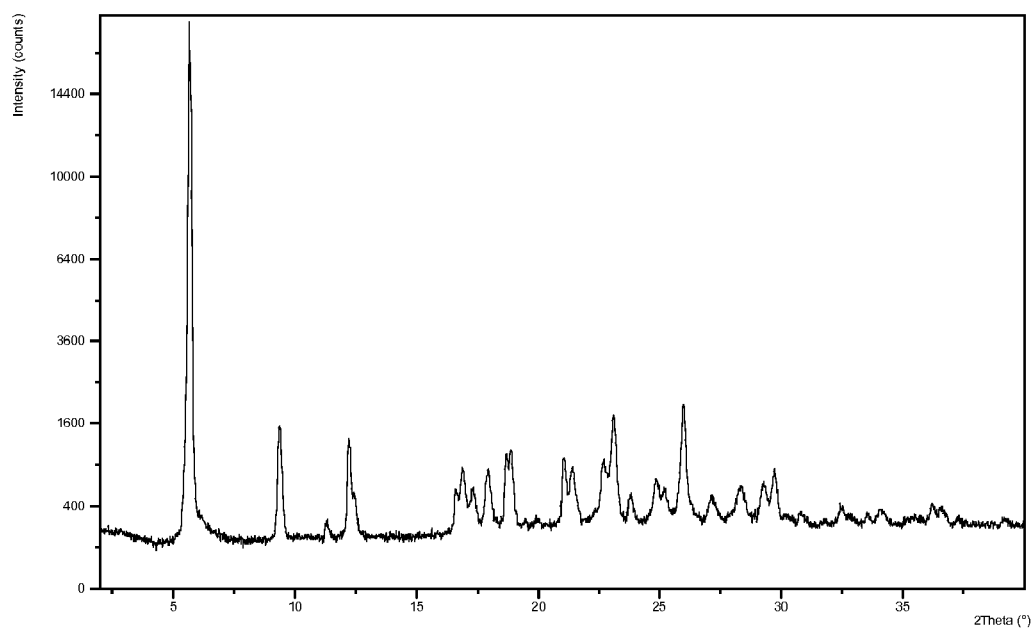
FIG. 4 shows an XRPD diffractogram of 6-amino-2-(butylamino)-9-(tetrahydro-3-furanylmethyl)-7,9-dihydro-8H-purin-8-one, Isomer 1.
Figure 5:
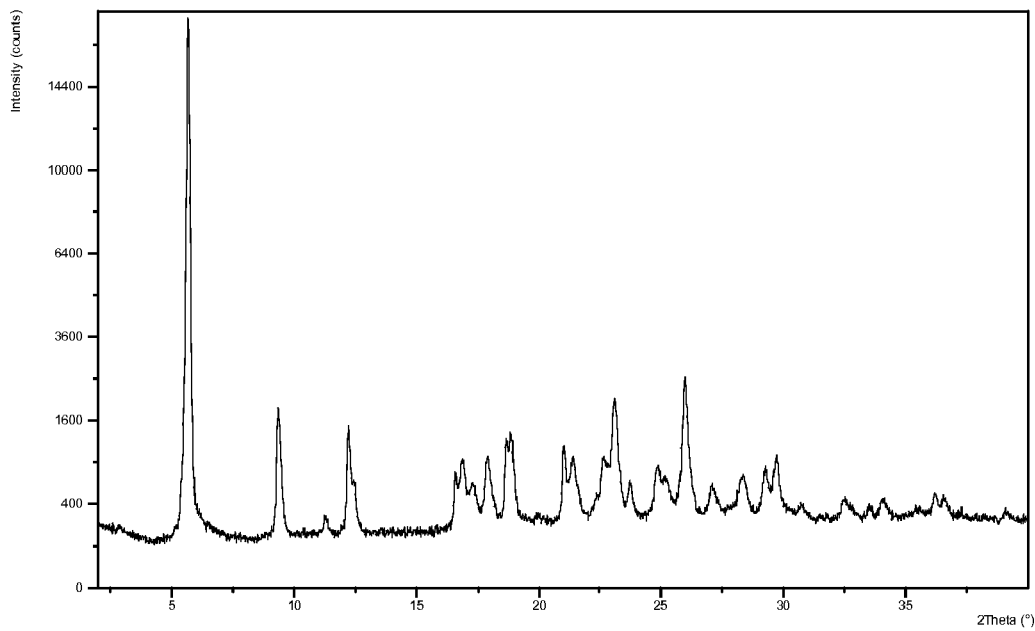
FIG. 5 shows an XRPD diffractogram of 6-amino-2-(butylamino)-9-(tetrahydro-3-furanylmethyl)-7,9-dihydro-8H-purin-8-one, Isomer 2.
Figure 6:
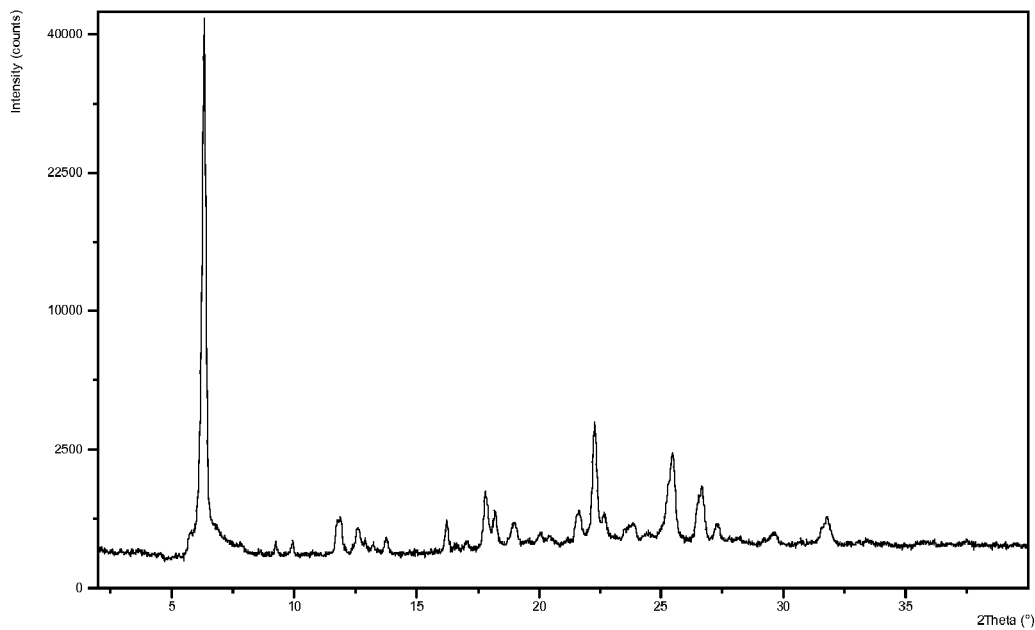
FIG. 6 shows an XRPD diffractogram of 6-amino-2-[(2-cyclopropylethyl)oxy]-9-(tetrahydro-3-furanylmethyl)-7,9-dihydro-8H-purin-8-one, Isomer 1
Figure 7:
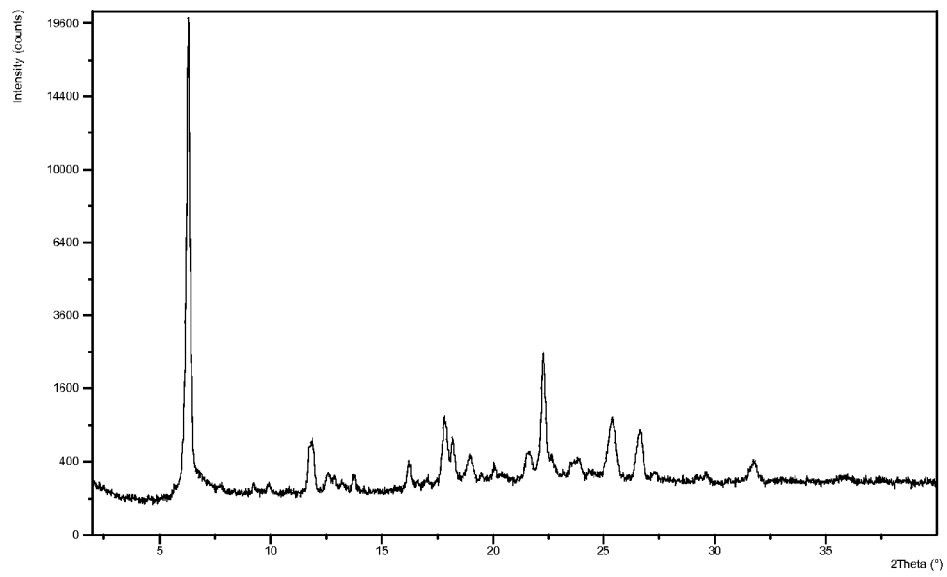
FIG. 7 shows an XRPD diffractogram of 6-amino-2-[(2-cyclopropylethyl)oxy]-9-[tetrahydro-3-furanylmethyl]-7,9-dihydro-8H-purin-8-one, Isomer 2.
Figure 8:
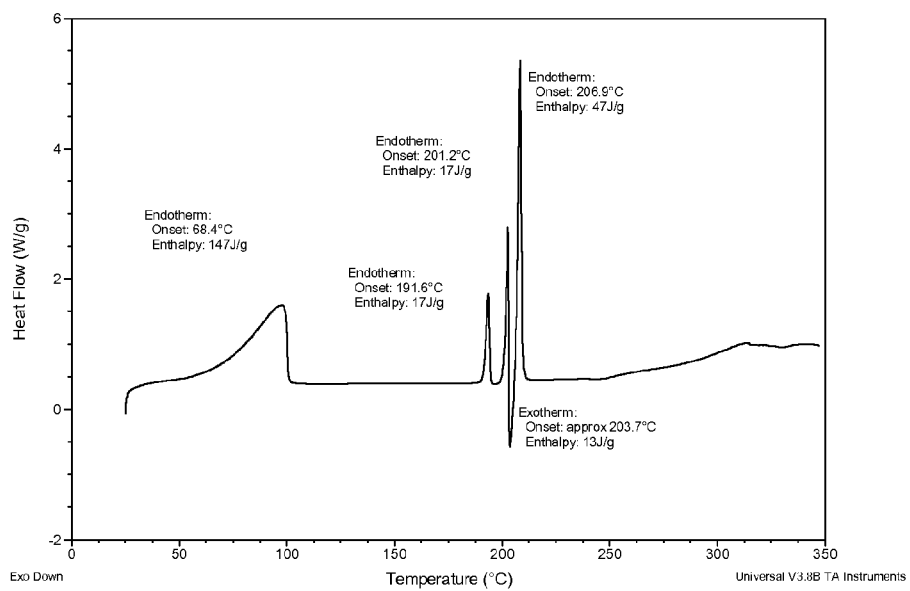
FIG. 8 shows a DSC thermogram of 6-amino-2-butylamino-9-(tetrahydro-2H-pyran-4-ylmethyl)-7,9-dihydro-8H-purin-8-one.
Figure 9:
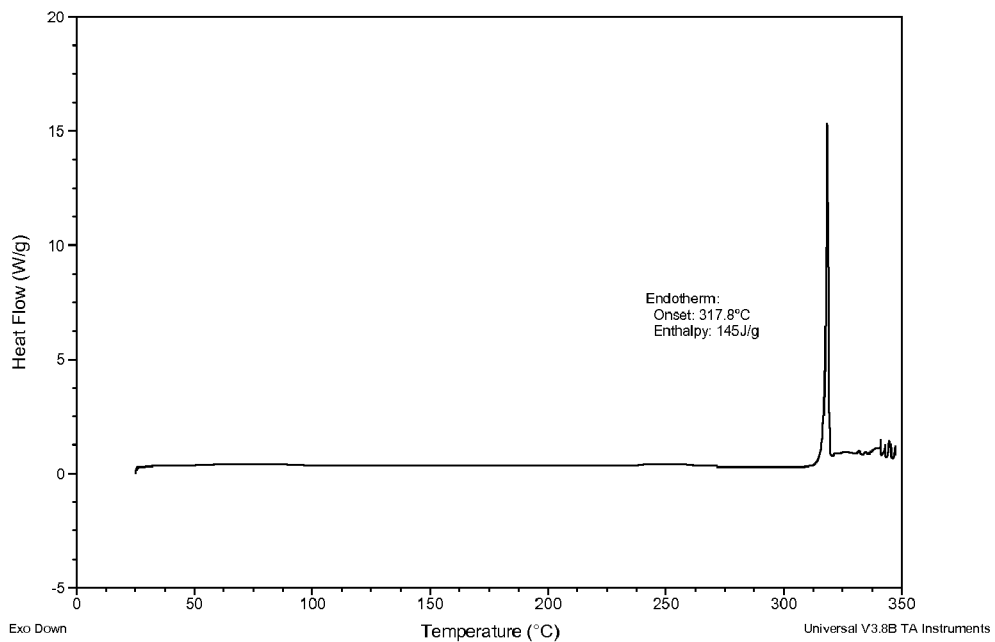
FIG. 9 shows a DSC thermogram of 6-amino-2-(butyloxy)-9-(tetrahydro-3-furanylmethyl)-7,9-dihydro-8H-purin-8-one, Isomer 1.
Figure 10:
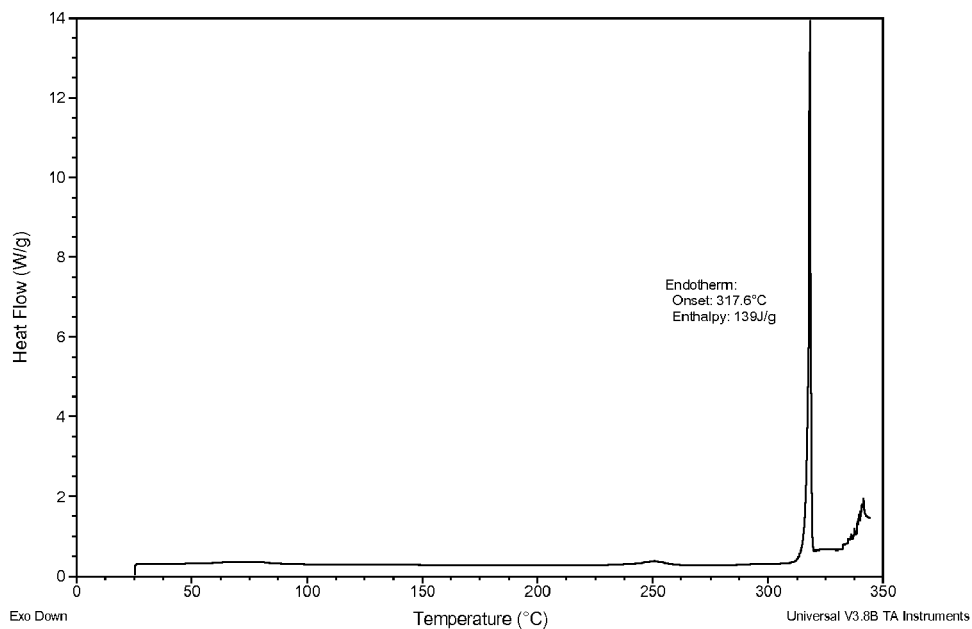
FIG. 10 shows a DSC thermogram of 6-amino-2-(butyloxy)-9-(tetrahydro-3-furanylmethyl)-7,9-dihydro-8H-purin-8-one, Isomer 2.
Figure 11:
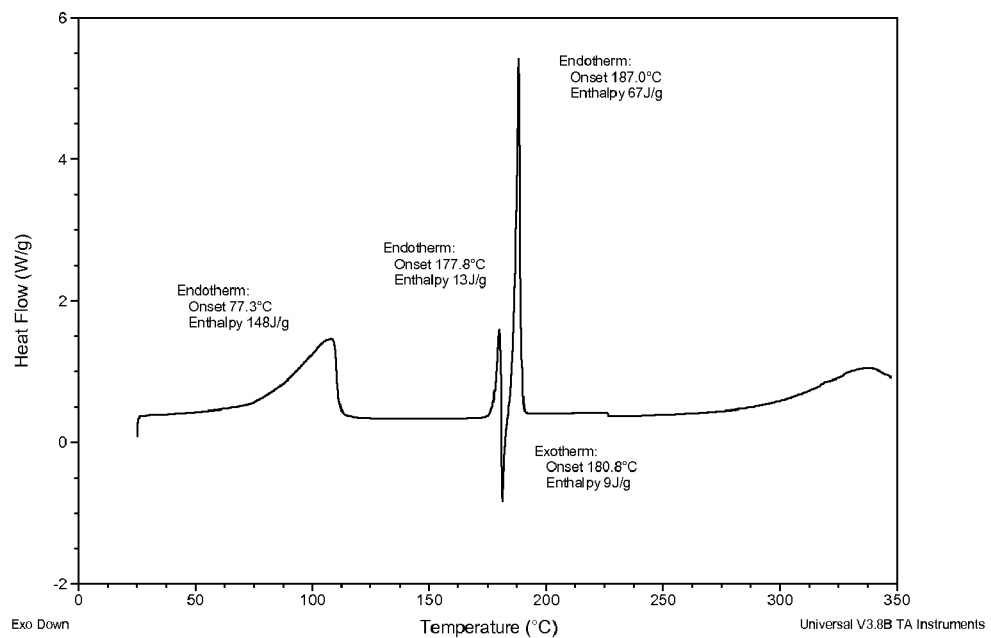
FIG. 11 shows a DSC thermogram of 6-amino-2-(butylamino)-9-(tetrahydro-3-furanylmethyl)-7,9-dihydro-8H-purin-8-one, Isomer 2.
Figure 12:
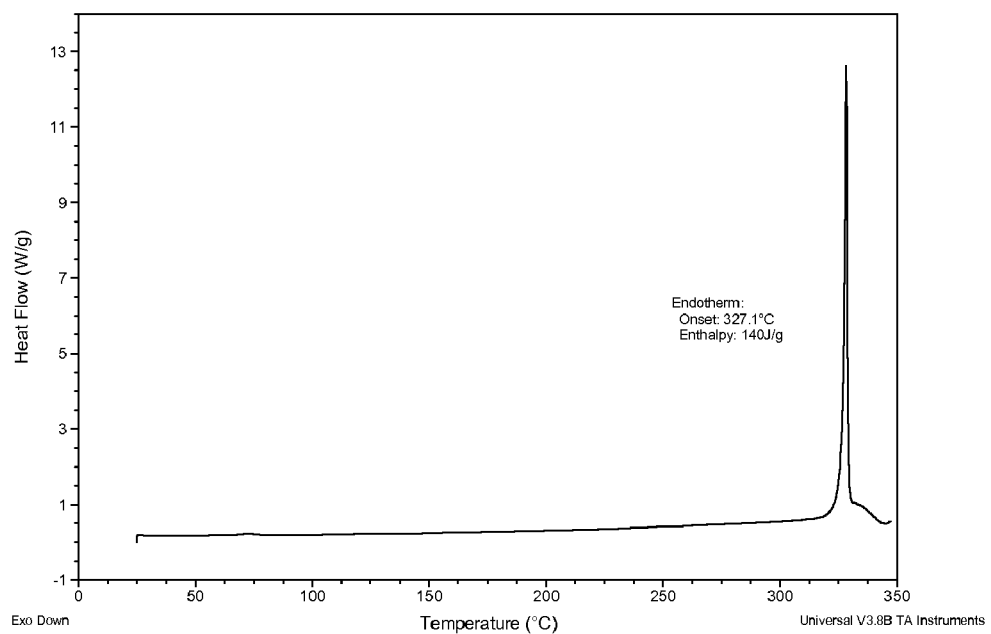
FIG. 12 shows a DSC thermogram of 6-amino-2-[(2-cyclopropylethyl)oxy]-9-(tetrahydro-3-furanylmethyl)-7,9-dihydro-8H-purin-8-one, Isomer 1.

Representative XRPD diffractograms of certain compounds of the invention are shown in FIGS. 1-7. Representative DSC thermograms of certain compounds of the invention are shown in FIGS. 8-12.

Biological Data

Compounds of the invention were tested for in vitro biological activity in accordance with the following assays:

Assays for the Induction of Interferon from Human PeriPheral Blood Mononuclear Cells (PBMC)

Assays based on stimulation of human donor blood derived peripheral blood mononuclear cells (PBMC) with test compounds were developed. After incubation of test compounds with freshly isolated PBMCs, cell supernatants were assayed for interferon alpha using an immunoassay with broad specificity for most IFNα isoforms. Some donor variability in responses to known interferon inducers was observed, hence resiquimod is included in these assays for normalisation purposes.

Interferon Induction Assay 'A'

Compound Preparation

Compounds were dissolved in DMSO. Serial 3-fold dilutions of compounds were prepared for each compound in growth medium (RPMI 1640 medium supplemented with 10% (v/v) foetal calf serum (FCS), 100 U/ml penicillin G, 100 μg/ml streptomycin, 10 mM L-glutamine and 1× non-essential amino acids) in sterile 96-well tissue culture plates. Each compound is assayed in duplicate for each PBMC donor.

Each assay included a positive control (resiquimod) and a negative control (growth medium). Data are expressed for each compound as $EC_{50}$ (calculated as the concentration of compound required to give 50% maximal induction of interferon alpha) and as relative activity compared with an $EC_{50}$ calculated for resiquimod in the same donor and experiment.

Preparation of PBMCs.

Blood samples were obtained from two human donors. 25 ml volumes of whole blood were overlaid onto 15 ml Histopaque® in ACCUSPIN™ tubes, centrifuged at 2100 rpm for 20 min and the band at the plasma/histopaque interface carefully removed. The collected cells were washed twice with PBS (centrifuged at 2100 rpm for 10 min) and resuspended in 10 ml growth medium. A 1:20 dilution of the cells in trypan blue was prepared and counted. The PBMCs were then diluted to give a final concentration in each well of 2×10$^6$ cells/ml in 100 μl/well when added to the diluted compounds.

The cell preparations were incubated for 24 h at 37° C. in 5% $CO_2$. The cell medium from each well was then transferred to a 96 well filter plate and the cell free supernatant was collected into a new 96 well plate under vacuum. These supernatants were stored at −20° C. prior to analysis.

Assay for Interferon Alpha

A multi-isoform immunoassay was used to quantify interferon alpha in PBMC supernatants. For direct quantification of interferon alpha, a standard line of recombinant human interferon alpha 2a (PBL laboratories) was included in each assay.

A rabbit polyclonal antibody against human IFN-alpha (catalogue number 31101, Stratech Scientific) was diluted 1:6400 in phosphate buffered saline (PBS) and 20 μl was added to each well of a Meso-Scale® Discovery (MSD®) single small-spot 96-well GAR plate. The plate was incubated for 1 h at room temperature with vigorous shaking. Following three washes with PBS, 20 μl of cell supernatant were added to each well of the plate. The plate was then incubated for 1 h at room temperature with vigorous shaking. A pair of monoclonal antibodies to IFN-alpha (catalogue numbers 21100 and 21112, Stratech Scientific), labelled with sulfo-TAG were diluted 1:500 in growth medium and 20 μl added to each well of the plate. The plate was further incubated for 1 h at room temperature with vigorous shaking. Following three washes with PBS, 150 μl of ×2 T buffer (MSD®) was added to each well and the plate was then read on an MSD® Sector 6000 plate reader.

IFNα concentrations in supernatants were quantified from a standard line constructed using recombinant IFNα2a. The limit of detection in this assay is approximately 1 pg/ml.

Interferon Induction Assay 'B'

Preparation of PBMCs.

Blood samples of up to 200 ml were obtained from healthy human donors. Whole blood in 25 ml volumes was overlaid onto 15 ml Ficoll® gradients in Leucosep® tubes, and centrifuged at 1000 g for 20 min. Cells in the band at the plasma/Histopaque® interface were carefully removed and washed twice with PBS (centrifuged at 400 g for 5 min to harvest). The final pellet was resuspended in freezing medium (90% Heat-inactivated serum, 10% DMSO) to a cell concentration of 4×10$^7$ cells/ml. The resuspended cells were then cryopreserved (frozen) using a rate controlled freezer, and stored at −140° C. for up to 4 months.

Assay for Interferon Alpha

Immediately prior to assay, vials of cryopreserved (frozen) PBMCs were thawed rapidly in a water bath at 37° C. A 1:10 dilution of the cells in trypan blue was prepared and counted. The PBMCs were then diluted in growth media [RPMI 1640 containing 10% fetal calf serum (invitrogen), Penicillin+Streptavidin (Gibco cat. # 25030-024, 1:50), L-Glutamine 2 mM, and 1000 units/ml recombinant human IFN-gamma (Preprotech catalogue #300-02)] to a density of 1×10$^6$ cells/ml, and dispensed to 384-well clear Greiner polypropylene plates containing 0.25 μl DMSO or test compound dissolved in neat DMSO. Top final concentration of compound was typically 50 μM. Plates were incubated for 24 h at 37° C. in 5% $CO_2$.

A multi-isoform immunoassay was used to quantify interferon-alpha in PBMC supernatants. Rabbit polyclonal antibody against human IFN-alpha (catalogue number 31101, Stratech Scientific) was diluted 1:10000 in assay buffer (RPMI 1640 containing 10% fetal calf serum, Invitrogen) and 20 μl was added to each well of an MSD® (Meso-Scale® Discovery) single small-spot 384-well GAR (goat anti-rabbit antibody coated) plate. The plate was incubated for 1 h at room temperature with vigorous shaking. Following three washes with PBS, 20 μl of cell supernatant were added to each well of the plate. The plate was then incubated for 1 h at room temperature with vigorous shaking. A pair of monoclonal antibodies to IFN-alpha (catalogue numbers 21100 and 21112, Stratech Scientific) were labelled with sulfo-TAG (MSD®), diluted 1:1000 in assay buffer and 20 μl added to each well of the plate. The plate was further incubated for 1 h at room temperature with vigorous shaking. Following three washes with PBS, 30 μl of ×2 T buffer (MSD®) was added to each well and the plate was read on an MSD® Sector 6000 plate reader.

Data were normalised to internal plate controls of 1 uM resiquimod (n=16) and DMSO (n=16). pEC50 values were derived by 4-parameter curve fit with IRLS in ActivityBase, from 11-point, two-fold serial dilution of test compounds.

Inhibition of Hepatitis C virus Replication by Supernatants from Compound-stimulated Human Peripheral Blood Mononuclear Cells (PBMC).

An assay was established to measure the antiviral activity in supernatants from human PBMC which had been previously stimulated with compounds.

Activity assays were conducted using an Huh-7 cell line stably-transfected with a dicistronic replicon, comprising the HCV Con 1-ET construct (Pietschmann et al., 2002 *J. Virol.* 2002 76(8):4008-21) and the firefly (*Photinus pyralis*) luciferase gene, obtained from ReBLikon GmbH, Germany.

$1.5 \times 10^4$ HCV ET replicon cells per well were grown in 96-well plates overnight in 90 microliters of cell culture medium. Ten microliters of three-fold dilutions of PBMC supernatants generated above (stimulation of human donor blood-derived peripheral blood mononuclear cells (PBMC) with test compounds) were added to the ET cells. Following a 48-hour incubation, assay medium was removed and luciferase activity measured in the cell monolayers using the SteadyLite™ assay system (Perkin Elmer). $EC_{50}$ values were calculated as the compound concentration giving a PBMC supernatant which was able to inhibit HCV replication by 50% compared with a supernatant from unstimulated PBMC cultures.

Inhibition of Ovalbumin (OVA)-Induced Acute Pulmonary Inflammation.

Female BALB/c mice (18-20 g) were inoculated on days 0 and 14, with 10 μg OVA adsorbed to 2 mg aluminium hydroxide in a volume of 0.2 ml phosphate buffered saline (PBS) via the intra-peritoneal route. On days 24-26, mice were intra-nasally challenged with 50 μl of either saline or OVA (formulated as above) under general anaesthesia.

Interferon-inducing test compounds were dosed at 5 mg/kg orally in a vehicle consisting of 0.2% Tween™ 80 in saline. Doses were given once daily on days 23 to 27 with the initial dose 24 h prior to the first challenge. On the days of challenge, animals were dosed with compound or vehicle one hour after challenge. Animals therefore received a total of 5 doses.

Dexamethasone was used as a positive control dosed at 10 mg/kg orally in the same vehicle once daily on days 24 to 27 with the initial dose 1 h prior to the first challenge. Animals therefore received a total of 4 doses.

Animals were killed on day 28 (48 hours post last saline or OVA challenge) and bronchoalveolar lavage (BAL) was performed with 5×1 ml (0.1% bovine serum albumin, 10 mM EDTA in PBS) and pooled. Numbers of lymphocytes, macrophages, eosinophils and neutrophils in BAL were identified by light scatter flow cytometry and quantified.

Results

In Interferon Induction Assay 'A', Examples 1 to 60 had a mean $EC_{50}$ of between 0.01 to 19 uM.

In Interferon Induction Assay 'B', Example 13 Isomer 1, Example 13 Isomer 2, Example 16 Isomer 1, Example 16 Isomer 2, Example 26 Isomer 1, Example 26 Isomer 2, Example 27 Isomer 1, Example 27 Isomer 2, and Examples 61-141 also had a mean $EC_{50}$ of between 0.01 to 10 uM.

Replicon Assay

In the above replicon assay, Examples 1 and 4 had a mean $EC_{50}$ of 0.043 uM and 1.05 uM respectively.

Ovalbumin-induced Acute Pulmonary Inflammation Model

In the above ovalbumin-induced acute pulmonary inflammation model, compared with saline treated controls, Example 4 reduced lymphocyte, eosinophil and neutrophil counts in BAL by 66%, 72% and 50% respectively. In the same experiment dexamethasone reduced lymphocyte, eosinophil and neutrophil counts in BAL by 87%, 92% and 68% respectively.

In the above ovalbumin-induced acute pulmonary inflammation model, compared with saline treated controls, Example 12 reduced lymphocyte, eosinophil and neutrophil counts in BAL by 68%, 67% and 58% respectively. In the same experiment dexamethasone reduced lymphocyte, eosinophil and neutrophil counts in BAL by 86%, 86% and 65% respectively.

The invention claimed is:

1. A compound of formula (I):

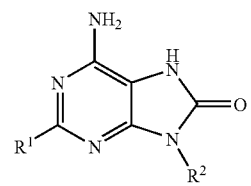

wherein;

$R^1$ is $C_{1-8}$alkylamino, $C_{1-8}$alkoxy, $C_{3-7}$cycloalkyl$C_{1-6}$alkylamino, $C_{3-7}$cycloalkyl$C_{1-6}$alkoxy, $C_{1-3}$alkoxy$C_{2-3}$alkoxy, or Het$^b$-$C_{1-3}$alkoxy;

Het$^b$ is a 5- or 6-membered saturated aliphatic heterocyle containing one oxygen atom;

$R^2$ is —$(CH_2)_n$-Het;

n is an integer having a value of 1 to 4;

Het is a 5- or 6-membered saturated aliphatic heterocycle containing one oxygen heteroatom, which heterocycle may be substituted by one or two $C_{1-4}$alkyl groups;

or salts or solvates thereof.

2. A compound according to claim 1 wherein $R^1$ is $C_{1-6}$alkylamino, $C_{1-8}$alkoxy, $C_{3-7}$cycloalkyl$C_{1-6}$alkylamino, $C_{3-7}$cycloalkyl$C_{1-6}$alkoxy, $C_{1-3}$alkoxy$C_{2-3}$alkoxy, or Het$^b$-$C_{1-3}$alkoxy.

3. A compound according to claim 1 or claim 2 wherein $R^1$ is n-butoxy, n-butylamino, 2,2-dimethylpentyloxy, n-pentylamino, 3-methylbutoxy, 2-methylbutoxy, 1-methylbutoxy, 2-methylbutylamino, 3-methylbutylamino, 1-methylbutylamino, 2-(cyclopropyl)ethoxy, 2-(ethoxy)ethoxy, (1-methyl-2-methoxy)ethoxy, cyclohexylmethylamino, cyclopentylmethylamino, 2-(cyclopropyl)ethylamino, 2-(methyl)propoxy, cyclohexylmethoxy, methoxyethoxy, (2-tetrahydrofuranyl)methoxy, (2-tetrahydro-2H-pyranyl)methoxy, or 2-(iso-propoxy)ethoxy.

4. A compound according to claim 1 wherein n is 1.

5. A compound according to claim 1 wherein n is 2.

6. A compound according to claim 1 wherein n is 3.

7. A compound according to claim 1 wherein n is 4.

8. A compound according to claim 1 wherein n is 1 and Het is tetrahydrofuran-3-yl, tetrahydro-2H-pyran-3-yl, tetrahydro-2H-pyran-4-yl, tetrahydrofuran-2-yl, 2,2-dimethyltetrahydro-2H-pyran-4-yl, or tetrahydro-2H-pyran-2-yl.

9. A compound according to claim 1 wherein n is 2 and Het is tetrahydro-2H-pyran-4-yl, tetrahydrofuran-2-yl, tetrahydro-2H-pyran-3-yl, tetrahydro-2H-pyran-2-yl, or tetrahydrofuran-3-yl.

10. A compound according to claim 1 wherein n is 3 and Het is tetrahydro-2H-pyran-3-yl.

11. A compound according to claim 1 wherein n is 4 and Het is tetrahydro-2H-pyran-3-yl.

12. A compound according to claim 1 wherein $R^1$ is n-butylamino, n-butoxy, or 2-(cyclopropyl)ethoxy.

13. A compound according to claim 1 wherein n is 1 and $R^2$ is tetrahydro-2H-pyran-4-yl or tetrahydrofuran-3-yl.

14. A compound according to claim 1 wherein $R^1$ is n-butylamino, n-butoxy, (R)-1-methyl butyloxy, (S)-1-methylbutyloxy, or 2-(cyclopropyl)ethoxy.

15. A compound according to claim 1 wherein Het is tetrahydrofuran-3-yl, tetrahydro-2H-pyran-3-yl, tetrahydro-2H-pyran-4-yl, tetrahydrofuran-2-yl, 2,2-dimethyltetrahydro-2H-pyran-4-yl, or tetrahydro-2H-pyran-2-yl.

16. A compound according to claim 1 wherein Het is tetrahydro-2H-pyran-4-yl, tetrahydrofuran-2-yl, tetrahydro-2H-pyran-3-yl, tetrahydro-2H-pyran-2-yl, or tetrahydrofuran-3-yl.

17. A compound according to claim 1 wherein Het is tetrahydro-2H-pyran-3-yl.

18. A compound according to claim 1 wherein Het is tetrahydro-2H-pyran-3-yl.

19. A compound according to claim 1 wherein Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydro-2H-pyran-2-yl.

20. A compound according to claim 1 wherein n is 2 and Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydrofuran-2-yl.

21. A compound according to claim 1 wherein n is 3 and Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydrofuran-2-yl.

22. A compound according to claim 1 wherein n is 4 and Het is tetrahydro-2H-pyran-4-yl, tetrahydro-2H-pyran-3-yl, tetrahydro-2H-pyran-2-yl, 2,2-dimethyltetrahydro-2H-pyran-4-yl, tetrahydrofuran-3-yl, or tetrahydrofuran-2-yl.

23. A compound selected from the list consisting of:
6-amino-2-butoxy-9-(tetrahydro-2H-pyran-4-ylmethyl)-7,9-dihydro-8H-purin-8-one;
6-amino-2-butoxy-9-(tetrahydro-2H-pyran-2-ylmethyl)-7,9-dihydro-8H-purin-8-one;
6-amino-2-butoxy-9-(tetrahydrofuran-2-ylmethyl)-7,9-dihydro-8H-purin-8-one;
6-amino-2-butylamino-9-(tetrahydro-2H-pyran-4-ylmethyl)-7,9-dihydro-8H-purin-8-one;
6-amino-2-butylamino-9-(tetrahydro-2H-pyran-2-ylmethyl)-7,9-dihydro-8H-purin-8-one;
6-amino-2-butylamino-9-(tetrahydrofuran-2-ylmethyl)-7,9-dihydro-8H-purin-8-one;
6-amino-2-butylamino-9-[2-(tetrahydro-2H-pyran-4-yl)ethyl]-7,9-dihydro-8H-purin-8-one;
6-amino-2-butylamino-9-(tetrahydrofuran-3-ylmethyl)-7,9-dihydro-8H-purin-8-one;
6-amino-2-butylamino-9-(tetrahydro-2H-pyran-3-ylmethyl)-7,9-dihydro-8H-purin-8-one;
6-amino-2-butoxy-9-(tetrahydrofuran-3-ylmethyl)-7,9-dihydro-8H-purin-8-one;
6-amino-2-butoxy-9-[2-(tetrahydro-2H-pyran-4-yl)ethyl]-7,9-dihydro-8H-purin-8-one;
6-amino-2-butoxy-9-(tetrahydro-2H-pyran-3-ylmethyl)-7,9-dihydro-8H-purin-8-one;
6-amino-2-butoxy-9-[2-(tetrahydrofuran-2-yl)ethyl]-7,9-dihydro-8H-purin-8-one;
6-amino-2-butylamino-9-[2-(tetrahydrofuran-2-yl)ethyl]-7,9-dihydro-8H-purin-8-one;
6-amino-2-butoxy-9-[2-(tetrahydro-2H-pyran-3-yl)ethyl]-7,9-dihydro-8H-purin-8-one;
6-amino-2-butylamino-9-[2-(tetrahydro-2H-pyran-3-yl)ethyl]-7,9-dihydro-8H-purin-8-one;
6-amino-2-[(2,2-dimethylpentyl)oxy]-9-(tetrahydro-2H-pyran-4-ylmethyl)-7,9-dihydro-8H-purin-8-one;
6-amino-2-(pentylamino)-9-(tetrahydro-2H-pyran-4-ylmethyl)-7,9-dihydro-8H-purin-8-one;
6-amino-2-[(3-methylbutyl)oxy]-9-(tetrahydro-2H-pyran-4-ylmethyl)-7,9-dihydro-8H-purin-8-one;
6-amino-2-[(2-methylbutyl)oxy]-9-(tetrahydro-2H-pyran-4-ylmethyl)-7,9-dihydro-8H-purin-8-one;
6-amino-2-[(1-methylbutyl)oxy]-9-(tetrahydro-2H-pyran-4-ylmethyl)-7,9-dihydro-8H-purin-8-one;
6-amino-2-[(2-methylbutyl)amino]-9-(tetrahydro-2H-pyran-4-ylmethyl)-7,9-dihydro-8H-purin-8-one;
6-amino-2-[(3-methylbutyl)amino]-9-(tetrahydro-2H-pyran-4-ylmethyl)-7,9-dihydro-8H-purin-8-one;
6-amino-2-[(1-methylbutyl)amino]-9-(tetrahydro-2H-pyran-4-ylmethyl)-7,9-dihydro-8H-purin-8-one;
6-amino-2-[(2-cyclopropylethyl)oxy]-9-(tetrahydro-3-furanylmethyl)-7,9-dihydro-8H-purin-8-one;
6-amino-2-butyloxy-9-[2-(tetrahydro-2H-pyran-2-yl)ethyl]-7,9-dihydro-8H-purin-8-one;
6-amino-2-butyloxy-9-[(2,2-dimethyltetrahydro-2H-pyran-4-yl)methyl]-7,9-dihydro-8H-purin-8-one;
6-amino-2-(butylamino)-9-[(2,2-dimethyltetrahydro-2H-pyran-4-yl)methyl]-7,9-dihydro-8H-purin-8-one;
6-amino-2-butyloxy-9-[2-(tetrahydro-3-furanyl)ethyl]-7,9-dihydro-8H-purin-8-one;
6-amino-2-(butylamino)-9-[2-(tetrahydro-2H-pyran-2-yl)ethyl]-7,9-dihydro-8H-purin-8-one;
6-amino-2-(butylamino)-9-[2-(tetrahydro-3-furanyl)ethyl]-7,9-dihydro-8H-purin-8-one;
6-amino-2-(butyloxy)-9-(tetrahydro-3-furanylmethyl)-7,9-dihydro-8H-purin-8-one, isomer 1;
6-amino-2-{[2-(ethyloxy)ethyl]oxy}-9-(tetrahydro-2H-pyran-4-ylmethyl)-7,9-dihydro-8H-purin-8-one;
6-amino-2-{[1-methyl-2-(methoxy)ethyl]oxy}-9-(tetrahydro-2H-pyran-4-ylmethyl)-7,9-dihydro-8H-purin-8-one;
6-amino-2-{[2-(ethyloxy)ethyl]oxy}-9-(tetrahydro-2H-pyran-3-ylmethyl)-7,9-dihydro-8H-purin-8-one;
6-amino-2-{[1-methyl-2-(methoxy)ethyl]oxy}-9-(tetrahydro-2H-pyran-3-ylmethyl)-7,9-dihydro-8H-purin-8-one;
6-amino-2-[(cyclohexylmethyl)amino]-9-(tetrahydro-2H-pyran-4-ylmethyl)-7,9-dihydro-8H-purin-8-one;
6-amino-2-[(cyclopentylmethyl)amino]-9-(tetrahydro-2H-pyran-4-ylmethyl)-7,9-dihydro-8H-purin-8-one;
6-amino-2-[(2-cyclopropylethyl)amino]-9-(tetrahydro-2H-pyran-4-ylmethyl)-7,9-dihydro-8H-purin-8-one;

6-amino-2-(butylamino)-9-(tetrahydro-3-furanylmethyl)-7,9-dihydro-8H-purin-8-one;
6-amino-2-[(2-methylpropyl)oxy]-9-(tetrahydro-2H-pyran-4-ylmethyl)-7,9-dihydro-8H-purin-8-one;
6-amino-2-[(2-cyclopropylethyl)oxy]-9-(tetrahydro-2H-pyran-4-ylmethyl)-7,9-dihydro-8H-purin-8-one;
6-amino-2-[(cyclohexyl methyl)oxy]-9-(tetrahydro-2H-pyran-4-ylmethyl)-7,9-dihydro-8H-purin-8-one;
6-amino-2-{[2-(methoxy)ethyl]oxy}-9-(tetrahydro-2H-pyran-4-ylmethyl)-7,9-dihydro-8H-purin-8-one;
6-amino-2-{[2-(methoxy)ethyl]oxy}-9-(tetrahydro-3-furanylmethyl)-7,9-dihydro-8H-purin-8-one;
6-amino-2-[(tetrahydro-2-furanylmethyl)oxy]-9-(tetrahydro-2H-pyran-4-ylmethyl)-7,9-dihydro-8H-purin-8-one;
6-amino-2-(butylamino)-9-[3-(tetrahydro-2H-pyran-3-yl)propyl]-7,9-dihydro-8H-purin-8-one;
6-amino-9-(tetrahydro-2H-pyran-4-ylmethyl)-2-[(tetrahydro-2H-pyran-2-yl methoxy]-7,9-dihydro-8H-purin-8-one;
6-amino-2-({2-[(1-methylethyl)oxy]ethyl}oxy)-9-(tetrahydro-2H-pyran-4-ylmethyl)-7,9-dihydro-8H-purin-8-one;
6-amino-2-(butylamino)-9-[4-(tetrahydro-2H-pyran-3-yl)butyl]-7,9-dihydro-8H-purin-8-one;
6-amino-2-[(2-cyclopropylethyl)amino]-9-(tetrahydro-3-furanylmethyl)-7,9-dihydro-8H-purin-8-one;
6-amino-2-[(2-cyclopropylethyl)amino]-9-(tetrahydro-2H-pyran-3-ylmethyl)-7,9-dihydro-8H-purin-8-one;
6-amino-2-[(2-cyclopropylethyl)oxy]-9-(tetrahydro-3-furanylmethyl)-7,9-dihydro-8H-purin-8-one;
and salts or solvates thereof.

24. A compound selected from the list consisting of:
6-amino-2-(butyloxy)-9-(tetrahydro-3-furanylmethyl)-7,9-dihydro-8H-purin-8-one;
6-amino-2-butylamino-9-(tetrahydro-2H-pyran-4-ylmethyl)-7,9-dihydro-8H-purin-8-one;
6-amino-2-(butylamino)-9-(tetrahydro-3-furanylmethyl)-7,9-dihydro-8H-purin-8-one;
6-amino-2-[(2-cyclopropylethyl)oxy]-9-(tetrahydro-3-furanylmethyl)-7,9-dihydro-8H-purin-8-one;
and salts or solvates thereof.

25. A compound selected from the list consisting of:
6-amino-2-butoxy-9-[2-(tetrahydrofuran-2-yl)ethyl]-7,9-dihydro-8H-purin-8-one;
6-amino-2-butylamino-9-[2-(tetrahydro-2H-pyran-3-yl)ethyl]-7,9-dihydro-8H-purin-8-one;
6-amino-2-butyloxy-9-[2-(tetrahydro-2H-pyran-2-yl)ethyl]-7,9-dihydro-8H-purin-8-one;
6-amino-2-butyloxy-9-[(2,2-dimethyltetrahydro-2H-pyran-4-yl)methyl]-7,9-dihydro-8H-purin-8-one;
6-amino-2-(butylamino)-9-[3-(tetrahydro-2-furanyl)propyl]-7,9-dihydro-8H-purin-8-one;
6-amino-2-(butylamino)-9-[4-(tetrahydro-2-furanyl)butyl]-7,9-dihydro-8H-purin-8-one;
6-amino-2-(butylamino)-9-{2-[(3S)-tetrahydro-3-furanyl]ethyl}-7,9-dihydro-8H-purin-8-one;
6-amino-2-(butylamino)-9-{2-[(3R)-tetrahydro-3-furanyl]ethyl}-7,9-dihydro-8H-purin-8-one;
6-amino-2-(butylamino)-9-[3-(tetrahydro-3-furanyl)propyl]-7,9-dihydro-8H-purin-8-one;
6-amino-2-(butylamino)-9-[4-(tetrahydro-3-furanyl)butyl]-7,9-dihydro-8H-purin-8-one;
6-amino-2-(butylamino)-9-[3-(tetrahydro-2H-pyran-2-yl)propyl]-7,9-dihydro-8H-purin-8-one;
6-amino-2-(butylamino)-9-[4-(tetrahydro-2H-pyran-2-yl)butyl]-7,9-dihydro-8H-purin-8-one;
6-amino-2-(butylamino)-9-[3-(tetrahydro-2H-pyran-4-yl)propyl]-7,9-dihydro-8H-purin-8-one;
6-amino-2-(butylamino)-9-[4-(tetrahydro-2H-pyran-4-yl)butyl]-7,9-dihydro-8H-purin-8-one;
6-amino-2-(butylamino)-9-[2-(2,2-dimethyltetrahydro-2H-pyran-4-yl)ethyl]-7,9-dihydro-8H-purin-8-one;
6-amino-2-(butylamino)-9-[3-(2,2-dimethyltetrahydro-2H-pyran-4-yl)propyl]-7,9-dihydro-8H-purin-8-one;
6-amino-2-(butylamino)-9-[4-(2,2-dimethyltetrahydro-2H-pyran-4-yl)butyl]-7,9-dihydro-8H-purin-8-one;
6-amino-2-(butyloxy)-9-[3-(tetrahydro-2-furanyl)propyl]-7,9-dihydro-8H-purin-8-one;
6-amino-2-(butyloxy)-9-[4-(tetrahydro-2-furanyl)butyl]-7,9-dihydro-8H-purin-8-one;
6-amino-2-(butyloxy)-9-{2-[(3S)-tetrahydro-3-furanyl]ethyl}-7,9-dihydro-8H-purin-8-one;
6-amino-2-(butyloxy)-9-{2-[(3R)-tetrahydro-3-furanyl]ethyl}-7,9-dihydro-8H-purin-8-one;
6-amino-2-(butyloxy)-9-[3-(tetrahydro-3-furanyl)propyl]-7,9-dihydro-8H-purin-8-one;
6-amino-2-(butyloxy)-9-[4-(tetrahydro-3-furanyl)butyl]-7,9-dihydro-8H-purin-8-one;
6-amino-2-(butyloxy)-9-[3-(tetrahydro-2H-pyran-2-yl)propyl]-7,9-dihydro-8H-purin-8-one;
6-amino-2-(butyloxy)-9-[4-(tetrahydro-2H-pyran-2-yl)butyl]-7,9-dihydro-8H-purin-8-one;
6-amino-2-(butyloxy)-9-[3-(tetrahydro-2H-pyran-3-yl)propyl]-7,9-dihydro-8H-purin-8-one;
6-amino-2-(butyloxy)-9-[4-(tetrahydro-2H-pyran-3-yl)butyl]-7,9-dihydro-8H-purin-8-one;
6-amino-2-(butyloxy)-9-[3-(tetrahydro-2H-pyran-4-yl)propyl]-7,9-dihydro-8H-purin-8-one;
6-amino-2-(butyloxy)-9-[4-(tetrahydro-2H-pyran-4-yl)butyl]-7,9-dihydro-8H-purin-8-one;
6-amino-2-(butyloxy)-9-[2-(2,2-dimethyltetrahydro-2H-pyran-4-yl)ethyl]-7,9-dihydro-8H-purin-8-one;
6-amino-2-(butyloxy)-9-[3-(2,2-dimethyltetrahydro-2H-pyran-4-yl)propyl]-7,9-dihydro-8H-purin-8-one;
6-amino-2-(butyloxy)-9-[4-(2,2-dimethyltetrahydro-2H-pyran-4-yl)butyl]-7,9-dihydro-8H-purin-8-one;
6-amino-2-[(2-cyclopropylethyl)oxy]-9-[2-(tetrahydro-2-furanyl)ethyl]-7,9-dihydro-8H-purin-8-one;
6-amino-2-[(2-cyclopropylethyl)oxy]-9-[3-(tetrahydro-2-furanyl)propyl]-7,9-dihydro-8H-purin-8-one;
6-amino-2-[(2-cyclopropylethyl)oxy]-9-[4-(tetrahydro-2-furanyl)butyl]-7,9-dihydro-8H-purin-8-one;
6-amino-2-[(2-cyclopropylethyl)oxy]-9-[2-(tetrahydro-3-furanyl)ethyl]-7,9-dihydro-8H-purin-8-one;
6-amino-2-[(2-cyclopropylethyl)oxy]-9-{2-[(3S)-tetrahydro-3-furanyl]ethyl}-7,9-dihydro-8H-purin-8-one;
6-amino-2-[(2-cyclopropylethyl)oxy]-9-{2-[(3R)-tetrahydro-3-furanyl]ethyl}-7,9-dihydro-8H-purin-8-one
6-amino-2-[(2-cyclopropylethyl)oxy]-9-[3-(tetrahydro-3-furanyl)propyl]-7,9-dihydro-8H-purin-8-one;
6-amino-2-[(2-cyclopropylethyl)oxy]-9-[4-(tetrahydro-3-furanyl)butyl]-7,9-dihydro-8H-purin-8-one;
6-amino-2-[(2-cyclopropylethyl)oxy]-9-[2-(tetrahydro-2H-pyran-2-yl)ethyl]-7,9-dihydro-8H-purin-8-one;
6-amino-2-[(2-cyclopropylethyl)oxy]-9-[3-(tetrahydro-2H-pyran-2-yl)propyl]-7,9-dihydro-8H-purin-8-one;
6-amino-2-[(2-cyclopropylethyl)oxy]-9-[4-(tetrahydro-2H-pyran-2-yl)butyl]-7,9-dihydro-8H-purin-8-one;
6-amino-2-[(2-cyclopropylethyl)oxy]-9-[2-(tetrahydro-2H-pyran-3-yl)ethyl]-7,9-dihydro-8H-purin-8-one;
6-amino-2-[(2-cyclopropylethyl)oxy]-9-[4-(tetrahydro-2H-pyran-3-yl)butyl]-7,9-dihydro-8H-purin-8-one;

6-amino-2-[(2-cyclopropylethyl)oxy]-9-[2-(tetrahydro-2H-pyran-4-yl)ethyl]-7,9-dihydro-8H-purin-8-one;
6-amino-2-[(2-cyclopropylethyl)oxy]-9-[3-(tetrahydro-2H-pyran-4-yl)propyl]-7,9-dihydro-8H-purin-8-one;
6-amino-2-[(2-cyclopropylethyl)oxy]-9-[4-(tetrahydro-2H-pyran-4-yl)butyl]-7,9-dihydro-8H-purin-8-one;
6-amino-2-[(2-cyclopropylethyl)oxy]-9-[2-(2,2-dimethyltetrahydro-2H-pyran-4-yl)ethyl]-7,9-dihydro-8H-purin-8-one;
6-amino-2-[(2-cyclopropylethyl)oxy]-9-[3-(2,2-dimethyltetrahydro-2H-pyran-4-yl)propyl]-7,9-dihydro-8H-purin-8-one;
6-amino-2-[(2-cyclopropylethyl)oxy]-9-[4-(2,2-dimethyltetrahydro-2H-pyran-4-yl)butyl]-7,9-dihydro-8H-purin-8-one;
6-amino-2-{[(1S)-1-methylbutyl]oxy}-9-[2-(tetrahydro-2-furanyl)ethyl]-7,9-dihydro-8H-purin-8-one;
6-amino-2-{[(1S)-1-methylbutyl]oxy}-9-[3-(tetrahydro-2-furanyl)propyl]-7,9-dihydro-8H-purin-8-one;
6-amino-2-{[(1S)-1-methylbutyl]oxy}-9-{2-[(3S)-tetrahydro-3-furanyl]ethyl}-7,9-dihydro-8H-purin-8-one;
6-amino-2-{[(1S)-1-methylbutyl]oxy}-9-{2-[(3R)-tetrahydro-3-furanyl]ethyl}-7,9-dihydro-8H-purin-8-one;
6-amino-2-{[(1S)-1-methylbutyl]oxy}-9-[3-(tetrahydro-3-furanyl)propyl]-7,9-dihydro-8H-purin-8-one;
6-amino-2-{[(1S)-1-methylbutyl]oxy}-9-[4-(tetrahydro-3-furanyl)butyl]-7,9-dihydro-8H-purin-8-one;
6-amino-2-{[(1S)-1-methylbutyl]oxy}-9-[2-(tetrahydro-2H-pyran-2-yl)ethyl]-7,9-dihydro-8H-purin-8-one;
6-amino-2-{[(1S)-1-methylbutyl]oxy}-9-[3-(tetrahydro-2H-pyran-2-yl)propyl]-7,9-dihydro-8H-purin-8-one;
6-amino-2-{[(1S)-1-methylbutyl]oxy}-9-[4-(tetrahydro-2H-pyran-2-yl)butyl]-7,9-dihydro-8H-purin-8-one;
6-amino-2-{[(1S)-1-methylbutyl]oxy}-9-[2-(tetrahydro-2H-pyran-3-yl)ethyl]-7,9-dihydro-8H-purin-8-one;
6-amino-2-{[(1S)-1-methylbutyl]oxy}-9-[4-(tetrahydro-2H-pyran-3-yl)butyl]-7,9-dihydro-8H-purin-8-one;
6-amino-2-{[(1S)-1-methylbutyl]oxy}-9-[2-(tetrahydro-2H-pyran-4-yl)ethyl]-7,9-dihydro-8H-purin-8-one;
6-amino-2-{[(1S)-1-methylbutyl]oxy}-9-[3-(tetrahydro-2H-pyran-4-yl)propyl]-7,9-dihydro-8H-purin-8-one;
6-amino-2-{[(1S)-1-methylbutyl]oxy}-9-[4-(tetrahydro-2H-pyran-4-yl)butyl]-7,9-dihydro-8H-purin-8-one;
6-amino-9-[2-(2,2-dimethyltetrahydro-2H-pyran-4-yl)ethyl]-2-{[(S)-1-methylbutyl]oxy}-7,9-dihydro-8H-purin-8-one;
6-amino-9-[3-(2,2-dimethyltetrahydro-2H-pyran-4-yl)propyl]-2-{[(1S)-1-methylbutyl]oxy}-7,9-dihydro-8H-purin-8-one;
6-amino-9-[4-(2,2-dimethyltetrahydro-2H-pyran-4-yl)butyl]-2-{[(1S)-1-methylbutyl]oxy}-7,9-dihydro-8H-purin-8-one;
6-amino-2-{[(1R)-1-methylbutyl]oxy}-9-[2-(tetrahydro-2-furanyl)ethyl]-7,9-dihydro-8H-purin-8-one;
6-amino-2-{[(1R)-1-methylbutyl]oxy}-9-[3-(tetrahydro-2-furanyl)propyl]-7,9-dihydro-8H-purin-8-one;
6-amino-2-{[(1R)-1-methylbutyl]oxy}-9-{2-[(3S)-tetrahydro-3-furanyl]ethyl}-7,9-dihydro-8H-purin-8-one;
6-amino-2-{[(1R)-1-methylbutyl]oxy}-9-{2-[(3R)-tetrahydro-3-furanyl]ethyl}-7,9-dihydro-8H-purin-8-one;
6-amino-2-{[(1R)-1-methylbutyl]oxy}-9-[3-(tetrahydro-3-furanyl)propyl]-7,9-dihydro-8H-purin-8-one;
6-amino-2-{[(1R)-1-methylbutyl]oxy}-9-[4-(tetrahydro-3-furanyl)butyl]-7,9-dihydro-8H-purin-8-one;
6-amino-2-{[(1R)-1-methylbutyl]oxy}-9-[2-(tetrahydro-2H-pyran-2-yl)ethyl]-7,9-dihydro-8H-purin-8-one;
6-amino-2-{[(1R)-1-methylbutyl]oxy}-9-[3-(tetrahydro-2H-pyran-2-yl)propyl]-7,9-dihydro-8H-purin-8-one;
6-amino-2-{[(1R)-1-methylbutyl]oxy}-9-[4-(tetrahydro-2H-pyran-2-yl)butyl]-7,9-dihydro-8H-purin-8-one;
6-amino-2-{[(1R)-1-methylbutyl]oxy}-9-[2-(tetrahydro-2H-pyran-3-yl)ethyl]-7,9-dihydro-8H-purin-8-one;
6-amino-2-{[(1R)-1-methylbutyl]oxy}-9-[4-(tetrahydro-2H-pyran-3-yl)butyl]-7,9-dihydro-8H-purin-8-one;
6-amino-2-{[(1R)-1-methylbutyl]oxy}-9-[2-(tetrahydro-2H-pyran-4-yl)ethyl]-7,9-dihydro-8H-purin-8-one;
6-amino-2-{[(1R)-1-methylbutyl]oxy}-9-[3-(tetrahydro-2H-pyran-4-yl)propyl]-7,9-dihydro-8H-purin-8-one;
6-amino-2-{[(1R)-1-methylbutyl]oxy}-9-[4-(tetrahydro-2H-pyran-4-yl)butyl]-7,9-dihydro-8H-purin-8-one;
6-amino-9-[2-(2,2-dimethyltetrahydro-2H-pyran-4-yl)ethyl]-2-{[(1R)-1-methylbutyl]oxy}-7,9-dihydro-8H-purin-8-one;
6-amino-9-[3-(2,2-dimethyltetrahydro-2H-pyran-4-yl)propyl]-2-{[(1R)-1-methylbutyl]oxy}-7,9-dihydro-8H-purin-8-one;
6-amino-9-[4-(2,2-dimethyltetrahydro-2H-pyran-4-yl)butyl]-2-{[(1R)-1-methylbutyl]oxy}-7,9-dihydro-8H-purin-8-one;
and salts and solvates thereof.

26. A method for the treatment of asthma, which method comprises administering an effective amount of a compound as defined in claim 1, or a pharmaceutically acceptable salt or solvate thereof.

27. A pharmaceutical composition comprising a compound as defined in claim 1, or a pharmaceutically acceptable salt or solvate thereof, and optionally one or more pharmaceutically acceptable diluents or carriers.

28. A compound selected from the list consisting of:
6-amino-2-(butyloxy)-9[4-(tetrahydro-2H-pyran-3-yl)butyl]-7,9-dihydro-8H-purin-8-one;
6-amino-2-(butyloxy)-9[3-(tetrahydro-2H-pyran-4-yl)propyl]-7,9-dihydro-8H-purin-8-one;
6-amino-2-(butyloxy)-9[4-(tetrahydro-2H-pyran-4-yl)butyl]-7,9-dihydro-8H-purin-8-one;
6-amino-2-[(2-cyclopropylethyl)oxy]-9-[3-(tetrahydro-2H-pyran-4-yl)propyl]-7, 9-dihydro-8H-purin-8-one;
6-amino-2-{[(1S)-1-methylbutyl]oxy}-9-[2-(tetrahydro-2H-pyran-4-yl)ethyl]-7,9-dihydro-8H-purin-8-one;
6-amino-2-{[(1S)-1-methylbutyl]oxy}-9-[3-(tetrahydro-2H-pyran-4-yl)propyl]-7,9-dihydro-8H-purin-8-one, and;
6-amino-2-{[(1S)-1-methylbutyl]oxy}-9-[4-(tetrahydro-2H-pyran-4-yl)butyl]-7,9-dihydro-8H-purin-8-one;
6-amino-2-[(2-cyclopropylethyl)oxy]-9-[2-(tetrahydro-2H-pyran-4-yl)ethyl]-7, 9-dihydro-8H-purin-8-one, and;
6-amino-2-[(2-cyclopropylethyl)oxy]-9-[4-(tetrahydro-2H-pyran-4-yl)butyl]-7,9-dihydro-8H-purin-8-one;
and salts or solvates thereof.

* * * * *